US010323253B2

(12) United States Patent
Abad et al.

(10) Patent No.: US 10,323,253 B2
(45) Date of Patent: Jun. 18, 2019

(54) TRANSGENIC PLANTS WITH ENHANCED TRAITS

(71) Applicant: Monsanto Technology LLC, St. Louis, MO (US)

(72) Inventors: Mark S. Abad, Webster Groves, MO (US); Erin Bell, St. Louis, MO (US); Paul S. Chomet, St. Louis, MO (US); Todd DeZwaan, Apex, NC (US); Stephen Duff, St. Louis, MO (US); Barry S. Goldman, St. Louis, MO (US); Hongwu Jia, Apex, NC (US); Lloyd Jones, Raleigh, NC (US); Balasulojini Karunanandaa, Creve Coeur, MO (US); Saritha V. Kuriakose, Kottavam (IN); Linda L. Lutfiyya, St. Louis, MO (US); Savitha Madappa, Bangalore (IN); Zoe P. McKiness, St. Louis, MO (US); Donald E. Nelson, Durham, NC (US); Sasha Preuss, Webster Groves, MO (US); Monnanda S. Rajani, Chesterfield, MO (US); Dhanalakshmi Ramachandra, Bangalore (IN); Aniruddha Raychaudhuri, Wildwood, MO (US); Daniel P. Schachtman, Lincoln, NE (US); Steven H. Schwartz, Davis, CA (US); Char Shobha, Bangalore (IN); Matthew M. Tanzer, Durham, NC (US); Tyamagondlu V. Venkatesh, St. Louis, MO (US); Huai Wang, Chesterfield, MO (US); Xiaoyun Wu, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/532,681

(22) PCT Filed: Dec. 2, 2015

(86) PCT No.: PCT/US2015/063306
§ 371 (c)(1),
(2) Date: Jun. 2, 2017

(87) PCT Pub. No.: WO2016/089931
PCT Pub. Date: Jun. 9, 2016

(65) Prior Publication Data

US 2017/0369894 A1  Dec. 28, 2017

Related U.S. Application Data

(60) Provisional application No. 62/086,918, filed on Dec. 3, 2014.

(51) Int. Cl.
*C12N 15/82* (2006.01)

(52) U.S. Cl.
CPC ..... *C12N 15/8261* (2013.01); *C12N 15/8243* (2013.01); *Y02A 40/146* (2018.01)

(58) Field of Classification Search
None
See application file for complete search history.

(56) References Cited

U.S. PATENT DOCUMENTS

| 2008/0090998 | A1 | 4/2008 | Abad et al. |
| 2012/0005773 | A1 | 1/2012 | Aasen et al. |
| 2012/0246748 | A1* | 9/2012 | Guo ..... C07K 14/415 800/260 |

FOREIGN PATENT DOCUMENTS

| WO | 1995002060 A1 | 1/1995 |
| WO | 2014102773 A1 | 7/2014 |

OTHER PUBLICATIONS

Whisstock J.C. et al. Prediction of protein function from protein sequence and structure. Q Rev Biophys. Aug. 2003;36(3):307-40. Review. (Year: 2003).*

* cited by examiner

*Primary Examiner* — Cynthia E Collins
(74) *Attorney, Agent, or Firm* — Dentons US LLP; Lawrence M. Lavin, Jr.

(57) ABSTRACT

This disclosure provides recombinant DNA constructs and transgenic plants having enhanced traits such as increased yield, increased nitrogen use efficiency and enhanced drought tolerance; propagules, progeny and field crops of such transgenic plants; and methods of making and using such transgenic plants. This disclosure also provides methods of producing seed from such transgenic plants, growing such seed and selecting progeny plants with enhanced traits. Also disclosed are transgenic plants with altered phenotypes which are useful for screening and selecting transgenic events for the desired enhanced trait.

15 Claims, No Drawings

Specification includes a Sequence Listing.

SEQUENCE LISTING

<160> NUMBER OF SEQ ID NOS: 104

<210> SEQ ID NO 1
<211> LENGTH: 165
<212> TYPE: DNA

<213> ORGANISM: Arabidopsis thaliana

<400> SEQUENCE: 1

| | | |
|---|---|---|
| atggtgaaca acgttgtctc tatcgaaaag atgaaagcac tctggcactc cgaggttcat | 60 |
| gatgaacaaa aatgggcggt gaacatgaaa cttctgcgag cacttggtat gtttgcagga | 120 |
| ggagtcgtcc tcatgcgtag ctatggggat ctcatgggag tttga | 165 |

<210> SEQ ID NO 2
<211> LENGTH: 948
<212> TYPE: DNA
<213> ORGANISM: Arabidopsis thaliana

<400> SEQUENCE: 2

| | | |
|---|---|---|
| atggtggggt gggcgattgc gctacacggc ggtgccggag acattccgat cgatctcccc | 60 |
| gacgagcgac gtatccctcg tgagagcgcc ctccgtcact gcctcgatct tggcatctcc | 120 |
| gccctcaaat ccggcaagcc tcccttggac gtcgccgaac ttgtcgttcg tgaacttgag | 180 |
| aaccaccegg acttcaatgc gggtaaagga tctgtcttaa ctgcacaagg cactgttgaa | 240 |
| atggaagctt ccattatgga cggtaaaacc aaaagatgtg agctgtctc cggcttgacc | 300 |
| actgttgtta atcccatttc tttagctcgc ctcgtcatgg agaaaactcc tcatatatat | 360 |
| cttgcattcg atgctgctga agcttttgca agagcacatg gtgttgagac ggtagattct | 420 |
| agccatttca taactcctga aaacattgca aggctaaagc aggccaaaga attcaatcga | 480 |
| gtccagttgg attacacagt ccctagtccg aaagtaccgg acaattgcgg tgacagccaa | 540 |
| ataggaacgg tcgatgtgt agctgtggac agtgctggaa atctagcttc ggctacatca | 600 |
| acgggcggtt atgtcaacaa aatggttggc agaattgggg atacgccagt cattggcgca | 660 |
| ggaacttacg ctaaccacct tgtgccatc tcagccacag gtaaaggaga ggatatcatc | 720 |
| cgtggaaccg tgctagaga cgtggctgca ctcatggaat ataaaggctt gtctttgact | 780 |
| gaggcagcgc cttatgttgt tgaccaatct gttcccagag aagctgtgg actcgttgct | 840 |
| gtctctgcca atggtgaagt cacaatgccg tttaacacta ccggaatgtt cagggcttgt | 900 |
| gctagcgaag atggttactc tgagatcgca atctggccaa acaattga | 948 |

<210> SEQ ID NO 3
<211> LENGTH: 2181
<212> TYPE: DNA
<213> ORGANISM: Arabidopsis thaliana

<400> SEQUENCE: 3

| | | |
|---|---|---|
| atgccctctc accccaactt catcttcagg tggattggac tgttttccga taagttccgt | 60 |
| cgacaaacga ctgggatcga tgaaaacagt aacctccaaa tcaacggtgg agattcgagc | 120 |
| agcagcggca gcgatgagac gccggtgcta agctccgtcg agtgttacgc ttgcacacaa | 180 |
| gtaggcgtcc cagcttttcca ttcaactagc tgcgatcaag ctcacgcgcc ggagtggcgt | 240 |
| gcctccgccg gctcttctct agttccgatc caggaaggat ctgtccctaa cccagcccga | 300 |
| accagattcc gacgtctcaa aggtccgttt ggtgaagttc tcgatcctag agcaagcgc | 360 |
| gtgcagagat ggaaccgcgc gttgctttta gctcgtggga tggctttagc ggtggatccg | 420 |
| ctcttcttct acgcgctttc catcggccga actaccggac cggcgtgtct ttacatggat | 480 |
| ggtgcgttcg ccgcggtggt cacggtgctc cgcacgtgtc tcgatgctgt tcatctttgg | 540 |
| cacgtgtggc ttcaattcag actggcctac gtctcgagag agtcgcttgt cgttggttgt | 600 |
| gggaagctcg tttgggatcc acgcgccatc gcgtctcact acgcacgctc tctcactggc | 660 |

```
ttctggtttg atgttatcgt catcctccct gtccctcagg cagtgttttg gttagttgtg      720
ccgaaactga taagagaaga gaaggttaag ctgataatga cgattctgct gctaatattc      780
ttgttccagt tcctccccaa gatttatcac tgcatctgtt tgatgagaag gatgcagaag      840
gtcactggtt acattttggg aactatttgg tggggtttt g ctcttaatct catcgcatat     900
ttcatcgctt tcatgttgc tgggggatgt tggtatgttc tcgcaataca gcgtgttgct       960
tcttgcataa gacaacaatg tatgagaacc gggaactgca atctgagtct ggcttgcaaa     1020
gaagaggtct gttaccaatt tgtgtcaccg acaagcacag ttggatatcc atgcttatct     1080
ggaaacctta ccagtgtggt caataagcct atgtgcttag actctaacgg accattccga     1140
tatggtatct accgttgggc acttccagtc atctccagca actctcttgc ggttaagatc     1200 ctttaccccca tcttctgggg cctaatgact ctcagcacat ttgcgaatga tcttgagccc    1260
acaagcaact ggctcgaggt tattttcagt atagttatgg ttctaagtgg cttgttactt    1320
ttcacgctgt tgataggaaa cattcagtg tttttgcatg cggtaatggc gaaaaaaagg     1380
aaaatgcaga tacggtgtag ggatatggaa tggtggatga aacgtaggca gttaccttcc     1440
cggttaagac agagggttag gcgatttgag cggcagagat ggaatgcctt gggtggtgaa     1500
gacgagctag aacttataca tgatttgcct ccgggtcttc gaagagatat caaacgatat     1560
ctttgctttg atctcattaa caaggtgcca ttgttcaggg gcatggacga cttgatcctc     1620
gacaacattt gcgatcgggc taagcctcga gtcttctcta aagacgaaaa gatcatccgt     1680
gaaggagatc ctgtacagag aatgatattc atcatgcgtg gacgagtcaa acgtatacag     1740
agcctaagca aaggcgtcct agccactagt acactagaac caggcggtta cttgggcgac     1800
gagctactct catggtgcct acgtcgcccg tttctggacc gtcttccccc ttcctcagca     1860
acatttgtct gcctagaaaa catcgaggca ttctccctcg gatccgaaga tcttaggtac     1920
attaccgatc atttccgtta taaattcgcg aacgagcggc ttaagcggac cgcaagatac     1980
tattcctcaa actggaggac gtgggcagcg gtaaatattc agatggcgtg cgccggcgt     2040 aggaaaagaa cccgtggtga aaacatcggc ggttcgatga gtcctgtgtc ggagaatagc     2100
attgaaggta acagtgaacg ccggttactt cagtatgcag ctatgttcat gtccattcga     2160
ccgcatgatc atctcgaata a                                              2181
```

<210> SEQ ID NO 4
<211> LENGTH: 1404
<212> TYPE: DNA
<213> ORGANISM: Arabidopsis thaliana

<400> SEQUENCE: 4

```
atgattcttg atttgggttt tccttgtttt gttcctcctc gaaccagctc tcgtgaggac       60
aacaaagctt ggcttctggc tgaaacagag ccgaagctta ttgactcaga acaacattcg      120
ttgcagtctt cgtttaggtt tagtctttgc tcacagttgg agctgagaa gattaaaaag       180 gagaaacctt cgttgtctta tcggaatttt ccagtgtctg aaggatcaga gacggttctg      240
ctagtgaatc tggagaatga gacaggagaa ttgacaggtg agatgaattg gtcgagaggc      300
ctttcactgg agaagagtat ttctccggtg gccgattctt tgatccgatt cagttaccgc      360
gaactcctca ctgccacgcg caatttctca aaacggaggg ttttgggaag aggagcttgt     420
agctatgttt ttaagggaag aatcgggatt tggcgtaaag ccgtggccat caaaagactt     480
gataaaaaag ataaagaatc tccaaagtcg ttttgcagag agttgatgat tgcaagctct     540
```

| | |
|---|---|
| cttaatagcc ccaacgttgt gcctctgcta ggtttctgta tcgatcccga tcaagggctt | 600 |
| ttcttggtgt acaagtatgt gtctggtggc agcctcgaac gctttttaca tgataagaag | 660 |
| aaaaagaaga gtaggaagac ccccttgaat ctgccttggt ctacaaggta caaggttgcc | 720 |
| ttaggtattg cagatgccat agcctattta cataatggca ctgagcaatg cgttgtgcat | 780 |
| agagacatta aaccctcaaa tattcttctt tcctcaaaca aaattccaaa gttgtgtgat | 840 |
| tttgggttgg ctacttggac cgctgcgcct tcggttcctt tcctctgtaa accgtgaaa | 900 |
| ggaactttttg gttatctggc tcctgagtat ttccaacacg gcaagatatc tgacaagacc | 960 |
| gatgtttacg catttggggt cgtgttgctt gagctaataa ctggtcggaa gccaattgaa | 1020 |
| gcaagaagac catctggtga agaaaatttg gtagtttggg caaaaccgtt gttgcataga | 1080 |
| gggatagaag ctacagagga gttgctagat ccaaggctga aatgtactag aaaaaactcg | 1140 |
| gcttcgatgg agcgtatgat ccgagctgcg gcagcgtgtg tgatcaatga ggaatcacga | 1200 |
| agaccgggga tgaaggagat actttcaatc ctaaaaggcg gtgaagggat agaactaagg | 1260 |
| acgttatcaa gccggaagaa atcaaatctt ccgggtataa tggactgtta tccgcagttg | 1320 |
| caacggacaa aatctgagat gaagagtcat cttacgcttg cgatgctcgg agtaacggaa | 1380 |
| tttgaagctg atgatctttt gtag | 1404 |

<210> SEQ ID NO 5
<211> LENGTH: 1065
<212> TYPE: DNA
<213> ORGANISM: Oryza sativa

<400> SEQUENCE: 5

| | |
|---|---|
| atggccggca gcgacgaggt caaccgcaac gagtgcaaga cggtggtgcc gctccacaca | 60 |
| tgggtgctca tctccaactt caagctgtcg tacaacattc tgcggcgggc ggacgggacg | 120 |
| ttcgagcggg acctcgggga gtacctggac aggagggtgc cggcgaacgc gcggccgctg | 180 |
| gagggggtgt cgtcgttcga ccacatcatc gaccagtcgg tggggctgga ggtgcgcatc | 240 |
| taccgggcgg cggcggaggg tgacgcggag gaggggcgg cggcggtgac gcggcccatc | 300 |
| cttgagttcc tgacggacgc gccagcggcg gagccgttcc cggtgatcat attcttccac | 360 |
| ggcggcagct tcgtgcactc gtcggccagc tcgaccatct acgacagtct gtgccgccgg | 420 |
| ttcgtgaagc tgagcaaggg cgtcgtggtg tccgtcaact accggcgcgc gccggagcac | 480 |
| cgctacccgt gcgcgtacga cgacgggtgg accgcgctca gtgggtcat gtcgcagccg | 540 |
| ttcatgcgca gcgcggcga cgcgcaggcc cgcgtgttcc tctccggcga cagctccggc | 600 |
| ggcaacatcg cccaccacgt cgccgtccgc gccgccgacg agggcgtcaa ggtctgcggc | 660 |
| aacatcctgc tcaacgccat gttcggcggc accgagcgca cggagtcgga gcggcggctc | 720 |
| gacggcaagt acttcgtgac gctccaggac agggactggt actggaaggc gtacctgccg | 780 |
| gaggacgccg accgggacca tccgcgtgc aacccgttcg gcccgaacgg ccggcggctc | 840 |
| gggggcctcc ccttcgccaa gagcctcatc atcgtgtcgg gcctggacct cacctgcgac | 900 |
| cggcagctcg cctacgccga cgccctccgg gaggacggcc accacgtcaa ggttgtccaa | 960 |
| tgcgagaacg ccacggtggg gttctacctg ttgcccaaca ccgtccacta ccacgaggtc | 1020 |
| atggaggaga tctccgactt cctcaacgct aacctctact actag | 1065 |

<210> SEQ ID NO 6
<211> LENGTH: 1173
<212> TYPE: DNA
<213> ORGANISM: Zea mays

<400> SEQUENCE: 6

```
atgcagagcg cggctgccat cgggctccta cggccatgtg ccgcgcggcc gctcgccgcc      60
tacactagcc cacgccgcgg cgccggcgcg tgcagcggcg gcacccagcc gatcatcacg     120
ccccgcggca tccgcctctc cgcccgcccc ggtctcgtgc cggcctcgcc gctggaggag     180
aaggagaacc ggagatgcag ggccagtatg cacgcggcgg cgtcggccgg agaggaagct     240
gggggagggc tcgccaagac gctgcagctg ggggcgcttt tcgggctctg gtacctcttc     300
aacatctact tcaacatcta caacaagcag gttctgaagg ttttgccata ccctataaac     360
atcacaacgg tgcagtttgc tgttggaagt gccattgctt tgttcatgtg atcactggt      420
atccataaaa ggccaaagat ttcgggtgcc cagcttttcg ctatccttcc tctagctatt     480
gtccatacca tgggcaatct tttcacaaac atgagccttg aaaggtggc agtgtcattt      540
acacatacta taaaggccat ggaacctttc ttctcagttc tcctttcagc aattttcctt     600
ggggagttgc ctacgccatg ggttgtgttg tctcttcttc cgattgttgg tggtgtagct     660
ttggcatccc ttactgaggc ctcctttaac tgggctggat tttggagtgc aatggcttca     720
aatgtaacct tccagtcaag gaatgtgcta agcaagaaac ttatggtgaa gaaagaggaa     780
tctctcgaca acattaacct attctcgatc attacagtca tgtcattctt cctgttggcc     840
ccagtaacct tacttacaga aggtgttaaa gttagtccag cagtgttgca gtctgctggt     900
ttgaacttga acaggtata cacaaggtca ttgattgctg cattctgctt ccatgcatac      960
caacaggtgt catacatgat cctcgccagg gtatccccag tcacacattc agtgggcaat    1020
tgcgtcaagc gtgtggtggt cattgtgacc tctgttctgt tcttcaggac ccctgtttct    1080
cccatcaact ctcttggtac cgggatcgct cttgctggag ttttcctata ctcgcaattg    1140
aagagactta agcccaagcc caagactgct tag                                 1173
```

<210> SEQ ID NO 7
<211> LENGTH: 1434
<212> TYPE: DNA
<213> ORGANISM: Arabidopsis thaliana

<400> SEQUENCE: 7

```
atggcgcatc tactttcagc ttcatgccct tcagttatct cacttagcag cagcagcagc      60
aagaattcag ttaagccgtt tgtttcaggg cagaccttct tcaatgctca gcttctttca     120
agatcttctc tcaaaggact tctcttccaa gagaagaaac cgagaaaaag ctgcgttttc     180
agagcaactg ctgtacctat aacccaacaa gcaccacccg aaacatctac caataactca     240
tcctctaaac caaagcgtgt tatggtcatt ggtggagatg gttattgcgg ttgggctact     300
gctctccact tgtccaagaa gaattacgaa gtttgcattg ttgacaacct tgtaagacgt     360
cttttcgacc accagcttgg acttgagtca ttgactccta ttgcctccat tcatgaccga     420
atcagccgat ggaaggcttt gacagggaaa tcaattgagt tgtacgttgg tgatatctgt     480
gatttcgaat tcttagctga gtctttcaag tcttttgagc cggattcagt tgtccacttt     540
ggggaacaga gatccgctcc ttactcgatg attgaccggt ccagagcagt ttatacacag    600
cacaacaatg tgattgggac tctcaacgtt ctctttgcta taaaagagtt tggagaggag    660
tgtcatcttg taaaacttgg gacgatgggt gagtatggaa ctccaaatat tgacatcgag    720
gaaggttata taaccataac ccacaacggt agaactgaca ctttgccata ccccaagcaa    780
gctagctcct tttatcatct tagcaaagtt catgattcgc acaacattgc tttactttgc    840
```

| | |
|---|---|
| aaggcttggg gtattagagc cactgatctc aaccaaggag ttgtttatgg agtgaagact | 900 |
| gatgagacag agatgcatga ggaactccgt aaccgactgg attacgatgc tgtgtttggt | 960 |
| acagcactta accggttctg tgtgcaagct gctgttggtc acccacttac agtttatggt | 1020 |
| aaaggtggtc agacgagagg ctacctcgat ataagagaca cggttcaatg tgttgagatc | 1080 |
| gctatagcaa acccggcaaa agctggtgag ttccgggtct caaccaatt tacagaacag | 1140 |
| ttttcagtca atgaactggc ttcactcgtc actaaagcgg gttcaaagct tgggctagac | 1200 |
| gtgaaaaaga tgacggtgcc taacccgaga gtggaggcag aagaacatta ctacaacgca | 1260 |
| aagcacacta agctgatgga acttggactt gagcctcact atctatctga ctcacttctt | 1320 |
| gattcgttgc tcaactttgc tgttcagttt aaagatcgtg tggacacgaa acaaatcatg | 1380 |
| cctagtgttt cctggaagaa gattggcgtc aagactaagt ccatgaccac atag | 1434 |

<210> SEQ ID NO 8
<211> LENGTH: 1515
<212> TYPE: DNA
<213> ORGANISM: Arabidopsis thaliana

<400> SEQUENCE: 8

| | |
|---|---|
| atggtgagtc ttctatcttt tttcttgctt ctactcgtcc ccattttctt cttgttaatc | 60 |
| ttcaccaaga agatcaagga gtcaaaacaa aatcttcctc ctggcccagc aaagcttccg | 120 |
| atcatcggaa acctacacca gctccaaggg ttgcttcata aatgtcttca cgatctctcc | 180 |
| aagaaacacg gacctgtgat gcatctccgt ctagggtttg ccccaatggt cgtaatttca | 240 |
| tcaagtgaag cagctgaaga agctcttaaa acacatgacc ttgagtgttg ttcaagacct | 300 |
| atcactatgg cctcaagggt ttttcgcgt aacggtaaag acatcggatt tggggtttac | 360 |
| ggtgatgaat ggagagagct gcgtaagctt tcggttcgcg aattctttag cgtgaaaaaa | 420 |
| gttcaatcct tcaagtatat tagagaggaa gagaatgact tgatgatcaa gaaactgaaa | 480 |
| gaattggctt cgaagcaatc tccggtggat ttgagcaaaa tcctctttgg tctcactgcg | 540 |
| agtatcatat tcagaaccgc ctttggacaa agtttctttg ataacaagca tgtcgatcag | 600 |
| gaaagcatca agaactgat gtttgaatct ctgagcaata tgacttttag attctctgat | 660 |
| ttttccccta ctgctggtct taaatggttt ataggctttg tgtcaggcca acataagagg | 720 |
| ctttacaacg tcttcaacag ggttgatact tttttttaatc atatagttga tgatcatcac | 780 |
| tcgaagaaag caactcaaga tcgtcctgat atggtcgacg ctatcttaga tatgatagat | 840 |
| aatgaacaac aatatgcatc tttcaagctc accgttgatc atctcaaagg agtcctctca | 900 |
| aatatatatc acgctggaat tgacacaagc gccatcacct tgatttgggc gatggcagag | 960 |
| ctcgttagaa acccgcgggt aatgaagaaa gctcaagacg agatccgaac ttgcattgga | 1020 |
| atcaaacagg aaggaagaat catggaagaa gatcttgata agcttcaata cttgaagctt | 1080 |
| gtggtgaaag aaaaccttaag actacaccca gcagctcctc tttacttcc tcgaaaaca | 1140 |
| atggctgata tcaagattca aggctacgac attcctcaga aaagagctct tcttgttaat | 1200 |
| gcatggtcta taggacgaga tccggaatcc tggaaaaatc ctgaagagtt taacccggag | 1260 |
| aggtttattg attgtcctgt ggattacaag ggacatagct tgagttgtt accatttggt | 1320 |
| tctggtcgga gaatttgtcc aggaatagct atggcgatcg caaccattga attggggctc | 1380 |
| ttgaatttgc tctacttctt tgattggaat atgcctgaga agaagaaaga tatggacatg | 1440 |
| gaagaagctg gtgatctcac tgttgataag aaagttcctc ttgagcttct gccagttatt | 1500 |
| cgcatcagtt tgtag | 1515 |

<210> SEQ ID NO 9
<211> LENGTH: 1170
<212> TYPE: DNA
<213> ORGANISM: Pseudomonas syringae pv. tomato str. DC3000

<400> SEQUENCE: 9

| | | | | | |
|---|---|---|---|---|---|
| atggtcatga | ccgtcttgaa | gatgaccgac | ctcgatctgc | aaggtaaacg | tgtactgatc | 60 |
| cgcgaagacc | tcaacgtccc | gataaaggac | ggcgttgtca | gcagcgatgc | acgtattctt | 120 |
| gcttcgctgc | cgaccatcag | gctggcgctg | aaaaaggcg | cggctgtcat | ggtctgctcg | 180 |
| caccttggcc | gtccgaccga | gggcgagttt | tctgctgaaa | acagcctcaa | gccggttgct | 240 |
| gaatacctga | gcaaggcatt | gggtcgtgac | gttccgctgg | tcgccgatta | cctggacggc | 300 |
| gttgacgtca | aggcgggcga | tatcgtgctg | ttcgagaacg | ttcgcttcaa | caagggcgag | 360 |
| aaaaagaacg | ccgacgagct | ggcgcagaag | tacgcggccc | tgtgcgacgt | gttcgtgatg | 420 |
| gacgcttttg | gcaccgctca | ccgcgctgaa | ggctcgaccc | acggcgtggc | caaatacgcc | 480 |
| aaggttgccg | ctgctggccc | gttgctggct | gccgaactgg | aagcgctggg | caaggcgctg | 540 |
| ggcgctccgg | ctcagccaat | ggctgctatt | gttgccggct | ccaaagtgtc | caccaagctg | 600 |
| gacgtgctca | acagcctgag | cgcgatctgc | gatcagttga | ttgttggcgg | cgggattgcc | 660 |
| aacaccttc | tggctgcagc | cggtcacaag | gtcggtaaat | cgctttacga | gccagacctg | 720 |
| ctcgacaccg | cgcgcgccat | tgccgccaag | gtcagcgtgc | cgttgccgac | tgacgtggtg | 780 |
| gttgccaagg | aattcgccga | gagtgccact | gcaaccgtca | agctgatcgc | cgatgtggcc | 840 |
| gacgacgaca | tgattctgga | tattggtcca | cagactgctg | cgcacttcgc | cgaactgttg | 900 |
| aaatcttccg | ggactatcct | gtggaacggt | ccggttggcg | tgttcgaatt | cgaccagttc | 960 |
| ggtgaaggca | ccaaaacgct | ggccaaggcc | attgctgaaa | gcaaagcgtt | ctccatcgcg | 1020 |
| ggtggtggcg | acaccctggc | cgcgatcgac | aagtacggtg | tggcagatca | gatttcctat | 1080 |
| atttcgaccg | gtggcggtgc | gttcctcgaa | ttcgtggaag | gcaaggttct | gccagcggtt | 1140 |
| gaaatgctcg | aacaacgtgc | cagggcctag | | | | 1170 |

<210> SEQ ID NO 10
<211> LENGTH: 1188
<212> TYPE: DNA
<213> ORGANISM: Zea mays

<400> SEQUENCE: 10

| | | | | | |
|---|---|---|---|---|---|
| atgagtctca | taagagggat | gggcaacgtt | gccaagagat | ggaaagaact | caatggcttg | 60 |
| aattactgga | agggcctagt | tgatccgctc | gacctcgacc | tccgtaggaa | catcatcaac | 120 |
| tacggtgagc | tctcccaggc | aacctacacc | gggctgaaca | gggagagaag | atcaaggtac | 180 |
| gctgggtctt | gcctcttcaa | ccgcagagac | ttcctcagca | gggtggatgt | atcaaacccg | 240 |
| aacctgtatg | agatcacgaa | gttcatatac | gcgatgtgca | ctgtcagctt | acctgacggg | 300 |
| ttcatggtca | agtctctctc | aaaggctgca | tggagcaggc | agtcgaattg | gatggggttt | 360 |
| gttgcagtag | ctacggacga | gggcaaggaa | ctgcttggga | ggcgggacgt | ggtggtggcg | 420 |
| tggcgtggca | ccataaggat | ggtagagtgg | gtcgatgatc | ttgatatttc | cttggtgcct | 480 |
| gcttcggaaa | tagttcttcc | aggcagcgca | gccaacccct | gtgtgcatgg | agggtggctt | 540 |
| tcagtctaca | cgagtgctga | tccagggtca | cagtacaaca | aagagagcgc | aagacatcag | 600 |
| gtgttaaacg | aggtgaaaag | gatacaggat | ctgtacaagc | cagaggagac | gagcatcacc | 660 |

```
ataacaggcc acagcctagg agcagcactt gccaccatca acgcaaccga catcgtctcc    720
aatggctaca acaggagctg ctgccctgtg tccgcgttcg tattcgggag ccccagagtc    780
ggaaaccctg atttccagaa ggcgttcgac agcgcggcgg acctgaggct gctccgcgtc    840
cggaactctc ccgacgtggt ccccaaatgg ccaaagctag ggtacagcga tgtcggcaca    900
gagctgatga tcgacacagg agaatcgccg tacctgaagg cccctggaaa cccctgaca    960 tggcatgaca tggagtgcta catgcacggg gtcgctgggg ctcaggggag cagcggaggg   1020
ttcgagctgt tggtcgatcg ggacgttgct ttggtgaaca agcatgaaga tgcgctgaga   1080
aatgagttcg ctgtcccacc gtcgtggtgg gtggtgcaga acaaaggtat ggtgaaaggc   1140
aaggatggcc ggtggcatct ggccgaccat gaggaggatg atgactag                1188
```

<210> SEQ ID NO 11
<211> LENGTH: 1539
<212> TYPE: DNA
<213> ORGANISM: Arabidopsis thaliana

<400> SEQUENCE: 11

```
atggctactc ttttagccac tcctatcttc tctcctttag cttcttctcc agcaaggaac     60 cgtcttctt gctctaagat ccgtttcggt tccaaaaatg ggaaaattct caattctgat    120
ggtgcccaga agttgaatct ctcaaaattc cgtaaacccg atggccaaag atttctacaa    180
atgggttctt ctaaagagat gaactttgag agaaaactct cagtccaagc tatggatggt    240
gcaggaacag gaaacacatc aacgatctct cgtaacgtaa ttgcgataag tcacttgttg    300
gtatcacttg ggatcattct tgctgcagac tatttcttga agcaggcgtt tgtagcagcg    360
tctattaagt tcccaagtgc tttgtttggg atgttctgta ttttctctgt tcttatgata    420
tttgattcgg ttgttcctgc tgctgcaaat ggtttgatga atttcttcga gcctgcgttt    480
ctgtttatcc aaagatggct tcctttgttc tatgttcctt ctcttgttgt tcttcctctt    540
tctgttagag atattccggc tgcttcaggt gtcaaaatct gctacattgt agccggtgga    600
tggttggcgt cactttgtgt agcagggtac acagctattg cagtgagaaa atggtgaaa    660 accgaaatga cggaagccga gcctatggca aaaccatcac cattttcaac acttgagcta    720
tggagttgga gtggaatctt tgttgtgtcg tttgttggtg ctctgttta ccctaattca    780 ttggggacaa gtgcaagaac ttctctccct ttccttcttt cttcaactgt gctaggttac    840
attgtaggtt ctgggttgcc atcttctatt aagaaagttt tccatccgat aatctgctgc    900
gcgctatctg cagtacttgc tgctctagct tttgggtatg cttcaggatc tggacttgat    960
cctgttttag gaaactacct taccaaagta gcatcagatc ctggtgctgg tgacatctta   1020
atgggttttc ttggctctgt cattctctct ttcgctttct ccatgttcaa acaaagaaag   1080
ctcgtgaaga ggcacgcagc tgagatcttc acatctgtga tagtttcaac ggtattctcg   1140
ctctactcca ctgctcttgt tggacgttta gtcggtttag aaccttcttt aacggtttca   1200
atcctacctc gctgcatcac ggttgcattg gcccttagca ttgtatcact ctttgaaggg   1260
accaattcgt ctcttacagc agctgtagtc gttgtgactg gtctgattgg agctaacttt   1320
gtacaagttt tccttgacaa actgcgttta cgtgatccaa ttgctcgggg aattgcaact   1380
gcttcaagtg ctcatggact tggaacagca gctttgtcgg ctaaggagcc agaggctctt   1440
cccttttgtg caatagctta tgctcttacc ggaatcttcg gatcgttact gtgttctgtt   1500
cctgccgtcc gacagagttt gctagcggtc gtcggctag                           1539
```

<210> SEQ ID NO 12
<211> LENGTH: 936
<212> TYPE: DNA
<213> ORGANISM: Zea mays

<400> SEQUENCE: 12

| | | | | | |
|---|---|---|---|---|---|
| atggctcgca | acgaggagaa | ggcgcagtca | atgctgaacc | gcttcatcac | gatgaagcag | 60 |
| gaggagaagc | gcaagccccg | agagcgccgg | ccctacctcg | cctccgagtg | ccgcgacctc | 120 |
| gccgacgccg | agcgctggcg | ctctgagatc | ctccgcgaga | tcggcgccaa | ggtcgccgag | 180 |
| atccagaacg | agggtctcgg | cgagcaccgc | ctccgcgacc | tcaacgacga | gatcaacaaa | 240 |
| ctcctccgcg | agcgcggcca | ctgggagcgc | cgcatcgtcg | agctcggcgg | ccgcgactac | 300 |
| tcccgcagct | ccaacgcgcc | gctcatgacc | gacctcgacg | caacatagt | cgccgtcccc | 360 |
| aacccctcgg | gtcgcggacc | ggggtaccgc | tactttggcg | cggccaggaa | gctccctggc | 420 |
| gtgcgggagc | tcttcgacaa | gccgcctgag | atgcggaagc | gacgcacccg | ctacgagatc | 480 |
| cacaagcgca | tcaacgccgg | gtactacgga | tactatgacg | atgaggacgg | cgtgctagag | 540 |
| cgccttgagg | gccctgccgg | gaagcgcatg | cgggaggaga | ttgtttcaga | gtggcaccgt | 600 |
| gtggaacggg | tgcggcggga | ggccatgaag | ggggtgatga | cggtgaggt | ggctgcggct | 660 |
| ggagggcgca | gcggggaggc | tgctagagag | gtgctgtttg | aggggtgga | ggaggaggtc | 720 |
| gaagaggaga | ggaagcgtga | ggaagagaag | agggagaggg | agaaaggcga | ggaagttggg | 780 |
| agggaattcg | ttgcacatgt | gccgctacct | gatgaaaagg | agattgagcg | catggtatta | 840 |
| gagaggaaga | agaaggagct | gcttagcaag | tatgccagtg | attccctgct | ggttgagcag | 900 |
| gaggaggcca | aggagatgct | caatgtccga | cgctag | | | 936 |

<210> SEQ ID NO 13
<211> LENGTH: 2049
<212> TYPE: DNA
<213> ORGANISM: Zea mays

<400> SEQUENCE: 13

| | | | | | |
|---|---|---|---|---|---|
| atggaccttg | cacggagagg | cggtgccgca | ggcgcggacg | acgaggggga | gatcgagagg | 60 |
| cacgagccgg | cgcccgagga | catggagtcc | gaccccgcag | cggcgcgcga | aaggagctg | 120 |
| gagctggagc | gggtgcagtc | gtggcgggag | caggtgactc | tgcgcggcgt | ggtggcggcg | 180 |
| ctgctgatcg | gcttcatgta | cagcgtgatc | gtgatgaaga | tcgcgctcac | cacggggctg | 240 |
| gtgcccacgc | tgaacgtctc | cgcggcgctg | atggcgttcc | tggcgctccg | cgggtggacg | 300 |
| cgcgtgctga | agcgcctcgg | cgtggcgcac | cgcccccttca | cgcgccagga | gaactgcgtc | 360 |
| atcgagacct | gcgccgtcgc | gtgctacacc | atcgcgttcg | gcggtgggtt | cggctccacg | 420 |
| ctgctgggcc | tggacaagaa | gacgtacgag | ctggccgggg | cctcgccggc | caacgttccg | 480 |
| ggcagctaca | aggaccctgg | gttcggctgg | atggccggat | cgtcgcggc | gatcagcttc | 540 |
| gccggcctcc | taagcctgat | cccctcaga | aaggttctgg | tcattgacta | caagctaact | 600 |
| tacccaagcg | ggactgcgac | cgctgttctc | ataaacgggt | tccacaccaa | gcaaggagac | 660 |
| aagaacgcaa | ggatgcaagt | ccgagggttc | ctcaagtact | tgggctcag | cttcgtgtgg | 720 |
| agctttttcc | agtggttcta | cacaggcggt | gaagtttgcg | gctttgttca | gtttcctacg | 780 |
| ttcggtctga | aggcctggaa | gcagacgttc | ttctttgatt | ttagcctcac | gtacgttggt | 840 |
| gcggggatga | tctgttcgca | cctcgtgaac | atctccaccc | tccttggtgc | catcctgtca | 900 |
| tgggggatac | tgtggccact | catcagcaag | cagaaagggg | agtggtaccc | tgcgaacata | 960 |

```
cctgagagta gcatgaaaag cttatacggt tacaaggcct tcctctgcat agctctgatc    1020
atgggagacg gtacatacca cttctttaaa gtcttcggtg tcactgttaa gagtctgcat    1080
caacggctga gccgcaaacg tgctaccaac agagtggcaa acggtggaga cgaaatggcc    1140
gcgcttgacg acctcagcg tgacgagatc ttcagcgacg gtctttccc cgcctgggca      1200 gcttacgccg ggtacgcggc gctgaccgtc gtctcagcgg tcatcatccc gcacatgttc    1260
cggcaggtca gtggtacta cgtgatcgtg gcctacgtcc tcgcccctct cctcggcttc     1320
gccaactcct acggcacggg gctcaccgac atcaacatgg cctacaacta cggcaagatc    1380
gcgctcttca tcttcgcggc ctgggccggc agggacaacg cgtcatcgc gggcctcgcc     1440 ggcggcaccc tggtgaagca gctggtgatg gcgtccgcgg acctgatgca cgacttcaag    1500
acgggccacc tgaccatgac gtcgcccagg tccctgctcg tggcgcagtt catcgggacg    1560
gccatgggct gcgtcgtcgc gcccctcacg ttcctgctct tctacaacgc gttcgacatc    1620
gggaacccca ccgggtactg gaaggcgccg tacggcctca tctaccgcaa catggcgatc    1680
ctcggcgtgg agggcttctc cgtgctgccc aggcactgcc tcgcgctctc cgctgggttc    1740
ttcgccttcg ccttcgtctt cagcgtcgcc cgggacgtcc tgccgcggaa gtacgccagg    1800
ttcgtgcccc tgcccatggc catggccgtg ccgttcctcg tgggcgggag cttcgcgatc    1860
gatatgtgcg tcgggagcct ggccgtcttt gtctgggaga aggtgaacag gaaggaggcc    1920
gtgttcatgg tgcctgcggt tgcgtccggt ttgatctgtg gagacggcat atggaccttc    1980
ccgtcttcca ttctcgctct ggccaagatc aagccaccga tttgcatgaa gttcactcct    2040
ggaagctag                                                            2049

<210> SEQ ID NO 14
<211> LENGTH: 1362
<212> TYPE: DNA
<213> ORGANISM: Arabidopsis thaliana

<400> SEQUENCE: 14
atggctaaag tttattggcc ttatttcgat cctgaatatg agaacttgag ctccagaatc      60
aatcctccaa gtgtttctat agataacact agctgcaaag aatgcactct tgtcaaggtg    120
gacagtatga acaaacctgg aatactactt gaagttgtgc aagtcctaac cgatctcgat    180
ctcactatca ctaaagctta tatctcttct gatggtggat ggttcatgga cgtattccat    240
gtcaccgatc aacaaggaaa caaggttact gatagcaaaa ccatcgatta catcgagaag    300
gtgttaggac caagggtca tgcttcggct tcacaaaaca cttggcctgg taaaagagtc     360
ggtgtccatt cattaggcga ccacacatcg atagagatta ttgctcgtga tcgtcctggt    420
ctcttgtcgg aggtttcagc cgtactagca gaccctcaaca ttaatgtggt ggcagctgaa    480
gcatggactc acaaccgtag gattgcgtgt gtcctctatg tgaatgacaa tgcaacttct    540
agagccgttg atgatccaga aagattgtct tccatggaag aacagcttaa caatgtgctg    600
cgtgggtgcg aagaacaaga tgagaaattt gctcggacga gtctctccat tgggtcgact    660
cacgttgatc gaaggcttca tcagatgttt ttcgctgata gagactacga agcagtgact    720
aagcttgatg attctgcttc ttgcggattc gagcccaaaa tcacggttga gcattgtgaa    780
gagaaaggtt actccgtgat aaacgtgagc tgcgaggatc gaccaaagct catgtttgac    840
attgtatgca cgcttacgga tatgcaatac attgtgtttc acgccacgat ttcatcaagc    900
ggctctcatg cttctcagga gtatttcatc agacacaaag acggttgcac tcttgacaca    960
gaaggagaga aagagagagt tgtcaaatgt ctggaagctg caatccatag acgagtcagc    1020
```

| | |
|---|---|
| gagggttgga gtttggagct ctgcgcaaag gacagagttg gattactgtc ggaagtgaca | 1080 |
| aggattctga gagagcacgg gctatcagtg tcgagagctg gtgtgacaac agtaggagaa | 1140 |
| caagccgtca acgttttcta tgtgaaagat gcttcaggga atccagtgga tgtgaagacg | 1200 |
| attgaggcgt tacgcggaga gattggacac agtatgatga ttgacttcaa gaataaagtt | 1260 |
| ccgagcagaa aatggaaaga agaaggtcaa gccggaacag gaggaggatg gccaaaacc | 1320 |
| agtttcttct ttgggaattt gctggagaag ttactgcctt ag | 1362 |

<210> SEQ ID NO 15
<211> LENGTH: 1005
<212> TYPE: DNA
<213> ORGANISM: Escherichia coli

<400> SEQUENCE: 15

| | |
|---|---|
| atggcgcaag ttagcagaat ctgcaatggt gtgcagaacc catctcttat ctccaatctc | 60 |
| tcgaaatcca gtcaacgcaa atctccctta tcggtttctc tgaagacgca gcagcatcca | 120 |
| cgagcttatc cgatttcgtc gtcgtgggga ttgaagaaga gtgggatgac gttaattggc | 180 |
| tctgagcttc gtcctcttaa ggtcatgtct tctgtttcca cggcgtgcat gatgaatcca | 240 |
| ttaattatca aactgggcgg cgtactgctg gatagtgaag aggcgctgga acgtctgttt | 300 |
| agcgcactgg tgaattatcg tgagtcacat cagcgtccgc tggtgattgt gcacggcggc | 360 |
| ggttgcgtgg tggatgagct gatgaaaggg ctgaatctgc cggtgaaaaa gaaaaacggc | 420 |
| ctgcgggtga cgcctgctga tcagatagac attatcaccg gagcactggc gggaacggca | 480 |
| aataaaaccc tgttggcatg ggcgaagaaa catcagattg cggccgtagg tttgtttctc | 540 |
| ggtgacggcg acagcgtcaa agtgacccag cttgatgaag agttaggtca tgttggactg | 600 |
| gcgcagccag gttcgcctaa gcttatcaac tccttgctgg agaacggtta tctgccggtg | 660 |
| gtcagctcca ttggcgtaac agacgaaggg caactgatga acgtcaatgc cgaccaggcg | 720 |
| gcaacggcgc tggcggcaac gctgggcgcg gatctgattt tgctctccga cgtcagcggc | 780 |
| attctcgacg gcaaagggca acgcattgcc gaaatgaccg ccgcgaaagc agaacaactg | 840 |
| attgagcagg gcattattac tgacggcatg atagtgaaag tgaacgcggc gctggatgcg | 900 |
| gcccgcacgc tgggccgtcc ggtagatatc gcctcctggc gtcatgcgga gcagcttccg | 960 |
| gcactgttta cgtatgcc gatgggtacg cggattttag cttag | 1005 |

<210> SEQ ID NO 16
<211> LENGTH: 1674
<212> TYPE: DNA
<213> ORGANISM: Glycine max

<400> SEQUENCE: 16

| | |
|---|---|
| atggcgctta aaccctatc cactttcctc tcacctcttt ctcttcccaa caccaaattc | 60 |
| ccgcaattcc tcaccaccaa gccttccctc attctctgcg agttccctcg ctctcagaaa | 120 |
| tcgcgtttgc tcgccgccga ttcggaaggc accggcgccg ccgctccttc tcccggcgag | 180 |
| aagttcctcg aacgccagca gtccttcgaa gatgctaaga tcattctcaa agaaaacaag | 240 |
| aagaagagaa agaagaaaga caatgctata aaagcttcta gagccgtcgc ttcttgctac | 300 |
| ggctgcggcg ctccgttaca cacttccgat gccgatgccc ctggctacgt tgatcccgaa | 360 |
| acctatgaat tgaagaagaa acaccaccag cttcgaaccg ttctgtgtag gcggtgccgg | 420 |
| cttttgtctc atggcaagat gataactgcc gttggagggc acggaggata tcctggcggt | 480 |

| | |
|---|---|
| aaattattcg tcactgctga agagcttcga gaaaagttgt ctcacctgcg tcacgagaaa | 540 |
| gctctaatcg tcaaattggt tgatattgtt gacttcaatg gcagttttt gtctcgtgtg | 600 |
| cgagatcttg ctggttctaa tccaataata ttggtggtga ctaaggttga tctccttcct | 660 |
| agagatactg atcttcattg tgttggggat tgggttgtag aggctactat gagaaagaag | 720 |
| ctaaatgttc tcagtgtcca tctgaccagt tccaaatcat tggttggaat aactggagtg | 780 |
| atatcggaaa tccagaaaga gaagaaggga cgagatgttt acattctggg ttcagctaat | 840 |
| gttgggaaat ctgctttcat caatgcttta ctaaaaacaa tggctataaa tgatccagtg | 900 |
| gctgcatctg cacaaagata caaaccaata caatctgcag ttcctggaac taccttaggg | 960 |
| ccaattcaaa ttaatgcttt cctaggagga gggaaattgt acgacactcc tggagttcat | 1020 |
| ctctaccata gcaaactgc agttgttcat tctgaagatc tacccatcct tgctccacaa | 1080 |
| agccgactga ggggcctgtc tttcccaagt tctatattat cttcagtaga ggaaggagct | 1140 |
| tccaccatag tgaatggctt gaatgcattt tcaatatttt ggggaggtct tgttagaatt | 1200 |
| gatgtcttga aggttctccc agaaacttgt ttgacatttt atggacccaa agaataccca | 1260 |
| attcatatgg tacccacaga gcaagcagtt gaatttatc agacagaact tggagttctg | 1320 |
| ctgaccccac caagtggagg agaaaatgct gagaactgga aaggacttga atcagaacga | 1380 |
| aaattgcaaa ttaaatttga agatgtggac agttatgatc ccaaaccagc ttgtgatata | 1440 |
| gctatatcag gtctaggatg gtttactgtt gagccagtta gtcggtcact caaaatctca | 1500 |
| caaccaaaac cggtagagac tgctggggaa ttgatttgg ctgtgcacgt ccccaaggct | 1560 |
| gttgagattt ttgtgaggtc accaatacca gtaggcaagg ctggagcaga gtggtaccag | 1620 |
| tatgtagaat taacagagaa acaagaggaa atgagaccaa aatggtactt ttag | 1674 |

<210> SEQ ID NO 17
<211> LENGTH: 1281
<212> TYPE: DNA
<213> ORGANISM: Zea mays

<400> SEQUENCE: 17

| | |
|---|---|
| atggcggcgg cgctcgcctc ctcccgctac tgctggagcc gcccgtcgct gccgccccaa | 60 |
| ccgacccgcg gccgccgctc cgtcactagc tgcgcgctct ccggacgaga gaaaagaaac | 120 |
| tcctttagct ggagagagtg tgcaatttct gttgcattgt cagttggact aatcactggt | 180 |
| gcaccaacgt ttggaccacc ggcctatgct tcttctcttg aacctgttct tccagatgtg | 240 |
| tctgttctta tctctggacc tcccattaaa gatccaggtg ctttattgag atatgcttta | 300 |
| ccaatagata ataaagctat ccgtgaagtt caaaagccgc tggaggatat cactgacagc | 360 |
| ctcaaggttg ctggtgttag agccttggat tcagttgaaa gaaatgtcag acaagcatcg | 420 |
| aaagcactga caatgggag aagcttaatt cttgctggcc ttgctgaacc aaaaagagca | 480 |
| aatggagaag agttgttgaa taagttggct gttggatttg aggagcttca agaattgtg | 540 |
| gaagacagaa atagggatgc agtagctcca aagcagaaag agcttctcca gtatgttgga | 600 |
| actgtagaag aagacatggt cgatggcttt cccttgaaa taccagaaga gtacagcaac | 660 |
| atgcctcttc tcaaaggaag agctactgtg atatgaagg ttaagattaa ggacaatccc | 720 |
| aacatggaag actgtgtatt taggatagtt ctggatggat ataatgctcc tgtgactgct | 780 |
| gggaacttcg tagatcttgt caaacgaaa ttctatgatg gcatggaaat ccaaagagct | 840 |
| gatggctttg ttgttcaaac tggagatcca gaggggccag ctgagggctt tatcgatccc | 900 |
| agcaccggca aaatccgtac ggtacctctt gaaattatgg ttgatggtga taggcgcct | 960 |

```
gtatatggtg aaacacttga agaacttggt cgctacaagg ctcaaacaaa actcccttct      1020 aacgctttg  gaacaatggc tatggcaaga agaagaatttg atgacaattc tgcttctagc    1080
caagtatttt ggctcttgaa agagagtgag ctaacaccaa gcaatgccaa tatattggac     1140
gggcggtacg cagtatttgg atatgtaact gagaatgagg actacctggc tgacgtcaaa     1200
gttggagatg tcatcgaatc aatccaagtc gtctcaggct tggacaacct tgtcaaccca     1260
agctacaaga ttgtaggata g                                               1281
```

<210> SEQ ID NO 18
<211> LENGTH: 435
<212> TYPE: DNA
<213> ORGANISM: Arabidopsis thaliana

<400> SEQUENCE: 18

```
atgatgcaag aattaggctt acaacgtttc tcaaacgacg tcgttcgctt agacctcact      60
cctccttctc aaacctcatc tacttctctt tccatcgacg aagaggaatc aacggaagcc     120
aagatccgac ggctgatatc ggagcatcct gtgatcatct tcagtagatc ttcatgttgc     180
atgtgccacg tcatgaagag actcttagca acgatcggcg taatccccac cgtcatcgag     240
ctcgatgatc acgaggtttc ctctcttccc acggctctac aagatgaata ttccggtggc     300
gtctccgtcg ttggtcctcc gccggcggtt tcattggcc gtgagtgcgt cggaggtctt      360
gagtcccttg tcgctcttca cttaagtggt caacttgttc ctaagcttgt ccaagttgga     420
gctctttggg tatag                                                      435
```

<210> SEQ ID NO 19
<211> LENGTH: 1530
<212> TYPE: DNA
<213> ORGANISM: Escherichia coli

<400> SEQUENCE: 19

```
atggcttcct ctatgctctc ttccgctact atggttgcct ctccggctca ggccactatg      60
gtcgctcctt tcaacggact taagtcctcc gctgccttcc cagccacccg caaggctaac     120
aacgacatta cttccatcac aagcaacggc ggaagagtta actgcatgca ggtgtggcct     180
ccgattggaa agaagaagtt tgagactctc tcttaccttc ctgaccttac cgattccggt     240
ggtcgcgtca actgcatgca ggccatgagc aacaatgaat ccatcagcg tcgtctttct     300 gccactccgc gcggggttgg cgtgatgtgt aacttcttcg cccagtcggc tgaaaacgcc     360
acgctgaagg atgttgaggg caacgagtac atcgatttcg ccgcaggcat tgcggtgctg     420
aataccggac atcgccaccc tgatctggtc gcggcggtgg agcagcaact gcaacagtttt    480 acccacaccg cgtatcagat tgtgccgtat gaaagctacg tcaccctggc ggagaaaatc     540
aacgcccttg ccccggtgag cgggcaggcc aaaaccgcgt tcttcaccac cggtgcggaa     600
gcggtggaaa acgcggtgaa aattgctcgc gcccataccg acgccctgg cgtgattgcg     660 tttagcggcg gctttcacgg tcgtacgtat atgaccatgg cgctgaccgg aaaagttgcg     720
ccgtacaaaa tcggcttcgg cccgttccct ggttcggtgt atcacgtacc ttatccgtca     780
gatttacacg gcatttcaac acaggactcc ctcgacgcca tcgaacgctt gtttaaatca     840
gacatcgaag cgaagcaggt ggcggcgatt attttcgaac cggtgcaggg cgagggcggt     900
ttcaacgttg cgccaaaaga gctggttgcc gctattcgcc gcctgtgcga cgagcacggt     960
attgtgatga ttgctgatga agtgcaaagc ggctttgcgc gtaccggtaa gctgtttgcc    1020
```

```
atggatcatt acgccgataa gccggattta atgacgatgg cgaaaagcct cgcgggcggg    1080
atgccgcttt cgggcgtggt cggtaacgcg aatattatgg acgcacccgc gccgggcggg    1140
cttggcggca cctacgccgg taacccgctg gcggtggctg ccgcgcacgc ggtgctcaac    1200
attatcgaca agaatcact ctgcgaacgc gcgaatcaac tgggccagcg tctcaaaaac     1260
acgttgattg atgccaaaga aagcgttccg gccattgctg cggtacgcgg cctggggtcg    1320
atgattgcgg tagagtttaa cgatccgcaa acgggcgagc cgtcagcggc gattgcacag    1380
aaaatccagc aacgcgcgct ggcgcagggg ctgctcctgc tgacctgtgg cgcatacggc    1440
aacgtgattc gcttcctgta tccgctgacc atcccggatg cgcaattcga tgcggcaatg    1500 aaaatttttgc aggatgcgct gagcgattag                                    1530

<210> SEQ ID NO 20
<211> LENGTH: 1473
<212> TYPE: DNA
<213> ORGANISM: Synechocystis sp.

<400> SEQUENCE: 20
atggcttcct ctatgctctc ttccgctact atggttgcct ctccggctca ggccactatg     60
gtcgctcctt tcaacggact taagtcctcc gctgccttcc cagccacccg caaggctaac    120
aacgacatta cttccatcac aagcaacggc ggaagagtta actgcatgca ggtgtggcct    180
ccgattggaa agaagaagtt tgagactctc tcttaccttc ctgaccttac cgattccggt    240
ggtcgcgtca actgcatgca ggccatgacc ccagaattga atcctaattt tcccgaagaa    300
actacctccg atgcttggct gaccccagca gatgccggcc aggatggtga tgcccaggaa    360
ccggcggaag atgggggaga agaaggagta gtgtcggaag aactggccct gcctgaggac    420
ttacctccta tggatgccat ggtggcggca gtggaagaaa tgactccggt ggtggtgccc    480
gaaactgtac cagaaacaga acccccagcc ttagaggatt tggtcgccca aagaccgcc     540 ctggaaaagg acattgccgc tctgcaacgg gaaaaagccc agtggtatgg ccagcagttc    600
cagcaattac agcgggaaat ggcccggtta gtggaggaag gcaccaggga attagggcaa    660
agaaaagcag ctctggaaaa ggaaattgag aagttagagc gccgtcagga acggattcaa    720
caggaaatgc gtaccacttt tgccggggct tcccaggagt tggccatccg cgtgcagggc    780
tttaaggatt atttggtggg gagttttgcag gatttggttt ccgccgccga ccagttggaa    840
ttaggggtgg gggacagttg ggagtcttcc tctacccatg gggatgcgat tattgaaaat    900
gccgacccaa ctccggtggt gagttttgcg gagcagggtt ttagtagcca aaaacgacaa    960
atccaagctt tgctggagca ataccgcact cgccctgatt attacggtcc cccttggcag    1020
ttgcgtcgta cctttgagcc agtccacgcc gaacggattg agaattggtt ctttaccctg    1080
ggcggtcggg gagcaatcct cagtttagac agtcgtttac aaaatatttt ggtgggttca    1140
gcggcgatcg ccattttgaa tcagctctac ggcgatcgtt gtcgggcgtt aattttggcg    1200
gccaccccag aaagattggg ggaatggcga cggggttac aggattgttt gggtatttcc    1260
cgcagtgact ttggcccaga ccggggcatt gttttgtttg aatcggccaa tgccttgatc    1320
cagcgggcgg aaagattggt cggcgatcgc caaatgccgt tggtgttggt ggatgaaaca    1380
gaggaacaaa ttgacttagc cctgttgcaa ttccccctttt actggccttt gcacctagt    1440 taccaagtcg gaggcagtaa ctattttttct tag                                1473

<210> SEQ ID NO 21
<211> LENGTH: 1215
```

```
<212> TYPE: DNA
<213> ORGANISM: Zea mays

<400> SEQUENCE: 21
atggccggcg aactgcgcca ccgccgcgcg ccgtcggagg acgagggcgt cgcctcctct      60
caaagactcg actccgcccc cgcaggcaac ggcaaggctg gcacttcgtc cggcggcggc     120 gaggggcgg agccgcgggg cgggaagagg acgcgctag ggtggctgga gtggtgccgc     180
ggttggatgg ccatcgtggg ggagttcctc ttccagcgca tcgccgccag ccacctggcc     240
aacccgctcg agttgccccc gctcgatggc gtctccatcg tcgtcaccgg cgccaccagc     300
ggcatcgggc tcgagatcgc aaggcaactc gctctcgctg gggcacatgt tgttatggct     360
gtaaggagac ccaaggtggc acaagagttg attcagaagt ggcagaatga aaattcagaa     420
acaggaagac cactaaatgc cgaggtgatg aacttgacc tgctctccct cgactcggtc     480
gtaaaatttg ctgatgcttg aatgctcgt atggcaccgc tgcacgtgtt gatcaacaat     540
gctggcatct tcgctatagg agaaccccaa cattttcga aggatggaca tgaagaacac     600
atgcaagtga accatcttgc acctgcatta ctggcgatgc tgcttatacc ttcccttctc     660
cgaggttctc ccagcagaat cgttaacgtt aattcaatca tgcacagtgt aggttttgtt     720
gatgctgaag atttcaactt gagaaaacat aaatatagaa gttggttggc gtattcaaat     780
agcaagttgg cacaggtaaa atttagtagc atgcttcata agagaattcc tgcagaagct     840
ggcatcagca taatttgtgc ttctcctgga attgtcgaca cgaatgttac aagagacctt     900
cctaagattt tgtagctgc ataccgtttt cttccctact tcatattcga tggtcaagaa     960
ggttctagga gtgcactgtt tgcggcatgt gacccccaag ttccagagta ctgtgagatg    1020
ctcaagtcgg aagactggcc agtctgtgct tgcattaact acgactgtaa tccgatgaac    1080
gcgtctgaag aagcgcacag ccttgaaacc tcgcagctgg tctgggagaa gacgctcgag    1140
atgatcggcc ttccgccgga tgccctggac aagctcatcg ccggagaaac agtgccgtgc    1200
cgttatggac aatag                                                    1215

<210> SEQ ID NO 22
<211> LENGTH: 2829
<212> TYPE: DNA
<213> ORGANISM: Zea mays

<400> SEQUENCE: 22
atggagggcg acgacttcac gccggagggc ggcaagctcc ccgagttcaa gctagatgcg      60
agacaagcgc agggtttcat ctccttcttc aagaagctgc cgcaggatcc ccgggccgtt     120
cgtctcttcg atcgcaggga ttattacact gcccatggcg agaatgctac gtttatcgca     180
aggacatact accacacaat gtctgcctta cgtcaactag gtagcaccct ctgatggaatc     240 ttaagtgcca gcgtgagcaa ggctatgttt gagaccattg cccgcaacat tttgttggaa     300
aggactgact gtacattgga actctatgag gaagtgggt caaattggag gttaacaaag     360
tccggaacac ctggaaatat tggtagtttt gaagacattc tgtttgcaaa caatgacatg     420
gaagattcac cagtgattgt tgcttttgttt ccagcgtgcc gggaaagtca gctgtatgta     480
gggcttagtt ttttggatat gaccaatagg aagcttgggt tggctgagtt tcccgaagat     540
agccgattca ctaatgttga atcagctctt gttgcattag gttgcaagga gtgtcttctc     600
ccagcagatt gtgaaaaatc cattgaccta aatccccttc aagacgtcat tagtaactgt     660
aatgttctgt tgactgagaa aaagaaggct gacttcaaat ccagggatct cgcacaagat     720
```

| | |
|---|---|
| cttggtagaa taatcagggg ttctgttgag cctgtacgtg atctactatc tcagtttgac | 780 |
| tatgctcttg gtccccttgg agctctttta tcttatgccg agttgctagc agatgacact | 840 |
| aactatggaa attacacaat tgagaagtac aatttgaact gctacatgcg acttgattct | 900 |
| gctgcagttc gagcattaaa cattgcagaa gggaaaactg atgtaaacaa gaacttcagt | 960 |
| ttgtttggtt tgatgaacag aacttgtact gttgggatgg gaaaaagatt gctgaacaga | 1020 |
| tggctgaaac aacctctatt agatgttaat gaaattaata accgactaga catggttcag | 1080 |
| gcttttgtag aagacccaga acttcgtcag ggactccggc aacaacttaa aaggatatca | 1140 |
| gatattgatc gtctaacaca tagtctccga aagaaatcag ctaatctgca gcctgttgtt | 1200 |
| aagctttatc agtcctgtag cagaatccca tacatcaagg gcattcttca gcaatataat | 1260 |
| ggccaatttt caacattgat aaggtcaaag tttcttgaac cgttagaaga atggatggca | 1320 |
| aagaatcgat ttggtcgttt ttcttctctt gttgagacag ctattgatct tgctcagctg | 1380 |
| gagaatggag agtacagaat atctcctcta tattcttctg acttgggtgt actaaaggat | 1440 |
| gagctttctg tggttgaaaa ccacataaac aatctgcacg tggatacagc tagtgatctg | 1500 |
| gatctttctg ttgataagca actgaagcta gaaaaaggat cccttggaca tgtgttcaga | 1560 |
| atgtcaaaga aagaggaaca gaaagtcagg aagaaactca ctggcagcta cttaatcata | 1620 |
| gaaactcgta aagatggtgt aaagttcaca aattctaagc tgaaaaatct aagtgatcaa | 1680 |
| taccaggcat tgtttggtga gtacacaagt tgtcagaaaa aggtggttgg tgatgtagtg | 1740 |
| agggtttcag gcacattctc agaggtattt gaaaattttg ctgcagttct gtcggagttg | 1800 |
| gatgttttac aaagttttgc tgatttggca actagttgcc cagttcctta tgttaggcca | 1860 |
| gacatcactg cgtcggatga aggagatatt gttctactgg gtagcagaca tccttgtcta | 1920 |
| gaggcacaag atggtgttaa ctttataccc aatgattgca ctctggtgag agggaaaagt | 1980 |
| tggtttcaga tcatcactgg accaaacatg ggaggaaaat ccacatttat aagacaggtt | 2040 |
| ggtgtaaatg tattgatggc acaagttggt tcctttgtac cttgtgatca agcaagtatt | 2100 |
| agtgtgaggg attgtatttt tgctcgtgtt ggcgctggtg attgccaact tcatggtgta | 2160 |
| tcaactttta tgcaagaaat gcttgaaaca gcatccatcc taaaaggcgc tctctgataag | 2220 |
| tctcttataa ttattgatga gctggggcgt ggaacttcca catatgatgg atttggtctt | 2280 |
| gcatgggcta tctgtgagca tcttatggaa gtgactcgag cgcctacctt gtttgcaacc | 2340 |
| catttccatg aactaactgc attagcacat agaaatgatg atgagcacca acacatttca | 2400 |
| gacatcggag ttgcaaatta tcacgtgggt gctcacatag acccattaag taggaagtta | 2460 |
| actatgcttt acaaggttga acctggtgca tgcgaccaaa gttttggtat tcatgttgca | 2520 |
| gaatttgcta attttccaga agctgttgtt gcccttgcga aaagcaaagc agcagagtta | 2580 |
| gaagactttt ctactacacc tacctttccc gatgatttga agacgaggt tggatcaaag | 2640 |
| cgcaagaggg tatttagccc agatgacatc accagaggag ctgcacgggc tcggctttc | 2700 |
| cttgaggaat tcgccgcatt gcctatggat gagatggatg ggagcaagat attggagatg | 2760 |
| gccaccaaga tgaaagctga cttgcagaaa gatgcagctg acaatccttg gctccagcag | 2820 |
| ttcttctag | 2829 |

<210> SEQ ID NO 23
<211> LENGTH: 1035
<212> TYPE: DNA
<213> ORGANISM: Arabidopsis thaliana

<400> SEQUENCE: 23

```
atggagtgga ttcgaggaga aactatcgga tacggaactt tttctacagt aagtctagcg    60
acgcggtcta ataacgattc cggcgagttt cctccgttaa tggctgtgaa atctgcagac   120
tcatacggcg ctgcttctct ggcaaacgag aaatcagttc tagataatct cggagacgat   180
tgcaacgaga tcgtacggtg tttcggcgag atcggacgg tcgaaaacgg tgaagagatg    240
cataatttgt tcttggaata cgcttctaga ggaagcttag agagttatct taagaaatta   300
gccggtgaag gtgtaccgga atccaccgtg cgtcgccaca caggatcggt gcttagaggt   360
ctacgacaca tccacgctaa cggattcgct cactgtgatt taaaactcgg gaatattctg   420
ttgttcggtg acgcgccgt taagattgcg gattttggat tggcgaagag aattggggat   480
ttaacggcgt taaattacgg tgtgcagatt agaggtacgc cgttgtacat ggcgccggaa   540
tctgttaacg ataacgagta cggatcagaa ggtgacgtgt gggctttagg atgcgtagta   600
gttgagatgt ttagtggtaa aacggcatgg agtttaaaag aagggtcgaa cttcatgtcg   660
ttgttgttac gcatcggtgt tggtgacgag gttccgatga ttcccgagga gttgtcggaa   720
caaggaagag atttttttgtc aaagtgtttc gttaaagatc ccaaaaagag atggacggct   780
gagatgcttc taaaccatcc atttgtaacc gtcgatgttg atcacgacgt tttagtcaaa   840
gaagaagatt tcgttgttaa tatgaaaaca gaggacgtct cgacatcgcc gagatgccca   900
ttcgaatttc ccgattgggt ttcggttttct tccggttcac aaacgatcga ttcgccggat   960
gagagagttg ctagtttggt gactgatatg atccctgatt ggtctgttac caatagctgg  1020
gtcaccgtac ggtga                                                   1035
```

<210> SEQ ID NO 24
<211> LENGTH: 3564
<212> TYPE: DNA
<213> ORGANISM: Arabidopsis thaliana

<400> SEQUENCE: 24

```
atgagaaacc attgcttaga actctcttcc aattgttcct ccatttttcgc ttcttccaaa    60
tccaatcctc gtttctctcc ttccaagctc tcctattcca ctttcttctc tcgtctgcc   120
atctattaca gatcaaaacc aaaacaagcc tcgtcttctt cttccttctc cactttcccc   180
ccatgtctca atcggaaaag ctccctcacg catgttctca aacccgtctc agagctcgcc   240
gacaccacta ccaagccttt ttctccggag atcgtcggca agagaaccga tctgaagaag   300
attatgattc tcggcgctgg tccgattgtc attggacaag cttgtgagtt tgattactct   360
ggtactcaag cttgtaaagc cttaagagaa gagggctatg aggttatcct gatcaattcg   420
aatcctgcca ctatcatgac tgatccggaa actgctaatc ggacttatat cgctccgatg   480
actcctgagc ttgtcgagca ggttattgag aaagagaggc ctgacgcttt gttaccaacc   540
atgggtggtc aaaccgcatt gaacctcgcg gttgctcttg ctgagagtgg tgctttggag   600
aaatacggtg ttgaattgat aggagctaag cttggtgcga ttaagaaagc tgaagatcgt   660
gagttgttca aggatgcgat gaagaacatt gggctaaaga ctccaccttc agggattggg  720
accactcttg atgagtgttt tgacattgct gagaaaattg tgagttccc tttgattatc   780
cgtcctgcgt ttactttagg tggtactggt ggtggaattc gtataacaa agaggagttt  840
gagtctatat gtaaatcggg tttggctgcg agtgcgacaa gtcaagttct tgtggagaaa  900
tccttgttgg gttggaaaga atatgagctt gaggtgatga gagacttagc tgacaatgtt   960
gtcattatct gttccattga gaatattgat cctatgggtg tgcacactgg tgattccatc  1020
```

```
actgtggcac ctgcacagac tctaacggat agagagtacc agcggcttag ggattattcc    1080
attgcgatta tacgggagat tggtgttgag tgtggtggat ctaatgtgca gtttgctgtc    1140
aacccggttg atggtgaagt tatgatcata gagatgaacc ctagggtctc aagatcttct    1200
gctcttgctt ccaaggctac agggtttccc attgctaaaa tggctgccaa gttgtctgtt    1260
ggctatacct tggatcagat tcctaatgat atcacgagga aaacaccggc tagcttcgag    1320
ccctccatcg attatgtggt gactaagatt cctcgatttg catttgaaaa gtttccagga    1380
tctcagccat tgctaacgac ccagatgaaa tctgttgggg aatctatggc tctcggccgt    1440
acattccaag aatctttcca gaaagctctg aggtctctgg agtgtggatt ctcgggttgg    1500
ggttgtgcaa aaattaaaga gctagattgg gactgggatc agctgaaata cagcctaaga    1560
gtcccaaatc ctgacaggat ccatgcgata tatgctgcca tgaaaaaggg tatgaaaatt    1620
gatgaaatct acgagttgag catggtggac aagtggttcc taacccagct taaagagctc    1680
gtggacgtcg aacagtatct tatgtccgga accttgtcag agattacaaa agaagacctt    1740
tacgaagtca aaaagcgggg atttagtgac aagcaaatcg cttttgctac aaagacaacc    1800
gaggaagaag tccgtaccaa gcggatttct ctaggagttg ttccatctta caagagagtg    1860
gatacatgtg ctgcagagtt cgaagcgcat acaccataca tgtactcttc atatgatgtt    1920
gaatgtgaat cagctccaaa caacaagaag aaggttttga ttttgggtgg agggccaaac    1980
cgcattggtc aagggattga atttgattac tgttgttgcc acacatcttt cgccttacag    2040
gatgctggat atgagaccat aatgttgaac tcaaatcctg aaacagtatc cacagattat    2100
gatacaagcg ataggctcta ttttgaacct ctcacaatcg aggatgttct caatgttatc    2160
gaccttgaga aacctgatgg cataatagtg caatttggtg gtcaaactcc tctgaaactt    2220
gctctgccga tcaaacatta tttggataag cacatgccca tgagcttgag cggagcggga    2280
cctgttcgca tctggggtac atcacctgac tccattgacg ctgctgaaga cagagagagg    2340
ttcaatgcaa ttctcgacga gctgaagatt gagcagccca agggaggcat tgcaaagagc    2400
gaagctgatg cattagccat agcaaaggag gtagggtacc cagttgtggt aagaccttct    2460
tatgttctag gtggacgagc aatggagatc gtttatgatg acagtagact aataacctat    2520
ttggaaaatg cggtacaagt tgacccagag agacctgttt tggtagataa atatctttct    2580
gatgccattg agatcgacgt tgatacccct actgattcct atggaaatgt ggtgattggt    2640
ggaataatgg agcatatcga acaagctggt gtgcattctg gtgactcagc ttgtatgctt    2700
ccaacacaaa ccatcccagc ttcttgtttg caaactattc gaacatggac cactaagctg    2760
gcgaagaagc taaatgtatg tgggctgatg aactgtcagt acgcaatcac aacatctggg    2820
gatgtttttt tgctggaagc caatccccga gcttcccgta ctgtcccttt tgtgtcaaaa    2880
gccattggac accctcttgc caagtatgca gcgctggtca tgtcgggcaa atctctcaaa    2940
gatcttaact ttgaaaaaga agttatccct aaacatgtct ctgtgaaaga agctgttttc    3000
ccgtttgaga agttccaagg atgcgatgtg atactcgggc agagatgag aagcacagga    3060 gaagtgatga gcatcagttc tgaattctca agtgcgtttg caatggctca gatcgctgca    3120
ggtcaaaagc tacctctatc aggcacagtc ttcctcagct aaacgatat gaccaaaccg    3180 cacctggaga aaatcgcggt gtccttcctc gagcttgggt tcaaaatagt tgccacctcg    3240
ggaacagctc atttcctgga actgaaaggc attccagtgg agagagtgtt gaagttgcat    3300
gaaggaagac cacatgctgc tgatatggtg gcgaatggtc agatccattt gatgttgatc    3360
acaagctcgg gtgatgctct tgatcagaaa gatgggagac agctcagaca aatggctcta    3420
```

```
gcatacaagg tacctgttat aaccactgtt gctggtgcat tggccactgc tgagggaatc    3480
aagagcttga agtcaagtgc cattaaaatg accgctcttc aggacttctt tgaggtaaag    3540
aatgtatctt ctttgctcgt ctga                                           3564
```

<210> SEQ ID NO 25
<211> LENGTH: 825
<212> TYPE: DNA
<213> ORGANISM: Glycine max

<400> SEQUENCE: 25

```
atgagagcca aattgtttgt gttcccaata cgaggcagga actggtgctt ctccagaacc     60
atcgatcact ctctctccgc ttcccatgct tcctctcaat cccccctcaac cctcaaagac   120 ttgtggacca acatcaacgt tggtgataaa cccctgaaca ccaaaactga gctctttgtc   180
gattacatcg ccaacaagat gaataatgct tggattggct tggagaaggc gccggagggg   240
tctttcaaga acaagattca tgggttgggg ttgcggctct tgtcgcgggt taagccctct   300
gagatatttt tgaagtctat atcgaaggaa atcactagtg ttgaaatcat ttatccatca   360
agtttgaatg ctcaacttgt tcgtcgaaga ctaagacaca ttgctgtgag gggagcagtt   420
atccatcgga attacttata cggtttagtt tcgttgattc cattgacttc agcacttagc   480
attttacctt tgcctaatgt tccgttcttc tgggttttat ttcgcactta ttctcattgg   540
agagccttgc agggaagtga gaggctgttt caactagtct cagataacag caagacttca   600
aacacttgta catatgaaaa gaaaactgag cacaaggaat ctaaaagtca agacatagt    660 tcaaatgaac cttgttgggt gttgaggcca tccaaagaac ttgagaatct tgtccatcta   720
gaagatggtc aagagagtct tagtcaacat gccatcataa acatttgcaa gatctatgac   780
ttgaacccag tagatgttat aaaatacgag aagtccgtct tttaa                    825
```

<210> SEQ ID NO 26
<211> LENGTH: 621
<212> TYPE: DNA
<213> ORGANISM: Arabidopsis thaliana

<400> SEQUENCE: 26

```
atggcgaaag agtccaccac catcgacgtc ggcgagccaa gcactgttac caaaagttca     60
agccatgtcg taaggacgc gaagaagaag ggctttgtgg cagtcgcctc aagaggtggt   120
gccaagagag gtttggctat attcgatttc ctcctccgtt tggcggccat agcagtcact   180 attgggctg cctctgtcat gtacaccgcc gaggaaactc ttcccttctt tactcagttc   240
ctccagttcc aagccggtta cgatgacctt cctgcgtttc agtactttgt gatagccgta   300
gccgtagtcg ctagctatct cgtcctttca cttccattct ccatcgtatc cattgtccgt   360
ccacatgctg tcgcgccccg gctgatcctc ctcatttgcg atactctggt cgtgacgctc   420
aacacatcag cagcagcagc ggcagcatca atcacctacc ttgcacacaa cggcaaccaa   480
agcaccaact ggctccctat ctgtcagcag tttggagact tctgccagaa cgttagcacc   540
gcggttgtgg ctgattctat cgcgattctc ttcttcatcg ttcttatcat catctcagcc   600
atcgccctca agaggcattg a                                              621
```

<210> SEQ ID NO 27
<211> LENGTH: 1236
<212> TYPE: DNA
<213> ORGANISM: Artificial
<220> FEATURE:

<223> OTHER INFORMATION: codon optimized Escherichia coli Asparagine synthetase A (AsnA) gene

<400> SEQUENCE: 27

```
atggcaacag caacatcagc ttctctgttt tcaactgttt cttcatctta ctccaaagct      60
agctccatac acattcaag actccaatct gtgaaattca actcagtccc tagcttcacc     120
ggtctcaaat caacctctct catctccgga tctgattcct cttccttagc caagactcta     180
cgcggttccg taacgaaagc acaaacatct gacaagaagc cttacggatt caaaatcaac     240
gctatgaaga ccgcctacat cgctaagcag cgccagatct ccttcgtgaa gtcccacttc     300
tctaggcagc tagaggagcg cctaggcctg atcgaggtgc aggcccccat ccttagccgc     360
gtgggtgacg gcacccagga caaccttagc ggctgcgaga aggccgtgca ggtgaaggtg     420
aaggccctcc ccgacgccca gttcgaggtg gtccactccc tcgccaagtg aagcgccag     480
accctcggcc agcacgactt cagcgccggc gagggcctct acacccacat gaaggccctc     540
cgccccgacg aggacaggct ctccccctc cactccgtgt acgtggacca gtgggactgg     600
gagagggtca tgggcgacgg cgagaggcag ttctccaccc tcaagagcac tgtcgaggcc     660
atctgggccg gcatcaaggc tactgaggct gcggtcagcg aggaattcgg cctcgctcct     720
ttcctccctg accagatcca ctttgtccac tctcaggagc tcctgtctag gtaccctgac     780
ctcgacgcta agggccggga gcgggctatc gctaaggacc tcggtgctgt ctttctggtc     840
ggtatcggtg ggaaactgtc tgacggtcac cggcacgatg tccgtgcgcc tgattatgat     900
gattggtcga ctccgtcgga gctgggtcat gcgggtctga acgggatat ctctggtttgg     960
aatccggttc tggaggatgc gtttgagctg tcgtcaatgg ggattcgtgt tgatgcggat    1020
acgctgaaac atcagctggc actgacgggg gatgaggata gacttgaact tgaatggcat    1080
caggcattac ttcgtgggga aatgccgcag acaattgggg gaggaattgg acaatcaaga    1140
cttacaatgc ttttgcttca attgccacat ataggacaag ttcaatgcgg agtttggcca    1200
gcagcagttc gagaaagtgt accaagtttg ttgtga                              1236
```

<210> SEQ ID NO 28
<211> LENGTH: 54
<212> TYPE: PRT
<213> ORGANISM: Arabidopsis thaliana

<400> SEQUENCE: 28

```
Met Val Asn Asn Val Val Ser Ile Glu Lys Met Lys Ala Leu Trp His
1               5                   10                  15
Ser Glu Val His Asp Glu Gln Lys Trp Ala Val Asn Met Lys Leu Leu
            20                  25                  30
Arg Ala Leu Gly Met Phe Ala Gly Gly Val Val Leu Met Arg Ser Tyr
        35                  40                  45
Gly Asp Leu Met Gly Val
    50
```

<210> SEQ ID NO 29
<211> LENGTH: 315
<212> TYPE: PRT
<213> ORGANISM: Arabidopsis thaliana

<400> SEQUENCE: 29

```
Met Val Gly Trp Ala Ile Ala Leu His Gly Gly Ala Gly Asp Ile Pro
1               5                   10                  15
Ile Asp Leu Pro Asp Glu Arg Arg Ile Pro Arg Glu Ser Ala Leu Arg
```

His Cys Leu Asp Leu Gly Ile Ser Ala Leu Lys Ser Gly Lys Pro Pro
                    35                  40                  45

Leu Asp Val Ala Glu Leu Val Arg Glu Leu Glu Asn His Pro Asp
 50                  55                  60

Phe Asn Ala Gly Lys Gly Ser Val Leu Thr Ala Gln Gly Thr Val Glu
 65                  70                  75                  80

Met Glu Ala Ser Ile Met Asp Gly Lys Thr Lys Arg Cys Gly Ala Val
                    85                  90                  95

Ser Gly Leu Thr Thr Val Val Asn Pro Ile Ser Leu Ala Arg Leu Val
                    100                 105                 110

Met Glu Lys Thr Pro His Ile Tyr Leu Ala Phe Asp Ala Ala Glu Ala
                    115                 120                 125

Phe Ala Arg Ala His Gly Val Glu Thr Val Asp Ser Ser His Phe Ile
 130                 135                 140

Thr Pro Glu Asn Ile Ala Arg Leu Lys Gln Ala Lys Glu Phe Asn Arg
 145                 150                 155                 160

Val Gln Leu Asp Tyr Thr Val Pro Ser Pro Lys Val Pro Asp Asn Cys
                    165                 170                 175

Gly Asp Ser Gln Ile Gly Thr Val Gly Cys Val Ala Val Asp Ser Ala
                    180                 185                 190

Gly Asn Leu Ala Ser Ala Thr Ser Thr Gly Gly Tyr Val Asn Lys Met
                    195                 200                 205

Val Gly Arg Ile Gly Asp Thr Pro Val Ile Gly Ala Gly Thr Tyr Ala
 210                 215                 220

Asn His Leu Cys Ala Ile Ser Ala Thr Gly Lys Gly Glu Asp Ile Ile
 225                 230                 235                 240

Arg Gly Thr Val Ala Arg Asp Val Ala Ala Leu Met Glu Tyr Lys Gly
                    245                 250                 255

Leu Ser Leu Thr Glu Ala Ala Ala Tyr Val Val Asp Gln Ser Val Pro
                    260                 265                 270

Arg Gly Ser Cys Gly Leu Val Ala Val Ser Ala Asn Gly Glu Val Thr
                    275                 280                 285

Met Pro Phe Asn Thr Thr Gly Met Phe Arg Ala Cys Ala Ser Glu Asp
                    290                 295                 300

Gly Tyr Ser Glu Ile Ala Ile Trp Pro Asn Asn
 305                 310                 315

<210> SEQ ID NO 30
<211> LENGTH: 726
<212> TYPE: PRT
<213> ORGANISM: Arabidopsis thaliana

<400> SEQUENCE: 30

Met Pro Ser His Pro Asn Phe Ile Phe Arg Trp Ile Gly Leu Phe Ser
 1               5                   10                  15

Asp Lys Phe Arg Arg Gln Thr Thr Gly Ile Asp Glu Asn Ser Asn Leu
                    20                  25                  30

Gln Ile Asn Gly Gly Asp Ser Ser Ser Gly Ser Asp Glu Thr Pro
                    35                  40                  45

Val Leu Ser Ser Val Glu Cys Tyr Ala Cys Thr Gln Val Gly Val Pro
 50                  55                  60

Ala Phe His Ser Thr Ser Cys Asp Gln Ala His Ala Pro Glu Trp Arg
 65                  70                  75                  80

```
Ala Ser Ala Gly Ser Ser Leu Val Pro Ile Gln Glu Gly Ser Val Pro
                85                  90                  95

Asn Pro Ala Arg Thr Arg Phe Arg Arg Leu Lys Gly Pro Phe Gly Glu
            100                 105                 110

Val Leu Asp Pro Arg Ser Lys Arg Val Gln Arg Trp Asn Arg Ala Leu
            115                 120                 125

Leu Leu Ala Arg Gly Met Ala Leu Ala Val Asp Pro Leu Phe Phe Tyr
        130                 135                 140

Ala Leu Ser Ile Gly Arg Thr Thr Gly Pro Ala Cys Leu Tyr Met Asp
145                 150                 155                 160

Gly Ala Phe Ala Ala Val Val Thr Val Leu Arg Thr Cys Leu Asp Ala
                165                 170                 175

Val His Leu Trp His Val Trp Leu Gln Phe Arg Leu Ala Tyr Val Ser
                180                 185                 190

Arg Glu Ser Leu Val Val Gly Cys Gly Lys Leu Val Trp Asp Pro Arg
            195                 200                 205

Ala Ile Ala Ser His Tyr Ala Arg Ser Leu Thr Gly Phe Trp Phe Asp
        210                 215                 220

Val Ile Val Ile Leu Pro Val Pro Gln Ala Val Phe Trp Leu Val Val
225                 230                 235                 240

Pro Lys Leu Ile Arg Glu Lys Val Lys Leu Ile Met Thr Ile Leu
                245                 250                 255

Leu Leu Ile Phe Leu Phe Gln Phe Leu Pro Lys Ile Tyr His Cys Ile
            260                 265                 270

Cys Leu Met Arg Arg Met Gln Lys Val Thr Gly Tyr Ile Phe Gly Thr
        275                 280                 285

Ile Trp Trp Gly Phe Ala Leu Asn Leu Ile Ala Tyr Phe Ile Ala Ser
290                 295                 300

His Val Ala Gly Gly Cys Trp Tyr Val Leu Ala Ile Gln Arg Val Ala
305                 310                 315                 320

Ser Cys Ile Arg Gln Gln Cys Met Arg Thr Gly Asn Cys Asn Leu Ser
            325                 330                 335

Leu Ala Cys Lys Glu Glu Val Cys Tyr Gln Phe Val Ser Pro Thr Ser
        340                 345                 350

Thr Val Gly Tyr Pro Cys Leu Ser Gly Asn Leu Thr Ser Val Val Asn
        355                 360                 365

Lys Pro Met Cys Leu Asp Ser Asn Gly Pro Phe Arg Tyr Gly Ile Tyr
        370                 375                 380

Arg Trp Ala Leu Pro Val Ile Ser Ser Asn Ser Leu Ala Val Lys Ile
385                 390                 395                 400

Leu Tyr Pro Ile Phe Trp Gly Leu Met Thr Leu Ser Thr Phe Ala Asn
            405                 410                 415

Asp Leu Glu Pro Thr Ser Asn Trp Leu Glu Val Ile Phe Ser Ile Val
        420                 425                 430

Met Val Leu Ser Gly Leu Leu Leu Phe Thr Leu Leu Ile Gly Asn Ile
        435                 440                 445

Gln Val Phe Leu His Ala Val Met Ala Lys Lys Arg Lys Met Gln Ile
        450                 455                 460

Arg Cys Arg Asp Met Glu Trp Trp Met Lys Arg Gln Leu Pro Ser
465                 470                 475                 480

Arg Leu Arg Gln Arg Val Arg Arg Phe Glu Arg Gln Arg Trp Asn Ala
            485                 490                 495

Leu Gly Gly Glu Asp Glu Leu Glu Leu Ile His Asp Leu Pro Pro Gly
```

```
                500             505             510
Leu Arg Arg Asp Ile Lys Arg Tyr Leu Cys Phe Asp Leu Ile Asn Lys
            515                 520                 525

Val Pro Leu Phe Arg Gly Met Asp Asp Leu Ile Leu Asp Asn Ile Cys
        530                 535                 540

Asp Arg Ala Lys Pro Arg Val Phe Ser Lys Asp Glu Lys Ile Ile Arg
545                 550                 555                 560

Glu Gly Asp Pro Val Gln Arg Met Ile Phe Ile Met Arg Gly Arg Val
                565                 570                 575

Lys Arg Ile Gln Ser Leu Ser Lys Gly Val Leu Ala Thr Ser Thr Leu
            580                 585                 590

Glu Pro Gly Gly Tyr Leu Gly Asp Glu Leu Leu Ser Trp Cys Leu Arg
        595                 600                 605

Arg Pro Phe Leu Asp Arg Leu Pro Pro Ser Ser Ala Thr Phe Val Cys
        610                 615                 620

Leu Glu Asn Ile Glu Ala Phe Ser Leu Gly Ser Glu Asp Leu Arg Tyr
625                 630                 635                 640

Ile Thr Asp His Phe Arg Tyr Lys Phe Ala Asn Glu Arg Leu Lys Arg
                645                 650                 655

Thr Ala Arg Tyr Tyr Ser Ser Asn Trp Arg Thr Trp Ala Ala Val Asn
            660                 665                 670

Ile Gln Met Ala Trp Arg Arg Arg Lys Arg Thr Arg Gly Glu Asn
            675                 680                 685

Ile Gly Gly Ser Met Ser Pro Val Ser Glu Asn Ser Ile Glu Gly Asn
        690                 695                 700

Ser Glu Arg Arg Leu Leu Gln Tyr Ala Ala Met Phe Met Ser Ile Arg
705                 710                 715                 720

Pro His Asp His Leu Glu
            725

<210> SEQ ID NO 31
<211> LENGTH: 467
<212> TYPE: PRT
<213> ORGANISM: Arabidopsis thaliana

<400> SEQUENCE: 31

Met Ile Leu Asp Leu Gly Phe Pro Cys Phe Val Pro Pro Arg Thr Ser
1               5                   10                  15

Ser Arg Glu Asp Asn Lys Ala Trp Leu Leu Ala Glu Thr Glu Pro Lys
            20                  25                  30

Leu Ile Asp Ser Glu Gln His Ser Leu Gln Ser Ser Phe Arg Phe Ser
        35                  40                  45

Leu Cys Ser Gln Leu Glu Leu Glu Lys Ile Lys Lys Glu Lys Pro Ser
    50                  55                  60

Leu Ser Tyr Arg Asn Phe Pro Val Ser Glu Gly Ser Glu Thr Val Leu
65                  70                  75                  80

Leu Val Asn Leu Glu Asn Glu Thr Gly Glu Leu Thr Gly Glu Met Asn
                85                  90                  95

Trp Ser Arg Gly Leu Ser Leu Glu Lys Ser Ile Ser Pro Val Ala Asp
            100                 105                 110

Ser Leu Ile Arg Phe Ser Tyr Arg Glu Leu Leu Thr Ala Thr Arg Asn
        115                 120                 125

Phe Ser Lys Arg Arg Val Leu Gly Arg Gly Ala Cys Ser Tyr Val Phe
    130                 135                 140
```

```
Lys Gly Arg Ile Gly Ile Trp Arg Lys Ala Val Ala Ile Lys Arg Leu
145                 150                 155                 160

Asp Lys Lys Asp Lys Glu Ser Pro Lys Ser Phe Cys Arg Glu Leu Met
            165                 170                 175

Ile Ala Ser Ser Leu Asn Ser Pro Asn Val Pro Leu Leu Gly Phe
        180                 185                 190

Cys Ile Asp Pro Asp Gln Gly Leu Phe Leu Val Tyr Lys Tyr Val Ser
        195                 200                 205

Gly Gly Ser Leu Glu Arg Phe Leu His Asp Lys Lys Lys Lys Ser
        210                 215                 220

Arg Lys Thr Pro Leu Asn Leu Pro Trp Ser Thr Arg Tyr Lys Val Ala
225                 230                 235                 240

Leu Gly Ile Ala Asp Ala Ile Ala Tyr Leu His Asn Gly Thr Glu Gln
                245                 250                 255

Cys Val Val His Arg Asp Ile Lys Pro Ser Asn Ile Leu Leu Ser Ser
            260                 265                 270

Asn Lys Ile Pro Lys Leu Cys Asp Phe Gly Leu Ala Thr Trp Thr Ala
        275                 280                 285

Ala Pro Ser Val Pro Phe Leu Cys Lys Thr Val Lys Gly Thr Phe Gly
290                 295                 300

Tyr Leu Ala Pro Glu Tyr Phe Gln His Gly Lys Ile Ser Asp Lys Thr
305                 310                 315                 320

Asp Val Tyr Ala Phe Gly Val Val Leu Leu Glu Leu Ile Thr Gly Arg
                325                 330                 335

Lys Pro Ile Glu Ala Arg Arg Pro Ser Gly Glu Glu Asn Leu Val Val
            340                 345                 350

Trp Ala Lys Pro Leu Leu His Arg Gly Ile Glu Ala Thr Glu Glu Leu
            355                 360                 365

Leu Asp Pro Arg Leu Lys Cys Thr Arg Lys Asn Ser Ala Ser Met Glu
        370                 375                 380

Arg Met Ile Arg Ala Ala Ala Cys Val Ile Asn Glu Glu Ser Arg
385                 390                 395                 400

Arg Pro Gly Met Lys Glu Ile Leu Ser Ile Leu Lys Gly Gly Glu Gly
                405                 410                 415

Ile Glu Leu Arg Thr Leu Ser Ser Arg Lys Ser Asn Leu Pro Gly
            420                 425                 430

Ile Met Asp Cys Tyr Pro Gln Leu Gln Arg Thr Lys Ser Glu Met Lys
        435                 440                 445

Ser His Leu Thr Leu Ala Met Leu Gly Val Thr Glu Phe Glu Ala Asp
    450                 455                 460

Asp Leu Leu
465

<210> SEQ ID NO 32
<211> LENGTH: 354
<212> TYPE: PRT
<213> ORGANISM: Oryza sativa

<400> SEQUENCE: 32

Met Ala Gly Ser Asp Glu Val Asn Arg Asn Glu Cys Lys Thr Val Val
1               5                   10                  15

Pro Leu His Thr Trp Val Leu Ile Ser Asn Phe Lys Leu Ser Tyr Asn
            20                  25                  30

Ile Leu Arg Arg Ala Asp Gly Thr Phe Glu Arg Asp Leu Gly Glu Tyr
        35                  40                  45
```

Leu Asp Arg Arg Val Pro Ala Asn Ala Arg Pro Leu Glu Gly Val Ser
 50                  55                  60

Ser Phe Asp His Ile Ile Asp Gln Ser Val Gly Leu Glu Val Arg Ile
 65                  70                  75                  80

Tyr Arg Ala Ala Ala Glu Gly Asp Ala Glu Gly Ala Ala Ala Val
                 85                  90                  95

Thr Arg Pro Ile Leu Glu Phe Leu Thr Asp Ala Pro Ala Ala Glu Pro
                100                 105                 110

Phe Pro Val Ile Ile Phe Phe His Gly Gly Ser Phe Val His Ser Ser
                115                 120                 125

Ala Ser Ser Thr Ile Tyr Asp Ser Leu Cys Arg Arg Phe Val Lys Leu
130                 135                 140

Ser Lys Gly Val Val Ser Val Asn Tyr Arg Arg Ala Pro Glu His
145                 150                 155                 160

Arg Tyr Pro Cys Ala Tyr Asp Asp Gly Trp Thr Ala Leu Lys Trp Val
                165                 170                 175

Met Ser Gln Pro Phe Met Arg Ser Gly Gly Asp Ala Gln Ala Arg Val
                180                 185                 190

Phe Leu Ser Gly Asp Ser Ser Gly Gly Asn Ile Ala His His Val Ala
                195                 200                 205

Val Arg Ala Ala Asp Glu Gly Val Lys Val Cys Gly Asn Ile Leu Leu
210                 215                 220

Asn Ala Met Phe Gly Gly Thr Glu Arg Thr Glu Ser Glu Arg Arg Leu
225                 230                 235                 240

Asp Gly Lys Tyr Phe Val Thr Leu Gln Asp Arg Asp Trp Tyr Trp Lys
                245                 250                 255

Ala Tyr Leu Pro Glu Asp Ala Asp Arg Asp His Pro Ala Cys Asn Pro
                260                 265                 270

Phe Gly Pro Asn Gly Arg Arg Leu Gly Gly Leu Pro Phe Ala Lys Ser
                275                 280                 285

Leu Ile Ile Val Ser Gly Leu Asp Leu Thr Cys Asp Arg Gln Leu Ala
290                 295                 300

Tyr Ala Asp Ala Leu Arg Glu Asp Gly His His Val Lys Val Val Gln
305                 310                 315                 320

Cys Glu Asn Ala Thr Val Gly Phe Tyr Leu Leu Pro Asn Thr Val His
                325                 330                 335

Tyr His Glu Val Met Glu Glu Ile Ser Asp Phe Leu Asn Ala Asn Leu
                340                 345                 350

Tyr Tyr

<210> SEQ ID NO 33
<211> LENGTH: 390
<212> TYPE: PRT
<213> ORGANISM: Zea mays

<400> SEQUENCE: 33

Met Gln Ser Ala Ala Ala Ile Gly Leu Leu Arg Pro Cys Ala Ala Arg
1               5                   10                  15

Pro Leu Ala Ala Tyr Thr Ser Pro Arg Arg Gly Ala Gly Ala Cys Ser
                20                  25                  30

Gly Gly Thr Gln Pro Ile Ile Thr Pro Arg Gly Ile Arg Leu Ser Ala
            35                  40                  45

Arg Pro Gly Leu Val Pro Ala Ser Pro Leu Glu Glu Lys Glu Asn Arg
 50                  55                  60

Arg Cys Arg Ala Ser Met His Ala Ala Ser Ala Gly Glu Glu Ala
65                  70                  75                  80

Gly Gly Gly Leu Ala Lys Thr Leu Gln Leu Gly Ala Leu Phe Gly Leu
                85                  90                  95

Trp Tyr Leu Phe Asn Ile Tyr Phe Asn Ile Tyr Asn Lys Gln Val Leu
                100                 105                 110

Lys Val Leu Pro Tyr Pro Ile Asn Ile Thr Thr Val Gln Phe Ala Val
                115                 120                 125

Gly Ser Ala Ile Ala Leu Phe Met Trp Ile Thr Gly Ile His Lys Arg
130                 135                 140

Pro Lys Ile Ser Gly Ala Gln Leu Phe Ala Ile Leu Pro Leu Ala Ile
145                 150                 155                 160

Val His Thr Met Gly Asn Leu Phe Thr Asn Met Ser Leu Gly Lys Val
                165                 170                 175

Ala Val Ser Phe Thr His Thr Ile Lys Ala Met Glu Pro Phe Phe Ser
                180                 185                 190

Val Leu Leu Ser Ala Ile Phe Leu Gly Glu Leu Pro Thr Pro Trp Val
                195                 200                 205

Val Leu Ser Leu Leu Pro Ile Val Gly Val Ala Leu Ala Ser Leu
                210                 215                 220

Thr Glu Ala Ser Phe Asn Trp Ala Gly Phe Trp Ser Ala Met Ala Ser
225                 230                 235                 240

Asn Val Thr Phe Gln Ser Arg Asn Val Leu Ser Lys Lys Leu Met Val
                245                 250                 255

Lys Lys Glu Glu Ser Leu Asp Asn Ile Asn Leu Phe Ser Ile Ile Thr
                260                 265                 270

Val Met Ser Phe Phe Leu Leu Ala Pro Val Thr Leu Leu Thr Glu Gly
                275                 280                 285

Val Lys Val Ser Pro Ala Val Leu Gln Ser Ala Gly Leu Asn Leu Lys
                290                 295                 300

Gln Val Tyr Thr Arg Ser Leu Ile Ala Ala Phe Cys Phe His Ala Tyr
305                 310                 315                 320

Gln Gln Val Ser Tyr Met Ile Leu Ala Arg Val Ser Pro Val Thr His
                325                 330                 335

Ser Val Gly Asn Cys Val Lys Arg Val Val Ile Val Thr Ser Val
                340                 345                 350

Leu Phe Phe Arg Thr Pro Val Ser Pro Ile Asn Ser Leu Gly Thr Gly
                355                 360                 365

Ile Ala Leu Ala Gly Val Phe Leu Tyr Ser Gln Leu Lys Arg Leu Lys
370                 375                 380

Pro Lys Pro Lys Thr Ala
385                 390

<210> SEQ ID NO 34
<211> LENGTH: 477
<212> TYPE: PRT
<213> ORGANISM: Arabidopsis thaliana

<400> SEQUENCE: 34

Met Ala His Leu Leu Ser Ala Ser Cys Pro Ser Val Ile Ser Leu Ser
1               5                   10                  15

Ser Ser Ser Ser Lys Asn Ser Val Lys Pro Phe Val Ser Gly Gln Thr
                20                  25                  30

Phe Phe Asn Ala Gln Leu Leu Ser Arg Ser Ser Leu Lys Gly Leu Leu

```
                35                  40                  45
Phe Gln Glu Lys Lys Pro Arg Lys Ser Cys Val Phe Arg Ala Thr Ala
 50                  55                  60
Val Pro Ile Thr Gln Gln Ala Pro Pro Glu Thr Ser Thr Asn Asn Ser
 65                  70                  75                  80
Ser Ser Lys Pro Lys Arg Val Met Val Ile Gly Gly Asp Gly Tyr Cys
                 85                  90                  95
Gly Trp Ala Thr Ala Leu His Leu Ser Lys Lys Asn Tyr Glu Val Cys
                100                 105                 110
Ile Val Asp Asn Leu Val Arg Arg Leu Phe Asp His Gln Leu Gly Leu
                115                 120                 125
Glu Ser Leu Thr Pro Ile Ala Ser Ile His Asp Arg Ile Ser Arg Trp
                130                 135                 140
Lys Ala Leu Thr Gly Lys Ser Ile Glu Leu Tyr Val Gly Asp Ile Cys
145                 150                 155                 160
Asp Phe Glu Phe Leu Ala Glu Ser Phe Lys Ser Phe Glu Pro Asp Ser
                165                 170                 175
Val Val His Phe Gly Glu Gln Arg Ser Ala Pro Tyr Ser Met Ile Asp
                180                 185                 190
Arg Ser Arg Ala Val Tyr Thr Gln His Asn Asn Val Ile Gly Thr Leu
                195                 200                 205
Asn Val Leu Phe Ala Ile Lys Glu Phe Gly Glu Cys His Leu Val
                210                 215                 220
Lys Leu Gly Thr Met Gly Glu Tyr Gly Thr Pro Asn Ile Asp Ile Glu
225                 230                 235                 240
Glu Gly Tyr Ile Thr Ile Thr His Asn Gly Arg Thr Asp Thr Leu Pro
                245                 250                 255
Tyr Pro Lys Gln Ala Ser Ser Phe Tyr His Leu Ser Lys Val His Asp
                260                 265                 270
Ser His Asn Ile Ala Phe Thr Cys Lys Ala Trp Gly Ile Arg Ala Thr
                275                 280                 285
Asp Leu Asn Gln Gly Val Val Tyr Gly Val Lys Thr Asp Glu Thr Glu
                290                 295                 300
Met His Glu Glu Leu Arg Asn Arg Leu Asp Tyr Asp Ala Val Phe Gly
305                 310                 315                 320
Thr Ala Leu Asn Arg Phe Cys Val Gln Ala Val Gly His Pro Leu
                325                 330                 335
Thr Val Tyr Gly Lys Gly Gly Gln Thr Arg Gly Tyr Leu Asp Ile Arg
                340                 345                 350
Asp Thr Val Gln Cys Val Glu Ile Ala Ile Ala Asn Pro Ala Lys Ala
                355                 360                 365
Gly Glu Phe Arg Val Phe Asn Gln Phe Thr Glu Gln Phe Ser Val Asn
                370                 375                 380
Glu Leu Ala Ser Leu Val Thr Lys Ala Gly Ser Lys Leu Gly Leu Asp
385                 390                 395                 400
Val Lys Lys Met Thr Val Pro Asn Pro Arg Val Glu Ala Glu His
                405                 410                 415
Tyr Tyr Asn Ala Lys His Thr Leu Met Glu Leu Gly Leu Glu Pro
                420                 425                 430
His Tyr Leu Ser Asp Ser Leu Leu Asp Ser Leu Leu Asn Phe Ala Val
                435                 440                 445
Gln Phe Lys Asp Arg Val Asp Thr Lys Gln Ile Met Pro Ser Val Ser
                450                 455                 460
```

Trp Lys Lys Ile Gly Val Lys Thr Lys Ser Met Thr Thr
465                 470                 475

<210> SEQ ID NO 35
<211> LENGTH: 504
<212> TYPE: PRT
<213> ORGANISM: Arabidopsis thaliana

<400> SEQUENCE: 35

Met Val Ser Leu Leu Ser Phe Phe Leu Leu Leu Val Pro Ile Phe
1               5                   10                  15

Phe Leu Leu Ile Phe Thr Lys Lys Ile Lys Glu Ser Lys Gln Asn Leu
                20                  25                  30

Pro Pro Gly Pro Ala Lys Leu Pro Ile Ile Gly Asn Leu His Gln Leu
            35                  40                  45

Gln Gly Leu Leu His Lys Cys Leu His Asp Leu Ser Lys Lys His Gly
        50                  55                  60

Pro Val Met His Leu Arg Leu Gly Phe Ala Pro Met Val Val Ile Ser
65                  70                  75                  80

Ser Ser Glu Ala Ala Glu Glu Ala Leu Lys Thr His Asp Leu Glu Cys
                85                  90                  95

Cys Ser Arg Pro Ile Thr Met Ala Ser Arg Val Phe Ser Arg Asn Gly
            100                 105                 110

Lys Asp Ile Gly Phe Gly Val Tyr Gly Asp Glu Trp Arg Glu Leu Arg
        115                 120                 125

Lys Leu Ser Val Arg Glu Phe Phe Ser Val Lys Val Gln Ser Phe
130                 135                 140

Lys Tyr Ile Arg Glu Glu Glu Asn Asp Leu Met Ile Lys Lys Leu Lys
145                 150                 155                 160

Glu Leu Ala Ser Lys Gln Ser Pro Val Asp Leu Ser Lys Ile Leu Phe
                165                 170                 175

Gly Leu Thr Ala Ser Ile Ile Phe Arg Thr Ala Phe Gly Gln Ser Phe
            180                 185                 190

Phe Asp Asn Lys His Val Asp Gln Glu Ser Ile Lys Glu Leu Met Phe
        195                 200                 205

Glu Ser Leu Ser Asn Met Thr Phe Arg Phe Ser Asp Phe Pro Thr
210                 215                 220

Ala Gly Leu Lys Trp Phe Ile Gly Phe Val Ser Gly Gln His Lys Arg
225                 230                 235                 240

Leu Tyr Asn Val Phe Asn Arg Val Asp Thr Phe Phe Asn His Ile Val
                245                 250                 255

Asp Asp His His Ser Lys Lys Ala Thr Gln Asp Arg Pro Asp Met Val
            260                 265                 270

Asp Ala Ile Leu Asp Met Ile Asp Asn Glu Gln Gln Tyr Ala Ser Phe
        275                 280                 285

Lys Leu Thr Val Asp His Leu Lys Gly Val Leu Ser Asn Ile Tyr His
        290                 295                 300

Ala Gly Ile Asp Thr Ser Ala Ile Thr Leu Ile Trp Ala Met Ala Glu
305                 310                 315                 320

Leu Val Arg Asn Pro Arg Val Met Lys Lys Ala Gln Asp Glu Ile Arg
                325                 330                 335

Thr Cys Ile Gly Ile Lys Gln Glu Gly Arg Ile Met Glu Glu Asp Leu
            340                 345                 350

Asp Lys Leu Gln Tyr Leu Lys Leu Val Val Lys Glu Thr Leu Arg Leu

```
                355                 360                 365
His Pro Ala Ala Pro Leu Leu Leu Pro Arg Glu Thr Met Ala Asp Ile
370                 375                 380

Lys Ile Gln Gly Tyr Asp Ile Pro Gln Lys Arg Ala Leu Leu Val Asn
385                 390                 395                 400

Ala Trp Ser Ile Gly Arg Asp Pro Glu Ser Trp Lys Asn Pro Glu Glu
                405                 410                 415

Phe Asn Pro Glu Arg Phe Ile Asp Cys Pro Val Asp Tyr Lys Gly His
                420                 425                 430

Ser Phe Glu Leu Leu Pro Phe Gly Ser Gly Arg Arg Ile Cys Pro Gly
            435                 440                 445

Ile Ala Met Ala Ile Ala Thr Ile Glu Leu Gly Leu Leu Asn Leu Leu
        450                 455                 460

Tyr Phe Phe Asp Trp Asn Met Pro Glu Lys Lys Asp Met Asp Met
465                 470                 475                 480

Glu Glu Ala Gly Asp Leu Thr Val Asp Lys Lys Val Pro Leu Glu Leu
                485                 490                 495

Leu Pro Val Ile Arg Ile Ser Leu
                500

<210> SEQ ID NO 36
<211> LENGTH: 389
<212> TYPE: PRT
<213> ORGANISM: Pseudomonas syringae pv. tomato str. DC3000

<400> SEQUENCE: 36

Met Val Met Thr Val Leu Lys Met Thr Asp Leu Asp Leu Gln Gly Lys
1               5                   10                  15

Arg Val Leu Ile Arg Glu Asp Leu Asn Val Pro Ile Lys Asp Gly Val
                20                  25                  30

Val Ser Ser Asp Ala Arg Ile Leu Ala Ser Leu Pro Thr Ile Arg Leu
            35                  40                  45

Ala Leu Glu Lys Gly Ala Ala Val Met Val Cys Ser His Leu Gly Arg
        50                  55                  60

Pro Thr Glu Gly Glu Phe Ser Ala Glu Asn Ser Leu Lys Pro Val Ala
65                  70                  75                  80

Glu Tyr Leu Ser Lys Ala Leu Gly Arg Asp Val Pro Leu Val Ala Asp
                85                  90                  95

Tyr Leu Asp Gly Val Asp Val Lys Ala Gly Asp Ile Val Leu Phe Glu
                100                 105                 110

Asn Val Arg Phe Asn Lys Gly Glu Lys Lys Asn Ala Asp Glu Leu Ala
            115                 120                 125

Gln Lys Tyr Ala Ala Leu Cys Asp Val Phe Val Met Asp Ala Phe Gly
        130                 135                 140

Thr Ala His Arg Ala Glu Gly Ser Thr His Gly Val Ala Lys Tyr Ala
145                 150                 155                 160

Lys Val Ala Ala Ala Gly Pro Leu Leu Ala Ala Glu Leu Glu Ala Leu
                165                 170                 175

Gly Lys Ala Leu Gly Ala Pro Ala Gln Pro Met Ala Ala Ile Val Ala
            180                 185                 190

Gly Ser Lys Val Ser Thr Lys Leu Asp Val Leu Asn Ser Leu Ser Ala
        195                 200                 205

Ile Cys Asp Gln Leu Ile Val Gly Gly Gly Ile Ala Asn Thr Phe Leu
    210                 215                 220
```

```
Ala Ala Ala Gly His Lys Val Gly Lys Ser Leu Tyr Glu Pro Asp Leu
225                 230                 235                 240

Leu Asp Thr Ala Arg Ala Ile Ala Ala Lys Val Ser Val Pro Leu Pro
            245                 250                 255

Thr Asp Val Val Val Ala Lys Glu Phe Ala Glu Ser Ala Thr Ala Thr
        260                 265                 270

Val Lys Leu Ile Ala Asp Val Ala Asp Asp Met Ile Leu Asp Ile
    275                 280                 285

Gly Pro Gln Thr Ala Ala His Phe Ala Glu Leu Leu Lys Ser Ser Gly
    290                 295                 300

Thr Ile Leu Trp Asn Gly Pro Val Gly Val Phe Glu Phe Asp Gln Phe
305                 310                 315                 320

Gly Glu Gly Thr Lys Thr Leu Ala Lys Ala Ile Ala Glu Ser Lys Ala
            325                 330                 335

Phe Ser Ile Ala Gly Gly Asp Thr Leu Ala Ala Ile Asp Lys Tyr
        340                 345                 350

Gly Val Ala Asp Gln Ile Ser Tyr Ile Ser Thr Gly Gly Gly Ala Phe
        355                 360                 365

Leu Glu Phe Val Glu Gly Lys Val Leu Pro Ala Val Glu Met Leu Glu
    370                 375                 380

Gln Arg Ala Arg Ala
385

<210> SEQ ID NO 37
<211> LENGTH: 395
<212> TYPE: PRT
<213> ORGANISM: Zea mays

<400> SEQUENCE: 37

Met Ser Leu Ile Arg Gly Met Gly Asn Val Ala Lys Arg Trp Lys Glu
1               5                   10                  15

Leu Asn Gly Leu Asn Tyr Trp Lys Gly Leu Val Asp Pro Leu Asp Leu
            20                  25                  30

Asp Leu Arg Arg Asn Ile Ile Asn Tyr Gly Glu Leu Ser Gln Ala Thr
        35                  40                  45

Tyr Thr Gly Leu Asn Arg Glu Arg Ser Arg Tyr Ala Gly Ser Cys
    50                  55                  60

Leu Phe Asn Arg Arg Asp Phe Leu Ser Arg Val Asp Val Ser Asn Pro
65                  70                  75                  80

Asn Leu Tyr Glu Ile Thr Lys Phe Ile Tyr Ala Met Cys Thr Val Ser
                85                  90                  95

Leu Pro Asp Gly Phe Met Val Lys Ser Leu Ser Lys Ala Ala Trp Ser
            100                 105                 110

Arg Gln Ser Asn Trp Met Gly Phe Val Ala Val Ala Thr Asp Glu Gly
        115                 120                 125

Lys Glu Leu Leu Gly Arg Arg Asp Val Val Ala Trp Arg Gly Thr
    130                 135                 140

Ile Arg Met Val Glu Trp Val Asp Asp Leu Asp Ile Ser Leu Val Pro
145                 150                 155                 160

Ala Ser Glu Ile Val Leu Pro Gly Ser Ala Ala Asn Pro Cys Val His
                165                 170                 175

Gly Gly Trp Leu Ser Val Tyr Thr Ser Ala Asp Pro Gly Ser Gln Tyr
            180                 185                 190

Asn Lys Glu Ser Ala Arg His Gln Val Leu Asn Glu Val Lys Arg Ile
        195                 200                 205
```

```
Gln Asp Leu Tyr Lys Pro Glu Glu Thr Ser Ile Thr Ile Thr Gly His
    210                 215                 220

Ser Leu Gly Ala Ala Leu Ala Thr Ile Asn Ala Thr Asp Ile Val Ser
225                 230                 235                 240

Asn Gly Tyr Asn Arg Ser Cys Cys Pro Val Ser Ala Phe Val Phe Gly
            245                 250                 255

Ser Pro Arg Val Gly Asn Pro Asp Phe Gln Lys Ala Phe Asp Ser Ala
        260                 265                 270

Ala Asp Leu Arg Leu Leu Arg Val Arg Asn Ser Pro Asp Val Val Pro
    275                 280                 285

Lys Trp Pro Lys Leu Gly Tyr Ser Asp Val Gly Thr Glu Leu Met Ile
290                 295                 300

Asp Thr Gly Glu Ser Pro Tyr Leu Lys Ala Pro Gly Asn Pro Leu Thr
305                 310                 315                 320

Trp His Asp Met Glu Cys Tyr Met His Gly Val Ala Gly Ala Gln Gly
            325                 330                 335

Ser Ser Gly Gly Phe Glu Leu Leu Val Asp Arg Asp Val Ala Leu Val
        340                 345                 350

Asn Lys His Glu Asp Ala Leu Arg Asn Glu Phe Ala Val Pro Pro Ser
    355                 360                 365

Trp Trp Val Val Gln Asn Lys Gly Met Val Lys Gly Lys Asp Gly Arg
370                 375                 380

Trp His Leu Ala Asp His Glu Glu Asp Asp Asp
385                 390                 395

<210> SEQ ID NO 38
<211> LENGTH: 512
<212> TYPE: PRT
<213> ORGANISM: Arabidopsis thaliana

<400> SEQUENCE: 38

Met Ala Thr Leu Leu Ala Thr Pro Ile Phe Ser Pro Leu Ala Ser Ser
1               5                   10                  15

Pro Ala Arg Asn Arg Leu Ser Cys Ser Lys Ile Arg Phe Gly Ser Lys
            20                  25                  30

Asn Gly Lys Ile Leu Asn Ser Asp Gly Ala Gln Lys Leu Asn Leu Ser
        35                  40                  45

Lys Phe Arg Lys Pro Asp Gly Gln Arg Phe Leu Gln Met Gly Ser Ser
    50                  55                  60

Lys Glu Met Asn Phe Glu Arg Lys Leu Ser Val Gln Ala Met Asp Gly
65                  70                  75                  80

Ala Gly Thr Gly Asn Thr Ser Thr Ile Ser Arg Asn Val Ile Ala Ile
                85                  90                  95

Ser His Leu Leu Val Ser Leu Gly Ile Ile Leu Ala Ala Asp Tyr Phe
            100                 105                 110

Leu Lys Gln Ala Phe Val Ala Ser Ile Lys Phe Pro Ser Ala Leu
    115                 120                 125

Phe Gly Met Phe Cys Ile Phe Ser Val Leu Met Ile Phe Asp Ser Val
130                 135                 140

Val Pro Ala Ala Ala Asn Gly Leu Met Asn Phe Glu Pro Ala Phe
145                 150                 155                 160

Leu Phe Ile Gln Arg Trp Leu Pro Leu Phe Tyr Val Pro Ser Leu Val
            165                 170                 175

Val Leu Pro Leu Ser Val Arg Asp Ile Pro Ala Ala Ser Gly Val Lys
```

```
            180                 185                 190
Ile Cys Tyr Ile Val Ala Gly Gly Trp Leu Ala Ser Leu Cys Val Ala
            195                 200                 205
Gly Tyr Thr Ala Ile Ala Val Arg Lys Met Val Lys Thr Glu Met Thr
            210                 215                 220
Glu Ala Glu Pro Met Ala Lys Pro Ser Pro Phe Ser Thr Leu Glu Leu
225                 230                 235                 240
Trp Ser Trp Ser Gly Ile Phe Val Val Ser Phe Val Gly Ala Leu Phe
                245                 250                 255
Tyr Pro Asn Ser Leu Gly Thr Ser Ala Arg Thr Ser Leu Pro Phe Leu
            260                 265                 270
Leu Ser Ser Thr Val Leu Gly Tyr Ile Val Gly Ser Gly Leu Pro Ser
            275                 280                 285
Ser Ile Lys Lys Val Phe His Pro Ile Ile Cys Cys Ala Leu Ser Ala
            290                 295                 300
Val Leu Ala Ala Leu Ala Phe Gly Tyr Ala Ser Gly Ser Gly Leu Asp
305                 310                 315                 320
Pro Val Leu Gly Asn Tyr Leu Thr Lys Val Ala Ser Asp Pro Gly Ala
                325                 330                 335
Gly Asp Ile Leu Met Gly Phe Leu Gly Ser Val Ile Leu Ser Phe Ala
                340                 345                 350
Phe Ser Met Phe Lys Gln Arg Lys Leu Val Lys Arg His Ala Ala Glu
            355                 360                 365
Ile Phe Thr Ser Val Ile Val Ser Thr Val Phe Ser Leu Tyr Ser Thr
            370                 375                 380
Ala Leu Val Gly Arg Leu Val Gly Leu Glu Pro Ser Leu Thr Val Ser
385                 390                 395                 400
Ile Leu Pro Arg Cys Ile Thr Val Ala Leu Ala Leu Ser Ile Val Ser
                405                 410                 415
Leu Phe Glu Gly Thr Asn Ser Ser Leu Thr Ala Ala Val Val Val Val
                420                 425                 430
Thr Gly Leu Ile Gly Ala Asn Phe Val Gln Val Val Leu Asp Lys Leu
            435                 440                 445
Arg Leu Arg Asp Pro Ile Ala Arg Gly Ile Ala Thr Ala Ser Ser Ala
            450                 455                 460
His Gly Leu Gly Thr Ala Ala Leu Ser Ala Lys Glu Pro Glu Ala Leu
465                 470                 475                 480
Pro Phe Cys Ala Ile Ala Tyr Ala Leu Thr Gly Ile Phe Gly Ser Leu
                485                 490                 495
Leu Cys Ser Val Pro Ala Val Arg Gln Ser Leu Leu Ala Val Val Gly
            500                 505                 510

<210> SEQ ID NO 39
<211> LENGTH: 311
<212> TYPE: PRT
<213> ORGANISM: Zea mays

<400> SEQUENCE: 39

Met Ala Arg Asn Glu Glu Lys Ala Gln Ser Met Leu Asn Arg Phe Ile
1               5                   10                  15
Thr Met Lys Gln Glu Glu Lys Arg Lys Pro Arg Glu Arg Arg Pro Tyr
            20                  25                  30
Leu Ala Ser Glu Cys Arg Asp Leu Ala Asp Ala Glu Arg Trp Arg Ser
        35                  40                  45
```

```
Glu Ile Leu Arg Glu Ile Gly Ala Lys Val Ala Glu Ile Gln Asn Glu
             50                  55                  60

Gly Leu Gly Glu His Arg Leu Arg Asp Leu Asn Asp Glu Ile Asn Lys
 65                  70                  75                  80

Leu Leu Arg Glu Arg Gly His Trp Glu Arg Ile Val Glu Leu Gly
                 85                  90                  95

Gly Arg Asp Tyr Ser Arg Ser Ser Asn Ala Pro Leu Met Thr Asp Leu
                100                 105                 110

Asp Gly Asn Ile Val Ala Val Pro Asn Pro Ser Gly Arg Gly Pro Gly
                115                 120                 125

Tyr Arg Tyr Phe Gly Ala Ala Arg Lys Leu Pro Gly Val Arg Glu Leu
130                 135                 140

Phe Asp Lys Pro Pro Glu Met Arg Lys Arg Thr Arg Tyr Glu Ile
145                 150                 155                 160

His Lys Arg Ile Asn Ala Gly Tyr Tyr Gly Tyr Tyr Asp Asp Glu Asp
                165                 170                 175

Gly Val Leu Glu Arg Leu Glu Gly Pro Ala Gly Lys Arg Met Arg Glu
                180                 185                 190

Glu Ile Val Ser Glu Trp His Arg Val Glu Arg Val Arg Arg Glu Ala
                195                 200                 205

Met Lys Gly Val Met Ser Gly Glu Val Ala Ala Gly Gly Arg Ser
210                 215                 220

Gly Glu Ala Ala Arg Glu Val Leu Phe Glu Gly Val Glu Glu Glu Val
225                 230                 235                 240

Glu Glu Glu Arg Lys Arg Glu Glu Lys Arg Glu Arg Glu Lys Gly
                245                 250                 255

Glu Glu Val Gly Arg Glu Phe Val Ala His Val Pro Leu Pro Asp Glu
                260                 265                 270

Lys Glu Ile Glu Arg Met Val Leu Glu Arg Lys Lys Lys Glu Leu Leu
                275                 280                 285

Ser Lys Tyr Ala Ser Asp Ser Leu Leu Val Glu Gln Glu Glu Ala Lys
                290                 295                 300

Glu Met Leu Asn Val Arg Arg
305                 310

<210> SEQ ID NO 40
<211> LENGTH: 682
<212> TYPE: PRT
<213> ORGANISM: Zea mays

<400> SEQUENCE: 40

Met Asp Leu Ala Arg Arg Gly Gly Ala Ala Gly Ala Asp Asp Glu Gly
 1               5                  10                  15

Glu Ile Glu Arg His Glu Pro Ala Pro Glu Asp Met Glu Ser Asp Pro
                 20                  25                  30

Ala Ala Ala Arg Glu Lys Glu Leu Glu Leu Glu Arg Val Gln Ser Trp
             35                  40                  45

Arg Glu Gln Val Thr Leu Arg Gly Val Val Ala Ala Leu Leu Ile Gly
 50                  55                  60

Phe Met Tyr Ser Val Ile Val Met Lys Ile Ala Leu Thr Thr Gly Leu
 65                  70                  75                  80

Val Pro Thr Leu Asn Val Ser Ala Ala Leu Met Ala Phe Leu Ala Leu
                 85                  90                  95

Arg Gly Trp Thr Arg Val Leu Glu Arg Leu Gly Val Ala His Arg Pro
                100                 105                 110
```

```
Phe Thr Arg Gln Glu Asn Cys Val Ile Glu Thr Cys Ala Val Ala Cys
            115                 120                 125

Tyr Thr Ile Ala Phe Gly Gly Phe Gly Ser Thr Leu Leu Gly Leu
130                 135                 140

Asp Lys Lys Thr Tyr Glu Leu Ala Gly Ala Ser Pro Ala Asn Val Pro
145                 150                 155                 160

Gly Ser Tyr Lys Asp Pro Gly Phe Gly Trp Met Ala Gly Phe Val Ala
                165                 170                 175

Ala Ile Ser Phe Ala Gly Leu Leu Ser Leu Ile Pro Leu Arg Lys Val
                180                 185                 190

Leu Val Ile Asp Tyr Lys Leu Thr Tyr Pro Ser Gly Thr Ala Thr Ala
                195                 200                 205

Val Leu Ile Asn Gly Phe His Thr Lys Gln Gly Asp Lys Asn Ala Arg
            210                 215                 220

Met Gln Val Arg Gly Phe Leu Lys Tyr Phe Gly Leu Ser Phe Val Trp
225                 230                 235                 240

Ser Phe Phe Gln Trp Phe Tyr Thr Gly Gly Glu Val Cys Gly Phe Val
                245                 250                 255

Gln Phe Pro Thr Phe Gly Leu Lys Ala Trp Lys Gln Thr Phe Phe Phe
                260                 265                 270

Asp Phe Ser Leu Thr Tyr Val Gly Ala Gly Met Ile Cys Ser His Leu
                275                 280                 285

Val Asn Ile Ser Thr Leu Leu Gly Ala Ile Leu Ser Trp Gly Ile Leu
            290                 295                 300

Trp Pro Leu Ile Ser Lys Gln Lys Gly Glu Trp Tyr Pro Ala Asn Ile
305                 310                 315                 320

Pro Glu Ser Ser Met Lys Ser Leu Tyr Gly Tyr Lys Ala Phe Leu Cys
                325                 330                 335

Ile Ala Leu Ile Met Gly Asp Gly Thr Tyr His Phe Phe Lys Val Phe
                340                 345                 350

Gly Val Thr Val Lys Ser Leu His Gln Arg Leu Ser Arg Lys Arg Ala
                355                 360                 365

Thr Asn Arg Val Ala Asn Gly Gly Asp Glu Met Ala Ala Leu Asp Asp
            370                 375                 380

Leu Gln Arg Asp Glu Ile Phe Ser Asp Gly Ser Phe Pro Ala Trp Ala
385                 390                 395                 400

Ala Tyr Ala Gly Tyr Ala Ala Leu Thr Val Val Ser Ala Val Ile Ile
                405                 410                 415

Pro His Met Phe Arg Gln Val Lys Trp Tyr Tyr Val Ile Val Ala Tyr
                420                 425                 430

Val Leu Ala Pro Leu Leu Gly Phe Ala Asn Ser Tyr Gly Thr Gly Leu
            435                 440                 445

Thr Asp Ile Asn Met Ala Tyr Asn Tyr Gly Lys Ile Ala Leu Phe Ile
450                 455                 460

Phe Ala Ala Trp Ala Gly Arg Asp Asn Gly Val Ile Ala Gly Leu Ala
465                 470                 475                 480

Gly Gly Thr Leu Val Lys Gln Leu Val Met Ala Ser Ala Asp Leu Met
                485                 490                 495

His Asp Phe Lys Thr Gly His Leu Thr Met Thr Ser Pro Arg Ser Leu
                500                 505                 510

Leu Val Ala Gln Phe Ile Gly Thr Ala Met Gly Cys Val Val Ala Pro
            515                 520                 525
```

```
Leu Thr Phe Leu Leu Phe Tyr Asn Ala Phe Asp Ile Gly Asn Pro Thr
    530                 535                 540

Gly Tyr Trp Lys Ala Pro Tyr Gly Leu Ile Tyr Arg Asn Met Ala Ile
545                 550                 555                 560

Leu Gly Val Glu Gly Phe Ser Val Leu Pro Arg His Cys Leu Ala Leu
                565                 570                 575

Ser Ala Gly Phe Phe Ala Phe Ala Phe Val Phe Ser Val Ala Arg Asp
            580                 585                 590

Val Leu Pro Arg Lys Tyr Ala Arg Phe Val Pro Leu Pro Met Ala Met
        595                 600                 605

Ala Val Pro Phe Leu Val Gly Gly Ser Phe Ala Ile Asp Met Cys Val
610                 615                 620

Gly Ser Leu Ala Val Phe Val Trp Glu Lys Val Asn Arg Lys Glu Ala
625                 630                 635                 640

Val Phe Met Val Pro Ala Val Ala Ser Gly Leu Ile Cys Gly Asp Gly
                645                 650                 655

Ile Trp Thr Phe Pro Ser Ser Ile Leu Ala Leu Ala Lys Ile Lys Pro
            660                 665                 670

Pro Ile Cys Met Lys Phe Thr Pro Gly Ser
        675                 680

<210> SEQ ID NO 41
<211> LENGTH: 453
<212> TYPE: PRT
<213> ORGANISM: Arabidopsis thaliana

<400> SEQUENCE: 41

Met Ala Lys Val Tyr Trp Pro Tyr Phe Asp Pro Glu Tyr Glu Asn Leu
1               5                   10                  15

Ser Ser Arg Ile Asn Pro Pro Ser Val Ser Ile Asp Asn Thr Ser Cys
            20                  25                  30

Lys Glu Cys Thr Leu Val Lys Val Asp Ser Met Asn Lys Pro Gly Ile
        35                  40                  45

Leu Leu Glu Val Val Gln Val Leu Thr Asp Leu Asp Leu Thr Ile Thr
    50                  55                  60

Lys Ala Tyr Ile Ser Ser Asp Gly Gly Trp Phe Met Asp Val Phe His
65                  70                  75                  80

Val Thr Asp Gln Gln Gly Asn Lys Val Thr Asp Ser Lys Thr Ile Asp
                85                  90                  95

Tyr Ile Glu Lys Val Leu Gly Pro Lys Gly His Ala Ser Ala Ser Gln
            100                 105                 110

Asn Thr Trp Pro Gly Lys Arg Val Gly Val His Ser Leu Gly Asp His
        115                 120                 125

Thr Ser Ile Glu Ile Ile Ala Arg Asp Arg Pro Gly Leu Leu Ser Glu
    130                 135                 140

Val Ser Ala Val Leu Ala Asp Leu Asn Ile Asn Val Val Ala Ala Glu
145                 150                 155                 160

Ala Trp Thr His Asn Arg Arg Ile Ala Cys Val Leu Tyr Val Asn Asp
                165                 170                 175

Asn Ala Thr Ser Arg Ala Val Asp Asp Pro Glu Arg Leu Ser Ser Met
            180                 185                 190

Glu Glu Gln Leu Asn Asn Val Leu Arg Gly Cys Glu Glu Gln Asp Glu
        195                 200                 205

Lys Phe Ala Arg Thr Ser Leu Ser Ile Gly Ser Thr His Val Asp Arg
    210                 215                 220
```

Arg Leu His Gln Met Phe Phe Ala Asp Arg Asp Tyr Glu Ala Val Thr
225                 230                 235                 240

Lys Leu Asp Asp Ser Ala Ser Cys Gly Phe Glu Pro Lys Ile Thr Val
            245                 250                 255

Glu His Cys Glu Glu Lys Gly Tyr Ser Val Ile Asn Val Ser Cys Glu
        260                 265                 270

Asp Arg Pro Lys Leu Met Phe Asp Ile Val Cys Thr Leu Thr Asp Met
    275                 280                 285

Gln Tyr Ile Val Phe His Ala Thr Ile Ser Ser Gly Ser His Ala
290                 295                 300

Ser Gln Glu Tyr Phe Ile Arg His Lys Asp Gly Cys Thr Leu Asp Thr
305                 310                 315                 320

Glu Gly Glu Lys Glu Arg Val Val Lys Cys Leu Glu Ala Ala Ile His
                325                 330                 335

Arg Arg Val Ser Glu Gly Trp Ser Leu Glu Leu Cys Ala Lys Asp Arg
            340                 345                 350

Val Gly Leu Leu Ser Glu Val Thr Arg Ile Leu Arg Glu His Gly Leu
        355                 360                 365

Ser Val Ser Arg Ala Gly Val Thr Thr Val Gly Glu Gln Ala Val Asn
370                 375                 380

Val Phe Tyr Val Lys Asp Ala Ser Gly Asn Pro Val Asp Val Lys Thr
385                 390                 395                 400

Ile Glu Ala Leu Arg Gly Glu Ile Gly His Ser Met Met Ile Asp Phe
                405                 410                 415

Lys Asn Lys Val Pro Ser Arg Lys Trp Lys Glu Gly Gln Ala Gly
            420                 425                 430

Thr Gly Gly Gly Trp Ala Lys Thr Ser Phe Phe Gly Asn Leu Leu
        435                 440                 445

Glu Lys Leu Leu Pro
    450

<210> SEQ ID NO 42
<211> LENGTH: 334
<212> TYPE: PRT
<213> ORGANISM: Escherichia coli

<400> SEQUENCE: 42

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Met Asn Pro
65                  70                  75                  80

Leu Ile Ile Lys Leu Gly Gly Val Leu Leu Asp Ser Glu Glu Ala Leu
                85                  90                  95

Glu Arg Leu Phe Ser Ala Leu Val Asn Tyr Arg Glu Ser His Gln Arg
            100                 105                 110

Pro Leu Val Ile Val His Gly Gly Cys Val Val Asp Glu Leu Met
        115                 120                 125

Lys Gly Leu Asn Leu Pro Val Lys Lys Lys Asn Gly Leu Arg Val Thr

```
                130                 135                 140
Pro Ala Asp Gln Ile Asp Ile Thr Gly Ala Leu Ala Gly Thr Ala
145                 150                 155                 160

Asn Lys Thr Leu Leu Ala Trp Ala Lys Lys His Gln Ile Ala Val
                165                 170                 175

Gly Leu Phe Leu Gly Asp Gly Asp Ser Val Lys Val Thr Gln Leu Asp
                180                 185                 190

Glu Glu Leu Gly His Val Gly Leu Ala Gln Pro Gly Ser Pro Lys Leu
                195                 200                 205

Ile Asn Ser Leu Leu Glu Asn Gly Tyr Leu Pro Val Val Ser Ser Ile
                210                 215                 220

Gly Val Thr Asp Glu Gly Gln Leu Met Asn Val Asn Ala Asp Gln Ala
225                 230                 235                 240

Ala Thr Ala Leu Ala Ala Thr Leu Gly Ala Asp Leu Ile Leu Leu Ser
                245                 250                 255

Asp Val Ser Gly Ile Leu Asp Gly Lys Gly Gln Arg Ile Ala Glu Met
                260                 265                 270

Thr Ala Ala Lys Ala Glu Gln Leu Ile Glu Gln Gly Ile Ile Thr Asp
                275                 280                 285

Gly Met Ile Val Lys Val Asn Ala Ala Leu Asp Ala Ala Arg Thr Leu
290                 295                 300

Gly Arg Pro Val Asp Ile Ala Ser Trp Arg His Ala Glu Gln Leu Pro
305                 310                 315                 320

Ala Leu Phe Asn Gly Met Pro Met Gly Thr Arg Ile Leu Ala
                325                 330

<210> SEQ ID NO 43
<211> LENGTH: 557
<212> TYPE: PRT
<213> ORGANISM: Glycine max

<400> SEQUENCE: 43

Met Ala Leu Lys Thr Leu Ser Thr Phe Leu Ser Pro Leu Ser Leu Pro
1               5                   10                  15

Asn Thr Lys Phe Pro Gln Phe Leu Thr Thr Lys Pro Ser Leu Ile Leu
                20                  25                  30

Cys Glu Phe Pro Arg Ser Gln Lys Ser Arg Leu Leu Ala Ala Asp Ser
                35                  40                  45

Glu Gly Thr Gly Ala Ala Ala Pro Ser Pro Gly Glu Lys Phe Leu Glu
            50                  55                  60

Arg Gln Gln Ser Phe Glu Asp Ala Lys Ile Ile Leu Lys Glu Asn Lys
65              70                  75                  80

Lys Lys Arg Lys Lys Lys Asp Asn Ala Ile Lys Ala Ser Arg Ala Val
                85                  90                  95

Ala Ser Cys Tyr Gly Cys Gly Ala Pro Leu His Thr Ser Asp Ala Asp
                100                 105                 110

Ala Pro Gly Tyr Val Asp Pro Glu Thr Tyr Glu Leu Lys Lys Lys His
                115                 120                 125

His Gln Leu Arg Thr Val Leu Cys Arg Arg Cys Arg Leu Leu Ser His
                130                 135                 140

Gly Lys Met Ile Thr Ala Val Gly Gly His Gly Tyr Pro Gly Gly
145                 150                 155                 160

Lys Leu Phe Val Thr Ala Glu Glu Leu Arg Glu Lys Leu Ser His Leu
                165                 170                 175
```

```
Arg His Glu Lys Ala Leu Ile Val Lys Leu Val Asp Ile Val Asp Phe
                180                 185                 190

Asn Gly Ser Phe Leu Ser Arg Val Arg Asp Leu Ala Gly Ser Asn Pro
            195                 200                 205

Ile Ile Leu Val Val Thr Lys Val Asp Leu Leu Pro Arg Asp Thr Asp
210                 215                 220

Leu His Cys Val Gly Asp Trp Val Val Glu Ala Thr Met Arg Lys Lys
225                 230                 235                 240

Leu Asn Val Leu Ser Val His Leu Thr Ser Ser Lys Ser Leu Val Gly
                245                 250                 255

Ile Thr Gly Val Ile Ser Glu Ile Gln Lys Glu Lys Lys Gly Arg Asp
            260                 265                 270

Val Tyr Ile Leu Gly Ser Ala Asn Val Gly Lys Ser Ala Phe Ile Asn
        275                 280                 285

Ala Leu Leu Lys Thr Met Ala Ile Asn Asp Pro Val Ala Ala Ser Ala
        290                 295                 300

Gln Arg Tyr Lys Pro Ile Gln Ser Ala Val Pro Gly Thr Thr Leu Gly
305                 310                 315                 320

Pro Ile Gln Ile Asn Ala Phe Leu Gly Gly Gly Lys Leu Tyr Asp Thr
                325                 330                 335

Pro Gly Val His Leu Tyr His Arg Gln Thr Ala Val Val His Ser Glu
            340                 345                 350

Asp Leu Pro Ile Leu Ala Pro Gln Ser Arg Leu Arg Gly Leu Ser Phe
        355                 360                 365

Pro Ser Ser Ile Leu Ser Ser Val Glu Glu Gly Ala Ser Thr Ile Val
370                 375                 380

Asn Gly Leu Asn Ala Phe Ser Ile Phe Trp Gly Gly Leu Val Arg Ile
385                 390                 395                 400

Asp Val Leu Lys Val Leu Pro Glu Thr Cys Leu Thr Phe Tyr Gly Pro
                405                 410                 415

Lys Arg Ile Pro Ile His Met Val Pro Thr Glu Gln Ala Val Glu Phe
            420                 425                 430

Tyr Gln Thr Glu Leu Gly Val Leu Leu Thr Pro Pro Ser Gly Gly Glu
        435                 440                 445

Asn Ala Glu Asn Trp Lys Gly Leu Glu Ser Glu Arg Lys Leu Gln Ile
        450                 455                 460

Lys Phe Glu Asp Val Asp Ser Tyr Asp Pro Lys Pro Ala Cys Asp Ile
465                 470                 475                 480

Ala Ile Ser Gly Leu Gly Trp Phe Thr Val Glu Pro Val Ser Arg Ser
                485                 490                 495

Leu Lys Ile Ser Gln Pro Lys Pro Val Glu Thr Ala Gly Glu Leu Ile
            500                 505                 510

Leu Ala Val His Val Pro Lys Ala Val Glu Ile Phe Val Arg Ser Pro
        515                 520                 525

Ile Pro Val Gly Lys Ala Gly Ala Glu Trp Tyr Gln Tyr Val Glu Leu
        530                 535                 540

Thr Glu Lys Gln Glu Glu Met Arg Pro Lys Trp Tyr Phe
545                 550                 555

<210> SEQ ID NO 44
<211> LENGTH: 426
<212> TYPE: PRT
<213> ORGANISM: Zea mays

<400> SEQUENCE: 44
```

```
Met Ala Ala Ala Leu Ala Ser Ser Arg Tyr Cys Trp Ser Arg Pro Ser
1               5                   10                  15

Leu Pro Pro Gln Pro Thr Arg Gly Arg Arg Ser Val Thr Ser Cys Ala
            20                  25                  30

Leu Ser Gly Arg Glu Lys Arg Asn Ser Phe Ser Trp Arg Glu Cys Ala
        35                  40                  45

Ile Ser Val Ala Leu Ser Val Gly Leu Ile Thr Gly Ala Pro Thr Phe
    50                  55                  60

Gly Pro Pro Ala Tyr Ala Ser Ser Leu Glu Pro Val Leu Pro Asp Val
65              70                  75                  80

Ser Val Leu Ile Ser Gly Pro Pro Ile Lys Asp Pro Gly Ala Leu Leu
                85                  90                  95

Arg Tyr Ala Leu Pro Ile Asp Asn Lys Ala Ile Arg Glu Val Gln Lys
                100                 105                 110

Pro Leu Glu Asp Ile Thr Asp Ser Leu Lys Val Ala Gly Val Arg Ala
            115                 120                 125

Leu Asp Ser Val Glu Arg Asn Val Arg Gln Ala Ser Lys Ala Leu Asn
    130                 135                 140

Asn Gly Arg Ser Leu Ile Leu Ala Gly Leu Ala Glu Pro Lys Arg Ala
145                 150                 155                 160

Asn Gly Glu Glu Leu Leu Asn Lys Leu Ala Val Gly Phe Glu Leu
                165                 170                 175

Gln Arg Ile Val Glu Asp Arg Asn Arg Asp Ala Val Ala Pro Lys Gln
                180                 185                 190

Lys Glu Leu Leu Gln Tyr Val Gly Thr Val Glu Glu Asp Met Val Asp
                195                 200                 205

Gly Phe Pro Phe Glu Ile Pro Glu Glu Tyr Ser Asn Met Pro Leu Leu
                210                 215                 220

Lys Gly Arg Ala Thr Val Asp Met Lys Val Lys Ile Lys Asp Asn Pro
225                 230                 235                 240

Asn Met Glu Asp Cys Val Phe Arg Ile Val Leu Asp Gly Tyr Asn Ala
                245                 250                 255

Pro Val Thr Ala Gly Asn Phe Val Asp Leu Val Lys Arg Lys Phe Tyr
                260                 265                 270

Asp Gly Met Glu Ile Gln Arg Ala Asp Gly Phe Val Val Gln Thr Gly
                275                 280                 285

Asp Pro Glu Gly Pro Ala Glu Gly Phe Ile Asp Pro Ser Thr Gly Lys
                290                 295                 300

Ile Arg Thr Val Pro Leu Glu Ile Met Val Asp Gly Asp Lys Ala Pro
305                 310                 315                 320

Val Tyr Gly Glu Thr Leu Glu Glu Leu Gly Arg Tyr Lys Ala Gln Thr
                325                 330                 335

Lys Leu Pro Phe Asn Ala Phe Gly Thr Met Ala Met Ala Arg Glu Glu
                340                 345                 350

Phe Asp Asp Asn Ser Ala Ser Ser Gln Val Phe Trp Leu Leu Lys Glu
                355                 360                 365

Ser Glu Leu Thr Pro Ser Asn Ala Asn Ile Leu Asp Gly Arg Tyr Ala
        370                 375                 380

Val Phe Gly Tyr Val Thr Glu Asn Glu Asp Tyr Leu Ala Asp Val Lys
385                 390                 395                 400

Val Gly Asp Val Ile Glu Ser Ile Gln Val Val Ser Gly Leu Asp Asn
                405                 410                 415
```

```
Leu Val Asn Pro Ser Tyr Lys Ile Val Gly
        420                 425
```

<210> SEQ ID NO 45
<211> LENGTH: 144
<212> TYPE: PRT
<213> ORGANISM: Arabidopsis thaliana

<400> SEQUENCE: 45

```
Met Met Gln Glu Leu Gly Leu Gln Arg Phe Ser Asn Asp Val Val Arg
1               5                   10                  15

Leu Asp Leu Thr Pro Pro Ser Gln Thr Ser Thr Ser Leu Ser Ile
            20                  25                  30

Asp Glu Glu Glu Ser Thr Glu Ala Lys Ile Arg Arg Leu Ile Ser Glu
        35                  40                  45

His Pro Val Ile Ile Phe Ser Arg Ser Ser Cys Cys Met Cys His Val
    50                  55                  60

Met Lys Arg Leu Leu Ala Thr Ile Gly Val Ile Pro Thr Val Ile Glu
65                  70                  75                  80

Leu Asp Asp His Glu Val Ser Ser Leu Pro Thr Ala Leu Gln Asp Glu
                85                  90                  95

Tyr Ser Gly Gly Val Ser Val Val Gly Pro Pro Ala Val Phe Ile
            100                 105                 110

Gly Arg Glu Cys Val Gly Gly Leu Glu Ser Leu Val Ala Leu His Leu
        115                 120                 125

Ser Gly Gln Leu Val Pro Lys Leu Val Gln Val Gly Ala Leu Trp Val
    130                 135                 140
```

<210> SEQ ID NO 46
<211> LENGTH: 509
<212> TYPE: PRT
<213> ORGANISM: Escherichia coli

<400> SEQUENCE: 46

```
Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Gly Lys
    50                  55                  60

Lys Lys Phe Glu Thr Leu Ser Tyr Leu Pro Asp Leu Thr Asp Ser Gly
65                  70                  75                  80

Gly Arg Val Asn Cys Met Gln Ala Met Ser Asn Asn Glu Phe His Gln
                85                  90                  95

Arg Arg Leu Ser Ala Thr Pro Arg Gly Val Gly Val Met Cys Asn Phe
            100                 105                 110

Phe Ala Gln Ser Ala Glu Asn Ala Thr Leu Lys Asp Val Glu Gly Asn
        115                 120                 125

Glu Tyr Ile Asp Phe Ala Ala Gly Ile Ala Val Leu Asn Thr Gly His
    130                 135                 140

Arg His Pro Asp Leu Val Ala Ala Val Glu Gln Gln Leu Gln Gln Phe
145                 150                 155                 160

Thr His Thr Ala Tyr Gln Ile Val Pro Tyr Glu Ser Tyr Val Thr Leu
                165                 170                 175
```

```
Ala Glu Lys Ile Asn Ala Leu Ala Pro Val Ser Gly Gln Ala Lys Thr
            180                 185                 190

Ala Phe Phe Thr Thr Gly Ala Glu Ala Val Glu Asn Ala Val Lys Ile
            195                 200                 205

Ala Arg Ala His Thr Gly Arg Pro Gly Val Ile Ala Phe Ser Gly Gly
            210                 215                 220

Phe His Gly Arg Thr Tyr Met Thr Met Ala Leu Thr Gly Lys Val Ala
225                 230                 235                 240

Pro Tyr Lys Ile Gly Phe Gly Pro Phe Pro Gly Ser Val Tyr His Val
            245                 250                 255

Pro Tyr Pro Ser Asp Leu His Gly Ile Ser Thr Gln Asp Ser Leu Asp
            260                 265                 270

Ala Ile Glu Arg Leu Phe Lys Ser Asp Ile Glu Ala Lys Gln Val Ala
            275                 280                 285

Ala Ile Ile Phe Glu Pro Val Gln Gly Glu Gly Gly Phe Asn Val Ala
            290                 295                 300

Pro Lys Glu Leu Val Ala Ala Ile Arg Arg Leu Cys Asp Glu His Gly
305                 310                 315                 320

Ile Val Met Ile Ala Asp Glu Val Gln Ser Gly Phe Ala Arg Thr Gly
            325                 330                 335

Lys Leu Phe Ala Met Asp His Tyr Ala Asp Lys Pro Asp Leu Met Thr
            340                 345                 350

Met Ala Lys Ser Leu Ala Gly Gly Met Pro Leu Ser Gly Val Val Gly
            355                 360                 365

Asn Ala Asn Ile Met Asp Ala Pro Ala Pro Gly Gly Leu Gly Gly Thr
            370                 375                 380

Tyr Ala Gly Asn Pro Leu Ala Val Ala Ala His Ala Val Leu Asn
385                 390                 395                 400

Ile Ile Asp Lys Glu Ser Leu Cys Glu Arg Ala Asn Gln Leu Gly Gln
            405                 410                 415

Arg Leu Lys Asn Thr Leu Ile Asp Ala Lys Glu Ser Val Pro Ala Ile
            420                 425                 430

Ala Ala Val Arg Gly Leu Gly Ser Met Ile Ala Val Glu Phe Asn Asp
            435                 440                 445

Pro Gln Thr Gly Glu Pro Ser Ala Ile Ala Gln Lys Ile Gln Gln
            450                 455                 460

Arg Ala Leu Ala Gln Gly Leu Leu Leu Leu Thr Cys Gly Ala Tyr Gly
465                 470                 475                 480

Asn Val Ile Arg Phe Leu Tyr Pro Leu Thr Ile Pro Asp Ala Gln Phe
            485                 490                 495

Asp Ala Ala Met Lys Ile Leu Gln Asp Ala Leu Ser Asp
            500                 505

<210> SEQ ID NO 47
<211> LENGTH: 490
<212> TYPE: PRT
<213> ORGANISM: Synechocystis sp.

<400> SEQUENCE: 47

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
            35                  40                  45
```

-continued

```
Asn Gly Gly Arg Val Asn Cys Met Gln Val Trp Pro Pro Ile Gly Lys
 50                  55                  60
Lys Lys Phe Glu Thr Leu Ser Tyr Leu Pro Asp Leu Thr Asp Ser Gly
 65                  70                  75                  80
Gly Arg Val Asn Cys Met Gln Ala Met Thr Pro Glu Leu Asn Pro Asn
                     85                  90                  95
Phe Pro Glu Glu Thr Thr Ser Asp Ala Trp Leu Thr Pro Ala Asp Ala
                    100                 105                 110
Gly Gln Asp Gly Asp Ala Gln Glu Pro Ala Glu Asp Gly Gly Glu Glu
                115                 120                 125
Gly Val Val Ser Glu Glu Leu Ala Leu Pro Glu Asp Leu Pro Pro Met
130                 135                 140
Asp Ala Met Val Ala Ala Val Glu Glu Met Thr Pro Val Val Val Pro
145                 150                 155                 160
Glu Thr Val Pro Glu Thr Glu Thr Pro Ala Leu Glu Asp Leu Val Ala
                165                 170                 175
Gln Lys Thr Ala Leu Glu Lys Asp Ile Ala Ala Leu Gln Arg Glu Lys
                180                 185                 190
Ala Gln Trp Tyr Gly Gln Gln Phe Gln Gln Leu Gln Arg Glu Met Ala
                195                 200                 205
Arg Leu Val Glu Glu Gly Thr Arg Glu Leu Gly Gln Arg Lys Ala Ala
210                 215                 220
Leu Glu Lys Glu Ile Glu Lys Leu Glu Arg Arg Gln Glu Arg Ile Gln
225                 230                 235                 240
Gln Glu Met Arg Thr Thr Phe Ala Gly Ala Ser Gln Glu Leu Ala Ile
                245                 250                 255
Arg Val Gln Gly Phe Lys Asp Tyr Leu Val Gly Ser Leu Gln Asp Leu
                260                 265                 270
Val Ser Ala Ala Asp Gln Leu Glu Leu Gly Val Gly Asp Ser Trp Glu
                275                 280                 285
Ser Ser Ser Thr His Gly Asp Ala Ile Ile Glu Asn Ala Asp Pro Thr
                290                 295                 300
Pro Val Val Ser Phe Ala Glu Gln Gly Phe Ser Ser Gln Lys Arg Gln
305                 310                 315                 320
Ile Gln Ala Leu Leu Glu Gln Tyr Arg Thr Arg Pro Asp Tyr Tyr Gly
                325                 330                 335
Pro Pro Trp Gln Leu Arg Arg Thr Phe Glu Pro Val His Ala Glu Arg
                340                 345                 350
Ile Glu Asn Trp Phe Phe Thr Leu Gly Gly Arg Gly Ala Ile Leu Ser
                355                 360                 365
Leu Asp Ser Arg Leu Gln Asn Ile Leu Val Gly Ser Ala Ala Ile Ala
                370                 375                 380
Ile Leu Asn Gln Leu Tyr Gly Asp Arg Cys Arg Ala Leu Ile Leu Ala
385                 390                 395                 400
Ala Thr Pro Glu Arg Leu Gly Glu Trp Arg Arg Gly Leu Gln Asp Cys
                405                 410                 415
Leu Gly Ile Ser Arg Ser Asp Phe Gly Pro Asp Arg Gly Ile Val Leu
                420                 425                 430
Phe Glu Ser Ala Asn Ala Leu Ile Gln Arg Ala Glu Arg Leu Val Gly
                435                 440                 445
Asp Arg Gln Met Pro Leu Val Leu Val Asp Glu Thr Glu Glu Gln Ile
450                 455                 460
```

```
Asp Leu Ala Leu Leu Gln Phe Pro Leu Leu Ala Phe Ala Pro Ser
465                 470                 475                 480

Tyr Gln Val Gly Gly Ser Asn Tyr Phe Ser
                485                 490

<210> SEQ ID NO 48
<211> LENGTH: 404
<212> TYPE: PRT
<213> ORGANISM: Zea mays

<400> SEQUENCE: 48

Met Ala Gly Glu Leu Arg His Arg Arg Ala Pro Ser Glu Asp Glu Gly
1               5                   10                  15

Val Ala Ser Ser Gln Arg Leu Asp Ser Ala Pro Ala Gly Asn Gly Lys
            20                  25                  30

Ala Gly Thr Ser Ser Gly Gly Glu Gly Ala Glu Pro Arg Gly Gly
        35                  40                  45

Lys Arg Asp Ala Leu Gly Trp Leu Glu Trp Cys Arg Gly Trp Met Ala
50                  55                  60

Ile Val Gly Glu Phe Leu Phe Gln Arg Ile Ala Ala Ser His Leu Ala
65                  70                  75                  80

Asn Pro Leu Glu Leu Pro Pro Leu Asp Gly Val Ser Ile Val Val Thr
                85                  90                  95

Gly Ala Thr Ser Gly Ile Gly Leu Glu Ile Ala Arg Gln Leu Ala Leu
            100                 105                 110

Ala Gly Ala His Val Val Met Ala Val Arg Arg Pro Lys Val Ala Gln
        115                 120                 125

Glu Leu Ile Gln Lys Trp Gln Asn Glu Asn Ser Glu Thr Gly Arg Pro
130                 135                 140

Leu Asn Ala Glu Val Met Glu Leu Asp Leu Leu Ser Leu Asp Ser Val
145                 150                 155                 160

Val Lys Phe Ala Asp Ala Trp Asn Ala Arg Met Ala Pro Leu His Val
                165                 170                 175

Leu Ile Asn Asn Ala Gly Ile Phe Ala Ile Gly Glu Pro Gln His Phe
            180                 185                 190

Ser Lys Asp Gly His Glu Glu His Met Gln Val Asn His Leu Ala Pro
        195                 200                 205

Ala Leu Leu Ala Met Leu Leu Ile Pro Ser Leu Leu Arg Gly Ser Pro
210                 215                 220

Ser Arg Ile Val Asn Val Asn Ser Ile Met His Ser Val Gly Phe Val
225                 230                 235                 240

Asp Ala Glu Asp Phe Asn Leu Arg Lys His Lys Tyr Arg Ser Trp Leu
                245                 250                 255

Ala Tyr Ser Asn Ser Lys Leu Ala Gln Val Lys Phe Ser Ser Met Leu
            260                 265                 270

His Lys Arg Ile Pro Ala Glu Ala Gly Ile Ser Ile Ile Cys Ala Ser
        275                 280                 285

Pro Gly Ile Val Asp Thr Asn Val Thr Arg Asp Leu Pro Lys Ile Val
290                 295                 300

Val Ala Ala Tyr Arg Phe Leu Pro Tyr Phe Ile Phe Asp Gly Gln Glu
305                 310                 315                 320

Gly Ser Arg Ser Ala Leu Phe Ala Ala Cys Asp Pro Gln Val Pro Glu
                325                 330                 335

Tyr Cys Glu Met Leu Lys Ser Glu Asp Trp Pro Val Cys Ala Cys Ile
            340                 345                 350
```

Asn Tyr Asp Cys Asn Pro Met Asn Ala Ser Glu Glu Ala His Ser Leu
            355                 360                 365

Glu Thr Ser Gln Leu Val Trp Glu Lys Thr Leu Glu Met Ile Gly Leu
    370                 375                 380

Pro Pro Asp Ala Leu Asp Lys Leu Ile Ala Gly Glu Thr Val Pro Cys
385                 390                 395                 400

Arg Tyr Gly Gln

<210> SEQ ID NO 49
<211> LENGTH: 942
<212> TYPE: PRT
<213> ORGANISM: Zea mays

<400> SEQUENCE: 49

Met Glu Gly Asp Asp Phe Thr Pro Glu Gly Gly Lys Leu Pro Glu Phe
1               5                   10                  15

Lys Leu Asp Ala Arg Gln Ala Gln Gly Phe Ile Ser Phe Phe Lys Lys
            20                  25                  30

Leu Pro Gln Asp Pro Arg Ala Val Arg Leu Phe Asp Arg Arg Asp Tyr
        35                  40                  45

Tyr Thr Ala His Gly Glu Asn Ala Thr Phe Ile Ala Arg Thr Tyr Tyr
    50                  55                  60

His Thr Met Ser Ala Leu Arg Gln Leu Gly Ser Thr Ser Asp Gly Ile
65                  70                  75                  80

Leu Ser Ala Ser Val Ser Lys Ala Met Phe Glu Thr Ile Ala Arg Asn
                85                  90                  95

Ile Leu Leu Glu Arg Thr Asp Cys Thr Leu Glu Leu Tyr Glu Gly Ser
            100                 105                 110

Gly Ser Asn Trp Arg Leu Thr Lys Ser Gly Thr Pro Gly Asn Ile Gly
        115                 120                 125

Ser Phe Glu Asp Ile Leu Phe Ala Asn Asn Asp Met Glu Asp Ser Pro
    130                 135                 140

Val Ile Val Ala Leu Phe Pro Ala Cys Arg Glu Ser Gln Leu Tyr Val
145                 150                 155                 160

Gly Leu Ser Phe Leu Asp Met Thr Asn Arg Lys Leu Gly Leu Ala Glu
                165                 170                 175

Phe Pro Glu Asp Ser Arg Phe Thr Asn Val Glu Ser Ala Leu Val Ala
            180                 185                 190

Leu Gly Cys Lys Glu Cys Leu Leu Pro Ala Asp Cys Glu Lys Ser Ile
        195                 200                 205

Asp Leu Asn Pro Leu Gln Asp Val Ile Ser Asn Cys Asn Val Leu Leu
    210                 215                 220

Thr Glu Lys Lys Lys Ala Asp Phe Lys Ser Arg Asp Leu Ala Gln Asp
225                 230                 235                 240

Leu Gly Arg Ile Ile Arg Gly Ser Val Glu Pro Val Arg Asp Leu Leu
                245                 250                 255

Ser Gln Phe Asp Tyr Ala Leu Gly Pro Leu Gly Ala Leu Leu Ser Tyr
            260                 265                 270

Ala Glu Leu Leu Ala Asp Asp Thr Asn Tyr Gly Asn Tyr Thr Ile Glu
        275                 280                 285

Lys Tyr Asn Leu Asn Cys Tyr Met Arg Leu Asp Ser Ala Ala Val Arg
    290                 295                 300

Ala Leu Asn Ile Ala Glu Gly Lys Thr Asp Val Asn Lys Asn Phe Ser
305                 310                 315                 320

```
Leu Phe Gly Leu Met Asn Arg Thr Cys Thr Val Gly Met Gly Lys Arg
                325                 330                 335

Leu Leu Asn Arg Trp Leu Lys Gln Pro Leu Leu Asp Val Asn Glu Ile
            340                 345                 350

Asn Asn Arg Leu Asp Met Val Gln Ala Phe Val Glu Asp Pro Glu Leu
            355                 360                 365

Arg Gln Gly Leu Arg Gln Gln Leu Lys Arg Ile Ser Asp Ile Asp Arg
    370                 375                 380

Leu Thr His Ser Leu Arg Lys Lys Ser Ala Asn Leu Gln Pro Val Val
385                 390                 395                 400

Lys Leu Tyr Gln Ser Cys Ser Arg Ile Pro Tyr Ile Lys Gly Ile Leu
                405                 410                 415

Gln Gln Tyr Asn Gly Gln Phe Ser Thr Leu Ile Arg Ser Lys Phe Leu
            420                 425                 430

Glu Pro Leu Glu Glu Trp Met Ala Lys Asn Arg Phe Gly Arg Phe Ser
            435                 440                 445

Ser Leu Val Glu Thr Ala Ile Asp Leu Ala Gln Leu Glu Asn Gly Glu
    450                 455                 460

Tyr Arg Ile Ser Pro Leu Tyr Ser Ser Asp Leu Gly Val Leu Lys Asp
465                 470                 475                 480

Glu Leu Ser Val Val Glu Asn His Ile Asn Asn Leu His Val Asp Thr
                485                 490                 495

Ala Ser Asp Leu Asp Leu Ser Val Asp Lys Gln Leu Lys Leu Glu Lys
            500                 505                 510

Gly Ser Leu Gly His Val Phe Arg Met Ser Lys Lys Glu Glu Gln Lys
            515                 520                 525

Val Arg Lys Lys Leu Thr Gly Ser Tyr Leu Ile Ile Glu Thr Arg Lys
    530                 535                 540

Asp Gly Val Lys Phe Thr Asn Ser Lys Leu Lys Asn Leu Ser Asp Gln
545                 550                 555                 560

Tyr Gln Ala Leu Phe Gly Glu Tyr Thr Ser Cys Gln Lys Lys Val Val
                565                 570                 575

Gly Asp Val Val Arg Val Ser Gly Thr Phe Ser Glu Val Phe Glu Asn
            580                 585                 590

Phe Ala Ala Val Leu Ser Glu Leu Asp Val Leu Gln Ser Phe Ala Asp
    595                 600                 605

Leu Ala Thr Ser Cys Pro Val Pro Tyr Val Arg Pro Asp Ile Thr Ala
610                 615                 620

Ser Asp Glu Gly Asp Ile Val Leu Leu Gly Ser Arg His Pro Cys Leu
625                 630                 635                 640

Glu Ala Gln Asp Gly Val Asn Phe Ile Pro Asn Asp Cys Thr Leu Val
                645                 650                 655

Arg Gly Lys Ser Trp Phe Gln Ile Ile Thr Gly Pro Asn Met Gly Gly
            660                 665                 670

Lys Ser Thr Phe Ile Arg Gln Val Gly Val Asn Val Leu Met Ala Gln
            675                 680                 685

Val Gly Ser Phe Val Pro Cys Asp Gln Ala Ser Ile Ser Val Arg Asp
    690                 695                 700

Cys Ile Phe Ala Arg Val Gly Ala Gly Asp Cys Gln Leu His Gly Val
705                 710                 715                 720

Ser Thr Phe Met Gln Glu Met Leu Glu Thr Ala Ser Ile Leu Lys Gly
                725                 730                 735
```

```
Ala Ser Asp Lys Ser Leu Ile Ile Ile Asp Glu Leu Gly Arg Gly Thr
            740                 745                 750

Ser Thr Tyr Asp Gly Phe Gly Leu Ala Trp Ala Ile Cys Glu His Leu
        755                 760                 765

Met Glu Val Thr Arg Ala Pro Thr Leu Phe Ala Thr His Phe His Glu
    770                 775                 780

Leu Thr Ala Leu Ala His Arg Asn Asp Glu His Gln His Ile Ser
785                 790                 795                 800

Asp Ile Gly Val Ala Asn Tyr His Val Gly Ala His Ile Asp Pro Leu
            805                 810                 815

Ser Arg Lys Leu Thr Met Leu Tyr Lys Val Glu Pro Gly Ala Cys Asp
            820                 825                 830

Gln Ser Phe Gly Ile His Val Ala Glu Phe Ala Asn Phe Pro Glu Ala
            835                 840                 845

Val Val Ala Leu Ala Lys Ser Lys Ala Ala Glu Leu Glu Asp Phe Ser
            850                 855                 860

Thr Thr Pro Thr Phe Ser Asp Asp Leu Lys Asp Glu Val Gly Ser Lys
865                 870                 875                 880

Arg Lys Arg Val Phe Ser Pro Asp Asp Ile Thr Arg Gly Ala Ala Arg
                885                 890                 895

Ala Arg Leu Phe Leu Glu Glu Phe Ala Ala Leu Pro Met Asp Glu Met
            900                 905                 910

Asp Gly Ser Lys Ile Leu Glu Met Ala Thr Lys Met Lys Ala Asp Leu
            915                 920                 925

Gln Lys Asp Ala Ala Asp Asn Pro Trp Leu Gln Phe Phe
930                 935                 940

<210> SEQ ID NO 50
<211> LENGTH: 344
<212> TYPE: PRT
<213> ORGANISM: Arabidopsis thaliana

<400> SEQUENCE: 50

Met Glu Trp Ile Arg Gly Glu Thr Ile Gly Tyr Gly Thr Phe Ser Thr
1               5                   10                  15

Val Ser Leu Ala Thr Arg Ser Asn Asn Asp Ser Gly Glu Phe Pro Pro
            20                  25                  30

Leu Met Ala Val Lys Ser Ala Asp Ser Tyr Gly Ala Ala Ser Leu Ala
        35                  40                  45

Asn Glu Lys Ser Val Leu Asp Asn Leu Gly Asp Asp Cys Asn Glu Ile
50                  55                  60

Val Arg Cys Phe Gly Glu Asp Arg Thr Val Glu Asn Gly Glu Glu Met
65                  70                  75                  80

His Asn Leu Phe Leu Glu Tyr Ala Ser Arg Gly Ser Leu Glu Ser Tyr
                85                  90                  95

Leu Lys Lys Leu Ala Gly Glu Gly Val Pro Glu Ser Thr Val Arg Arg
            100                 105                 110

His Thr Gly Ser Val Leu Arg Gly Leu Arg His Ile His Ala Asn Gly
        115                 120                 125

Phe Ala His Cys Asp Leu Lys Leu Gly Asn Ile Leu Leu Phe Gly Asp
    130                 135                 140

Gly Ala Val Lys Ile Ala Asp Phe Gly Leu Ala Lys Arg Ile Gly Asp
145                 150                 155                 160

Leu Thr Ala Leu Asn Tyr Gly Val Gln Ile Arg Gly Thr Pro Leu Tyr
                165                 170                 175
```

Met Ala Pro Glu Ser Val Asn Asp Asn Glu Tyr Gly Ser Glu Gly Asp
            180                 185                 190

Val Trp Ala Leu Gly Cys Val Val Glu Met Phe Ser Gly Lys Thr
        195                 200                 205

Ala Trp Ser Leu Lys Glu Gly Ser Asn Phe Met Ser Leu Leu Arg
    210                 215                 220

Ile Gly Val Gly Asp Glu Val Pro Met Ile Pro Glu Glu Leu Ser Glu
225                 230                 235                 240

Gln Gly Arg Asp Phe Leu Ser Lys Cys Phe Val Lys Asp Pro Lys Lys
                245                 250                 255

Arg Trp Thr Ala Glu Met Leu Leu Asn His Pro Phe Val Thr Val Asp
                260                 265                 270

Val Asp His Asp Val Leu Val Lys Glu Glu Asp Phe Val Val Asn Met
            275                 280                 285

Lys Thr Glu Asp Val Ser Thr Ser Pro Arg Cys Pro Phe Glu Phe Pro
            290                 295                 300

Asp Trp Val Ser Val Ser Ser Gly Ser Gln Thr Ile Asp Ser Pro Asp
305                 310                 315                 320

Glu Arg Val Ala Ser Leu Val Thr Asp Met Ile Pro Asp Trp Ser Val
                325                 330                 335

Thr Asn Ser Trp Val Thr Val Arg
            340

<210> SEQ ID NO 51
<211> LENGTH: 1187
<212> TYPE: PRT
<213> ORGANISM: Arabidopsis thaliana

<400> SEQUENCE: 51

Met Arg Asn His Cys Leu Glu Leu Ser Ser Asn Cys Ser Ser Ile Phe
1               5                   10                  15

Ala Ser Ser Lys Ser Asn Pro Arg Phe Ser Pro Ser Lys Leu Ser Tyr
            20                  25                  30

Ser Thr Phe Phe Ser Arg Ser Ala Ile Tyr Tyr Arg Ser Lys Pro Lys
        35                  40                  45

Gln Ala Ser Ser Ser Ser Phe Ser Thr Phe Pro Pro Cys Leu Asn
    50                  55                  60

Arg Lys Ser Ser Leu Thr His Val Leu Lys Pro Val Ser Glu Leu Ala
65                  70                  75                  80

Asp Thr Thr Thr Lys Pro Phe Ser Pro Glu Ile Val Gly Lys Arg Thr
                85                  90                  95

Asp Leu Lys Lys Ile Met Ile Leu Gly Ala Gly Pro Ile Val Ile Gly
            100                 105                 110

Gln Ala Cys Glu Phe Asp Tyr Ser Gly Thr Gln Ala Cys Lys Ala Leu
        115                 120                 125

Arg Glu Glu Gly Tyr Glu Val Ile Leu Ile Asn Ser Asn Pro Ala Thr
    130                 135                 140

Ile Met Thr Asp Pro Glu Thr Ala Asn Arg Thr Tyr Ile Ala Pro Met
145                 150                 155                 160

Thr Pro Glu Leu Val Glu Gln Val Ile Glu Lys Glu Arg Pro Asp Ala
                165                 170                 175

Leu Leu Pro Thr Met Gly Gly Gln Thr Ala Leu Asn Leu Ala Val Ala
            180                 185                 190

Leu Ala Glu Ser Gly Ala Leu Glu Lys Tyr Gly Val Glu Leu Ile Gly

```
            195                 200                 205
Ala Lys Leu Gly Ala Ile Lys Lys Ala Glu Asp Arg Glu Leu Phe Lys
210                 215                 220

Asp Ala Met Lys Asn Ile Gly Leu Lys Thr Pro Pro Ser Gly Ile Gly
225                 230                 235                 240

Thr Thr Leu Asp Glu Cys Phe Asp Ile Ala Glu Lys Ile Gly Glu Phe
                245                 250                 255

Pro Leu Ile Ile Arg Pro Ala Phe Thr Leu Gly Gly Thr Gly Gly Gly
                260                 265                 270

Ile Ala Tyr Asn Lys Glu Glu Phe Glu Ser Ile Cys Lys Ser Gly Leu
                275                 280                 285

Ala Ala Ser Ala Thr Ser Gln Val Leu Val Glu Lys Ser Leu Leu Gly
290                 295                 300

Trp Lys Glu Tyr Glu Leu Glu Val Met Arg Asp Leu Ala Asp Asn Val
305                 310                 315                 320

Val Ile Ile Cys Ser Ile Glu Asn Ile Asp Pro Met Gly Val His Thr
                325                 330                 335

Gly Asp Ser Ile Thr Val Ala Pro Ala Gln Thr Leu Thr Asp Arg Glu
                340                 345                 350

Tyr Gln Arg Leu Arg Asp Tyr Ser Ile Ala Ile Ile Arg Glu Ile Gly
                355                 360                 365

Val Glu Cys Gly Gly Ser Asn Val Gln Phe Ala Val Asn Pro Val Asp
370                 375                 380

Gly Glu Val Met Ile Ile Glu Met Asn Pro Arg Val Ser Arg Ser Ser
385                 390                 395                 400

Ala Leu Ala Ser Lys Ala Thr Gly Phe Pro Ile Ala Lys Met Ala Ala
                405                 410                 415

Lys Leu Ser Val Gly Tyr Thr Leu Asp Gln Ile Pro Asn Asp Ile Thr
                420                 425                 430

Arg Lys Thr Pro Ala Ser Phe Glu Pro Ser Ile Asp Tyr Val Val Thr
                435                 440                 445

Lys Ile Pro Arg Phe Ala Phe Glu Lys Phe Pro Gly Ser Gln Pro Leu
450                 455                 460

Leu Thr Thr Gln Met Lys Ser Val Gly Glu Ser Met Ala Leu Gly Arg
465                 470                 475                 480

Thr Phe Gln Glu Ser Phe Gln Lys Ala Leu Arg Ser Leu Glu Cys Gly
                485                 490                 495

Phe Ser Gly Trp Gly Cys Ala Lys Ile Lys Glu Leu Asp Trp Asp Trp
                500                 505                 510

Asp Gln Leu Lys Tyr Ser Leu Arg Val Pro Asn Pro Asp Arg Ile His
                515                 520                 525

Ala Ile Tyr Ala Ala Met Lys Lys Gly Met Lys Ile Asp Glu Ile Tyr
530                 535                 540

Glu Leu Ser Met Val Asp Lys Trp Phe Leu Thr Gln Leu Lys Glu Leu
545                 550                 555                 560

Val Asp Val Glu Gln Tyr Leu Met Ser Gly Thr Leu Ser Glu Ile Thr
                565                 570                 575

Lys Glu Asp Leu Tyr Glu Val Lys Lys Arg Gly Phe Ser Asp Lys Gln
                580                 585                 590

Ile Ala Phe Ala Thr Lys Thr Thr Glu Glu Glu Val Arg Thr Lys Arg
                595                 600                 605

Ile Ser Leu Gly Val Val Pro Ser Tyr Lys Arg Val Asp Thr Cys Ala
                610                 615                 620
```

```
Ala Glu Phe Glu Ala His Thr Pro Tyr Met Tyr Ser Ser Tyr Asp Val
625                 630                 635                 640

Glu Cys Glu Ser Ala Pro Asn Asn Lys Lys Val Leu Ile Leu Gly
            645                 650                 655

Gly Gly Pro Asn Arg Ile Gly Gln Gly Ile Glu Phe Asp Tyr Cys Cys
                660                 665                 670

Cys His Thr Ser Phe Ala Leu Gln Asp Ala Gly Tyr Glu Thr Ile Met
            675                 680                 685

Leu Asn Ser Asn Pro Glu Thr Val Ser Thr Asp Tyr Asp Thr Ser Asp
690                 695                 700

Arg Leu Tyr Phe Glu Pro Leu Thr Ile Glu Asp Val Leu Asn Val Ile
705                 710                 715                 720

Asp Leu Glu Lys Pro Asp Gly Ile Ile Val Gln Phe Gly Gly Gln Thr
                725                 730                 735

Pro Leu Lys Leu Ala Leu Pro Ile Lys His Tyr Leu Asp Lys His Met
            740                 745                 750

Pro Met Ser Leu Ser Gly Ala Gly Pro Val Arg Ile Trp Gly Thr Ser
            755                 760                 765

Pro Asp Ser Ile Asp Ala Ala Glu Asp Arg Glu Arg Phe Asn Ala Ile
770                 775                 780

Leu Asp Glu Leu Lys Ile Glu Gln Pro Lys Gly Gly Ile Ala Lys Ser
785                 790                 795                 800

Glu Ala Asp Ala Leu Ala Ile Ala Lys Glu Val Gly Tyr Pro Val Val
                805                 810                 815

Val Arg Pro Ser Tyr Val Leu Gly Gly Arg Ala Met Glu Ile Val Tyr
            820                 825                 830

Asp Asp Ser Arg Leu Ile Thr Tyr Leu Glu Asn Ala Val Gln Val Asp
            835                 840                 845

Pro Glu Arg Pro Val Leu Val Asp Lys Tyr Leu Ser Asp Ala Ile Glu
850                 855                 860

Ile Asp Val Asp Thr Leu Thr Asp Ser Tyr Gly Asn Val Val Ile Gly
865                 870                 875                 880

Gly Ile Met Glu His Ile Glu Gln Ala Gly Val His Ser Gly Asp Ser
                885                 890                 895

Ala Cys Met Leu Pro Thr Gln Thr Ile Pro Ala Ser Cys Leu Gln Thr
            900                 905                 910

Ile Arg Thr Trp Thr Thr Lys Leu Ala Lys Lys Leu Asn Val Cys Gly
            915                 920                 925

Leu Met Asn Cys Gln Tyr Ala Ile Thr Thr Ser Gly Asp Val Phe Leu
            930                 935                 940

Leu Glu Ala Asn Pro Arg Ala Ser Arg Thr Val Pro Phe Val Ser Lys
945                 950                 955                 960

Ala Ile Gly His Pro Leu Ala Lys Tyr Ala Ala Leu Val Met Ser Gly
                965                 970                 975

Lys Ser Leu Lys Asp Leu Asn Phe Glu Lys Glu Val Ile Pro Lys His
            980                 985                 990

Val Ser Val Lys Glu Ala Val Phe Pro Phe Glu Lys Phe Gln Gly Cys
            995                 1000                1005

Asp Val Ile Leu Gly Pro Glu Met Arg Ser Thr Gly Glu Val Met
    1010                1015                1020

Ser Ile Ser Ser Glu Phe Ser Ala Phe Ala Met Ala Gln Ile
    1025                1030                1035
```

Ala Ala Gly Gln Lys Leu Pro Leu Ser Gly Thr Val Phe Leu Ser
    1040                1045                1050

Leu Asn Asp Met Thr Lys Pro His Leu Glu Lys Ile Ala Val Ser
    1055                1060                1065

Phe Leu Glu Leu Gly Phe Lys Ile Val Ala Thr Ser Gly Thr Ala
    1070                1075                1080

His Phe Leu Glu Leu Lys Gly Ile Pro Val Glu Arg Val Leu Lys
    1085                1090                1095

Leu His Glu Gly Arg Pro His Ala Ala Asp Met Val Ala Asn Gly
    1100                1105                1110

Gln Ile His Leu Met Leu Ile Thr Ser Ser Gly Asp Ala Leu Asp
    1115                1120                1125

Gln Lys Asp Gly Arg Gln Leu Arg Gln Met Ala Leu Ala Tyr Lys
    1130                1135                1140

Val Pro Val Ile Thr Thr Val Ala Gly Ala Leu Ala Thr Ala Glu
    1145                1150                1155

Gly Ile Lys Ser Leu Lys Ser Ser Ala Ile Lys Met Thr Ala Leu
    1160                1165                1170

Gln Asp Phe Phe Glu Val Lys Asn Val Ser Ser Leu Leu Val
    1175                1180                1185

<210> SEQ ID NO 52
<211> LENGTH: 274
<212> TYPE: PRT
<213> ORGANISM: Glycine max

<400> SEQUENCE: 52

Met Arg Ala Lys Leu Phe Val Phe Pro Ile Arg Gly Arg Asn Trp Cys
1               5                   10                  15

Phe Ser Arg Thr Ile Asp His Ser Leu Ser Ala Ser His Ala Ser Ser
            20                  25                  30

Gln Ser Pro Ser Thr Leu Lys Asp Leu Trp Thr Asn Ile Asn Val Gly
        35                  40                  45

Asp Lys Pro Leu Asn Thr Lys Thr Glu Leu Phe Val Asp Tyr Ile Ala
    50                  55                  60

Asn Lys Met Asn Asn Ala Trp Ile Gly Leu Glu Lys Ala Pro Glu Gly
65                  70                  75                  80

Ser Phe Lys Asn Lys Ile His Gly Leu Gly Leu Arg Leu Leu Ser Arg
                85                  90                  95

Val Lys Pro Ser Glu Ile Phe Leu Lys Ser Ile Ser Lys Glu Ile Thr
            100                 105                 110

Ser Val Glu Ile Ile Tyr Pro Ser Ser Leu Asn Ala Gln Leu Val Arg
        115                 120                 125

Arg Arg Leu Arg His Ile Ala Val Arg Gly Ala Val Ile His Arg Asn
    130                 135                 140

Tyr Leu Tyr Gly Leu Val Ser Leu Ile Pro Leu Thr Ser Ala Leu Ser
145                 150                 155                 160

Ile Leu Pro Leu Pro Asn Val Pro Phe Phe Trp Val Leu Phe Arg Thr
                165                 170                 175

Tyr Ser His Trp Arg Ala Leu Gln Gly Ser Glu Arg Leu Phe Gln Leu
            180                 185                 190

Val Ser Asp Asn Ser Lys Thr Ser Asn Thr Cys Thr Tyr Glu Lys Lys
        195                 200                 205

Thr Glu His Lys Glu Ser Lys Ser Gln Arg His Ser Ser Asn Glu Pro
    210                 215                 220

```
Cys Trp Val Leu Arg Pro Ser Lys Glu Leu Glu Asn Leu Val His Leu
225                 230                 235                 240

Glu Asp Gly Gln Glu Ser Leu Ser Gln His Ala Ile Ile Asn Ile Cys
            245                 250                 255

Lys Ile Tyr Asp Leu Asn Pro Val Asp Val Ile Lys Tyr Glu Lys Ser
            260                 265                 270

Val Phe

<210> SEQ ID NO 53
<211> LENGTH: 206
<212> TYPE: PRT
<213> ORGANISM: Arabidopsis thaliana

<400> SEQUENCE: 53

Met Ala Lys Glu Ser Thr Thr Ile Asp Val Gly Glu Pro Ser Thr Val
1               5                   10                  15

Thr Lys Ser Ser Ser His Val Val Lys Asp Ala Lys Lys Gly Phe
            20                  25                  30

Val Ala Val Ala Ser Arg Gly Gly Ala Lys Arg Gly Leu Ala Ile Phe
        35                  40                  45

Asp Phe Leu Leu Arg Leu Ala Ala Ile Ala Val Thr Ile Gly Ala Ala
    50                  55                  60

Ser Val Met Tyr Thr Ala Glu Glu Thr Leu Pro Phe Phe Thr Gln Phe
65                  70                  75                  80

Leu Gln Phe Gln Ala Gly Tyr Asp Asp Leu Pro Ala Phe Gln Tyr Phe
                85                  90                  95

Val Ile Ala Val Ala Val Ala Ser Tyr Leu Val Leu Ser Leu Pro
            100                 105                 110

Phe Ser Ile Val Ser Ile Val Arg Pro His Ala Val Ala Pro Arg Leu
        115                 120                 125

Ile Leu Leu Ile Cys Asp Thr Leu Val Val Thr Leu Asn Thr Ser Ala
    130                 135                 140

Ala Ala Ala Ala Ala Ser Ile Thr Tyr Leu Ala His Asn Gly Asn Gln
145                 150                 155                 160

Ser Thr Asn Trp Leu Pro Ile Cys Gln Gln Phe Gly Asp Phe Cys Gln
                165                 170                 175

Asn Val Ser Thr Ala Val Val Ala Asp Ser Ile Ala Ile Leu Phe Phe
            180                 185                 190

Ile Val Leu Ile Ile Ile Ser Ala Ile Ala Leu Lys Arg His
        195                 200                 205

<210> SEQ ID NO 54
<211> LENGTH: 411
<212> TYPE: PRT
<213> ORGANISM: Escherichia coli

<400> SEQUENCE: 54

Met Ala Thr Ala Thr Ser Ala Ser Leu Phe Ser Thr Val Ser Ser Ser
1               5                   10                  15

Tyr Ser Lys Ala Ser Ser Ile Pro His Ser Arg Leu Gln Ser Val Lys
            20                  25                  30

Phe Asn Ser Val Pro Ser Phe Thr Gly Leu Lys Ser Thr Ser Leu Ile
        35                  40                  45

Ser Gly Ser Asp Ser Ser Ser Leu Ala Lys Thr Leu Arg Gly Ser Val
    50                  55                  60
```

```
Thr Lys Ala Gln Thr Ser Asp Lys Lys Pro Tyr Gly Phe Lys Ile Asn
 65                  70                  75                  80

Ala Met Lys Thr Ala Tyr Ile Ala Lys Gln Arg Gln Ile Ser Phe Val
                 85                  90                  95

Lys Ser His Phe Ser Arg Gln Leu Glu Glu Arg Leu Gly Leu Ile Glu
            100                 105                 110

Val Gln Ala Pro Ile Leu Ser Arg Val Gly Asp Gly Thr Gln Asp Asn
        115                 120                 125

Leu Ser Gly Cys Glu Lys Ala Val Gln Val Lys Val Lys Ala Leu Pro
130                 135                 140

Asp Ala Gln Phe Glu Val Val His Ser Leu Ala Lys Trp Lys Arg Gln
145                 150                 155                 160

Thr Leu Gly Gln His Asp Phe Ser Ala Gly Glu Gly Leu Tyr Thr His
                165                 170                 175

Met Lys Ala Leu Arg Pro Asp Glu Asp Arg Leu Ser Pro Leu His Ser
            180                 185                 190

Val Tyr Val Asp Gln Trp Asp Trp Glu Arg Val Met Gly Asp Gly Glu
        195                 200                 205

Arg Gln Phe Ser Thr Leu Lys Ser Thr Val Glu Ala Ile Trp Ala Gly
210                 215                 220

Ile Lys Ala Thr Glu Ala Ala Val Ser Glu Glu Phe Gly Leu Ala Pro
225                 230                 235                 240

Phe Leu Pro Asp Gln Ile His Phe Val His Ser Gln Glu Leu Leu Ser
                245                 250                 255

Arg Tyr Pro Asp Leu Asp Ala Lys Gly Arg Glu Arg Ala Ile Ala Lys
            260                 265                 270

Asp Leu Gly Ala Val Phe Leu Val Gly Ile Gly Gly Lys Leu Ser Asp
        275                 280                 285

Gly His Arg His Asp Val Arg Ala Pro Asp Tyr Asp Asp Trp Ser Thr
290                 295                 300

Pro Ser Glu Leu Gly His Ala Gly Leu Asn Gly Asp Ile Leu Val Trp
305                 310                 315                 320

Asn Pro Val Leu Glu Asp Ala Phe Glu Leu Ser Ser Met Gly Ile Arg
                325                 330                 335

Val Asp Ala Asp Thr Leu Lys His Gln Leu Ala Leu Thr Gly Asp Glu
            340                 345                 350

Asp Arg Leu Glu Leu Glu Trp His Gln Ala Leu Leu Arg Gly Glu Met
        355                 360                 365

Pro Gln Thr Ile Gly Gly Gly Ile Gly Gln Ser Arg Leu Thr Met Leu
370                 375                 380

Leu Leu Gln Leu Pro His Ile Gly Gln Val Gln Cys Gly Val Trp Pro
385                 390                 395                 400

Ala Ala Val Arg Glu Ser Val Pro Ser Leu Leu
                405                 410

<210> SEQ ID NO 55
<211> LENGTH: 1173
<212> TYPE: DNA
<213> ORGANISM: Zea mays

<400> SEQUENCE: 55
atgcagagcg cggctgccat cgggctccta cggccatgtg ccgcgcggcc gctcgccgcc      60
tacactagcc cacgccgcgg cgccggcgcg tgcagcggcg gcacccagcc gctcatcacg     120
ccccgcggca tccgcctctc cgcccgcccc ggtctcgtgc cggcctcgcc gctggaggag     180
```

```
aaggagaacc ggagatgcag ggccagtatg cacgcggcgg cgtcggccgg agaggaagct      240
gggggagggc tcgccaagac gctgcagctg ggggcgcttt tcgggctctg gtacctcttc      300
aacatctact tcaacatcta caacaagcag gttctgaagg ttttgccata ccctataaac      360
atcacaacgg tgcagtttgc tgttggaagt gccattgctt tgttcatgtg atcactggt       420 atccataaaa ggccaaagat ttcgggtgcc cagcttttcg ctatccttcc tctagctatt      480
gtccatacca tgggcaatct tttcacaaac atgagccttg aaaggttgc agtgtcattt       540 acacatacta taaaggccat ggaacctttc ttctcagttc tcctttcagc aattttcctt      600
ggggagttgc ctacgccatg ggttgtgttg tctcttcttc cgattgttgg tggtgtagct      660
ttggcatccc ttactgaggc ctcctttaac tgggctggat tttggagtgc aatggcttca      720
aatgtaacct tccagtcaag gaatgtgcta agcaagaaac ttatggtgaa gaaagaggaa      780
tctctcgaca acattaacct attctcgatc attacagtca tgtcattctt cctgttggcc      840
ccagtaacct tacttacaga aggtgttaaa gttagtccag cagtgttgca gtctgctggt      900
ttgaacttga acaggtata cacaaggtca ttgattgctg cattctgctt ccatgcatac       960
caacaggtat catacatgat cctcgccagg gtatccccag tcacacattc agtgggcaat     1020
tgcgtcaagc gtgtggtggt cattgtgacc tctgttctgt tcttcaggac ccctgtttct     1080
cccatcaact ctcttggtac cgggatcgct cttgctggag ttttcctata ctcgcaattg     1140
aagagactta agcccaagcc caagactgct tga                                   1173

<210> SEQ ID NO 56
<211> LENGTH: 720
<212> TYPE: DNA
<213> ORGANISM: Glycine max

<400> SEQUENCE: 56
atggctgctg ctagtactat gatcacactc aagttctcat tcctctggag tctccttctc       60
tcagtttcac tcttgggtgt aaagtcatca catagccacc aaaatggtgg agaagaaca       120 attcctccaa catgcaagcg cattgagtgc cccacccatg atgtgattga agtgggtgat      180
ggctatgaaa tccgacgcta taataataat tcaactgtgt ggatgtcaac ttctcccatt      240
caagacattt ctctggttga agctacaaga actggcttca ggagtctatt tgattatatc      300
caaggcaaga caactacaa gcaaaaaatt gagatgacag cgcctgtgat cacagaagtt       360
tcacctagtg atggacccct ttgtaaatcc tcatttgttg tcagcttctt tgtgccaaaa      420
ttgaaccaag caaaccctcc tcctgcaaag ggtctccatg tccaaagatg aacaatatg       480 tatgtggcag caaggcagtt tggtggacac gtaaacgatt caaatgttgc ggtggaagcc      540
gctgtgttgc gagctagtat tgaaggcaca aaatggtctg gtgccattga caaaaaccag      600
aaagctggcc atgcttctgt ttacactgtg gcacaataca tgacccttt tgaatatcag       660 aatagggtga tgagatatg gttcttgttt gaaatggaaa gtgaaaggca tgcaatttga      720

<210> SEQ ID NO 57
<211> LENGTH: 981
<212> TYPE: DNA
<213> ORGANISM: Glycine max

<400> SEQUENCE: 57
atggaacgaa gtggcggaat ggtaacgggg tcgcatgaaa ggaacgaact tgttagagtt       60
agacacggtt ctgacagtgg gtctaaaccc ttgaagaatt taaatggtca gatttgtcaa      120
```

```
atatgtggtg acaccattgg attaacggct actggtgacc tctttgttgc ttgtcatgag    180
tgtggcttcc cactttgtca ttcttgttac gagtatgagc tgaaaaatgt gagccaatct    240
tgtccccagt gcaagactac attcacaagt cgccaagagg gtgctgaagt ggagggagat    300
gatgatgacg aagacgatgc tgatgatcta gataatggga tcaactatgg ccaaggaaac    360
aattccaagt cggggatgct gtgggaagaa gatgctgacc tctcttcatc ttctggacat    420
gattctcata taccaaaccc ccatctagta acgggcaac cgatgtctgg tgagtttcca    480
tgtgctactt ctgatgctca atctatgcaa actacatcag atcctatggg tcaatccgaa    540
aaggttcact cacttccata tgctgatcca aagcaaccag gtcctgagag tgatgaagag    600
ataagaagag tgccggagat tggaggtgaa agcgctggaa cttcagcctc tcggccagat    660
gccggttcaa atgctggtac agaacgtgct caggggacag ggacagcca aagaagaga    720 gggagaagcc cagctgataa agaaagcaag cggctaaaga ggctactgag gaatagagtt    780
tcggctcagc aagcaaggga gaggaagaag gcatatttga ttgatttgga aacaagagtc    840
aaagacttag agaagaagaa ctcagagctc aaagaaagac tttccacttt gcagaatgaa    900
aaccaaatgc ttagacaaat attgaagaac acaacagcaa gcaggagagg gagcaatagt    960
ggtaccaata atgctgagta a                                              981

<210> SEQ ID NO 58
<211> LENGTH: 792
<212> TYPE: DNA
<213> ORGANISM: Zea mays

<400> SEQUENCE: 58
atgttggagc tacgtctcgt gcagggctct ctcctgaaga aggttctcga atcgatcaag     60
gatctcgtca acgacgccaa cttcgactgc tccaccaccg gcttctccct ccaagccatg    120
gactccagcc acgtggcgct cgtctccctc ctgctcagat ccgaaggctt cgagcactac    180
cgctgcgacc gtaacctttc catggggatg aatctcggaa acatgtcgaa gatgctcaaa    240
tgcgccggaa acgacgacat catcaccatc aaagccgatg acggcggcga caccgtcacc    300
ttcatgttcg agagtcccaa gcaagacaag attgcagatt ttgagatgaa gctgatggat    360
atagacagtg agcatttggg gatacctgat gctgagtatc attcgattgt taggatgccg    420
tctaatgagt tctctagaat ctgcaaagat ctcagtacca tcggtgacac tgttgtgata    480
tctgtgacta agaagggggt taagttctct actgctggtg acattgggac agctaacatt    540
gtgttgagac agaacacaac tgttgacaag ccggaagatg cgattgtaat agagatgaac    600
gagccggtgt cactctcgtt tgccttgagg tatatgaatt ccttcacaaa ggcgactcct    660
ttgtcagaca cggtgacgat cagcttatcg tcggagctgc cagttgtggt ggagtataag    720
gtggctgaga tgggttacat tcgttactac ttggctccta agattgaaga agatgaagaa    780
gacaaggctt aa                                                        792

<210> SEQ ID NO 59
<211> LENGTH: 902
<212> TYPE: DNA
<213> ORGANISM: Zea mays

<400> SEQUENCE: 59
atggcggcgc cgcgcgtcct cctcctcctc gccgccgcgg cccttctcgc cgtcgcctcc     60
ctcggggacg cttcgggcga gggccccgc gggcgcaagc tgctggtgct cgtcgacgat    120
ctggccgtcc gctcatccca ctcggccttc ttcggctcgc tccaggcccg cgggctagat    180
```

```
ctggagttcc gcctcgccga cgacccaag ctctcgctcc accgctacgg tcagtacctc    240
tacgacggcc tcgtgctctt cgccccatcg accccgcgct tcggcggatc ggtggaccag    300
aatgctgttc tggagtttat cgatgccggg catgatatga ttctggcagc agatcattcg    360
gcttcagatc tgatccgcgg catcgcgacg gagtgtgggg ttgactttga tgaggacccg    420
gaagcaatgg ttattgacca catcaattat gcctccagtg aggttgaagg tgaccacacc    480
ttgattgctg gcgatgacct gattcagtca gatgtgatat tggggtccaa aaagattgag    540
gctcctgtgc tgtttcgagg gattgggcat gcggccaatc catccaacag cttggtttta    600
aaggttctat ctgcctcgcc atcagcgtat tcagcaaacc cggaggctaa gtggcatctg    660
ttccatctct cactgggtcg gccatatcgc tggtttctgt tatgcaggct aggaataatg    720
ctcgtgtgtt gatatctgga tcactggatt tgtttagcaa caggttccta agtctggtg     780 tgcagaaggc tggcagcaaa atgagccatg acaaagctgg aaatgaacaa tttgtgacag    840
agacgagcaa atgggtcttc catgagaggg ggcatctgaa ggcagggaat gtcaagcacc    900
at                                                                  902

<210> SEQ ID NO 60
<211> LENGTH: 2184
<212> TYPE: DNA
<213> ORGANISM: Zea mays

<400> SEQUENCE: 60
atggccgcgg ggtcgatccg ggtcaccatg gaggtgggcg ccgacggcgt cgcgctcatc     60
accatcgcca acccgcccgt caacgcgctc caccccatca tcatcgcggg gctcaaggac    120
aagtacgcgg aggccttgcg ccgtgacgac gttaaggcaa tcgtgctcac tggtgctgga    180
ggcaagttct gtggaggatt tgatatcaac gttttcacaa aggttcatca gactggggat    240
gtatcactta tgccggacgt atccgtgag cttgtgtcaa acatgatgga gagggaaaa      300 aaaccttctg ttgcagccat tcaaggtctt gcattgggtg gtggcctaga gttgactatg    360
ggttgtcatg ctcggatatc tactcctgaa gctcaacttg gattgccaga gctaaccctt    420
ggcatcatcc ctgatttggg aggtacccag cgtttgccga ggcttgtagg tctacccaaa    480
gcaattgaaa tgatgctgca agtaagttc attacggcaa aggaagggaa tgaacgtggt    540
ttgattgatg ccctttgctc tcctgatgaa ttgataaaga catcacgtct ttgggctctg    600
gaaattgcta attgccgtaa accttggatg aggtctcttg gcagaacaga taggcttgga    660
ccactctctg aagctcgtgc tgtgttaaat gcagcaagac agcaagcaat gaagatcgca    720
ccaaacatgc cacaaaaacca ggcctgcctg gatgtgatgg aggaaggcat attatgtgga    780
ggccaagctg gtgttttgaa ggaggccgtg gttttcaagg agctggtgat agcaccaaca    840
tcaaaggctc ttgtccatgt tttctttgca caacgttcca cgacaaaggt gccaggtgta    900
actgatgttc aactgaaacc aaggccaatt agaaagttg ctgttattgg tggtggtctg     960
atgggatctg gaattgccac atcacttctt gttagcaaca tttctgttgt gctcaaggaa    1020 gtaaacccctc agtttctgca aggggagag aaaacaatag caggtaatct tgagggcctg    1080
gtcaaaagag gttcactaac aaaggatagg atgcacaagg ccatgccct tctcaagggt    1140 gctttggatt attcagattt caaggatgtt gatatggtta ttgaggctgt tattgagaag    1200
attcctttga gcaatcaat atttgctgac attgagaaaa tctgtccaaa acattgcata    1260
cttgcaacaa acacatccac cattgatttg aatgttgttg gcaagaagac aaattctcaa    1320
```

```
gatagaatta tagggggctca cttttttcagc cctgctcata ttatgccctt gcttgaaatt    1380
gttcggacgg agaagacatc accacaagct atccttgatc tcatcaccat tgggaagata    1440
ataaagaaag tccctattgt ggtcggcaac tgcacaggat ttgcagtcaa ccgtacattt    1500
tttccttaca cacagggttc tcatcttcta gttagtcttg gtattgatgt tttcagaatt    1560
gatcgagtaa taagcaccct tggcatgcca atgggacctt ttcaactcca agatgtggct    1620
gggtatggag ttgccttggc agtaaaggat atctacgctg atgcctttgg agaaagaaat    1680
ttggactctg accttgtgga tttgatggta aaggatggac gacaaggaaa ggtgaacggc    1740
aaaggttact acatttatga gaagggtggg aagccaaagc cagatcctag tgttaagcat    1800
gttatcgagg agtaccgaaa gcacgcaaac acaatgcctg gtggaaagcc tgttacttta    1860
acggatcaag atattttgga gatgattttc ttcccagttg tgaatgaggc atgcagggtt    1920
atggatgaaa atgttgtaat tcgagcttct gatcttgata ttgcttctgt tcttggaatg    1980
ggctttccta aatacagggg tggtcttgtc ttctgggctg acactgttgg agcaccttac    2040
atacattcta agctaagcaa gtgggctgaa atttatggcc ccttcttcaa accatcatca    2100
tatttggaac agcgagctaa gagtggtgta ccattgagcg caccaggagc ttcgcagcaa    2160
ggttcggcga ggtcacgcat gtga                                            2184
```

<210> SEQ ID NO 61
<211> LENGTH: 390
<212> TYPE: PRT
<213> ORGANISM: Zea mays

<400> SEQUENCE: 61

```
Met Gln Ser Ala Ala Ile Gly Leu Leu Arg Pro Cys Ala Ala Arg
1               5                  10                 15

Pro Leu Ala Ala Tyr Thr Ser Pro Arg Arg Gly Ala Gly Ala Cys Ser
            20                  25                  30

Gly Gly Thr Gln Pro Leu Ile Thr Pro Arg Gly Ile Arg Leu Ser Ala
        35                  40                  45

Arg Pro Gly Leu Val Pro Ala Ser Pro Leu Glu Glu Lys Glu Asn Arg
    50                  55                  60

Arg Cys Arg Ala Ser Met His Ala Ala Ser Ala Gly Glu Glu Ala
65                  70                  75                  80

Gly Gly Gly Leu Ala Lys Thr Leu Gln Leu Gly Ala Leu Phe Gly Leu
                85                  90                  95

Trp Tyr Leu Phe Asn Ile Tyr Phe Asn Ile Tyr Asn Lys Gln Val Leu
            100                 105                 110

Lys Val Leu Pro Tyr Pro Ile Asn Ile Thr Thr Val Gln Phe Ala Val
        115                 120                 125

Gly Ser Ala Ile Ala Leu Phe Met Trp Ile Thr Gly Ile His Lys Arg
    130                 135                 140

Pro Lys Ile Ser Gly Ala Gln Leu Phe Ala Ile Leu Pro Leu Ala Ile
145                 150                 155                 160

Val His Thr Met Gly Asn Leu Phe Thr Asn Met Ser Leu Gly Lys Val
                165                 170                 175

Ala Val Ser Phe Thr His Thr Ile Lys Ala Met Glu Pro Phe Phe Ser
            180                 185                 190

Val Leu Leu Ser Ala Ile Phe Leu Gly Glu Leu Pro Thr Pro Trp Val
        195                 200                 205

Val Leu Ser Leu Leu Pro Ile Val Gly Gly Val Ala Leu Ala Ser Leu
    210                 215                 220
```

```
Thr Glu Ala Ser Phe Asn Trp Ala Gly Phe Trp Ser Ala Met Ala Ser
225                 230                 235                 240

Asn Val Thr Phe Gln Ser Arg Asn Val Leu Ser Lys Lys Leu Met Val
            245                 250                 255

Lys Lys Glu Glu Ser Leu Asp Asn Ile Asn Leu Phe Ser Ile Ile Thr
        260                 265                 270

Val Met Ser Phe Phe Leu Leu Ala Pro Val Thr Leu Leu Thr Glu Gly
    275                 280                 285

Val Lys Val Ser Pro Ala Val Leu Gln Ser Ala Gly Leu Asn Leu Lys
290                 295                 300

Gln Val Tyr Thr Arg Ser Leu Ile Ala Ala Phe Cys Phe His Ala Tyr
305                 310                 315                 320

Gln Gln Val Ser Tyr Met Ile Leu Ala Arg Val Ser Pro Val Thr His
                325                 330                 335

Ser Val Gly Asn Cys Val Lys Arg Val Val Ile Val Thr Ser Val
            340                 345                 350

Leu Phe Phe Arg Thr Pro Val Ser Pro Ile Asn Ser Leu Gly Thr Gly
        355                 360                 365

Ile Ala Leu Ala Gly Val Phe Leu Tyr Ser Gln Leu Lys Arg Leu Lys
370                 375                 380

Pro Lys Pro Lys Thr Ala
385                 390

<210> SEQ ID NO 62
<211> LENGTH: 239
<212> TYPE: PRT
<213> ORGANISM: Glycine max

<400> SEQUENCE: 62

Met Ala Ala Ala Ser Thr Met Ile Thr Leu Lys Phe Ser Phe Leu Trp
1               5                   10                  15

Ser Leu Leu Leu Ser Val Ser Leu Leu Gly Val Lys Ser Ser His Ser
            20                  25                  30

His Gln Asn Gly Gly Arg Arg Thr Ile Pro Pro Thr Cys Lys Arg Ile
        35                  40                  45

Glu Cys Pro Thr His Asp Val Ile Glu Val Gly Asp Gly Tyr Glu Ile
    50                  55                  60

Arg Arg Tyr Asn Asn Asn Ser Thr Val Trp Met Ser Thr Ser Pro Ile
65                  70                  75                  80

Gln Asp Ile Ser Leu Val Glu Ala Thr Arg Thr Gly Phe Arg Ser Leu
                85                  90                  95

Phe Asp Tyr Ile Gln Gly Lys Asn Asn Tyr Lys Gln Lys Ile Glu Met
            100                 105                 110

Thr Ala Pro Val Ile Thr Glu Val Ser Pro Ser Asp Gly Pro Phe Cys
        115                 120                 125

Lys Ser Ser Phe Val Val Ser Phe Phe Val Pro Lys Leu Asn Gln Ala
    130                 135                 140

Asn Pro Pro Pro Ala Lys Gly Leu His Val Gln Arg Trp Asn Asn Met
145                 150                 155                 160

Tyr Val Ala Ala Arg Gln Phe Gly Gly His Val Asn Asp Ser Asn Val
                165                 170                 175

Ala Val Glu Ala Ala Val Leu Arg Ala Ser Ile Glu Gly Thr Lys Trp
            180                 185                 190

Ser Gly Ala Ile Asp Lys Asn Gln Lys Ala Gly His Ala Ser Val Tyr
```

```
                  195                 200                 205
Thr Val Ala Gln Tyr Asn Asp Pro Phe Glu Tyr Gln Asn Arg Val Asn
210                 215                 220

Glu Ile Trp Phe Leu Phe Glu Met Glu Ser Glu Arg His Ala Ile
225                 230                 235

<210> SEQ ID NO 63
<211> LENGTH: 326
<212> TYPE: PRT
<213> ORGANISM: Glycine max

<400> SEQUENCE: 63

Met Glu Arg Ser Gly Gly Met Val Thr Gly Ser His Glu Arg Asn Glu
1               5                   10                  15

Leu Val Arg Val Arg His Gly Ser Asp Ser Gly Ser Lys Pro Leu Lys
                20                  25                  30

Asn Leu Asn Gly Gln Ile Cys Gln Ile Cys Gly Asp Thr Ile Gly Leu
            35                  40                  45

Thr Ala Thr Gly Asp Leu Phe Val Ala Cys His Glu Cys Gly Phe Pro
        50                  55                  60

Leu Cys His Ser Cys Tyr Glu Tyr Glu Leu Lys Asn Val Ser Gln Ser
65                  70                  75                  80

Cys Pro Gln Cys Lys Thr Thr Phe Thr Ser Arg Gln Glu Gly Ala Glu
                85                  90                  95

Val Glu Gly Asp Asp Asp Glu Asp Ala Asp Asp Leu Asp Asn
                100                 105                 110

Gly Ile Asn Tyr Gly Gln Gly Asn Asn Ser Lys Ser Gly Met Leu Trp
            115                 120                 125

Glu Glu Asp Ala Asp Leu Ser Ser Ser Gly His Asp Ser His Ile
130                 135                 140

Pro Asn Pro His Leu Val Asn Gly Gln Pro Met Ser Gly Glu Phe Pro
145                 150                 155                 160

Cys Ala Thr Ser Asp Ala Gln Ser Met Gln Thr Thr Ser Asp Pro Met
                165                 170                 175

Gly Gln Ser Glu Lys Val His Ser Leu Pro Tyr Ala Asp Pro Lys Gln
            180                 185                 190

Pro Gly Pro Glu Ser Asp Glu Glu Ile Arg Arg Val Pro Glu Ile Gly
        195                 200                 205

Gly Glu Ser Ala Gly Thr Ser Ala Ser Arg Pro Asp Ala Gly Ser Asn
210                 215                 220

Ala Gly Thr Glu Arg Ala Gln Gly Thr Gly Asp Ser Gln Lys Lys Arg
225                 230                 235                 240

Gly Arg Ser Pro Ala Asp Lys Glu Ser Lys Arg Leu Lys Arg Leu Leu
                245                 250                 255

Arg Asn Arg Val Ser Ala Gln Gln Ala Arg Glu Arg Lys Lys Ala Tyr
            260                 265                 270

Leu Ile Asp Leu Glu Thr Arg Val Lys Asp Leu Glu Lys Lys Asn Ser
        275                 280                 285

Glu Leu Lys Glu Arg Leu Ser Thr Leu Gln Asn Glu Asn Gln Met Leu
    290                 295                 300

Arg Gln Ile Leu Lys Asn Thr Thr Ala Ser Arg Arg Gly Ser Asn Ser
305                 310                 315                 320

Gly Thr Asn Asn Ala Glu
            325
```

-continued

```
<210> SEQ ID NO 64
<211> LENGTH: 263
<212> TYPE: PRT
<213> ORGANISM: Zea mays

<400> SEQUENCE: 64

Met Leu Glu Leu Arg Leu Val Gln Gly Ser Leu Leu Lys Lys Val Leu
1               5                   10                  15

Glu Ser Ile Lys Asp Leu Val Asn Asp Ala Asn Phe Asp Cys Ser Thr
            20                  25                  30

Thr Gly Phe Ser Leu Gln Ala Met Asp Ser Ser His Val Ala Leu Val
        35                  40                  45

Ser Leu Leu Arg Ser Glu Gly Phe Glu His Tyr Arg Cys Asp Arg
    50                  55                  60

Asn Leu Ser Met Gly Met Asn Leu Gly Asn Met Ser Lys Met Leu Lys
65                  70                  75                  80

Cys Ala Gly Asn Asp Asp Ile Ile Thr Ile Lys Ala Asp Asp Gly Gly
                85                  90                  95

Asp Thr Val Thr Phe Met Phe Glu Ser Pro Lys Gln Asp Lys Ile Ala
            100                 105                 110

Asp Phe Glu Met Lys Leu Met Asp Ile Asp Ser Glu His Leu Gly Ile
        115                 120                 125

Pro Asp Ala Glu Tyr His Ser Ile Val Arg Met Pro Ser Asn Glu Phe
    130                 135                 140

Ser Arg Ile Cys Lys Asp Leu Ser Thr Ile Gly Asp Thr Val Val Ile
145                 150                 155                 160

Ser Val Thr Lys Glu Gly Val Lys Phe Ser Thr Ala Gly Asp Ile Gly
                165                 170                 175

Thr Ala Asn Ile Val Leu Arg Gln Asn Thr Thr Val Asp Lys Pro Glu
            180                 185                 190

Asp Ala Ile Val Ile Glu Met Asn Glu Pro Val Ser Leu Ser Phe Ala
        195                 200                 205

Leu Arg Tyr Met Asn Ser Phe Thr Lys Ala Thr Pro Leu Ser Asp Thr
    210                 215                 220

Val Thr Ile Ser Leu Ser Ser Glu Leu Pro Val Val Glu Tyr Lys
225                 230                 235                 240

Val Ala Glu Met Gly Tyr Ile Arg Tyr Tyr Leu Ala Pro Lys Ile Glu
                245                 250                 255

Glu Asp Glu Glu Asp Lys Ala
            260

<210> SEQ ID NO 65
<211> LENGTH: 243
<212> TYPE: PRT
<213> ORGANISM: Zea mays

<400> SEQUENCE: 65

Met Ala Ala Pro Arg Val Leu Leu Leu Ala Ala Ala Leu Leu
1               5                   10                  15

Ala Val Ala Ser Leu Gly Asp Ala Ser Gly Glu Gly Pro Arg Gly Arg
            20                  25                  30

Lys Leu Leu Val Leu Val Asp Asp Leu Ala Val Arg Ser Ser His Ser
        35                  40                  45

Ala Phe Phe Gly Ser Leu Gln Ala Arg Gly Leu Asp Leu Glu Phe Arg
    50                  55                  60
```

-continued

Leu Ala Asp Asp Pro Lys Leu Ser Leu His Arg Tyr Gly Gln Tyr Leu
65                  70                  75                  80

Tyr Asp Gly Leu Val Leu Phe Ala Pro Ser Thr Pro Arg Phe Gly Gly
                85                  90                  95

Ser Val Asp Gln Asn Ala Val Leu Glu Phe Ile Asp Ala Gly His Asp
            100                 105                 110

Met Ile Leu Ala Ala Asp His Ser Ala Ser Asp Leu Ile Arg Gly Ile
        115                 120                 125

Ala Thr Glu Cys Gly Val Asp Phe Asp Glu Asp Pro Glu Ala Met Val
    130                 135                 140

Ile Asp His Ile Asn Tyr Ala Ser Ser Glu Val Glu Gly Asp His Thr
145                 150                 155                 160

Leu Ile Ala Gly Asp Asp Leu Ile Gln Ser Asp Val Ile Leu Gly Ser
                165                 170                 175

Lys Lys Ile Glu Ala Pro Val Leu Phe Arg Gly Ile Gly His Ala Ala
            180                 185                 190

Asn Pro Ser Asn Ser Leu Val Leu Lys Val Leu Ser Ala Ser Pro Ser
        195                 200                 205

Ala Tyr Ser Ala Asn Pro Glu Ala Lys Trp His Leu Phe His Leu Ser
    210                 215                 220

Leu Gly Arg Pro Tyr Arg Trp Phe Leu Leu Cys Arg Leu Gly Ile Met
225                 230                 235                 240

Leu Val Cys

<210> SEQ ID NO 66
<211> LENGTH: 727
<212> TYPE: PRT
<213> ORGANISM: Zea mays

<400> SEQUENCE: 66

Met Ala Ala Gly Ser Ile Arg Val Thr Met Glu Val Gly Ala Asp Gly
1               5                   10                  15

Val Ala Leu Ile Thr Ile Ala Asn Pro Pro Val Asn Ala Leu His Pro
                20                  25                  30

Ile Ile Ile Ala Gly Leu Lys Asp Lys Tyr Ala Glu Ala Leu Arg Arg
            35                  40                  45

Asp Asp Val Lys Ala Ile Val Leu Thr Gly Ala Gly Gly Lys Phe Cys
        50                  55                  60

Gly Gly Phe Asp Ile Asn Val Phe Thr Lys Val His Gln Thr Gly Asp
65                  70                  75                  80

Val Ser Leu Met Pro Asp Val Ser Val Glu Leu Val Ser Asn Met Met
                85                  90                  95

Glu Glu Gly Lys Lys Pro Ser Val Ala Ala Ile Gln Gly Leu Ala Leu
            100                 105                 110

Gly Gly Gly Leu Glu Leu Thr Met Gly Cys His Ala Arg Ile Ser Thr
        115                 120                 125

Pro Glu Ala Gln Leu Gly Leu Pro Glu Leu Thr Leu Gly Ile Ile Pro
    130                 135                 140

Gly Phe Gly Gly Thr Gln Arg Leu Pro Arg Leu Val Gly Leu Pro Lys
145                 150                 155                 160

Ala Ile Glu Met Met Leu Gln Ser Lys Phe Ile Thr Ala Lys Glu Gly
                165                 170                 175

Asn Glu Arg Gly Leu Ile Asp Ala Leu Cys Ser Pro Asp Glu Leu Ile
            180                 185                 190

```
Lys Thr Ser Arg Leu Trp Ala Leu Glu Ile Ala Asn Cys Arg Lys Pro
        195                 200                 205

Trp Met Arg Ser Leu Gly Arg Thr Asp Arg Leu Gly Pro Leu Ser Glu
210                 215                 220

Ala Arg Ala Val Leu Asn Ala Ala Arg Gln Gln Ala Met Lys Ile Ala
225                 230                 235                 240

Pro Asn Met Pro Gln Asn Gln Ala Cys Leu Asp Val Met Glu Glu Gly
                245                 250                 255

Ile Leu Cys Gly Gly Gln Ala Gly Val Leu Lys Glu Ala Val Val Phe
            260                 265                 270

Lys Glu Leu Val Ile Ala Pro Thr Ser Lys Ala Leu Val His Val Phe
        275                 280                 285

Phe Ala Gln Arg Ser Thr Thr Lys Val Pro Gly Val Thr Asp Val Gln
290                 295                 300

Leu Lys Pro Arg Pro Ile Arg Lys Val Ala Val Ile Gly Gly Gly Leu
305                 310                 315                 320

Met Gly Ser Gly Ile Ala Thr Ser Leu Leu Val Ser Asn Ile Ser Val
            325                 330                 335

Val Leu Lys Glu Val Asn Pro Gln Phe Leu Gln Arg Gly Glu Lys Thr
        340                 345                 350

Ile Ala Gly Asn Leu Glu Gly Leu Val Lys Arg Gly Ser Leu Thr Lys
        355                 360                 365

Asp Arg Met His Lys Ala Met Ala Leu Leu Lys Gly Ala Leu Asp Tyr
        370                 375                 380

Ser Asp Phe Lys Asp Val Asp Met Val Ile Glu Ala Val Ile Glu Lys
385                 390                 395                 400

Ile Pro Leu Lys Gln Ser Ile Phe Ala Asp Ile Glu Lys Ile Cys Pro
                405                 410                 415

Lys His Cys Ile Leu Ala Thr Asn Thr Ser Thr Ile Asp Leu Asn Val
            420                 425                 430

Val Gly Lys Lys Thr Asn Ser Gln Asp Arg Ile Ile Gly Ala His Phe
        435                 440                 445

Phe Ser Pro Ala His Ile Met Pro Leu Leu Glu Ile Val Arg Thr Glu
450                 455                 460

Lys Thr Ser Pro Gln Ala Ile Leu Asp Leu Ile Thr Ile Gly Lys Ile
465                 470                 475                 480

Ile Lys Lys Val Pro Ile Val Val Gly Asn Cys Thr Gly Phe Ala Val
                485                 490                 495

Asn Arg Thr Phe Phe Pro Tyr Thr Gln Gly Ser His Leu Leu Val Ser
                500                 505                 510

Leu Gly Ile Asp Val Phe Arg Ile Asp Arg Val Ile Ser Thr Phe Gly
        515                 520                 525

Met Pro Met Gly Pro Phe Gln Leu Gln Asp Val Ala Gly Tyr Gly Val
530                 535                 540

Ala Leu Ala Val Lys Asp Ile Tyr Ala Asp Ala Phe Gly Glu Arg Asn
545                 550                 555                 560

Leu Asp Ser Asp Leu Val Asp Leu Met Val Lys Asp Gly Arg Gln Gly
                565                 570                 575

Lys Val Asn Gly Lys Gly Tyr Tyr Ile Tyr Glu Lys Gly Lys Pro
            580                 585                 590

Lys Pro Asp Pro Ser Val Lys His Val Ile Glu Glu Tyr Arg Lys His
                595                 600                 605

Ala Asn Thr Met Pro Gly Gly Lys Pro Val Thr Leu Thr Asp Gln Asp
```

|     |     |     |     |     |     |     |     |     |     |     |     |     |     |     |
| --- | --- | --- | --- | --- | --- | --- | --- | --- | --- | --- | --- | --- | --- | --- |
|     |     | 610 |     |     |     | 615 |     |     |     |     |     | 620 |     |     |
| Ile | Leu | Glu | Met | Ile | Phe | Phe | Pro | Val | Val | Asn | Glu | Ala | Cys | Arg | Val |
| 625 |     |     |     | 630 |     |     |     |     | 635 |     |     |     |     | 640 |

| Met | Asp | Glu | Asn | Val | Val | Ile | Arg | Ala | Ser | Asp | Leu | Asp | Ile | Ala | Ser |
| --- | --- | --- | --- | --- | --- | --- | --- | --- | --- | --- | --- | --- | --- | --- | --- |
|     |     |     |     | 645 |     |     |     |     | 650 |     |     |     |     | 655 |     |

| Val | Leu | Gly | Met | Gly | Phe | Pro | Lys | Tyr | Arg | Gly | Gly | Leu | Val | Phe | Trp |
| --- | --- | --- | --- | --- | --- | --- | --- | --- | --- | --- | --- | --- | --- | --- | --- |
|     |     |     | 660 |     |     |     |     | 665 |     |     |     |     | 670 |     |     |

| Ala | Asp | Thr | Val | Gly | Ala | Pro | Tyr | Ile | His | Ser | Lys | Leu | Ser | Lys | Trp |
| --- | --- | --- | --- | --- | --- | --- | --- | --- | --- | --- | --- | --- | --- | --- | --- |
|     |     | 675 |     |     |     |     | 680 |     |     |     |     | 685 |     |     |     |

| Ala | Glu | Ile | Tyr | Gly | Pro | Phe | Phe | Lys | Pro | Ser | Ser | Tyr | Leu | Glu | Gln |
| --- | --- | --- | --- | --- | --- | --- | --- | --- | --- | --- | --- | --- | --- | --- | --- |
|     |     | 690 |     |     |     |     | 695 |     |     |     |     | 700 |     |     |     |

| Arg | Ala | Lys | Ser | Gly | Val | Pro | Leu | Ser | Ala | Pro | Gly | Ala | Ser | Gln | Gln |
| --- | --- | --- | --- | --- | --- | --- | --- | --- | --- | --- | --- | --- | --- | --- | --- |
| 705 |     |     |     | 710 |     |     |     |     | 715 |     |     |     |     | 720 |     |

| Gly | Ser | Ala | Arg | Ser | Arg | Met |
| --- | --- | --- | --- | --- | --- | --- |
|     |     |     | 725 |     |     |     |

<210> SEQ ID NO 67
<211> LENGTH: 328
<212> TYPE: DNA
<213> ORGANISM: Artificial
<220> FEATURE:
<223> OTHER INFORMATION: Engineered miRNA precursor

<400> SEQUENCE: 67

| ggcagagccg tgcccgtctc atccctgcc cgtgcaagca gctaggtagg acgatttgag | 60 |
| --- | --- |
| cgtggtgtta ggccgaaccg ctgaaggaag attgctccac tgttgactgc attagatgtt | 120 |
| gaagaggtac caaaaatgta ttgcttatat tcagcaatat aatgttcttg gtacctaggc | 180 |
| aacatctaat atagtcgata gtggaagaac ggtaacatat gtggtttgca gcaggtgagc | 240 |
| aggatgggtg tggatgattg aatatctctg ttcagtgttt tcatcatctg actgaacact | 300 |
| gaatcagctt gctgacgtta gaggttag | 328 |

<210> SEQ ID NO 68
<211> LENGTH: 328
<212> TYPE: DNA
<213> ORGANISM: Artificial
<220> FEATURE:
<223> OTHER INFORMATION: Engineered miRNA precursor

<400> SEQUENCE: 68

| ggcagagccg tgcccgtctc atccctgcc cgtgcaagca gctaggtagg acgatttgag | 60 |
| --- | --- |
| cgtggtgtta ggccgaaccg ctgaaggaag attgctccac tgttgactgc atttcatagc | 120 |
| catcacccac ttcaaatgta ttgcttatat tcagcaatat aatgttcgaa gtgggttcgg | 180 |
| gctatgaaat atagtcgata gtggaagaac ggtaacatat gtggtttgca gcaggtgagc | 240 |
| aggatgggtg tggatgattg aatatctctg ttcagtgttt tcatcatctg actgaacact | 300 |
| gaatcagctt gctgacgtta gaggttag | 328 |

<210> SEQ ID NO 69
<211> LENGTH: 325
<212> TYPE: DNA
<213> ORGANISM: Artificial
<220> FEATURE:
<223> OTHER INFORMATION: Engineered miRNA precursor

<400> SEQUENCE: 69

| ggcagagccg tgcccgtctc atccctgcc cgtgcaagca gctaggtagg acgatttgag | 60 |
| --- | --- |

```
cgtggtgtta ggccgaaccg ctgaaggaag attgctccac tgttgactgc attgacaagc    120
aacaaagagg tcaaaatgta ttgcttatat tcagcaatat aatgttctga cctcttgtgt    180
gcttgtcaat atagtcgata gtggaagaac ggtaacatat gtggtttgca gcaggtgagc    240
aggatgggtg tggatgattg aatatctctg ttcagtgttt tcatcatctg actgaacact    300
gaatcagctt gctgacgtta gaggt                                          325

<210> SEQ ID NO 70
<211> LENGTH: 325
<212> TYPE: DNA
<213> ORGANISM: Artificial
<220> FEATURE:
<223> OTHER INFORMATION: Engineered miRNA precursor

<400> SEQUENCE: 70
ggcagagccg tgcccgtctc atccctgcc cgtgcaagca gctaggtagg acgatttgag     60
cgtggtgtta ggccgaaccg ctgaaggaag attgctccac tgttgactgc atttatactc    120
caccacaact ggcaaatgta ttgcttatat tcagcaatat aatgttcgcc agttgtttgg    180
gagtataaat atagtcgata gtggaagaac ggtaacatat gtggtttgca gcaggtgagc    240
aggatgggtg tggatgattg aatatctctg ttcagtgttt tcatcatctg actgaacact    300
gaatcagctt gctgacgtta gaggt                                          325

<210> SEQ ID NO 71
<211> LENGTH: 408
<212> TYPE: DNA
<213> ORGANISM: Artificial
<220> FEATURE:
<223> OTHER INFORMATION: Engineered miRNA precursor

<400> SEQUENCE: 71
ggcagagccg tgcccgtctc atccctgcc cgtgcaagca gctaggtagg acgatttgag     60
cgtggtgtta ggccgaaccg ctgaaggaag attgctccac tgttgactgc attgagagat    120
ggaacagatg cccaaatgta ttgcttatat tcagcaatat aatgttcggg catctgggac    180
atctctcaat atagtcgata gtggaagaac ggtaacatat gtggtttgca gcaggtgagc    240
aggatgggtg tggatgattg aatatctctg ttcagtgttt tcatcatctg actgaacact    300
gaatcagctt gctgacgtta gaggtttcag tttacctaat ttatggtctg tacccatgaa    360 aagtggggaaa aggctgaaga attcgatttc tttctttctt tcaatgtt              408

<210> SEQ ID NO 72
<211> LENGTH: 408
<212> TYPE: DNA
<213> ORGANISM: Artificial
<220> FEATURE:
<223> OTHER INFORMATION: Engineered miRNA precursor

<400> SEQUENCE: 72
ggcagagccg tgcccgtctc atccctgcc cgtgcaagca gctaggtagg acgatttgag     60
cgtggtgtta ggccgaaccg ctgaaggaag attgctccac tgttgactgc attagaagat    120
gagaaccctg tgcaaatgta ttgcttatat tcagcaatat aatgttcgca cagggtgagc    180
atcttctaat atagtcgata gtggaagaac ggtaacatat gtggtttgca gcaggtgagc    240
aggatgggtg tggatgattg aatatctctg ttcagtgttt tcatcatctg actgaacact    300
gaatcagctt gctgacgtta gaggtttcag tttacctaat ttatggtctg tacccatgaa    360 aagtggggaaa aggctgaaga attcgatttc tttctttctt tcaatgtt              408
```

```
<210> SEQ ID NO 73
<211> LENGTH: 21
<212> TYPE: DNA
<213> ORGANISM: Artificial
<220> FEATURE:
<223> OTHER INFORMATION: miRNA recognition site

<400> SEQUENCE: 73
tagatgttga agaggtacca a                                              21

<210> SEQ ID NO 74
<211> LENGTH: 21
<212> TYPE: DNA
<213> ORGANISM: Artificial
<220> FEATURE:
<223> OTHER INFORMATION: miRNA recognition site

<400> SEQUENCE: 74
ttcatagcca tcacccactt c                                              21

<210> SEQ ID NO 75
<211> LENGTH: 21
<212> TYPE: DNA
<213> ORGANISM: Artificial
<220> FEATURE:
<223> OTHER INFORMATION: miRNA recognition site

<400> SEQUENCE: 75
tgacaagcaa caaagaggtc a                                              21

<210> SEQ ID NO 76
<211> LENGTH: 21
<212> TYPE: DNA
<213> ORGANISM: Artificial
<220> FEATURE:
<223> OTHER INFORMATION: miRNA recognition site

<400> SEQUENCE: 76
ttatactcca ccacaactgg c                                              21

<210> SEQ ID NO 77
<211> LENGTH: 21
<212> TYPE: DNA
<213> ORGANISM: Artificial
<220> FEATURE:
<223> OTHER INFORMATION: miRNA recognition site

<400> SEQUENCE: 77
tgagagatgg aacagatgcc c                                              21

<210> SEQ ID NO 78
<211> LENGTH: 21
<212> TYPE: DNA
<213> ORGANISM: Artificial
<220> FEATURE:
<223> OTHER INFORMATION: miRNA recognition site

<400> SEQUENCE: 78
tagaagatga gaaccctgtg c                                              21

<210> SEQ ID NO 79
<211> LENGTH: 315
<212> TYPE: PRT
<213> ORGANISM: Arabidopsis thaliana
```

<400> SEQUENCE: 79

Met Val Gly Trp Ala Ile Ala Leu His Gly Gly Ala Gly Asp Ile Pro
1               5                   10                  15

Ile Asp Leu Pro Asp Glu Arg Arg Ile Pro Arg Glu Ser Ala Leu Arg
            20                  25                  30

His Cys Leu Asp Leu Gly Ile Ser Ala Leu Lys Ser Gly Lys Pro Pro
        35                  40                  45

Leu Asp Val Ala Glu Leu Val Val Arg Glu Leu Glu Asn His Pro Asp
    50                  55                  60

Phe Asn Ala Gly Lys Gly Ser Val Leu Thr Ala Gln Gly Thr Val Glu
65                  70                  75                  80

Met Glu Ala Ser Ile Met Asp Gly Lys Thr Lys Arg Cys Gly Ala Val
                85                  90                  95

Ser Gly Leu Thr Thr Val Val Asn Pro Ile Ser Leu Ala Arg Leu Val
            100                 105                 110

Met Glu Lys Thr Pro His Ile Tyr Leu Ala Phe Asp Ala Ala Glu Ala
        115                 120                 125

Phe Ala Arg Ala His Gly Val Glu Thr Val Tyr Ser Ser His Phe Ile
    130                 135                 140

Thr Pro Glu Asn Ile Ala Arg Leu Lys Gln Ala Lys Glu Phe Asn Arg
145                 150                 155                 160

Val Gln Leu Asp Tyr Thr Val Pro Ser Pro Lys Val Pro Asp Asn Cys
                165                 170                 175

Gly Asp Ser Gln Ile Gly Thr Val Gly Cys Val Ala Val Asp Ser Ala
            180                 185                 190

Gly Asn Leu Ala Ser Ala Thr Ser Thr Gly Gly Tyr Val Asn Lys Met
        195                 200                 205

Val Gly Arg Ile Gly Asp Thr Pro Val Ile Gly Ala Gly Thr Tyr Ala
    210                 215                 220

Asn His Leu Cys Ala Ile Ser Ala Thr Gly Lys Gly Glu Asp Ile Ile
225                 230                 235                 240

Arg Gly Thr Val Ala Arg Asp Val Ala Ala Leu Met Glu Tyr Lys Gly
                245                 250                 255

Leu Ser Leu Thr Glu Ala Ala Ala Tyr Val Val Asp Gln Ser Val Pro
            260                 265                 270

Arg Gly Ser Cys Gly Leu Val Ala Val Ser Ala Asn Gly Glu Val Thr
        275                 280                 285

Met Pro Phe Asn Thr Thr Gly Met Phe Arg Ala Cys Ala Ser Glu Asp
    290                 295                 300

Gly Tyr Ser Glu Ile Ala Ile Trp Pro Asn Asn
305                 310                 315

<210> SEQ ID NO 80
<211> LENGTH: 726
<212> TYPE: PRT
<213> ORGANISM: Arabidopsis thaliana

<400> SEQUENCE: 80

Met Pro Ser His Pro Asn Phe Ile Phe Arg Trp Ile Gly Leu Phe Ser
1               5                   10                  15

Asp Lys Phe Arg Arg Gln Thr Thr Gly Ile Asp Glu Asn Ser Asn Leu
            20                  25                  30

Gln Ile Asn Gly Gly Asp Ser Ser Ser Gly Ser Asp Glu Thr Pro
        35                  40                  45

-continued

Val Leu Ser Ser Ile Glu Cys Tyr Ala Cys Thr Gln Val Gly Val Pro
 50                  55                  60

Ala Phe His Ser Thr Ser Cys Asp Gln Ala His Ala Pro Glu Trp Arg
 65                  70                  75                  80

Ala Ser Ala Gly Ser Ser Leu Val Pro Ile Gln Glu Gly Ser Val Pro
                 85                  90                  95

Asn Pro Ala Arg Thr Arg Phe Arg Arg Leu Lys Gly Pro Phe Gly Glu
            100                 105                 110

Val Leu Asp Pro Arg Ser Lys Arg Val Gln Arg Trp Asn Arg Ala Leu
        115                 120                 125

Leu Leu Ala Arg Gly Met Ala Leu Ala Val Asp Pro Leu Phe Phe Tyr
130                 135                 140

Ala Leu Ser Ile Gly Arg Thr Thr Gly Pro Ala Cys Leu Tyr Met Asp
145                 150                 155                 160

Gly Ala Phe Ala Ala Val Val Thr Val Leu Arg Thr Cys Leu Asp Ala
                165                 170                 175

Val His Leu Trp His Val Trp Leu Gln Phe Arg Leu Ala Tyr Val Ser
            180                 185                 190

Arg Glu Ser Leu Val Val Gly Cys Gly Lys Leu Val Trp Asp Pro Arg
        195                 200                 205

Ala Ile Ala Ser His Tyr Ala Arg Ser Leu Thr Gly Phe Trp Phe Asp
210                 215                 220

Val Ile Val Ile Leu Pro Val Pro Gln Ala Val Phe Trp Leu Val Val
225                 230                 235                 240

Pro Lys Leu Ile Arg Glu Glu Lys Val Lys Leu Ile Met Thr Ile Leu
                245                 250                 255

Leu Leu Ile Phe Leu Phe Gln Phe Leu Pro Lys Ile Tyr His Cys Ile
            260                 265                 270

Cys Leu Met Arg Arg Met Gln Lys Val Thr Gly Tyr Ile Phe Gly Thr
        275                 280                 285

Ile Trp Trp Gly Phe Ala Leu Asn Leu Ile Ala Tyr Phe Ile Ala Ser
290                 295                 300

His Val Ala Gly Gly Cys Trp Tyr Val Leu Ala Ile Gln Arg Val Ala
305                 310                 315                 320

Ser Cys Ile Arg Gln Gln Cys Met Arg Thr Gly Asn Cys Asn Leu Ser
                325                 330                 335

Leu Ala Cys Lys Glu Glu Val Cys Tyr Gln Phe Val Ser Pro Thr Ser
            340                 345                 350

Thr Val Gly Tyr Pro Cys Leu Ser Gly Asn Leu Thr Ser Val Val Asn
        355                 360                 365

Lys Pro Met Cys Leu Asp Ser Asn Gly Pro Phe Arg Tyr Gly Ile Tyr
370                 375                 380

Arg Trp Ala Leu Pro Val Ile Ser Ser Asn Ser Leu Ala Val Lys Ile
385                 390                 395                 400

Leu Tyr Pro Ile Phe Trp Gly Leu Met Thr Leu Ser Thr Phe Ala Asn
                405                 410                 415

Asp Leu Glu Pro Thr Ser Asn Trp Leu Glu Val Ile Phe Ser Ile Val
            420                 425                 430

Met Val Leu Ser Gly Leu Leu Leu Phe Thr Leu Leu Ile Gly Asn Ile
        435                 440                 445

Gln Val Phe Leu His Ala Val Met Ala Lys Lys Arg Lys Met Gln Ile
450                 455                 460

Arg Cys Arg Asp Met Glu Trp Trp Met Lys Arg Arg Gln Leu Pro Ser

```
                465                 470                 475                 480
        Arg Leu Arg Gln Arg Val Arg Phe Glu Arg Gln Arg Trp Asn Ala
                        485                 490                 495

Leu Gly Gly Glu Asp Glu Leu Glu Leu Ile His Asp Leu Pro Pro Gly
                        500                 505                 510

Leu Arg Arg Asp Ile Lys Arg Tyr Leu Cys Phe Asp Leu Ile Asn Lys
                        515                 520                 525

Val Pro Leu Phe Arg Gly Met Asp Asp Leu Ile Leu Asp Asn Ile Cys
        530                 535                 540

Asp Arg Ala Lys Pro Arg Val Phe Ser Lys Asp Glu Lys Ile Ile Arg
        545                 550                 555                 560

Glu Gly Asp Pro Val Gln Arg Met Ile Phe Ile Met Arg Gly Arg Val
                        565                 570                 575

Lys Arg Ile Gln Ser Leu Ser Lys Gly Val Leu Ala Thr Ser Thr Leu
                        580                 585                 590

Glu Pro Gly Gly Tyr Leu Gly Asp Glu Leu Leu Ser Trp Cys Leu Arg
                        595                 600                 605

Arg Pro Phe Leu Asp Arg Leu Pro Ser Ser Ala Thr Phe Val Cys
        610                 615                 620

Leu Glu Asn Ile Glu Ala Phe Ser Leu Gly Ser Glu Asp Leu Arg Tyr
        625                 630                 635                 640

Ile Thr Asp His Phe Arg Tyr Lys Phe Ala Asn Glu Arg Leu Lys Arg
                        645                 650                 655

Thr Ala Arg Tyr Tyr Ser Ser Asn Trp Arg Thr Trp Ala Ala Val Asn
                        660                 665                 670

Ile Gln Met Ala Trp Arg Arg Arg Lys Arg Thr Arg Gly Glu Asn
                        675                 680                 685

Ile Gly Gly Ser Met Ser Pro Val Ser Glu Asn Ser Ile Glu Gly Asn
                        690                 695                 700

Ser Glu Arg Arg Leu Leu Gln Tyr Ala Ala Met Phe Met Ser Ile Arg
        705                 710                 715                 720

Pro His Asp His Leu Glu
                        725

<210> SEQ ID NO 81
<211> LENGTH: 365
<212> TYPE: PRT
<213> ORGANISM: Oryza sativa Japonica Group

<400> SEQUENCE: 81

Ala Gly Ser Asp Glu Val Asn Arg Asn Glu Cys Lys Thr Val Val Pro
        1               5                   10                  15

Leu His Thr Trp Val Leu Ile Ser Asn Phe Lys Leu Ser Tyr Asn Ile
                        20                  25                  30

Leu Arg Arg Ala Asp Gly Thr Phe Glu Arg Asp Leu Gly Glu Tyr Leu
                        35                  40                  45

Asp Arg Arg Val Pro Ala Asn Ala Arg Pro Leu Glu Gly Val Ser Ser
                        50                  55                  60

Phe Asp His Ile Ile Asp Gln Ser Val Gly Leu Glu Val Arg Ile Tyr
        65                  70                  75                  80

Arg Ala Ala Ala Glu Gly Asp Ala Glu Glu Gly Ala Ala Val Thr
                        85                  90                  95

Arg Pro Ile Leu Glu Phe Leu Thr Asp Ala Pro Ala Ala Glu Pro Phe
                        100                 105                 110
```

```
Pro Val Ile Ile Phe His Gly Gly Ser Phe Val Ser Ser Ala
            115                 120                 125

Ser Ser Thr Ile Tyr Asp Ser Leu Cys Arg Arg Phe Val Lys Leu Ser
130                 135                 140

Lys Gly Val Val Val Ser Val Asn Tyr Arg Arg Ala Pro Glu His Arg
145                 150                 155                 160

Tyr Pro Cys Ala Tyr Asp Asp Gly Trp Thr Ala Leu Lys Trp Val Met
                165                 170                 175

Ser Gln Pro Phe Met Arg Ser Gly Gly Asp Ala Gln Ala Arg Val Phe
            180                 185                 190

Leu Ser Gly Asp Ser Ser Gly Gly Asn Ile Ala His His Val Ala Val
                195                 200                 205

Arg Ala Ala Asp Glu Gly Val Lys Val Cys Gly Asn Ile Leu Leu Asn
210                 215                 220

Ala Met Phe Gly Gly Thr Glu Arg Thr Glu Ser Glu Arg Arg Leu Asp
225                 230                 235                 240

Gly Lys Tyr Phe Val Thr Leu Gln Asp Arg Asp Trp Tyr Trp Lys Ala
                245                 250                 255

Tyr Leu Pro Glu Asp Ala Asp Arg Asp His Pro Ala Cys Asn Pro Phe
            260                 265                 270

Gly Pro Asn Gly Arg Arg Leu Gly Gly Leu Pro Phe Ala Lys Ser Leu
                275                 280                 285

Ile Ile Val Ser Gly Leu Asp Leu Thr Cys Asp Arg Gln Leu Ala Tyr
            290                 295                 300

Ala Asp Ala Leu Arg Glu Asp Gly His His Val Lys Val Val Gln Cys
305                 310                 315                 320

Glu Asn Ala Thr Val Gly Phe Tyr Leu Leu Pro Asn Thr Val His Tyr
                325                 330                 335

His Glu Val Met Glu Glu Ile Ser Asp Phe Leu Asn Ala Asn Leu Tyr
                340                 345                 350

Tyr Gly Ser His His His His His His His His
            355                 360                 365

<210> SEQ ID NO 82
<211> LENGTH: 390
<212> TYPE: PRT
<213> ORGANISM: Zea mays

<400> SEQUENCE: 82

Met Gln Ser Ala Ala Ala Ile Gly Leu Leu Arg Pro Cys Ala Ala Arg
1               5                   10                  15

Pro Leu Ala Ala Tyr Thr Ser Pro Arg Arg Gly Ala Gly Ala Cys Ser
            20                  25                  30

Gly Gly Thr Gln Pro Ile Ile Thr Pro Arg Gly Ile Arg Leu Ser Ala
        35                  40                  45

Arg Pro Gly Leu Val Pro Ala Ser Pro Leu Glu Glu Lys Glu Asn Arg
50                  55                  60

Arg Cys Arg Ala Ser Met His Thr Ala Ala Ser Ala Gly Glu Glu Ala
65                  70                  75                  80

Gly Gly Gly Leu Ala Lys Thr Leu Gln Leu Gly Ala Leu Phe Gly Leu
                85                  90                  95

Trp Tyr Leu Phe Asn Ile Tyr Phe Asn Ile Tyr Asn Lys Gln Val Leu
            100                 105                 110

Lys Val Leu Pro Tyr Pro Ile Asn Ile Thr Thr Val Gln Phe Ala Val
            115                 120                 125
```

Gly Ser Ala Ile Ala Leu Phe Met Trp Ile Thr Gly Ile His Lys Arg
                130                 135                 140

Pro Lys Ile Ser Gly Ala Gln Leu Phe Ala Ile Leu Pro Leu Ala Ile
145                 150                 155                 160

Val His Thr Met Gly Asn Leu Phe Thr Asn Met Ser Leu Gly Lys Val
                165                 170                 175

Ala Val Ser Phe Thr His Thr Ile Lys Ala Met Glu Pro Phe Phe Ser
            180                 185                 190

Val Leu Leu Ser Ala Ile Phe Leu Gly Glu Leu Pro Thr Pro Trp Val
        195                 200                 205

Val Leu Ser Leu Leu Pro Ile Val Gly Val Ala Leu Ala Ser Leu
    210                 215                 220

Thr Glu Ala Ser Phe Asn Trp Ala Gly Phe Trp Ser Ala Met Ala Ser
225                 230                 235                 240

Asn Val Thr Phe Gln Ser Arg Asn Val Leu Ser Lys Lys Leu Met Val
                245                 250                 255

Lys Lys Glu Glu Ser Leu Asp Asn Ile Asn Leu Phe Ser Ile Ile Thr
            260                 265                 270

Val Met Ser Phe Phe Leu Leu Ala Pro Val Thr Leu Leu Thr Glu Gly
        275                 280                 285

Val Lys Val Ser Pro Ala Val Leu Gln Ser Ala Gly Leu Asn Leu Lys
    290                 295                 300

Gln Val Tyr Thr Arg Ser Leu Ile Ala Ala Cys Cys Phe His Ala Tyr
305                 310                 315                 320

Gln Gln Val Ser Tyr Met Ile Leu Ala Arg Val Ser Pro Val Thr His
                325                 330                 335

Ser Val Gly Asn Cys Val Lys Arg Val Val Ile Val Thr Ser Val
            340                 345                 350

Leu Phe Phe Arg Thr Pro Val Ser Pro Ile Asn Ser Leu Gly Thr Gly
        355                 360                 365

Ile Ala Leu Ala Gly Val Phe Leu Tyr Ser Gln Leu Lys Arg Leu Lys
    370                 375                 380

Pro Lys Pro Lys Thr Ala
385                 390

<210> SEQ ID NO 83
<211> LENGTH: 504
<212> TYPE: PRT
<213> ORGANISM: Arabidopsis thaliana

<400> SEQUENCE: 83

Met Val Ser Leu Leu Ser Phe Phe Leu Leu Leu Val Pro Ile Phe
1               5                   10                  15

Phe Leu Leu Ile Phe Thr Lys Lys Ile Lys Glu Ser Lys Gln Asn Leu
                20                  25                  30

Pro Pro Gly Pro Ala Lys Leu Pro Ile Ile Gly Asn Leu His Gln Leu
            35                  40                  45

Gln Gly Leu Leu His Lys Cys Leu His Asp Leu Ser Lys Lys His Gly
        50                  55                  60

Pro Val Met His Leu Arg Leu Gly Phe Ala Pro Met Val Val Ile Ser
65                  70                  75                  80

Ser Ser Glu Ala Ala Glu Glu Ala Leu Lys Thr His Asp Leu Glu Cys
                85                  90                  95

Cys Ser Arg Pro Ile Thr Met Ala Ser Arg Val Phe Ser Arg Asn Gly

```
            100                 105                 110
Lys Asp Ile Gly Phe Gly Val Tyr Gly Asp Glu Trp Arg Glu Leu Arg
            115                 120                 125
Lys Leu Ser Val Arg Glu Phe Phe Ser Val Lys Lys Val Gln Ser Phe
            130                 135                 140
Lys Tyr Ile Arg Glu Glu Asn Asp Leu Met Ile Lys Lys Leu Lys
145                 150                 155                 160
Glu Leu Ala Ser Lys Gln Ser Pro Val Asp Leu Ser Lys Ile Leu Phe
            165                 170                 175
Gly Leu Thr Ala Ser Ile Ile Phe Arg Thr Ala Phe Gly Gln Ser Phe
            180                 185                 190
Phe Asp Asn Lys His Val Asp Gln Glu Ser Ile Lys Glu Leu Met Phe
            195                 200                 205
Glu Ser Leu Ser Asn Met Thr Phe Arg Phe Ser Asp Phe Phe Pro Thr
            210                 215                 220
Ala Gly Leu Lys Trp Phe Ile Gly Phe Val Ser Gly Gln His Lys Arg
225                 230                 235                 240
Leu Tyr Asn Val Phe Asn Arg Val Asp Thr Phe Phe Asn His Ile Val
            245                 250                 255
Asp Asp His His Ser Lys Lys Ala Thr Gln Asp Arg Pro Asp Met Val
            260                 265                 270
Asp Ala Ile Leu Asp Met Ile Asp Asn Glu Gln Gln Tyr Ala Ser Phe
            275                 280                 285
Lys Leu Thr Val Asp His Leu Lys Gly Val Leu Ser Asn Ile Tyr His
            290                 295                 300
Ala Gly Ile Asp Thr Ser Ala Ile Thr Leu Ile Trp Ala Met Ala Glu
305                 310                 315                 320
Leu Val Arg Asn Pro Arg Val Met Lys Lys Ala Gln Asp Glu Ile Arg
            325                 330                 335
Thr Cys Ile Gly Ile Lys Gln Glu Gly Arg Ile Met Glu Glu Asp Leu
            340                 345                 350
Asp Lys Leu Gln Tyr Leu Lys Leu Val Val Lys Glu Thr Leu Arg Leu
            355                 360                 365
His Pro Ala Ala Pro Leu Leu Leu Pro Arg Glu Thr Met Ala Asp Ile
            370                 375                 380
Lys Ile Gln Gly Tyr Asp Ile Pro Gln Lys Arg Ala Leu Leu Val Asn
385                 390                 395                 400
Ala Trp Ser Ile Gly Arg Asp Pro Glu Ser Trp Lys Asn Pro Glu Glu
            405                 410                 415
Phe Asn Pro Glu Arg Phe Ile Asp Cys Pro Val Asp Tyr Lys Gly His
            420                 425                 430
Ser Cys Glu Leu Leu Pro Phe Gly Ser Gly Arg Arg Ile Cys Pro Gly
            435                 440                 445
Ile Ala Met Ala Ile Ala Thr Ile Glu Leu Gly Leu Leu Asn Leu Leu
            450                 455                 460
Tyr Phe Phe Asp Trp Asn Met Pro Glu Lys Lys Lys Asp Met Asp Met
465                 470                 475                 480
Glu Glu Ala Gly Asp Leu Thr Val Asp Lys Lys Val Pro Leu Glu Leu
            485                 490                 495
Leu Pro Val Ile Arg Ile Ser Leu
            500

<210> SEQ ID NO 84
```

```
<211> LENGTH: 387
<212> TYPE: PRT
<213> ORGANISM: Pseudomonas syringae pv. tomato str. DC3000

<400> SEQUENCE: 84
```

| | | | | | | | | | | | | | | |
|---|---|---|---|---|---|---|---|---|---|---|---|---|---|---|
|Met|Thr|Val|Leu|Lys|Met|Thr|Asp|Leu|Asp|Leu|Gln|Gly|Lys|Arg|Val
|1| | | |5| | | | |10| | | | |15|

Leu Ile Arg Glu Asp Leu Asn Val Pro Ile Lys Asp Gly Val Val Ser
            20                  25                  30

Ser Asp Ala Arg Ile Leu Ala Ser Leu Pro Thr Ile Arg Leu Ala Leu
        35                  40                  45

Glu Lys Gly Ala Ala Val Met Val Cys Ser His Leu Gly Arg Pro Thr
    50                  55                  60

Glu Gly Glu Phe Ser Ala Glu Asn Ser Leu Lys Pro Val Ala Glu Tyr
65                  70                  75                  80

Leu Ser Lys Ala Leu Gly Arg Asp Val Pro Leu Val Ala Asp Tyr Leu
                85                  90                  95

Asp Gly Val Asp Val Lys Ala Gly Asp Ile Val Leu Phe Glu Asn Val
            100                 105                 110

Arg Phe Asn Lys Gly Glu Lys Lys Asn Ala Asp Glu Leu Ala Gln Lys
        115                 120                 125

Tyr Ala Ala Leu Cys Asp Val Phe Val Met Asp Ala Phe Gly Thr Ala
    130                 135                 140

His Arg Ala Glu Gly Ser Thr His Gly Val Ala Lys Tyr Ala Lys Val
145                 150                 155                 160

Ala Ala Ala Gly Pro Leu Leu Ala Ala Glu Leu Glu Ala Leu Gly Lys
                165                 170                 175

Ala Leu Gly Ala Pro Ala Gln Pro Met Ala Ala Ile Val Ala Gly Ser
            180                 185                 190

Lys Val Ser Thr Lys Leu Asp Val Leu Asn Ser Leu Ser Ala Ile Cys
        195                 200                 205

Asp Gln Leu Ile Val Gly Gly Gly Ile Ala Asn Thr Phe Leu Ala Ala
    210                 215                 220

Ala Gly His Lys Val Gly Lys Ser Leu Tyr Glu Pro Asp Leu Leu Asp
225                 230                 235                 240

Thr Ala Arg Ala Ile Ala Ala Lys Val Ser Val Pro Leu Pro Thr Asp
                245                 250                 255

Val Val Val Ala Lys Glu Phe Ala Glu Ser Ala Thr Ala Thr Val Lys
            260                 265                 270

Leu Ile Ala Asp Val Ala Asp Asp Met Ile Leu Asp Ile Gly Pro
        275                 280                 285

Gln Thr Ala Ala His Phe Ala Glu Leu Leu Lys Ser Ser Gly Thr Ile
    290                 295                 300

Leu Trp Asn Gly Pro Val Gly Val Phe Glu Phe Asp Gln Phe Gly Glu
305                 310                 315                 320

Gly Thr Lys Thr Leu Ala Lys Ala Ile Ala Glu Ser Lys Ala Phe Ser
                325                 330                 335

Ile Ala Gly Gly Gly Asp Thr Leu Ala Ala Ile Asp Lys Tyr Gly Val
            340                 345                 350

Ala Asp Gln Ile Ser Tyr Ile Ser Thr Gly Gly Gly Ala Phe Leu Glu
        355                 360                 365

Phe Val Glu Gly Lys Val Leu Pro Ala Val Glu Met Leu Glu Gln Arg
    370                 375                 380

Ala Arg Ala

385

<210> SEQ ID NO 85
<211> LENGTH: 387
<212> TYPE: PRT
<213> ORGANISM: Pseudomonas syringae pv. phaseolicola 1448A

<400> SEQUENCE: 85

Met Thr Val Leu Lys Met Thr Asp Leu Asp Leu Gln Gly Lys Arg Val
1               5                   10                  15

Leu Ile Arg Glu Asp Leu Asn Val Pro Val Lys Asp Gly Val Val Ser
            20                  25                  30

Ser Asp Ala Arg Ile Leu Ala Ser Leu Pro Thr Ile Arg Leu Ala Leu
        35                  40                  45

Glu Lys Gly Ala Ala Val Met Val Cys Ser His Leu Gly Arg Pro Thr
50                  55                  60

Glu Gly Glu Phe Ser Ala Glu Asn Ser Leu Lys Pro Val Ala Asp Tyr
65                  70                  75                  80

Leu Ser Lys Ala Leu Gly Arg Asp Val Pro Leu Val Ala Asp Tyr Leu
                85                  90                  95

Asp Gly Val Asp Val Lys Ala Gly Asp Val Val Leu Phe Glu Asn Val
            100                 105                 110

Arg Phe Asn Lys Gly Glu Lys Lys Asn Ala Asp Glu Leu Ala Gln Lys
        115                 120                 125

Tyr Ala Ala Leu Cys Asp Val Phe Val Met Asp Ala Phe Gly Thr Ala
130                 135                 140

His Arg Ala Glu Gly Ser Thr His Gly Val Ala Lys Phe Ala Lys Val
145                 150                 155                 160

Ala Ala Ala Gly Pro Leu Leu Ala Ala Glu Leu Glu Ala Leu Gly Lys
                165                 170                 175

Ala Leu Gly Ala Pro Ala Gln Pro Met Thr Ala Ile Val Ala Gly Ser
            180                 185                 190

Lys Val Ser Thr Lys Leu Asp Val Leu Asn Ser Leu Ser Gly Ile Cys
        195                 200                 205

Asn Gln Leu Ile Val Gly Gly Gly Ile Ala Asn Thr Phe Leu Ala Ala
    210                 215                 220

Ala Gly His Lys Val Gly Lys Ser Leu Tyr Glu Pro Asp Leu Leu Asp
225                 230                 235                 240

Thr Ala Arg Ala Ile Ala Ala Lys Val Ser Val Pro Leu Pro Thr Asp
                245                 250                 255

Val Val Val Ala Lys Glu Phe Ala Glu Ser Ala Thr Ala Thr Val Lys
            260                 265                 270

Leu Ile Ala Asp Val Ala Asp Asp Met Ile Leu Asp Ile Gly Pro
        275                 280                 285

Gln Thr Ala Ala His Phe Ala Glu Leu Leu Lys Ser Ser Gly Thr Ile
290                 295                 300

Leu Trp Asn Gly Pro Val Gly Val Phe Glu Phe Asp Gln Phe Gly Glu
305                 310                 315                 320

Gly Thr Lys Thr Leu Ala Lys Ala Ile Gly Glu Ser Gln Ala Phe Ser
                325                 330                 335

Ile Ala Gly Gly Gly Asp Thr Leu Ala Ala Ile Asp Lys Tyr Gly Val
            340                 345                 350

Ala Glu Gln Ile Ser Tyr Ile Ser Thr Gly Gly Gly Ala Phe Leu Glu
        355                 360                 365

```
Phe Val Glu Gly Lys Val Leu Pro Ala Val Glu Val Leu Glu Gln Arg
                370                 375                 380

Ala Lys Ala
385

<210> SEQ ID NO 86
<211> LENGTH: 387
<212> TYPE: PRT
<213> ORGANISM: Pseudomonas syringae pv. syringae B728a

<400> SEQUENCE: 86

Met Thr Val Leu Lys Met Thr Asp Leu Asp Leu Gln Gly Lys Arg Val
1               5                   10                  15

Leu Ile Arg Glu Asp Leu Asn Val Pro Val Lys Asp Gly Val Val Ser
                20                  25                  30

Ser Asp Ala Arg Ile Leu Ala Ser Leu Pro Thr Ile Arg Leu Ala Leu
            35                  40                  45

Glu Lys Gly Ala Ala Val Met Val Cys Ser His Leu Gly Arg Pro Thr
50                  55                  60

Glu Gly Glu Phe Ser Ala Glu Asn Ser Leu Lys Pro Val Ala Asp Tyr
65                  70                  75                  80

Leu Ser Lys Ala Leu Gly Arg Asp Val Pro Leu Val Ala Asp Tyr Leu
                85                  90                  95

Asp Gly Val Asp Val Lys Ala Gly Glu Val Val Leu Phe Glu Asn Val
            100                 105                 110

Arg Phe Asn Lys Gly Glu Lys Lys Asn Ala Asp Glu Leu Ala Gln Gln
        115                 120                 125

Tyr Ala Ala Leu Cys Asp Val Phe Val Met Asp Ala Phe Gly Thr Ala
130                 135                 140

His Arg Ala Glu Gly Ser Thr His Gly Val Ala Lys Phe Ala Lys Val
145                 150                 155                 160

Ala Ala Ala Gly Pro Leu Leu Ala Ala Glu Leu Glu Ala Leu Gly Lys
                165                 170                 175

Ala Leu Gly Ala Pro Ala Gln Pro Met Thr Ala Ile Val Ala Gly Ser
            180                 185                 190

Lys Val Ser Thr Lys Leu Asp Val Leu Asn Ser Leu Ser Gly Ile Cys
        195                 200                 205

Asn Gln Leu Ile Val Gly Gly Gly Ile Ala Asn Thr Phe Leu Ala Ala
210                 215                 220

Ala Gly His Lys Val Gly Lys Ser Leu Tyr Glu Pro Asp Leu Leu Asp
225                 230                 235                 240

Thr Ala Arg Ala Ile Ala Ala Lys Val Ser Val Pro Leu Pro Thr Asp
                245                 250                 255

Val Val Val Ala Lys Glu Phe Ala Glu Ser Ala Ala Thr Val Lys
            260                 265                 270

Leu Ile Ala Asp Val Ala Asp Asp Met Ile Leu Asp Ile Gly Pro
        275                 280                 285

Gln Thr Ala Ala His Phe Ala Glu Leu Leu Lys Ser Ser Gly Thr Ile
290                 295                 300

Leu Trp Asn Gly Pro Val Gly Val Phe Glu Phe Asp Gln Phe Gly Glu
305                 310                 315                 320

Gly Thr Lys Thr Leu Ala Lys Ala Ile Ala Glu Ser Gln Ala Phe Ser
                325                 330                 335

Ile Ala Gly Gly Gly Asp Thr Leu Ala Ala Ile Asp Lys Tyr Gly Val
            340                 345                 350
```

Ala Gln Gln Ile Ser Tyr Ile Ser Thr Gly Gly Ala Phe Leu Glu
        355                 360                 365

Phe Val Glu Gly Lys Val Leu Pro Ala Val Glu Val Leu Glu Gln Arg
    370                 375                 380

Ala Lys Ala
385

<210> SEQ ID NO 87
<211> LENGTH: 393
<212> TYPE: PRT
<213> ORGANISM: Sorghum bicolor

<400> SEQUENCE: 87

Met Ser Leu Ile Arg Gly Met Gly Asn Ile Ala Lys Arg Trp Lys Glu
1               5                   10                  15

Leu Asn Gly Leu Asn Tyr Trp Lys Gly Leu Val Asp Pro Leu Asp Leu
            20                  25                  30

Asp Leu Arg Arg Asn Ile Ile Asn Tyr Gly Glu Leu Ser Gln Ala Ala
        35                  40                  45

Tyr Thr Gly Leu Asn Arg Glu Arg Arg Ser Arg Tyr Ala Gly Ser Cys
    50                  55                  60

Leu Phe Asn Arg Arg Asp Phe Leu Ser Arg Val Asp Val Ser Asn Pro
65                  70                  75                  80

Asn Leu Tyr Glu Ile Thr Lys Phe Ile Tyr Ala Met Cys Thr Val Ser
                85                  90                  95

Leu Pro Asp Gly Phe Met Val Lys Ser Leu Ser Lys Ala Ala Trp Ser
            100                 105                 110

Arg Gln Ser Asn Trp Met Gly Phe Val Ala Val Ala Thr Asp Glu Gly
        115                 120                 125

Lys Glu Val Leu Gly Arg Arg Asp Val Val Val Ala Trp Arg Gly Thr
    130                 135                 140

Ile Arg Met Val Glu Trp Met Asp Asp Leu Asp Ile Ser Leu Val Pro
145                 150                 155                 160

Ala Ser Glu Ile Val Leu Pro Gly Ser Ala Thr Asn Pro Cys Val His
                165                 170                 175

Gly Gly Trp Leu Ser Val Tyr Thr Ser Ala Asp Pro Gly Ser Gln Tyr
            180                 185                 190

Asn Lys Glu Ser Ala Arg His Gln Val Leu Asn Glu Val Lys Arg Ile
        195                 200                 205

Gln Asp Leu Tyr Lys Thr Glu Glu Thr Ser Ile Ser Ile Thr Gly His
    210                 215                 220

Ser Leu Gly Ala Ala Leu Ala Thr Ile Asn Ala Ile Asp Ile Val Ser
225                 230                 235                 240

Asn Gly Tyr Asn Arg Ser Cys Pro Val Ser Ala Phe Val Phe Gly Ser
                245                 250                 255

Pro Arg Val Gly Asn Pro Asp Phe Gln Glu Ala Phe Ser Ala Ala
            260                 265                 270

Asp Leu Arg Leu Leu Arg Val Arg Asn Ser Pro Asp Val Val Pro Lys
        275                 280                 285

Trp Pro Lys Leu Gly Tyr Ser Asp Val Gly Thr Glu Leu Arg Ile Asp
    290                 295                 300

Thr Gly Glu Ser Pro Tyr Leu Lys Ser Pro Gly Asn Pro Leu Thr Trp
305                 310                 315                 320

His Asp Met Glu Cys Tyr Met His Gly Val Ala Gly Ala Gln Gly Ser

```
                    325                 330                 335

Ser Gly Gly Phe Glu Leu Ala Val Asp Arg Asp Ile Ala Leu Val Asn
                340                 345                 350

Lys His Glu Asp Ala Leu Lys Asn Glu Phe Ala Val Pro Ser Ser Trp
            355                 360                 365

Trp Val Val Gln Asn Lys Asp Met Val Lys Gly Lys Asp Gly Arg Trp
370                 375                 380

His Leu Ala Asp His Glu Asp Asp
385                 390

<210> SEQ ID NO 88
<211> LENGTH: 512
<212> TYPE: PRT
<213> ORGANISM: Arabidopsis thaliana

<400> SEQUENCE: 88

Met Ala Thr Leu Leu Ala Thr Pro Ile Phe Ser Pro Leu Ala Ser Ser
1               5                   10                  15

Pro Ala Arg Asn Arg Leu Ser Cys Ser Asn Ile Arg Phe Gly Ser Lys
            20                  25                  30

Asn Gly Lys Ile Leu Asn Ser Asp Gly Ala Gln Lys Leu Asn Leu Ser
        35                  40                  45

Lys Phe Arg Lys Pro Asp Gly Gln Arg Phe Leu Gln Met Gly Ser Ser
    50                  55                  60

Lys Glu Met Asn Phe Glu Arg Lys Leu Ser Val Gln Ala Met Asp Gly
65                  70                  75                  80

Ala Gly Thr Gly Asn Thr Ser Thr Ile Ser Arg Asn Val Ile Ala Ile
                85                  90                  95

Ser His Leu Leu Val Ser Leu Gly Ile Ile Leu Ala Ala Asp Tyr Phe
            100                 105                 110

Leu Lys Gln Ala Phe Val Ala Ala Ser Ile Lys Phe Pro Ser Ala Leu
        115                 120                 125

Phe Gly Met Phe Cys Ile Phe Ser Val Leu Met Ile Phe Asp Ser Val
    130                 135                 140

Val Pro Ala Ala Ala Asn Gly Leu Met Asn Phe Phe Glu Pro Ala Phe
145                 150                 155                 160

Leu Phe Ile Gln Arg Trp Leu Pro Leu Phe Tyr Val Pro Ser Leu Val
                165                 170                 175

Val Leu Pro Leu Ser Val Arg Asp Ile Pro Ala Ala Ser Gly Val Lys
            180                 185                 190

Ile Cys Tyr Ile Val Ala Gly Gly Trp Leu Ala Ser Leu Cys Val Ala
        195                 200                 205

Gly Tyr Thr Ala Ile Ala Val Arg Lys Met Val Lys Thr Glu Met Thr
    210                 215                 220

Glu Ala Glu Pro Met Ala Lys Pro Ser Pro Phe Ser Thr Leu Glu Leu
225                 230                 235                 240

Trp Ser Trp Ser Gly Ile Phe Val Val Ser Phe Val Gly Ala Leu Phe
                245                 250                 255

Tyr Pro Asn Ser Leu Gly Thr Ser Ala Arg Thr Ser Leu Pro Phe Leu
            260                 265                 270

Leu Ser Ser Thr Val Leu Gly Tyr Ile Val Gly Ser Gly Leu Pro Ser
        275                 280                 285

Ser Ile Lys Lys Val Phe His Pro Ile Ile Cys Cys Ala Leu Ser Ala
    290                 295                 300
```

```
Val Leu Ala Ala Leu Ala Phe Gly Tyr Ala Ser Gly Ser Gly Leu Asp
305                 310                 315                 320

Pro Val Leu Gly Asn Tyr Leu Thr Lys Val Ala Ser Asp Pro Gly Ala
            325                 330                 335

Gly Asp Ile Leu Met Gly Phe Leu Gly Ser Val Ile Leu Ser Phe Ala
            340                 345                 350

Phe Ser Met Phe Lys Gln Arg Lys Leu Val Lys Arg His Ala Ala Glu
            355                 360                 365

Ile Phe Thr Ser Val Ile Val Ser Thr Val Phe Ser Leu Tyr Ser Thr
            370                 375                 380

Ala Leu Val Gly Arg Leu Val Gly Leu Glu Pro Ser Leu Thr Val Ser
385                 390                 395                 400

Ile Leu Pro Arg Cys Ile Thr Val Ala Leu Ala Leu Ser Ile Val Ser
            405                 410                 415

Leu Phe Glu Gly Thr Asn Ser Ser Leu Thr Ala Ala Val Val Val Val
            420                 425                 430

Thr Gly Leu Ile Gly Ala Asn Phe Val Gln Val Val Leu Asp Lys Leu
            435                 440                 445

Arg Leu Arg Asp Pro Ile Ala Arg Gly Ile Ala Thr Ala Ser Ser Ala
450                 455                 460

His Gly Leu Gly Thr Ala Ala Leu Ser Ala Lys Glu Pro Glu Ala Leu
465                 470                 475                 480

Pro Phe Cys Ala Ile Ala Tyr Ala Leu Thr Gly Ile Phe Gly Ser Leu
            485                 490                 495

Leu Cys Ser Val Pro Ala Val Arg Gln Ser Leu Leu Ala Val Val Gly
            500                 505                 510

<210> SEQ ID NO 89
<211> LENGTH: 311
<212> TYPE: PRT
<213> ORGANISM: Zea mays

<400> SEQUENCE: 89

Met Ala Arg Asn Glu Glu Lys Ala Gln Ser Met Leu Asn Arg Phe Ile
1               5                   10                  15

Thr Met Lys Gln Glu Glu Lys Arg Lys Pro Arg Glu Arg Arg Pro Tyr
            20                  25                  30

Leu Ala Ser Glu Cys Arg Asp Leu Ala Asp Ala Glu Arg Trp Arg Ser
            35                  40                  45

Glu Ile Leu Arg Glu Ile Gly Ala Lys Val Ala Glu Ile Gln Asn Glu
        50                  55                  60

Gly Leu Gly Glu His Arg Leu Arg Asp Leu Asn Asp Glu Ile Asn Lys
65                  70                  75                  80

Leu Leu Arg Glu Arg Gly His Trp Glu Arg Arg Ile Val Glu Leu Gly
            85                  90                  95

Gly Arg Asp Tyr Ser Arg Ser Ser Asn Ala Pro Leu Met Thr Asp Leu
            100                 105                 110

Asp Gly Asn Ile Val Ala Val Pro Asn Pro Ser Gly Arg Gly Pro Gly
            115                 120                 125

Tyr Arg Tyr Phe Gly Ala Ala Arg Lys Leu Pro Gly Val Arg Glu Leu
130                 135                 140

Phe Asp Lys Pro Pro Glu Met Arg Lys Arg Thr Arg Tyr Glu Ile
145                 150                 155                 160

His Lys Arg Ile Asn Ala Gly Tyr Tyr Gly Tyr Tyr Asp Asp Glu Asp
            165                 170                 175
```

Gly Val Leu Glu Arg Leu Glu Gly Pro Ala Glu Lys Arg Met Arg Glu
            180                 185                 190

Glu Ile Val Ser Glu Trp His Arg Val Glu Arg Val Arg Arg Glu Ala
        195                 200                 205

Met Lys Gly Val Met Ser Gly Glu Val Ala Ala Gly Gly Arg Ser
    210                 215                 220

Gly Glu Ala Ala Arg Glu Val Leu Phe Glu Gly Val Glu Glu Val
225                 230                 235                 240

Glu Glu Glu Arg Lys Arg Glu Glu Lys Arg Glu Arg Glu Lys Gly
                245                 250                 255

Glu Glu Val Gly Arg Glu Phe Val Ala His Val Pro Leu Pro Asp Glu
            260                 265                 270

Lys Glu Ile Glu Arg Met Val Leu Glu Arg Lys Lys Lys Glu Leu Leu
275                 280                 285

Ser Lys Tyr Ala Ser Asp Ser Leu Leu Val Glu Gln Glu Ala Lys
    290                 295                 300

Glu Met Leu Asn Val Arg Arg
305                 310

<210> SEQ ID NO 90
<211> LENGTH: 309
<212> TYPE: PRT
<213> ORGANISM: Sorghum bicolor

<400> SEQUENCE: 90

Met Ala Arg Asn Glu Glu Lys Ala Gln Ser Met Leu Asn Arg Phe Ile
1               5                   10                  15

Thr Met Lys Gln Glu Glu Lys Arg Lys Pro Arg Glu Arg Arg Pro Tyr
            20                  25                  30

Leu Ala Ser Glu Cys Arg Asp Leu Ala Asp Ala Glu Arg Trp Arg Ser
        35                  40                  45

Glu Ile Leu Arg Glu Ile Gly Ala Lys Val Ala Glu Ile Gln Asn Glu
    50                  55                  60

Gly Leu Gly Glu His Arg Leu Arg Asp Leu Asn Asp Glu Ile Asn Lys
65                  70                  75                  80

Leu Leu Arg Glu Arg Gly His Trp Glu Arg Arg Ile Val Glu Leu Gly
                85                  90                  95

Gly Arg Asp Tyr Ser Arg Ser Ser Asn Ala Pro Leu Met Thr Asp Leu
            100                 105                 110

Asp Gly Asn Ile Val Ala Val Pro Asn Pro Ser Gly Arg Gly Pro Gly
        115                 120                 125

Tyr Arg Tyr Phe Gly Ala Ala Arg Lys Leu Pro Gly Val Arg Glu Leu
    130                 135                 140

Phe Asp Lys Pro Pro Glu Met Arg Lys Arg Arg Thr Arg Tyr Glu Ile
145                 150                 155                 160

His Lys Arg Ile Asn Ala Gly Tyr Tyr Gly Tyr Tyr Asp Asp Glu Asp
                165                 170                 175

Gly Val Leu Glu Arg Leu Glu Ala Pro Ala Glu Lys Arg Met Arg Glu
            180                 185                 190

Glu Ile Val Ser Glu Trp His Arg Val Glu Arg Val Arg Arg Glu Ala
        195                 200                 205

Met Lys Gly Val Val Ser Gly Glu Val Ala Ala Gly Gly Arg Ser
    210                 215                 220

Gly Glu Ala Ala Arg Glu Val Leu Phe Glu Gly Val Glu Glu Val

```
                        225                 230                 235                 240
Glu Glu Glu Arg Lys Arg Glu Glu Lys Arg Glu Arg Glu Lys Gly
                245                 250                 255
Glu Glu Ala Glu Phe Val Ala His Val Pro Leu Pro Asp Glu Lys Glu
            260                 265                 270
Ile Glu Arg Met Val Leu Glu Arg Lys Lys Glu Leu Leu Ser Lys
        275                 280                 285
Tyr Ala Ser Asp Ser Leu Leu Val Glu Gln Glu Glu Ala Lys Glu Met
        290                 295                 300
Leu Asn Val Arg Arg
305

<210> SEQ ID NO 91
<211> LENGTH: 453
<212> TYPE: PRT
<213> ORGANISM: Arabidopsis thaliana
<220> FEATURE:
<221> NAME/KEY: misc_feature
<222> LOCATION: (327)..(327)
<223> OTHER INFORMATION: Xaa can be any naturally occurring amino acid

<400> SEQUENCE: 91

Met Ala Lys Val Tyr Trp Pro Tyr Phe Asp Pro Glu Tyr Glu Asn Leu
1               5                   10                  15
Ser Ser Arg Ile Asn Pro Pro Ser Val Ser Ile Asp Asn Thr Ser Cys
            20                  25                  30
Lys Glu Cys Thr Leu Val Lys Val Asp Ser Met Asn Lys Pro Gly Ile
        35                  40                  45
Leu Leu Glu Val Val Gln Val Leu Thr Asp Leu Asp Leu Thr Ile Thr
    50                  55                  60
Lys Ala Tyr Ile Ser Ser Asp Gly Gly Trp Phe Met Asp Val Phe His
65                  70                  75                  80
Val Thr Asp Gln Gln Gly Asn Lys Val Thr Asp Ser Lys Thr Ile Asp
                85                  90                  95
Tyr Ile Glu Lys Val Leu Gly Pro Lys Gly His Ala Ser Ala Ser Gln
            100                 105                 110
Asn Thr Trp Pro Gly Lys Arg Val Gly Val His Ser Leu Gly Asp His
        115                 120                 125
Thr Ser Ile Glu Ile Ile Ala Arg Asp Arg Pro Gly Leu Leu Ser Glu
    130                 135                 140
Val Ser Ala Val Leu Ala Asp Leu Asn Ile Asn Val Val Ala Ala Glu
145                 150                 155                 160
Ala Trp Thr His Asn Arg Arg Ile Ala Cys Val Leu Tyr Val Asn Asp
                165                 170                 175
Asn Ala Thr Ser Arg Ala Val Asp Asp Pro Glu Arg Leu Ser Ser Met
            180                 185                 190
Glu Glu Gln Leu Asn Asn Val Leu Arg Gly Cys Glu Glu Gln Asp Glu
        195                 200                 205
Lys Phe Ala Arg Thr Ser Leu Ser Ile Gly Ser Thr His Val Asp Arg
    210                 215                 220
Arg Leu His Gln Met Phe Phe Ala Asp Arg Asp Tyr Glu Ala Val Thr
225                 230                 235                 240
Lys Leu Asp Asp Ser Ala Ser Cys Gly Phe Glu Pro Lys Ile Thr Val
                245                 250                 255
Glu His Cys Glu Glu Lys Gly Tyr Ser Val Ile Asn Val Ser Cys Glu
            260                 265                 270
```

```
Asp Arg Pro Lys Leu Met Phe Asp Ile Val Cys Thr Leu Thr Asp Met
        275                 280                 285

Gln Tyr Ile Val Phe His Ala Thr Ile Ser Ser Ser Gly Ser His Ala
    290                 295                 300

Ser Gln Glu Tyr Phe Ile Arg His Lys Asp Gly Cys Thr Leu Asp Thr
305                 310                 315                 320

Glu Gly Glu Lys Glu Arg Xaa Val Lys Cys Leu Glu Ala Ala Ile His
                325                 330                 335

Arg Arg Val Ser Glu Gly Trp Ser Leu Glu Leu Cys Ala Lys Asp Arg
            340                 345                 350

Val Gly Leu Leu Ser Glu Val Thr Arg Ile Leu Arg Glu His Gly Leu
        355                 360                 365

Ser Val Ser Arg Ala Gly Val Thr Thr Val Gly Glu Gln Ala Val Asn
    370                 375                 380

Val Phe Tyr Val Lys Asp Ala Ser Gly Asn Pro Val Asp Val Lys Thr
385                 390                 395                 400

Ile Glu Ala Leu Arg Gly Glu Ile Gly His Ser Met Met Ile Asp Phe
                405                 410                 415

Lys Asn Lys Val Pro Ser Arg Lys Trp Lys Glu Glu Gly Gln Ala Gly
            420                 425                 430

Thr Gly Gly Gly Trp Ala Lys Thr Ser Phe Phe Gly Asn Leu Leu
        435                 440                 445

Glu Lys Leu Leu Pro
    450

<210> SEQ ID NO 92
<211> LENGTH: 143
<212> TYPE: PRT
<213> ORGANISM: Arabidopsis thaliana

<400> SEQUENCE: 92

Met Gln Glu Leu Gly Leu Gln Arg Phe Ser Asn Asp Val Val Arg Leu
1               5                   10                  15

Asp Leu Thr Pro Pro Ser Gln Thr Ser Ser Thr Ser Leu Ser Ile Asp
            20                  25                  30

Glu Glu Glu Ser Thr Glu Ala Lys Ile Arg Arg Leu Ile Ser Glu His
        35                  40                  45

Pro Val Ile Ile Phe Ser Arg Ser Ser Cys Cys Met Cys His Val Met
    50                  55                  60

Lys Arg Leu Leu Ala Thr Ile Gly Val Ile Pro Thr Val Ile Glu Leu
65                  70                  75                  80

Asp Asp His Glu Val Ser Ser Leu Pro Thr Ala Leu Gln Asp Glu Tyr
                85                  90                  95

Ser Gly Gly Val Ser Val Val Gly Pro Pro Ala Val Phe Ile Gly
            100                 105                 110

Arg Glu Cys Val Gly Gly Leu Glu Ser Leu Val Ala Leu His Leu Ser
        115                 120                 125

Gly Gln Leu Val Pro Lys Leu Val Gln Val Gly Ala Leu Trp Val
    130                 135                 140

<210> SEQ ID NO 93
<211> LENGTH: 942
<212> TYPE: PRT
<213> ORGANISM: Zea mays

<400> SEQUENCE: 93
```

```
Met Glu Gly Asp Asp Phe Thr Pro Glu Gly Lys Leu Pro Glu Phe
1               5                   10                  15

Lys Leu Asp Ala Arg Gln Ala Gln Gly Phe Ile Ser Phe Lys Lys
                20                  25                  30

Leu Pro Gln Asp Pro Arg Ala Val Arg Leu Phe Asp Arg Arg Asp Tyr
            35                  40                  45

Tyr Thr Ala His Gly Glu Asn Ala Thr Phe Ile Ala Arg Thr Tyr Tyr
    50                  55                  60

His Thr Met Ser Ala Leu Arg Gln Leu Gly Ser Ser Asp Gly Ile
65                  70                  75                  80

Leu Ser Ala Ser Val Ser Lys Ala Met Phe Glu Thr Ile Ala Arg Asn
                85                  90                  95

Ile Leu Leu Glu Arg Thr Asp Cys Thr Leu Glu Leu Tyr Glu Gly Ser
            100                 105                 110

Gly Ser Asn Trp Arg Leu Thr Lys Ser Gly Thr Pro Gly Asn Ile Gly
        115                 120                 125

Ser Phe Glu Asp Ile Leu Phe Ala Asn Asn Asp Met Glu Asp Ser Pro
    130                 135                 140

Val Ile Val Ala Leu Phe Pro Ala Cys Arg Glu Ser Gln Leu Tyr Val
145                 150                 155                 160

Gly Leu Ser Phe Leu Asp Met Thr Asn Arg Lys Leu Gly Leu Ala Glu
            165                 170                 175

Phe Pro Glu Asp Ser Arg Phe Thr Asn Val Glu Ser Ala Leu Val Ala
        180                 185                 190

Leu Gly Cys Lys Glu Cys Leu Leu Pro Ala Asp Cys Glu Lys Ser Ile
    195                 200                 205

Asp Leu Asn Pro Leu Gln Asp Val Ile Ser Asn Cys Asn Val Leu Leu
210                 215                 220

Thr Glu Lys Lys Lys Ala Asp Phe Lys Ser Arg Asp Leu Ala Gln Asp
225                 230                 235                 240

Leu Gly Arg Ile Ile Arg Gly Ser Val Glu Pro Val Arg Asp Leu Leu
            245                 250                 255

Ser Gln Phe Asp Tyr Ala Leu Gly Pro Leu Gly Ala Leu Leu Ser Tyr
        260                 265                 270

Ala Glu Leu Leu Ala Asp Asp Thr Asn Tyr Gly Asn Tyr Thr Ile Glu
    275                 280                 285

Lys Tyr Asn Leu Asn Cys Tyr Met Arg Leu Asp Ser Ala Ala Val Arg
    290                 295                 300

Ala Leu Asn Ile Ala Glu Gly Lys Thr Asp Val Asn Lys Asn Phe Ser
305                 310                 315                 320

Leu Phe Gly Leu Met Asn Arg Thr Cys Thr Val Gly Met Gly Lys Arg
            325                 330                 335

Leu Leu Asn Arg Trp Leu Lys Gln Pro Leu Leu Asp Val Asn Glu Ile
        340                 345                 350

Asn Asn Arg Leu Asp Met Val Gln Ala Phe Val Glu Asp Pro Glu Leu
        355                 360                 365

Arg Gln Gly Leu Arg Gln Gln Leu Lys Arg Ile Ser Asp Ile Asp Arg
    370                 375                 380

Leu Thr His Ser Leu Arg Lys Lys Ser Ala Asn Leu Gln Pro Val Val
385                 390                 395                 400

Lys Leu Tyr Gln Ser Cys Ser Arg Ile Pro Tyr Ile Lys Gly Ile Leu
            405                 410                 415
```

```
Gln Gln Tyr Asn Gly Gln Phe Ser Thr Leu Ile Arg Ser Lys Phe Leu
            420                 425                 430
Glu Pro Leu Glu Glu Trp Met Ala Lys Asn Arg Phe Gly Arg Phe Ser
                435                 440                 445
Ser Leu Val Glu Thr Ala Ile Asp Leu Ala Gln Leu Glu Asn Gly Glu
        450                 455                 460
Tyr Arg Ile Ser Pro Leu Tyr Ser Ser Asp Leu Gly Val Leu Lys Asp
465                 470                 475                 480
Glu Leu Ser Val Val Glu Asn His Ile Asn Asn Leu His Val Asp Thr
                485                 490                 495
Ala Ser Asp Leu Asp Leu Ser Val Asp Lys Gln Leu Lys Leu Glu Lys
        500                 505                 510
Gly Ser Leu Gly His Val Phe Arg Met Ser Lys Lys Glu Glu Gln Lys
        515                 520                 525
Val Arg Lys Lys Leu Thr Gly Ser Tyr Leu Ile Ile Glu Thr Arg Lys
        530                 535                 540
Asp Gly Val Lys Phe Thr Asn Ser Lys Leu Lys Asn Leu Ser Asp Gln
545                 550                 555                 560
Tyr Gln Ala Leu Phe Gly Glu Tyr Thr Ser Cys Gln Lys Lys Val Val
                565                 570                 575
Gly Asp Val Val Arg Val Ser Gly Thr Phe Ser Glu Val Phe Glu Asn
            580                 585                 590
Phe Ala Ala Val Leu Ser Glu Leu Asp Val Leu Gln Ser Phe Ala Asp
                595                 600                 605
Leu Ala Thr Ser Cys Pro Val Pro Tyr Val Arg Pro Asp Ile Thr Ala
        610                 615                 620
Ser Asp Glu Gly Asp Ile Val Leu Leu Gly Ser Arg His Pro Cys Leu
625                 630                 635                 640
Glu Ala Gln Asp Gly Val Asn Phe Ile Pro Asn Asp Cys Thr Leu Val
                645                 650                 655
Arg Gly Lys Ser Trp Phe Gln Ile Ile Thr Gly Pro Asn Met Gly Gly
                660                 665                 670
Lys Ser Thr Phe Ile Arg Gln Val Gly Val Asn Val Leu Met Ala Gln
        675                 680                 685
Val Gly Ser Phe Val Pro Cys Asp Gln Ala Ser Ile Ser Val Arg Asp
        690                 695                 700
Cys Ile Phe Ala Arg Val Gly Ala Gly Asp Cys Gln Leu His Gly Val
705                 710                 715                 720
Ser Thr Phe Met Gln Glu Met Leu Glu Thr Ala Ser Ile Leu Lys Gly
                725                 730                 735
Ala Ser Asp Lys Ser Leu Ile Ile Ile Asp Glu Leu Gly Arg Gly Thr
            740                 745                 750
Ser Thr Tyr Asp Gly Phe Gly Leu Ala Trp Ala Ile Cys Glu His Leu
        755                 760                 765
Met Glu Val Thr Arg Ala Pro Thr Leu Phe Ala Thr His Phe His Glu
        770                 775                 780
Leu Thr Ala Leu Ala His Arg Asn Asp Glu His Gln His Ile Ser
785                 790                 795                 800
Asp Ile Gly Val Ala Asn Tyr His Val Gly Ala His Ile Asp Pro Leu
                805                 810                 815
Ser Arg Lys Leu Thr Met Leu Tyr Lys Val Glu Pro Gly Ala Cys Asp
            820                 825                 830
Gln Ser Phe Gly Ile His Val Ala Glu Phe Ala Asn Phe Pro Glu Ala
```

```
                  835                 840                 845
        Val Val Ala Leu Ala Lys Ser Lys Ala Ala Glu Leu Glu Asp Phe Ser
        850                 855                 860

Thr Thr Pro Thr Phe Ser Asp Asp Leu Lys Asp Glu Val Gly Ser Lys
        865                 870                 875                 880

Arg Lys Arg Val Phe Ser Pro Asp Asp Ile Thr Arg Gly Ala Ala Arg
                            885                 890                 895

Ala Arg Leu Phe Leu Glu Glu Phe Ala Ala Leu Pro Met Asp Glu Met
                            900                 905                 910

Asp Gly Ser Lys Ile Leu Glu Met Ala Thr Lys Met Lys Ala Asp Leu
                            915                 920                 925

Gln Lys Asp Ala Ala Asp Asn Pro Trp Leu Gln Gln Phe Phe
                            930                 935                 940

<210> SEQ ID NO 94
<211> LENGTH: 942
<212> TYPE: PRT
<213> ORGANISM: Sorghum bicolor

<400> SEQUENCE: 94

Met Glu Gly Asp Asp Phe Thr Pro Glu Gly Lys Leu Pro Glu Phe
1               5                   10                  15

Lys Leu Asp Ala Arg Gln Ala Gln Gly Phe Ile Ser Phe Phe Lys Arg
                20                  25                  30

Leu Pro Gln Asp Pro Arg Ala Val Arg Leu Phe Asp Arg Arg Asp Tyr
                35                  40                  45

Tyr Thr Ala His Gly Glu Asn Ala Thr Phe Ile Ala Arg Thr Tyr Tyr
            50                  55                  60

His Thr Met Ser Ala Leu Arg Gln Leu Gly Ser Ser Asp Gly Ile
65              70                  75                  80

Ser Ser Val Ser Val Ser Lys Ala Met Phe Glu Thr Ile Ala Arg Asn
                85                  90                  95

Ile Leu Leu Glu Arg Thr Asp Cys Thr Leu Glu Leu Tyr Glu Gly Ser
                100                 105                 110

Gly Ser Asn Trp Arg Leu Thr Lys Ser Gly Thr Pro Gly Asn Ile Gly
                115                 120                 125

Ser Phe Glu Asp Leu Leu Phe Ala Asn Asn Asp Met Gln Asp Ser Pro
130                 135                 140

Val Ile Val Ala Leu Phe Pro Val Cys Arg Glu Ser Gln Leu Tyr Val
145                 150                 155                 160

Gly Leu Ser Phe Leu Asp Met Thr Asn Arg Lys Leu Gly Leu Ala Glu
                165                 170                 175

Phe Pro Glu Asp Ser Arg Phe Thr Asn Val Glu Ser Ala Leu Val Ala
                180                 185                 190

Leu Gly Cys Lys Glu Cys Leu Leu Ser Glu Asp Cys Glu Lys Ser Ile
                195                 200                 205

Asp Leu Asn Pro Leu Arg Asp Ala Ile Ser Asn Cys Asn Val Leu Leu
                210                 215                 220

Thr Val Lys Lys Lys Ala Asp Phe Lys Ser Arg Asp Leu Ala Gln Asp
225                 230                 235                 240

Leu Gly Arg Ile Ile Arg Gly Ser Val Glu Pro Val Arg Asp Leu Leu
                245                 250                 255

Ser Gln Phe Asp Tyr Ala Leu Gly Pro Leu Gly Ala Leu Leu Ser Tyr
                260                 265                 270
```

```
Ala Glu Leu Leu Ala Asp Asp Thr Asn Tyr Gly Asn Tyr Thr Ile Glu
            275                 280                 285

Lys Tyr Asn Leu Asn Cys Tyr Met Arg Leu Asp Ser Ala Ala Val Arg
    290                 295                 300

Ala Leu Asn Ile Ser Glu Arg Lys Thr Asp Val Asn Lys Asn Phe Ser
305                 310                 315                 320

Leu Phe Gly Leu Met Asn Arg Thr Cys Thr Val Gly Met Gly Lys Arg
                325                 330                 335

Leu Leu Asn Arg Trp Leu Lys Gln Pro Leu Leu Asp Val Asn Glu Ile
            340                 345                 350

Asn Asn Arg Leu Asp Met Val Gln Ala Phe Val Glu Asp Pro Glu Leu
            355                 360                 365

Arg Gln Gly Leu Arg Gln Leu Lys Arg Ile Ser Asp Ile Asp Arg
    370                 375                 380

Leu Thr His Ala Leu Arg Lys Lys Ser Ala Thr Leu Gln Pro Val Val
385                 390                 395                 400

Lys Leu Tyr Gln Ser Cys Cys Arg Ile Ser Tyr Ile Lys Gly Ile Leu
                405                 410                 415

Glu Gln Tyr Asn Gly Gln Phe Ser Thr Leu Ile Arg Ser Lys Phe Leu
            420                 425                 430

Glu Pro Leu Glu Glu Trp Met Ala Glu Asp Arg Phe Gly Arg Phe Ser
        435                 440                 445

Ser Leu Val Glu Thr Thr Ile Asp Leu Gly Gln Leu Glu Asn Gly Glu
        450                 455                 460

Tyr Arg Ile Ser Pro Leu Tyr Ser Ser Asp Leu Gly Val Leu Lys Asp
465                 470                 475                 480

Glu Leu Ser Val Val Glu Asn His Ile Asn Asn Leu His Val Asp Thr
                485                 490                 495

Ala Ser Asp Leu Asp Leu Ser Val Asp Lys Gln Leu Lys Leu Glu Lys
            500                 505                 510

Gly Pro Leu Gly His Val Phe Arg Met Ser Lys Lys Glu Glu Gln Lys
            515                 520                 525

Val Arg Lys Lys Leu Thr Gly Ser Tyr Leu Ile Ile Glu Thr Arg Lys
    530                 535                 540

Asp Gly Val Lys Phe Thr Ser Ser Lys Leu Lys Lys Leu Ser Asp Gln
545                 550                 555                 560

Tyr Gln Ala Leu Phe Ala Glu Tyr Thr Ser Cys Gln Lys Lys Val Val
                565                 570                 575

Gly Asp Val Val Arg Val Ser Gly Ser Tyr Ser Glu Val Phe Glu Asn
            580                 585                 590

Phe Ala Ala Val Leu Ser Glu Leu Asp Val Leu Gln Ser Phe Ala Asp
            595                 600                 605

Leu Ala Thr Ser Cys Pro Val Pro Tyr Val Arg Pro Asp Ile Thr Val
    610                 615                 620

Ser Asp Glu Gly Asp Ile Val Leu Leu Gly Ser Arg His Pro Cys Leu
625                 630                 635                 640

Glu Ala Gln Asp Gly Val Asn Phe Ile Pro Asn Asp Cys Thr Leu Val
                645                 650                 655

Arg Gly Lys Ser Trp Phe Gln Ile Ile Thr Gly Pro Asn Met Gly Gly
            660                 665                 670

Lys Ser Thr Phe Ile Arg Gln Val Gly Val Asn Val Leu Met Ala Gln
            675                 680                 685

Val Gly Ser Phe Val Pro Cys Asp Gln Ala Ser Val Ser Val Arg Asp
```

```
                690               695               700
    Cys Ile Phe Ala Arg Val Gly Ala Gly Asp Cys Gln Leu His Gly Val
    705                 710                 715                 720

Ser Thr Phe Met Gln Glu Met Leu Glu Thr Ala Ser Ile Leu Lys Gly
                        725                 730                 735

Ala Ser Asp Lys Ser Leu Ile Ile Ile Asp Glu Leu Gly Arg Gly Thr
                    740                 745                 750

Ser Thr Tyr Asp Gly Phe Gly Leu Ala Trp Ala Ile Cys Glu His Leu
                755                 760                 765

Met Glu Val Thr Arg Ala Pro Thr Leu Phe Ala Thr His Phe His Glu
    770                 775                 780

Leu Thr Ala Leu Ala His Lys Asn Asp Glu His Gln Arg Val Ser
    785                 790                 795                 800

Asn Ile Gly Ile Ala Asn Tyr His Val Gly Ala His Ile Asp Pro Ser
                    805                 810                 815

Ser Arg Lys Leu Thr Met Leu Tyr Lys Val Glu Pro Gly Ala Cys Asp
                820                 825                 830

Gln Ser Phe Gly Ile His Val Ala Glu Phe Ala Asn Phe Pro Glu Ala
                835                 840                 845

Val Val Ala Leu Ala Lys Ser Lys Ala Ala Glu Leu Glu Asp Phe Ser
    850                 855                 860

Thr Thr Pro Thr Phe Ser Asp Asp Ser Lys Asp Glu Val Gly Ser Lys
    865                 870                 875                 880

Arg Lys Arg Val Phe Ser Pro Asp Asp Val Thr Arg Gly Ala Ala Arg
                    885                 890                 895

Ala Arg Leu Phe Leu Glu Asp Phe Ala Ala Leu Pro Val Asp Glu Met
                900                 905                 910

Asp Arg Ser Lys Ile Val Glu Met Val Thr Lys Met Lys Ser Asp Leu
                915                 920                 925

Gln Lys Asp Ala Ala Asp Asn Pro Trp Leu Gln Gln Phe Phe
    930                 935                 940

<210> SEQ ID NO 95
<211> LENGTH: 274
<212> TYPE: PRT
<213> ORGANISM: Glycine max

<400> SEQUENCE: 95

Met Arg Ala Lys Leu Phe Val Phe Pro Ile Arg Gly Arg Asn Trp Cys
    1               5                   10                  15

Phe Ser Arg Thr Ile Asp His Ser Leu Ser Ala Ser His Ala Ser Ser
                    20                  25                  30

Gln Ser Pro Ser Thr Leu Lys Asp Leu Trp Thr Asn Ile Asn Val Gly
                35                  40                  45

Asp Lys Pro Leu Asn Thr Lys Thr Glu Leu Phe Val Asp Tyr Ile Ala
    50                  55                  60

Asn Lys Met Asn Asn Ala Trp Ile Gly Leu Glu Lys Ala Pro Glu Gly
    65                  70                  75                  80

Ser Phe Lys Asn Lys Ile His Gly Leu Gly Leu Arg Leu Leu Ser Arg
                    85                  90                  95

Val Lys Pro Ser Glu Ile Phe Leu Lys Ser Ile Ser Lys Glu Ile Thr
                    100                 105                 110

Ser Val Glu Ile Ile Tyr Pro Ser Ser Leu Asn Ala Gln Leu Val Arg
                115                 120                 125
```

Arg Arg Leu Arg His Ile Ala Val Arg Gly Ala Val Ile His Arg Asn
    130                 135                 140

Tyr Leu Tyr Gly Leu Val Ser Leu Ile Pro Leu Thr Ser Ala Leu Ser
145                 150                 155                 160

Ile Leu Pro Leu Pro Asn Val Pro Phe Phe Trp Val Leu Phe Arg Thr
                165                 170                 175

Tyr Ser His Trp Arg Ala Leu Gln Gly Ser Glu Arg Leu Phe Gln Leu
                180                 185                 190

Val Ser Asp Asn Ser Lys Thr Ser Asn Thr Cys Thr Tyr Glu Lys Lys
            195                 200                 205

Thr Glu His Lys Glu Ser Lys Ser Gln Arg His Ser Ser Asn Glu Pro
    210                 215                 220

Cys Trp Val Leu Arg Pro Ser Lys Glu Leu Glu Asn Leu Val His Leu
225                 230                 235                 240

Glu Asp Gly Gln Glu Ser Phe Ser Gln His Ala Ile Ile Asn Ile Cys
                245                 250                 255

Lys Ile Tyr Asp Leu Asn Pro Val Asp Val Ile Lys Tyr Glu Lys Ser
            260                 265                 270

Val Phe

<210> SEQ ID NO 96
<211> LENGTH: 390
<212> TYPE: PRT
<213> ORGANISM: Zea mays

<400> SEQUENCE: 96

Met Gln Ser Ala Ala Ile Gly Leu Leu Arg Pro Cys Ala Ala Arg
1               5                   10                  15

Pro Leu Ala Ala Tyr Thr Ser Pro Arg Arg Gly Ala Gly Ala Cys Ser
                20                  25                  30

Gly Gly Thr Gln Pro Ile Ile Thr Pro Arg Gly Ile Arg Leu Ser Ala
            35                  40                  45

Arg Pro Gly Leu Val Pro Ala Ser Pro Leu Glu Glu Lys Glu Asn Arg
50                  55                  60

Arg Cys Arg Ala Ser Met His Ala Ala Ser Ala Gly Glu Glu Ala
65                  70                  75                  80

Gly Gly Gly Leu Ala Lys Thr Leu Gln Leu Gly Ala Leu Phe Gly Leu
                85                  90                  95

Trp Tyr Leu Phe Asn Ile Tyr Phe Asn Ile Tyr Asn Lys Gln Val Leu
                100                 105                 110

Lys Val Leu Pro Tyr Pro Ile Asn Ile Thr Thr Val Gln Phe Ala Val
            115                 120                 125

Gly Ser Ala Ile Ala Leu Phe Met Trp Ile Thr Gly Ile His Lys Arg
130                 135                 140

Pro Lys Ile Ser Gly Ala Gln Leu Phe Ala Ile Leu Pro Leu Ala Ile
145                 150                 155                 160

Val His Thr Met Gly Asn Leu Phe Thr Asn Met Ser Leu Gly Lys Val
                165                 170                 175

Ala Val Ser Phe Thr His Thr Ile Lys Ala Met Glu Pro Phe Phe Ser
            180                 185                 190

Val Leu Leu Ser Ala Ile Phe Leu Gly Glu Leu Pro Thr Pro Trp Val
            195                 200                 205

Val Leu Ser Leu Leu Pro Ile Val Gly Gly Val Ala Leu Ala Ser Leu
            210                 215                 220

```
Thr Glu Ala Ser Phe Asn Trp Ala Gly Phe Trp Ser Ala Met Ala Ser
225                 230                 235                 240

Asn Val Thr Phe Gln Ser Arg Asn Val Leu Ser Lys Lys Leu Met Val
            245                 250                 255

Lys Lys Glu Glu Ser Leu Asp Asn Ile Asn Leu Phe Ser Ile Ile Thr
        260                 265                 270

Val Met Ser Phe Phe Leu Leu Ala Pro Val Thr Leu Leu Thr Glu Gly
    275                 280                 285

Val Lys Val Ser Pro Ala Val Leu Gln Ser Ala Gly Leu Asn Leu Lys
290                 295                 300

Gln Val Tyr Thr Arg Ser Leu Ile Ala Ala Phe Cys Phe His Ala Tyr
305                 310                 315                 320

Gln Gln Val Ser Tyr Met Ile Leu Ala Arg Val Ser Pro Val Thr His
                325                 330                 335

Ser Val Gly Asn Cys Val Lys Arg Val Val Ile Val Thr Ser Val
            340                 345                 350

Leu Phe Phe Arg Thr Pro Val Ser Pro Ile Asn Ser Leu Gly Thr Gly
            355                 360                 365

Ile Ala Leu Ala Gly Val Phe Leu Tyr Ser Gln Leu Lys Arg Leu Lys
370                 375                 380

Pro Lys Pro Lys Thr Ala
385             390
```

<210> SEQ ID NO 97
<211> LENGTH: 2092
<212> TYPE: DNA
<213> ORGANISM: Artificial
<220> FEATURE:
<223> OTHER INFORMATION: Cold inducible promoter

<400> SEQUENCE: 97

```
cagatccacg ctcgctcggg tgtcgggtca gatcgatcca gttggcgcac gtaataatcc      60
ttttccccag aaggagtcga accccctcctc cccgtccaat ccaatcaaag cgaccaatcg    120
actggctgtc ctacacacac acaaaaccga ccgaggcgac acaccgcagc agtgatcatt    180
ctgagcattt gcagaaaaag gagaacgtcc cgaaatcctg gtggttgtat tgtgtgattg    240
ctcactcagt ccgtgcaggg tcagggtgaa gccaagccaa caacccaacg ctcgctggga    300
gtagggtcca ccggatttat tggcagtaca tcgctgtttg gtcctcctgc ccttcgctta    360
ttttttaatt cggcagacgt gcacagacag ggcaccaccg gaccaaggaa gggcgcacac    420
cgtcgtcagt caccaggtgg gtgtgatcag cagccgcttc tcttgtgctg ctttatagcg    480
tatgaaattc cagtgtccct gttccacctg catgcaattg gtttgactga caacatgat    540
agcaagtgat actatatata ttttataga ggaacacagt gaaaaaatat ttagtattat    600
tacgtgcatg aaattgtatt cacagttatc cctgatgcaa cgcaattgtt caatatatag    660
cagtatatat tatacgaagt atatatgtat atctaattt atgagaccgg gagaaggtgt    720
attcacagta cagtgcaggg ccatggccat gcagcccttg gggcctgaaa agggtcgcgt    780
gaagtggcca acgctgtgca attgcaacca aacaaacttt tggtggcggg gtccctgtcc    840
ctggccggct tgcccacag gccacagcgc atcacaccac cgctttatag cgccacccca    900
ccaccctcgt ctctccccc gtcgagcaca caacacaccc tcctcgtcct ccaatccaat    960
caacctggta gactcgcttc gcttctcccc cagctcggaa cggagctcct cgcagcagcc   1020
gccgatcaac ctgcgctcgg gctcagcgct ggaaggtgag agctcagtgc ctcgtcccgc   1080
```

```
ccgccccaaa tctggttctt gtgctggctc tggctgtgcg ctgcacgaat tctgcatctg    1140
gttctttcga gacgcaattc ccggaccgtg ggctttggtt tcggaggggg ccgagagtaa    1200
ggcgttagga ctttctccga gctgcaaggc cgctcgtcgt tgcggcattt ttcgtttcgc    1260
ttgtcctgtg atgagagatg tgcatttccc tttggcgggc ttaccgttcc ctgctcgtct    1320
gtatgtgtgt atgtttgtgt gacctttccc tcaacgccag gctcttctcc cctcttgctg    1380
tttctttcag cagtacagac gcgcatctgt acagcgcctt tcttcggtcc tgggttatga    1440
ttgatccgtt aacagttggt caccaagtgc tggctgttta atatgtacta aagcttctt     1500 ggtgccgctg cctctgccta tacgactttg tcgctgcct gcacaagtct cagccatctg     1560
tgggaacgtg tgtctctcac ctacctttca tattgcacta gctggattga atcattctgc    1620
tttggagaga tgtccggtca ttttttttta aatcattttc atctcgcgta ctagtttttg    1680
ttttgttttg cgagagagta attttttttt aatatttact gtctcctgtc ccatttgctg    1740
tttctttacc cagaaatttc caccagattc agtcaaacga aactcctgtg ctctttttt     1800 tctccctttc aaaagggtgt gtaaccgact accgactcag ataatataag tgcggtcaca    1860
tatcacatga tatcatctcg cctctctccc ttctcctgtg ttttattttc cttttttcta    1920
accacagcgt gatgaacttc ttttttttt ggggggggg gggggggtaa ctacagctta      1980
gcgaacatga atgggtagtt ttacaactaa tgcaacggct ggttcactga acaactgtag    2040
gtgttggaag agaatagcct gaaggttcac agtaaccttc atctgtcgga ag            2092
```

<210> SEQ ID NO 98
<211> LENGTH: 2516
<212> TYPE: DNA
<213> ORGANISM: Artificial
<220> FEATURE:
<223> OTHER INFORMATION: Seed preferred promoter

<400> SEQUENCE: 98

```
acactttat tatcgcgtca aatcagtacc tcaatcgata ttgtagccta gtgttcttat      60
taaatgggaa gaattcgagg acacactaat tccttgctaa cacacactta tgctccattt    120
ggatgtcgat attggagggc atggaactga attggtttca attacaaatc agccatgata    180
ttgtaatgag atgtaatttc aattctattc tttggatgtc actgaattgg agtttggaat    240
tgtgtggtcc aattccacct tatatagaag agggatgctc tgtattggga gagtgagttt    300
ctagttatag tctagcttcg ggaaattgag tctctcgttc caaatctcaa ttccatgtgc    360
aaccaaacaa tagaattctg gaaagctgat tccaattcct aattccgtgc tccaatatct    420
acatccaaac gggtgttaca taaatataga aatgacatat caaccatgca aaaccacatt    480
ggcgatgttg aacaaaggcg aacacccaca tactatgtac cgcacacggc atctcttcct   540
caaaggtcga accacgtgtg ttccatgcat gcgtggaaca tgcaaggttg tcacgtatag    600
ggaatgatga cacacgagag cgcctacaag gcaacaaaca ccttacgtac cacgtagagt    660
gcattttgct accacctgcc accggatgac atgtatgcat gcatgcgttg tgtacgcata    720
cactgctgtc tgctggtgcc caaagaccat ctagaacagc atcttttaat tctccatttc    780
cctcacgcca ttgctagtgc cttgcacatg ctcgcactcc ctaacacatc ttcctcccct    840
tatttttcgt tgccaattgc tagttgttca atgccacgt tttccttaca cagctgtagg     900
gcaccgtacc acgtagaatg cattcctcgc caccaacaga caacacggcc gggcatatgt    960
acgtcttacg ccggaccatc accagtatat atgatgctag gatcagtgg gcgcccttt      1020 tgcctcgtcc tcccggggcg gcattcctat gtcctaactg aagcaaccca cgcgccgcca    1080
```

```
tttctgttgc gaatgagtcc atggacatat gtgccaacag aacccctcgg aaggcaccat    1140
ctatctatct atctctcaag caatattata tttggcacct acgctcaagt acatagacag    1200
tgtgcacggc attgtgcagc tggaaagccc gcccgacacg agggctgcca atcgacagc     1260 tccgcgccct tggaaatcct agtcacttgt tcacaattga ccaatctacc cttgaagcac    1320
acggtggatg gtactgccac atttggctta tagggcata gaggacaatg aatgcaactg     1380
gagcgggaag gagagcttta atttgtaagt actcggtgaa cacggcacct gatgatgatg    1440
atgatggaca gcgaggaatt gttataaaag gcgcccgtcc ctcccatggc tcaagaacaa    1500
gggaatcgaa gccattccct cttcaagagg ggatcatcag attgggctta ttattcctta    1560
ttactccagg taattcttag tttgttgccc ttccaaacct ttacatctca tataagaatg    1620
attattacat gcaagattat gttgacatgc gtcgtcatgg tatttttttt aggcaaggat    1680
cggagttgct ctgaattgac tgaaccagat ctaccgtctt cggtacgcgc tcactccgcc    1740
ctctgccttt gttactgcca cgtttctctg aatgctctct tgtgtggtga ttgctgagag    1800
tggtttagct ggatctagaa ttacactctg aaatcgtgtt ctgcctgtgc tgattacttg    1860
ccgtcctttg tagcagcaaa atataggac atggtagtac gaaacgaaga tagaacctac     1920
acagcaatac gagaaatgtg taatttggtg cttagcggta tttatttaag cacatgttgg    1980
tgttataggg cacttggatt cagaagtttg ctgttaattt aggcacaggc ttcatactac    2040
atgggtcaat agtataggga ttcatattat aggcgatact ataataattt gttcgtctgc    2100
agagcttatt atttgccaaa attagatatt cctattctgt ttttgtttgt gtgctgttaa    2160
attgttaacg cctgaaggaa taaatataaa tgacgaaatt ttgatgttta tctctgctcc    2220
tttattgtga ccataagtca agatcagatg cacttgtttt aaatattgtt gtctgaagaa    2280
ataagtactg acagtatttt gatgcattga tctgcttgtt tgttgtaaca aaatttaaaa    2340
ataaagagtt tccttttttgt tgctctcctt acctcctgat ggtatctagt atctaccaac   2400
tgacactata ttgcttctct ttacatacgt atcttgctcg atgccttctc cctagtgttg    2460
accagtgtta ctcacatagt ctttgctcat ttcattgtaa tgcagatacc aagcgg        2516
```

<210> SEQ ID NO 99
<211> LENGTH: 1761
<212> TYPE: DNA
<213> ORGANISM: Artificial
<220> FEATURE:
<223> OTHER INFORMATION: Leaf preferred promoter

<400> SEQUENCE: 99

```
gacatggagg tggaaggcct gacgtagata gagaagatgc tcttagcttt cattgtcttt      60
cttttgtagt catctgattt acctctctcg tttatacaac tggtttttta aacactcctt     120
aacttttcaa attgtctctt tctttaccct agactagata attttaatgg tgattttgct     180
aatgtggcgc catgttagat agaggtaaaa tgaactagtt aaaagctcag agtgataaat     240
caggctctca aaaattcata aactgttttt taaatatcca atattttta catggaaaat      300 aataaaattt agtttagtat taaaaaattc agttgaatat agttttgtct tcaaaaatta     360
tgaaactgat cttaattatt tttccttaaa accgtgctct atcttgatg tctagtttga      420 gacgattata taatttttttt tgtgcttaac tacgacgagc tgaagtacgt agaaatacta    480
gtggagtcgt gccgcgtgtg cctgtagcca ctcgtacgct acagcccaag cgctagagcc     540
caagaggccg gaggtggaag gcgtcgcggc actatagcca ctcgccgcaa gagcccaaga     600
```

```
gaccggagct ggaaggatga gggtctgggt gttcacgaat tgcctggagg caggaggctc    660
gtcgtccgga gccacaggcg tggagacgtc cgggataagg tgagcagccg ctgcgatagg    720
ggcgcgtgtg aaccccgtcg cgccccacgg atggtataag aataaaggca ttccgcgtgc    780
aggattcacc cgttcgcctc tcaccttttc gctgtactca ctcgccacac acacccccctc    840 tccagctccg ttggagctcc ggacagcagc aggcgcgggg cggtcacgta gtaagcagct    900
ctcggctccc tctccccttg ctccatttga tagtgcaacc catcgagcta cgggcccacc    960
gtcttcggta cgcgctcact ccgccctctg cctttgttac tgccacgttt ctctgaatgc   1020
tctcttgtgt ggtgattgct gagagtggtt tagctggatc tagaattaca ctctgaaatc   1080
gtgttctgcc tgtgctgatt acttgccgtc ctttgtagca gcaaaatata gggacatggt   1140
agtacgaaac gaagatagaa cctacacagc aatacgagaa atgtgtaatt tggtgcttag   1200
cggtatttat ttaagcacat gttggtgtta tagggcactt ggattcagaa gtttgctgtt   1260
aatttaggca caggcttcat actacatggg tcaatagtat agggattcat attataggcg   1320
atactataat aatttgttcg tctgcagagc ttattatttg ccaaaattag atattcctat   1380
tctgtttttg tttgtgtgct gttaaattgt taacgcctga ggaataaat ataaatgacg   1440 aaattttgat gtttatctct gctcctttat tgtgaccata agtcaagatc agatgcactt   1500
gttttaaata ttgttgtctg aagaaataag tactgacagt attttgatgc attgatctgc   1560
ttgtttgttg taacaaaatt taaaaataaa gagtttcctt tttgttgctc tccttacctc   1620
ctgatggtat ctagtatcta ccaactgaca ctatattgct tctctttaca tacgtatctt   1680
gctcgatgcc ttctccctag tgttgaccag tgttactcac atagtctttg ctcatttcat   1740
tgtaatgcag ataccaagcg g                                              1761
```

<210> SEQ ID NO 100
<211> LENGTH: 2924
<212> TYPE: DNA
<213> ORGANISM: Artificial
<220> FEATURE:
<223> OTHER INFORMATION: Leaf preferred promoter

<400> SEQUENCE: 100

```
atgtgctggt gccccataag gtaggcacct aggtctgtgt ttgaagcatc gacagatttg     60
taaacatgtt cctatgaacc tatttctgat tgataatttg tcaaaactca tcatttgtct    120
tcatccttgc ctgcttgcgt tcacgtgaca aagtacgtgt atgtcttcgg cctttgctgt    180
gtatgtttcg cattgcttag atgtggtgaa agaacatcag aagatgcatt gatggcgtgc    240
ttaaaccagt gatgtgctcc aggtgttcct gcagtctgca gagatattta ctcttgtagt    300
cttgttgaca gcacagttgt atgtgatttc ttggatgtaa tgtaaaccaa atgaaagata    360
ggaacagttc gtcctcttcc gtatacgaag gtcactgtat catttgtcgt ggcacaagat    420
gatctgcagg caggactgca acatggtttc ttggactgtc ctgaatgccc gttcttgttc    480
tttagttgag ccagagcagc agcctggtgt cggtgcctga cctgacga agcacacggc    540 aaacaaacaa gtcgcagcag ctagcagggg cgttgccatc gccacaagcc cccaagagac    600
ccgccgagga aaagaaaaaa aaactacggc cgccgttgcc aagccgagcg tgcgaaccga    660
tccacggatg ggagatcaga gatcacccac cgcaggcggg cggcagtggc tggcgaggtg    720
cgtccacaga acctgctgca ggtccctgtc cgtcccggcg accccttttc taggcgagca    780
actccccatg gcagagctgc acgcagcagg gcccgtcgtt ggttgcagct taacccttt    840 ttgtttaac catacaatgc agagtcgcag aggtgaaaca ggacggaaat tacagaaaag    900
```

```
atggtggtgt gccagcagcc ccagcatgaa gaagatcagg acaaaagaaa agcttgtgat    960
tggtgacagc aacaggattg gattggagcc aagctaggca gtgagaggca ggcagcaaga   1020
cgcgtcagcc actgaaatcc agagggcaac ctcggcctca caactcatat cccttgtgc   1080
tgttgcgcgc cgtggttagc caggtgtgct gcagggggta ccatggcatg catcgataga   1140
tctcgaggga tccaaagaca tggaggtgga aggcctgacg tagatagaga agatgctctt   1200
agctttcatt gtctttcttt tgtagtcatc tgatttacct ctctcgttta tacaactggt   1260
ttttttaaaca ctccttaact tttcaaattg tctctttctt taccctagac tagataattt   1320
taatggtgat tttgctaatg tggcgccatg ttagatagag gtaaaatgaa ctagttaaaa   1380
gctcagagtg ataaatcagg ctctcaaaaa ttcataaact gttttttaaa tatccaaata   1440
tttttacatg gaaaataata aaatttagtt tagtattaaa aaattcagtt gaatatagtt   1500
ttgtcttcaa aaattatgaa actgatctta attattttttc cttaaaaccg tgctctatct   1560
ttgatgtcta gtttgagacg attatataat tttttttgtg cttaactacg acagctgaa   1620
gtacgtagaa atactagtgg agtcgtgccg cgtgtgcctg tagccactcg tacgctacag   1680
cccaagcgct agagcccaag aggccggagg tggaaggcgt cgcggcacta tagccactcg   1740
ccgcaagagc ccaagagacc ggagctggaa ggatgagggt ctgggtgttc acgaattgcc   1800
tggaggcagg aggctcgtcg tccggagcca caggcgtgga gacgtccggg ataaggtgag   1860
cagccgctgc gatagggggcg cgtgtgaacc ccgtcgcgcc ccacggatgg tataagaata   1920
aaggcattcc gcgtgcagga ttcacccgtt cgcctctcac cttttcgctg tactcactcg   1980
ccacacacac cccctctcca gctccgttgg agctccggac agcagcaggc gcggggcggt   2040
cacgtagtaa gcagctctcg gctccctctc cccttgctcc atttgatagt gcaacccatc   2100
gagctacacc ggtgcggccc accgtcttcg gtacgcgctc actccgccct ctgcctttgt   2160
tactgccacg tttctctgaa tgctctcttg tgtggtgatt gctgagagtg gtttagctgg   2220
atctagaatt acactctgaa atcgtgttct gcctgtgctg attacttgcc gtcctttgta   2280
gcagcaaaat atagggacat ggtagtacga aacgaagata gaacctacac agcaatacga   2340
gaaatgtgta atttggtgct tagcggtatt tatttaagca catgttggtg ttatagggca   2400
cttggattca gaagtttgct gttaatttag gcacaggctt catactacat gggtcaatag   2460
tatagggatt catattatag gcgatactat aataatttgt tcgtctgcag agcttattat   2520
ttgccaaaat tagatattcc tattctgttt ttgtttgtgt gctgttaaat tgttaacgcc   2580
tgaaggaata aatataaatg acgaaatttt gatgtttatc tctgctcctt tattgtgacc   2640
ataagtcaag atcagatgca cttgttttaa atattgttgt ctgaagaaat aagtactgac   2700
agtatttga tgcattgatc tgcttgtttg ttgtaacaaa atttaaaaat aaagagtttc   2760
cttttttgttg ctctccttac ctcctgatgg tatctagtat ctaccaactg acactatatt   2820
gcttctcttt acatacgtat cttgctcgat gccttctccc tagtgttgac cagtgttact   2880
cacatagtct ttgctcattt cattgtaatg cagataccaa gcgg                    2924
```

<210> SEQ ID NO 101
<211> LENGTH: 408
<212> TYPE: DNA
<213> ORGANISM: Oryza sativa

<400> SEQUENCE: 101

```
ggcagagccg tgcccgtctc atcccctgcc cgtgcaagca gctaggtagg acgatttgag    60
```

-continued

```
cgtggtgtta ggccgaaccg ctgaaggaag attgctccac tgttgactgc attaggattc        120
aatccttgct gctaaatgta ttgcttatat tcagcaatat aatgttcagc agcaagaact        180
ggatcttaat atagtcgata gtggaagaac ggtaacatat gtggtttgca gcaggtgagc        240
aggatgggtg tggatgattg aatatctctg ttcagtgttt tcatcatctg actgaacact        300
gaatcagctt gctgacgtta gaggtttcag tttacctaat ttatggtctg tacccatgaa        360
aagtgggaaa aggctgaaga attcgatttc tttctttctt tcaatgtt                     408

<210> SEQ ID NO 102
<211> LENGTH: 325
<212> TYPE: DNA
<213> ORGANISM: Oryza sativa

<400> SEQUENCE: 102
ggcagagccg tgcccgtctc atccctgcc cgtgcaagca gctaggtagg acgatttgag         60
cgtggtgtta ggccgaaccg ctgaaggaag attgctccac tgttgactgc attaggattc        120
aatccttgct gctaaatgta ttgcttatat tcagcaatat aatgttcagc agcaagaact        180
ggatcttaat atagtcgata gtggaagaac ggtaacatat gtggtttgca gcaggtgagc        240
aggatgggtg tggatgattg aatatctctg ttcagtgttt tcatcatctg actgaacact        300
gaatcagctt gctgacgtta gaggt                                              325

<210> SEQ ID NO 103
<211> LENGTH: 280
<212> TYPE: DNA
<213> ORGANISM: Oryza sativa

<400> SEQUENCE: 103
ggcagagccg tgcccgtctc atccctgcc cgtgcaagca gctaggtagg acgatttgag         60
cgtggtgtta ggccgaaccg ctgaaggaag attgctccac tgttgactgc attaggattc        120
aatccttgct gctaaatgta ttgcttatat tcagcaatat aatgttcagc agcaagaact        180
ggatcttaat atagtcgata gtggaagaac ggtaacatat gtggtttgca gcaggtgagc        240
aggatgggtg tggatgattg aatatctctg ttcagtgttt                              280

<210> SEQ ID NO 104
<211> LENGTH: 249
<212> TYPE: DNA
<213> ORGANISM: Oryza sativa

<400> SEQUENCE: 104
ggcagagccg tgcccgtctc atccctgcc cgtgcaagca gctaggtagg acgatttgag         60
cgtggtgtta ggccgaaccg ctgaaggaag attgctccac tgttgactgc attaggattc        120
aatccttgct gctaaatgta ttgcttatat tcagcaatat aatgttcagc agcaagaact        180
ggatcttaat atagtcgata gtggaagaac ggtaacatat gtggtttgca gcaggtgagc        240
aggatgggt                                                                249
```

TRANSGENIC PLANTS WITH ENHANCED TRAITS

CROSS REFERENCE TO RELATED APPLICATIONS

This application is a U.S. National Stage filing under 35 U.S.C. § 371 of International Application No. PCT/US2015/063306 filed 2 Dec. 2015, which claims benefit and priority to U.S. Provisional Application No. 62/086,918 filed on 3 Dec. 2014, which are incorporated herein by reference.

INCORPORATION OF SEQUENCE LISTING

The Sequence Listing accompanying this application is contained within the computer readable file "60803US0001_ST25.txt" submitted electronically and contemporaneously with the filing of this application through the USPTO EFS-Web. The file is 270 KB (measured in MS-Windows), was created on 31 May 2017, and is incorporated herein by reference.

FIELD OF THE INVENTION

Disclosed herein are recombinant DNA constructs, plants having enhanced traits such as increased yield, increased nitrogen use efficiency and increased water use efficiency; propagules, progenies and field crops of such plants; and methods of making and using such plants. Also disclosed are methods of producing seed from such plants, growing such seed and/or selecting progeny plants with enhanced traits.

SUMMARY OF THE INVENTION

In one aspect, the disclosure provides a recombinant DNA construct comprising a heterologous promoter functional in a plant cell and operably linked to:
  a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-27 and 55;
  b) a DNA encoding RNA for suppressing the expression of a target mRNA transcribed from a polynucleotide having a nucleic acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 6 and 55-60;
  c) a polynucleotide that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 28-54, 61, 79-96; or
  d) a DNA encoding RNA for suppressing the expression of a target protein having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 33, 61-66, 82, and 96.

In another aspect, the disclosure provides a suppression recombinant DNA construct that transcribes into a double-stranded RNA, an antisense RNA, a miRNA or a ta-siRNA.

In another aspect, the disclosure provides a suppression recombinant DNA construct that transcribes into a miRNA precursor that produces a mature miRNA having a nucleic acid sequence with at least 95%, at least 96%, at least 97%, at least 98%, at least 99%, or 100% identity to a fragment of at least 19, 20, 21, 22, 23, 24, 25, 26 or 27 consecutive nucleotides of a sequence selected from the group consisting of SEQ ID NOs: 6 and 55-60.

In another aspect, the disclosure provides a suppression recombinant DNA construct that transcribes into a miRNA precursor that produces a mature miRNA having a nucleic acid sequence with at least 95%, at least 96%, at least 97%, at least 98%, at least 99%, or 100% complimentarity to a fragment of at least 19, 20, 21, 22, 23, 24, 25, 26 or 27 consecutive nucleotides of a sequence selected from the group consisting of SEQ ID NOs: 6 and 55-60.

In another aspect, the disclosure provides a suppression recombinant DNA construct that transcribes into a miRNA precursor that produces a mature miRNA having a nucleic acid sequence with 100% identity or 100% complementarity to a fragment of 21 consecutive nucleotides of a sequence selected from the group consisting of SEQ ID NOs: 6 and 55-60.

In another aspect, the disclosure provides a suppression recombinant DNA construct comprising a sequence selected from the group consisting of SEQ ID NOs: 67-72.

In another aspect, the disclosure provides a plant comprising a recombinant DNA construct comprising a heterologous promoter functional in a plant cell and operably linked to:
  a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-27 and 55;
  b) a DNA encoding RNA for suppressing the expression of a target mRNA transcribed from a polynucleotide having a nucleic acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 6 and 55-60;
  c) a polynucleotide that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 28-54, 61, 79-96; or
  d) a DNA encoding RNA for suppressing the expression of a target protein having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 33, 61-66, 82, and 96.

In another aspect, the disclosure provides a plant comprising a recombinant DNA construct of the present disclosure, and having at least one altered phenotype or at least one enhanced trait as compared to a control plant. Such phenotype is characterized or measured by anthocyanin content, biomass, canopy area, chlorophyll content, plant height, water applied, water content or water use efficiency. Such enhanced trait is increased yield, increased nitrogen use efficiency, or increased water use efficiency.

In another aspect, the disclosure provides a plant comprising a recombinant DNA construct of the present disclosure, wherein the plant is a progeny, a propagule, or a field crop.

In another aspect, the disclosure provides a field crop comprising a recombinant DNA construct of the present disclosure, wherein the field crop is selected from the group consisting of corn, soybean, cotton, canola, rice, barley, oat, wheat, turf grass, alfalfa, sugar beet, sunflower, quinoa and sugar cane.

In another aspect, the disclosure provides a propagule comprising a recombinant DNA construct the present disclosure, wherein the propagule is selected from the group consisting of cell, pollen, ovule, flower, embryo, leaf, root, stem, shoot, meristem, grain and seed.

In another aspect, the disclosure provides a plant comprising a recombinant DNA construct of the present disclosure, wherein the plant is a monocot plant or is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, brome-grass plant, *Miscanthus* plant, pampas grass plant, switchgrass (*Panicum*) plant, and/or teosinte plant, or is a member of the family Alliaceae, onion plant, leek plant, garlic plant; or wherein the plant is a dicot plant or is a member of the family Amaranthaceae, spinach plant, quinoa plant, a member of the family Anacardiaceae, mango plant, a member of the family Asteraceae, sunflower plant, endive plant, lettuce plant, artichoke plant, a member of the family Brassicaceae, *Arabidopsis thaliana* plant, rape plant, oilseed rape plant, broccoli plant, Brussels sprouts plant, cabbage plant, canola plant, cauliflower plant, kohlrabi plant, turnip plant, radish plant, a member of the family Bromeliaceae, pineapple plant, a member of the family Caricaceae, papaya plant, a member of the family Chenopodiaceae, beet plant, a member of the family Curcurbitaceae, melon plant, cantaloupe plant, squash plant, watermelon plant, honeydew plant, cucumber plant, pumpkin plant, a member of the family Dioscoreaceae, yam plant, a member of the family Ericaceae, blueberry plant, a member of the family Euphorbiaceae, cassava plant, a member of the family Fabaceae, alfalfa plant, clover plant, peanut plant, a member of the family Grossulariaceae, currant plant, a member of the family Juglandaceae, walnut plant, a member of the family Lamiaceae, mint plant, a member of the family Lauraceae, avocado plant, a member of the family Leguminosae, soybean plant, bean plant, pea plant, a member of the family Malvaceae, cotton plant, a member of the family Marantaceae, arrowroot plant, a member of the family Myrtaceae, guava plant, eucalyptus plant, a member of the family Rosaceae, peach plant, apple plant, cherry plant, plum plant, pear plant, prune plant, blackberry plant, raspberry plant, strawberry plant, a member of the family Rubiaceae, coffee plant, a member of the family Rutaceae, citrus plant, orange plant, lemon plant, grapefruit plant, tangerine plant, a member of the family Salicaceae, poplar plant, willow plant, a member of the family Solanaceae, potato plant, sweet potato plant, tomato plant, *Capsicum* plant, tobacco plant, tomatillo plant, eggplant plant, *Atropa belladona* plant, *Datura stramonium* plant, a member of the family Vitaceae, grape plant, a member of the family Umbelliferae, carrot plant, or a member of the family Musaceae, banana plant; or wherein the plant is a member of the family Pinaceae, cedar plant, fir plant, hemlock plant, larch plant, pine plant, or spruce plant.

In another aspect, the disclosure provides a method for increasing yield, increasing nitrogen use efficiency, or increasing water use efficiency in a plant comprising producing a plant comprising a recombinant DNA construct comprising a heterologous promoter functional in a plant cell and operably linked to:

a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-27 and 55;

b) a DNA encoding RNA for suppressing the expression of a target mRNA transcribed from a polynucleotide having a nucleic acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 6 and 55-60;

c) a polynucleotide that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 28-54, 61, 79-96; or d) a DNA encoding RNA for suppressing the expression of a target protein having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 33, 61-66, 82, and 96.

In another aspect, the disclosure provides a method for producing a plant by transforming a plant cell or tissue with the recombinant DNA construct of the present disclosure and regenerating a plant from said cell or tissue containing said recombinant DNA construct. In another aspect, the disclosure provides a method for producing a plant by crossing said plant through breeding with:

a) itself;
b) a second plant from the same plant line;
c) a wild type plant; or
d) a second plant from a different line of plants to produce a seed, growing said seed to produce a plurality of progeny plants; and selecting a progeny plant with increased yield, increased nitrogen use efficiency, or increased water use efficiency as compared to a control plant.

DETAILED DESCRIPTION OF THE INVENTION

In the attached sequence listing:

SEQ ID NOs 1 to 27 are nucleotide sequences of the coding strand of the DNA used in the recombinant DNA constructs imparting an enhanced trait in plants, each representing a coding sequence for a protein.

SEQ ID NOs 28 to 54 are amino acid sequences of the cognate proteins of the DNA molecules with nucleotide sequences of SEQ ID NOs 1 to 27 respectively in the same order.

SEQ ID NOs: 55 to 60 are nucleotide sequences, each representing a coding sequence of a suppression target gene.

SEQ ID NOs 61 to 66 are amino acid sequences of the cognate proteins of the DNA molecules with nucleotide sequences of SEQ ID NOs 55 to 60 respectively in the same order.

SEQ ID NOs 67 to 72 are nucleotide sequences of DNA molecules used in the recombinant DNA constructs imparting an enhanced trait or altered phenotype in plants, each representing an engineered miRNA precursor sequence.

SEQ ID NOs: 73 to 78 are nucleotide sequences of the target recognition sites of the engineered miRNA precursors with nucleotide sequences of SEQ ID NOs 67 to 72 respectively in the same order.

SEQ ID NOs 79 to 96 are amino acid sequences of proteins homologous to the proteins with amino acid sequences of SEQ ID NOs 28 to 54, and 61 to 66.

SEQ ID NOs 97 to 100 are nucleotide sequences of DNA molecules used in the recombinant DNA constructs imparting an enhanced trait or altered phenotype in plants, each representing a promoter with a specific expression pattern.

SEQ ID NOs 101 to 104 are nucleotide sequences of variants of a rice MIR gene.

Unless otherwise stated, nucleic acid sequences in the text of this specification are given, when read from left to right, in the 5' to 3' direction. One of skill in the art would be aware that a given DNA sequence is understood to define a corresponding RNA sequence which is identical to the DNA sequence except for replacement of the thymine (T) nucleotide of the DNA with uracil (U) nucleotide. Thus, providing a specific DNA sequence is understood to define the exact RNA equivalent. A given first polynucleotide sequence, whether DNA or RNA, further defines the sequence of its exact complement (which can be DNA or RNA), i.e., a second polynucleotide that hybridizes perfectly to the first polynucleotide by forming Watson-Crick base-pairs. By "essentially identical" or "essentially complementary" to a target gene or a fragment of a target gene is meant that a polynucleotide strand (or at least one strand of a double-stranded polynucleotide) is designed to hybridize (generally under physiological conditions such as those found in a living plant or animal cell) to a target gene or to a fragment of a target gene or to the transcript of the target gene or the fragment of a target gene; one of skill in the art would understand that such hybridization does not necessarily require 100% sequence identity or complementarity. A first nucleic acid sequence is "operably" connected or "linked" with a second nucleic acid sequence when the first nucleic acid sequence is placed in a functional relationship with the second nucleic acid sequence. For example, a promoter sequence is "operably linked" to DNA if the promoter provides for transcription or expression of the DNA. Generally, operably linked DNA sequences are contiguous.

As used herein, the term "expression" refers to the production of a polynucleotide or a protein by a plant, plant cell or plant tissue which can give rise to an altered phenotype or enhanced trait. Expression can also refer to the process by which information from a gene is used in the synthesis of functional gene products, which may include but are not limited to other polynucleotides or proteins which may serve, e.g., an enzymatic, structural or regulatory function. Gene products having a regulatory function include but are not limited to elements that affect the occurrence or level of transcription or translation of a target protein. In some cases, the expression product is a non-coding functional RNA.

"Modulation" of expression refers to the process of effecting either overexpression or suppression of a polynucleotide or a protein.

The term "suppression" as used herein refers to a lower expression level of a target polynucleotide or target protein in a plant, plant cell or plant tissue, as compared to the expression in a wild-type or control plant, cell or tissue, at any developmental or temporal stage for the gene. The term "target protein" as used in the context of suppression refers to a protein which is suppressed; similarly, "target mRNA" refers to a polynucleotide which can be suppressed or, once expressed, degraded so as to result in suppression of the target protein it encodes. The term "target gene" as used in the context of suppression refers to either "target protein" or "target mRNA". In alternate non-limiting embodiments, the target protein or target polynucleotide is one the suppression of which can give rise to an enhanced trait or altered phenotype directly or indirectly. In one exemplary embodiment, the target protein is one which can indirectly increase or decrease the expression of one or more other proteins, the increased or decreased expression, respectively, of which is associated with an enhanced trait or an altered phenotype. In another exemplary embodiment, the target protein can bind to one or more other proteins associated with an altered phenotype or enhanced trait to enhance or inhibit their function and thereby affect the altered phenotype or enhanced trait indirectly.

Suppression can be applied using numerous approaches. Non limiting examples include: suppressing an endogenous gene(s) or a subset of genes in a pathway, suppressing one or more mutation that has resulted in decreased activity of a protein, suppressing the production of an inhibitory agent, to elevate, reducing or eliminating the level of substrate that an enzyme requires for activity, producing a new protein, activating a normally silent gene; or accumulating a product that does not normally increase under natural conditions.

Conversely, the term "overexpression" as used herein refers to a greater expression level of a polynucleotide or a protein in a plant, plant cell or plant tissue, compared to expression in a wild-type plant, cell or tissue, at any developmental or temporal stage for the gene. Overexpression can take place in plant cells normally lacking expression of polypeptides functionally equivalent or identical to the present polypeptides. Overexpression can also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "target protein" as used herein in the context of overexpression refers to a protein which is overexpressed; "target mRNA" refers to an mRNA which encodes and is translated to produce the target protein, which can also be overexpressed. The term "target gene" as used in the context of overexpression refers to either "target protein" or "target mRNA". In alternative embodiments, the target protein can effect an enhanced trait or altered phenotype directly or indirectly. In the latter case it may do so, for example, by affecting the expression, function or substrate available to one or more other proteins. In an exemplary embodiment, the target protein can bind to one or more other proteins associated with an altered phenotype or enhanced trait to enhance or inhibit their function.

Overexpression can be achieved using numerous approaches. In one embodiment, overexpression can be achieved by placing the DNA sequence encoding one or more polynucleotides or polypeptides under the control of a promoter, examples of which include but are not limited to endogenous promoters, heterologous promoters, inducible promoters and tissue specific promoters. In one exemplary embodiment, the promoter is a constitutive promoter, for example, the cauliflower mosaic virus 35S transcription initiation region. Thus, depending on the promoter used, overexpression can occur throughout a plant, in specific tissues of the plant, or in the presence or absence of different inducing or inducible agents, such as hormones or environmental signals.

Gene Suppression Elements: The gene suppression element can be transcribable DNA of any suitable length, and generally includes at least about 19 to about 27 nucleotides (for example 19, 20, 21, 22, 23, or 24 nucleotides) for every target gene that the recombinant DNA construct is intended to suppress. In many embodiments the gene suppression element includes more than 23 nucleotides (for example, more than about 30, about 50, about 100, about 200, about 300, about 500, about 1000, about 1500, about 2000, about 3000, about 4000, or about 5000 nucleotides) for every target gene that the recombinant DNA construct is intended to suppress.

Suitable gene suppression elements useful in the recombinant DNA constructs of the invention include at least one element (and, in some embodiments, multiple elements) selected from the group consisting of:
(a) DNA that includes at least one anti-sense DNA segment that is anti-sense to at least one segment of the at least one first target gene; (b) DNA that includes multiple copies of at least one anti-sense DNA segment that is anti-sense to at least one segment of the at least one first target gene; (c) DNA that includes at least one sense DNA segment that is at least one segment of the at least one first target gene; (d) DNA that includes multiple copies of at least one sense DNA segment that is at least one segment of the at least one first target gene; (e) DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene; (f) DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene; (g) DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats; (h) DNA that includes nucleotides derived from a miRNA, preferably a plant miRNA; (i) DNA that includes nucleotides of a siRNA; (j) DNA that transcribes to an RNA aptamer capable of binding to a ligand; and (k) DNA that transcribes to an RNA aptamer capable of binding to a ligand, and DNA that transcribes to regulatory RNA capable of regulating expression of the first target gene, wherein the regulation is dependent on the conformation of the regulatory RNA, and the conformation of the regulatory RNA is allosterically affected by the binding state of the RNA aptamer.

Any of these gene suppression elements, whether transcribing to a single double-stranded RNA or to multiple double-stranded RNAs, can be designed to suppress more than one target gene, including, for example, more than one allele of a target gene, multiple target genes (or multiple segments of at least one target gene) from a single species, or target genes from different species.

Anti-Sense DNA Segments: In one embodiment, the at least one anti-sense DNA segment that is anti-sense to at least one segment of the at least one first target gene includes DNA sequence that is anti-sense or complementary to at least a segment of the at least one first target gene, and can include multiple anti-sense DNA segments, that is, multiple copies of at least one anti-sense DNA segment that is anti-sense to at least one segment of the at least one first target gene. Multiple anti-sense DNA segments can include DNA sequence that is anti-sense or complementary to multiple segments of the at least one first target gene, or to multiple copies of a segment of the at least one first target gene, or to segments of multiple first target genes, or to any combination of these. Multiple anti-sense DNA segments can be fused into a chimera, e.g., including DNA sequences that are anti-sense to multiple segments of one or more first target genes and fused together.

The anti-sense DNA sequence that is anti-sense or complementary to (that is, can form Watson-Crick base-pairs with) at least a segment of the at least one first target gene has at least about 80%, or at least about 85%, or at least about 90%, or at least about 95% complementarity to at least a segment of the at least one first target gene. In one embodiment, the DNA sequence that is anti-sense or complementary to at least a segment of the at least one first target gene has between about 95% to about 100% complementarity to at least a segment of the at least one first target gene. Where the at least one anti-sense DNA segment includes multiple anti-sense DNA segments, the degree of complementarity can be, but need not be, identical for all of the multiple anti-sense DNA segments.

Sense DNA Segments: In another embodiment, the at least one sense DNA segment that is at least one segment of the at least one first target gene includes DNA sequence that corresponds to (that is, has a sequence that is identical or substantially identical to) at least a segment of the at least one first target gene, and can include multiple sense DNA segments, that is, multiple copies of at least one sense DNA segment that corresponds to (that is, has the nucleotide sequence of) at least one segment of the at least one first target gene. Multiple sense DNA segments can include DNA sequence that is or that corresponds to multiple segments of the at least one first target gene, or to multiple copies of a segment of the at least one first target gene, or to segments of multiple first target genes, or to any combination of these. Multiple sense DNA segments can be fused into a chimera, that is, can include DNA sequences corresponding to multiple segments of one or more first target genes and fused together.

The sense DNA sequence that corresponds to at least a segment of the target gene has at least about 80%, or at least about 85%, or at least about 90%, or at least about 95% sequence identity to at least a segment of the target gene. In one embodiment, the DNA sequence that corresponds to at least a segment of the target gene has between about 95% to about 100% sequence identity to at least a segment of the target gene. Where the at least one sense DNA segment includes multiple sense DNA segments, the degree of sequence identity can be, but need not be, identical for all of the multiple sense DNA segments.

Multiple Copies: Where the gene suppression element includes multiple copies of anti-sense or multiple copies of sense DNA sequence, these multiple copies can be arranged serially in tandem repeats. In some embodiments, these multiple copies can be arranged serially end-to-end, that is, in directly connected tandem repeats. In some embodiments, these multiple copies can be arranged serially in interrupted tandem repeats, where one or more spacer DNA segment can be located adjacent to one or more of the multiple copies. Tandem repeats, whether directly connected or interrupted or a combination of both, can include multiple copies of a single anti-sense or multiple copies of a single sense DNA sequence in a serial arrangement or can include multiple copies of more than one anti-sense DNA sequence or of more than one sense DNA sequence in a serial arrangement.

Double-stranded RNA: In those embodiments wherein the gene suppression element includes either at least one anti-sense DNA segment that is anti-sense to at least one segment of the at least one target gene or at least one sense DNA segment that is at least one segment of the at least one target gene, RNA transcribed from either the at least one anti-sense or at least one sense DNA may become double-stranded by the action of an RNA-dependent RNA polymerase. See, for example, U.S. Pat. No. 5,283,184, which is incorporated by reference herein.

In yet other embodiments, the gene suppression element can include DNA that transcribes to RNA for suppressing the at least one first target gene by forming double-stranded RNA and includes at least one anti-sense DNA segment that is anti-sense to at least one segment of the at least one target gene (as described above under the heading "Anti-sense DNA Segments") and at least one sense DNA segment that is at least one segment of the at least one first target gene (as described above under the heading "Sense DNA Segments"). Such a gene suppression element can further include spacer DNA segments. Each at least one anti-sense DNA segment is complementary to at least part of a sense DNA segment in order to permit formation of double-stranded RNA by intramolecular hybridization of the at least one anti-sense DNA segment and the at least one sense DNA segment. Such complementarity between an anti-sense DNA segment and a sense DNA segment can be, but need not be, 100% complementarity; in some embodiments, this complementarity can be preferably at least about 80%, or at least about 85%, or at least about 90%, or at least about 95% complementarity.

The double-stranded RNA can be in the form of a single dsRNA "stem" (region of base-pairing between sense and anti-sense strands), or can have multiple dsRNA "stems". In one embodiment, the gene suppression element can include DNA that transcribes to RNA for suppressing the at least one first target gene by forming essentially a single double-stranded RNA and includes multiple serial anti-sense DNA segments that are anti-sense to at least one segment of the at least one first target gene and multiple serial sense DNA segments that are at least one segment of the at least one first target gene; the multiple serial anti-sense and multiple serial sense segments can form a single double-stranded RNA "stem" or multiple "stems" in a serial arrangement (with or without non-base paired spacer DNA separating the multiple "stems"). In another embodiment, the gene suppression element includes DNA that transcribes to RNA for suppressing the at least one first target gene by forming multiple dsRNA "stems" of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of dsRNA "stems" (such as, but not limited to "inverted repeats"). Such multiple dsRNA "stems" can further be arranged in series or clusters to form tandem inverted repeats, or structures resembling "hammerhead" or "cloverleaf" shapes. Any of these gene suppression elements can further include spacer DNA segments found within a dsRNA "stem" (for example, as a spacer between multiple anti-sense or sense DNA segments or as a spacer between a base-pairing anti-sense DNA segment and a sense DNA segment) or outside of a double-stranded RNA "stem" (for example, as a loop region separating a pair of inverted repeats). In cases where base-pairing anti-sense and sense DNA segment are of unequal length, the longer segment can act as a spacer.

miRNAs: In a further embodiment, the gene suppression element can include DNA that includes nucleotides derived from a miRNA (microRNA), that is, a DNA sequence that corresponds to a miRNA native to a virus or a eukaryote of interest (including plants and animals, especially invertebrates), or a DNA sequence derived from such a native miRNA but modified to include nucleotide sequences that do not correspond to the native miRNA. While miRNAs have not to date been reported in fungi, fungal miRNAs, should they exist, are also suitable for use in the invention. An embodiment includes a gene suppression element containing DNA that includes nucleotides derived from a viral or plant miRNA.

In a non-limiting example, the nucleotides derived from a miRNA can include DNA that includes nucleotides corresponding to the loop region of a native miRNA and nucleotides that are selected from a target gene sequence. In another non-limiting example, the nucleotides derived from a miRNA can include DNA derived from a miRNA precursor sequence, such as a native pri-miRNA or pre-miRNA sequence, or nucleotides corresponding to the regions of a native miRNA and nucleotides that are selected from a target gene sequence number such that the overall structure (e.g., the placement of mismatches in the stem structure of the pre-miRNA) is preserved to permit the pre-miRNA to be processed into a mature miRNA. In yet another embodiment, the gene suppression element can include DNA that includes nucleotides derived from a miRNA and capable of inducing or guiding in-phase cleavage of an endogenous transcript into trans-acting siRNAs, as described by Allen et al. (2005) Cell, 121:207-221, which is incorporated by reference in its entirety herein. Thus, the DNA that includes nucleotides derived from a miRNA can include sequence naturally occurring in a miRNA or a miRNA precursor molecule, synthetic sequence, or both.

siRNAs: In yet another embodiment, the gene suppression element can include DNA that includes nucleotides of a small interfering RNA (siRNA). The siRNA can be one or more native siRNAs (such as siRNAs isolated from a non-transgenic eukaryote or from a transgenic eukaryote), or can be one or more DNA sequences predicted to have siRNA activity (such as by use of predictive tools known in the art, see, for example, Reynolds et al. (2004) Nature Biotechnol., 22:326-330, which is incorporated by reference in its entirety herein). Multiple native or predicted siRNA sequences can be joined in a chimeric siRNA sequence for gene suppression. Such a DNA that includes nucleotides of a siRNA includes at least 19 nucleotides, and in some embodiments includes at least 20, at least 21, at least 22, at least 23, or at least 24 nucleotides. In other embodiments, the DNA that includes nucleotides of a siRNA can contain substantially more than 21 nucleotides, for example, more than about 50, about 100, about 300, about 500, about 1000, about 3000, or about 5000 nucleotides or greater.

Engineered miRNAs and trans-acting siRNAs (ta-siR-NAs) are useful for gene suppression with increased specificity. The invention provides recombinant DNA constructs, each including a transcribable engineered miRNA precursor designed to suppress a target sequence, wherein the transcribable engineered miRNA precursor is derived from the fold-back structure of a MIR gene, preferably a plant MIR sequence. These miRNA precursors are also useful for directing in-phase production of siRNAs (e.g., heterologous sequence designed to be processed in a trans-acting siRNA suppression mechanism in planta). The invention further provides a method to suppress expression of a target sequence in a plant cell, including transcribing in a plant cell a recombinant DNA including a transcribable engineered miRNA precursor designed to suppress a target sequence, wherein the transcribable engineered miRNA precursor is derived from the fold-back structure of a MIR gene, preferably a plant MIR sequence, whereby expression of the target sequence is suppressed relative to its expression in the absence of transcription of the recombinant DNA construct. In specifically claimed embodiments, the transcribable engineered miRNA precursor is derived from the fold-back structure of a rice MIR sequence selected from the group consisting of SEQ ID NOs. 101-104, and their complements.

The mature miRNAs produced, or predicted to be produced, from these miRNA precursors may be engineered for use in suppression of a target gene, e.g., in transcriptional suppression by the miRNA, or to direct in-phase production of siRNAs in a trans-acting siRNA suppression mechanism (see Allen et al. (2005) Cell, 121:207-221, Vaucheret (2005) Science STKE, 2005:pe43, and Yoshikawa et al. (2005) Genes Dev., 19:2164-2175, all of which are incorporated by reference herein). Plant miRNAs generally have near-perfect complementarity to their target sequences (see, for example, Llave et al. (2002) Science, 297:2053-2056, Rhoades et al. (2002) Cell, 110:513-520, Jones-Rhoades and Bartel (2004) Mol. Cell, 14:787-799, all of which are incorporated by reference herein). Thus, the mature miRNAs can be engineered to serve as sequences useful for gene suppression of a target sequence, by replacing nucleotides of the mature miRNA sequence with nucleotides of the sequence that is targeted for suppression; see, for example, methods disclosed by Parizotto et al. (2004) Genes Dev., 18:2237-2242 and especially U.S. Patent Application Publications US2004/0053411A1, US2004/0268441A1, US2005/0144669, and US2005/0037988 all of which are incorporated by reference herein. When engineering a novel miRNA to target a specific sequence, one strategy is to select within the target sequence a region with sequence that is as similar as possible to the native miRNA sequence. Alternatively, the native miRNA sequence can be replaced with a region of the target sequence, preferably a region that meets structural and thermodynamic criteria believed to be important for miRNA function (see, for example, U.S. Patent Application Publication US2005/0037988). Sequences are preferably engineered such that the number and placement of mismatches in the stem structure of the fold-back region or pre-miRNA is preserved. Thus, an engineered miRNA or engineered miRNA precursor can be derived from any of the mature miRNA sequences, or their corresponding miRNA precursors (including the fold-back portions of the corresponding MIR genes) disclosed herein. The engineered miRNA precursor can be cloned and expressed (transiently or stably) in a plant cell or tissue or intact plant.

The construction and description of recombinant DNA constructs to modulate small non-coding RNA activities are disclosed in US Patent Application Publication US 2009/0070898 A1, US2011/0296555 A1, US2011/0035839 A1, all of which are incorporated herein by reference in their entirety. In particular, with respect to US2011/0035839 A1, see e.g., sections under the headings "Gene Suppression Elements" in paragraphs 122 to 135, and "Engineered Heterologous miRNA for Controlling Gene Expression in paragraphs 188 to 190.

As used herein a "plant" includes a whole plant, a transgenic plant, meristematic tissue, a shoot organ/structure (for example, leaf, stem and tuber), a root, a flower, a floral organ/structure (for example, a bract, a sepal, a petal, a stamen, a carpel, an anther and an ovule), a seed (including an embryo, endosperm, and a seed coat) and a fruit (the mature ovary), plant tissue (for example, vascular tissue, ground tissue, and the like) and a cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and multicellular algae.

As used herein a "transgenic plant cell" means a plant cell that is transformed with stably-integrated, recombinant DNA, for example, by *Agrobacterium*-mediated transformation or by bombardment using microparticles coated with recombinant DNA or by other means. A plant cell of this disclosure can be an originally-transformed plant cell that exists as a microorganism or as a progeny plant cell that is regenerated into differentiated tissue, for example, into a transgenic plant with stably-integrated, recombinant DNA, or seed or pollen derived from a progeny transgenic plant.

As used herein a "control plant" means a plant that does not contain the recombinant DNA of the present disclosure that imparts an enhanced trait or altered phenotype. A control plant is used to identify and select a transgenic plant that has an enhanced trait or altered phenotype. A suitable control plant can be a non-transgenic plant of the parental line used to generate a transgenic plant, for example, a wild type plant devoid of a recombinant DNA. A suitable control plant can also be a transgenic plant that contains recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, or a negative isogenic line.

As used herein a "propagule" includes all products of meiosis and mitosis, including but not limited to, plant, seed and part of a plant able to propagate a new plant. Propagules include whole plants, cells, pollen, ovules, flowers, embryos, leaves, roots, stems, shoots, meristems, grains or seeds, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

As used herein a "progeny" includes any plant, seed, plant cell, and/or regenerable plant part comprising a recombinant DNA of the present disclosure derived from an ancestor plant. A progeny can be homozygous or heterozygous for the transgene. Progeny can be grown from seeds produced by a transgenic plant comprising a recombinant DNA of the present disclosure, and/or from seeds produced by a plant fertilized with pollen or ovule from a transgenic plant comprising a recombinant DNA of the present disclosure.

As used herein a "trait" is a physiological, morphological, biochemical, or physical characteristic of a plant or particular plant material or cell. In some instances, this characteristic is visible to the human eye, such as seed or plant size, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance. In some specific aspects of this disclosure an enhanced trait is selected from the group consisting of drought tolerance, increased water use efficiency, cold tolerance, increased nitrogen use efficiency and increased yield as shown in Tables 7 and 9, and altered phenotypes as shown in Tables 4-6. In another aspect of the disclosure the trait is increased yield under non-stress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a recombinant DNA of the present disclosure relative to a plant not comprising the recombinant DNA, such as a wild-type plant, or a negative segregant. In some cases, the trait modification can be evaluated quantitatively. For example, the trait modification can entail an increase or decrease, in an observed trait as compared to a control plant. It is known that there can be natural variations in a modified trait. Therefore, the trait modification observed entails a change of the normal distribution and magnitude of the trait in the plants as compared to a control plant.

The present disclosure relates to a plant with improved economically important characteristics, more specifically increased yield. More specifically the present disclosure relates to a plant comprising a polynucleotide of this disclosure, wherein the plant has increased yield as compared to a control plant. Many plants of this disclosure exhibited increased yield as compared to a control plant. In an embodiment, a plant of the present disclosure exhibited an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, etc.), seed production and more. Root development, photosynthetic efficiency, nutrient uptake, stress tolerance, early vigor, delayed senescence and functional stay green phenotypes can be important factors in determining yield. Optimizing the above mentioned factors can therefore contribute to increasing crop yield.

Reference herein to an increase in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. For example, corn yield can be measured as production of shelled corn kernels per unit of production area, for example in bushels per acre or metric tons per hectare. This is often also reported on a moisture adjusted basis, for example at 15.5 percent moisture. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens. This disclosure can also be used to provide plants with improved growth and development, and ultimately increased yield, as the result of modified expression of plant growth regulators or modification of cell cycle or photosynthesis pathways. Also of interest is the generation of plants that demonstrate increased yield with respect to a seed component that may or may not correspond to an increase in overall plant yield.

In an embodiment, "alfalfa yield" can also be measured in forage yield, the amount of above ground biomass at harvest. Factors leading contributing to increased biomass include increased vegetative growth, branches, nodes and internodes, leaf area, and leaf area index.

In another embodiment, "canola yield" can also be measured in pod number, number of pods per plant, number of pods per node, number of internodes, incidence of pod shatter, seeds per silique, seed weight per silique, improved seed, oil, or protein composition.

Additionally, "corn or maize yield" can also be measured as production of shelled corn kernels per unit of production area, ears per acre, number of kernel rows per ear and number of kernels per row, kernel number or weight per ear, weight per kernel, ear number, ear weight, fresh or dry ear biomass (weight).

In yet another embodiment, "cotton yield" can be measured as bolls per plant, size of bolls, fiber quality, seed cotton yield in g/plant, seed cotton yield in lb/acre, lint yield in lb/acre, and number of bales.

Specific embodiment for "rice yield" can also include panicles per hill, grain per hill, and filled grains per panicle.

Still further embodiment for "soybean yield" can also include pods per plant, pods per acre, seeds per plant, seeds per pod, weight per seed, weight per pod, pods per node, number of nodes, and the number of internodes per plant.

In still further embodiment, "sugarcane yield" can be measured as cane yield (tons per acre; kg/hectare), total recoverable sugar (pounds per ton), and sugar yield (tons/acre).

In yet still further embodiment, "wheat yield" can include: cereal per unit area, grain number, grain weight, grain size, grains per head, seeds per head, seeds per plant, heads per acre, number of viable tillers per plant, composition of seed (for example, carbohydrates, starch, oil, and protein) and characteristics of seed fill.

The terms "yield", "seed yield" are defined above for a number of core crops. The terms "increased", "improved", "enhanced" are interchangeable and are defined herein.

In another embodiment, the present disclosure provides a method for the production of plants having increased yield; performance of the method gives plants increased yield. "Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination. "Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor in corn, for example, is a combination of the ability of corn seeds to germinate and emerge after planting and the ability of the young corn plants to grow and develop after emergence. Plants having early vigor also show increased seedling survival and better establishment of the crop, which often results in highly uniform fields with the majority of the plants reaching the various stages of development at substantially the same time, which often results in increased yield. Therefore early vigor can be determined by measuring various factors, such as kernel weight, percentage germination, percentage emergence, seedling growth, seedling height, root length, root and shoot biomass, canopy size and color and others.

Further, increased yield can also manifest as (iii) increased total seed yield, which may result from one or more of an increase in seed biomass (seed weight) due to an increase in the seed weight on a per plant and/or on an individual seed basis an increased number of panicles per plant; an increased number of pods; an increased number of nodes; an increased number of flowers ("florets") per panicle/plant; increased seed fill rate; an increased number of filled seeds; increased seed size (length, width, area, perimeter), which can also influence the composition of seeds; and/or increased seed volume, which can also influence the composition of seeds.

Increased yield can also (iv) result in modified architecture, or can occur because of modified plant architecture.

Increased yield can also manifest as (v) increased harvest index, which is expressed as a ratio of the yield of harvestable parts, such as seeds, over the total biomass Increased yield can also manifest as (vi) increased kernel weight, which is extrapolated from the number of filled seeds counted and their total weight. An increased kernel weight can result from an increased seed size and/or seed weight, an increase in embryo size, increased endosperm size, aleurone and/or scutellum, or an increase with respect to other parts of the seed that result in increased kernel weight.

Increased yield can also manifest as (vii) increased ear biomass, which is the weight of the ear and can be represented on a per ear, per plant or per plot basis.

In one embodiment, increased yield can be increased seed yield, and is selected from one of the following: (i) increased seed weight; (ii) increased number of filled seeds; and (iii) increased harvest index.

The disclosure also extends to harvestable parts of a plant such as, but not limited to, seeds, leaves, fruits, flowers, bolls, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

This disclosure further provides a method of increasing yield in a plant by producing a plant comprising a polynucleic acid sequence of this disclosure where the plant can be crossed with itself, a second plant from the same plant line, a wild type plant, or a plant from a different line of plants to produce a seed. The seed of the resultant plant can be harvested from fertile plants and be used to grow progeny generations of plant(s) of this disclosure. In addition to direct transformation of a plant with a recombinant DNA construct, transgenic plants can be prepared by crossing a first plant having a stably integrated recombinant DNA construct with a second plant lacking the DNA. For example, recombinant DNA can be introduced into a first plant line that is amenable to transformation to produce a transgenic plant which can be crossed with a second plant line to introgress the recombinant DNA into the second plant line.

Selected transgenic plants transformed with a recombinant DNA construct and having the polynucleotide of this disclosure provides the enhanced trait of increased yield compared to a control plant. Use of genetic markers associated with the recombinant DNA can facilitate production of transgenic progeny that is homozygous for the desired recombinant DNA. Progeny plants carrying DNA for both parental traits can be back-crossed into a parent line multiple times, for example usually 6 to 8 generations, to produce a progeny plant with substantially the same genotype as the one reoccurring original transgenic parental line but having the recombinant DNA of the other transgenic parental line.

The term "progeny" denotes the offspring of any generation of a parent plant prepared by the methods of this disclosure containing the recombinant polynucleotides as described herein.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance, and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein "water deficit" refers to the conditions or environments that provide less than optimal amounts of water needed for adequate/successful growth and development of plants.

As used herein "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein a "polynucleotide" is a nucleic acid molecule comprising a plurality of polymerized nucleotides. A polynucleotide may be referred to as a nucleic acid, a oligonucleotide, or any fragment thereof. In many instances, a polynucleotide encodes a polypeptide (or protein) or a domain or a fragment thereof. Additionally, a polynucleotide can comprise a promoter, an intron, an enhancer region, a polyadenylation site, a translation initiation site, 5' or 3' untranslated regions, a reporter gene, a selectable marker, a scorable marker, or the like. A polynucleotide can be single-stranded or double-stranded DNA or RNA. A polynucleotide optionally comprises modified bases or a modified backbone. A polynucleotide can be, for example, genomic DNA or RNA, a transcript (such as an mRNA), a cDNA, a PCR product, a cloned DNA, a synthetic DNA or RNA, or the like. A polynucleotide can be combined with carbohydrate(s), lipid(s), protein(s), or other materials to perform a particular activity such as transformation or form a composition such as a peptide nucleic acid (PNA). A polynucleotide can comprise a sequence in either sense or antisense orientations. "Oligonucleotide" is substantially equivalent to the terms amplimer, primer, oligomer, element, target, and probe and is preferably single-stranded.

As used herein a "recombinant polynucleotide" or "recombinant DNA" is a polynucleotide that is not in its native state, for example, a polynucleotide comprises a series of nucleotides (represented as a nucleotide sequence) not found in nature, or a polynucleotide is in a context other than that in which it is naturally found; for example, separated from polynucleotides with which it typically is in proximity in nature, or adjacent (or contiguous with) polynucleotides with which it typically is not in proximity. The "recombinant polynucleotide" or "recombinant DNA" refers to polynucleotide or DNA which has been genetically engineered and constructed outside of a cell including DNA containing naturally occurring DNA or cDNA or synthetic DNA. For example, the polynucleotide at issue can be cloned into a vector, or otherwise recombined with one or more additional nucleic acids.

As used herein a "polypeptide" comprises a plurality of consecutive polymerized amino acid residues for example, at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein "protein" refers to a series of amino acids, oligopeptide, peptide, polypeptide or portions thereof whether naturally occurring or synthetic.

As used herein a "recombinant polypeptide" is a polypeptide produced by translation of a recombinant polynucleotide.

A "synthetic polypeptide" is a polypeptide created by consecutive polymerization of isolated amino acid residues using methods known in the art.

An "isolated polypeptide", whether a naturally occurring or a recombinant polypeptide, is more enriched in (or out of) a cell than the polypeptide in its natural state in a wild-type cell, for example, more than about 5% enriched, more than about 10% enriched, or more than about 20%, or more than about 50%, or more, enriched, for example, alternatively denoted: 105%, 110%, 120%, 150% or more, enriched relative to wild type standardized at 100%. Such enrichment is not the result of a natural response of a wild-type plant. Alternatively, or additionally, the isolated polypeptide is separated from other cellular components, with which it is typically associated, for example, by any of the various protein purification methods.

As used herein, a "functional fragment" refers to a portion of a polypeptide provided herein which retains full or partial molecular, physiological or biochemical function of the full length polypeptide. A functional fragment often contains the domain(s), such as Pfam domains (see below), identified in the polypeptide provided in the sequence listing.

A "recombinant DNA construct" as used in the present disclosure comprises at least one expression cassette having a promoter operable in plant cells and a polynucleotide of the present disclosure. DNA constructs can be used as a means of delivering recombinant DNA constructs to a plant cell in order to effect stable integration of the recombinant molecule into the plant cell genome. In one embodiment, the polynucleotide can encode a protein or variant of a protein or fragment of a protein that is functionally defined to maintain activity in transgenic host cells including plant cells, plant parts, explants and whole plants. In another embodiment, the polynucleotide can encode a non-coding RNA that interferes with the functioning of endogenous classes of small RNAs that regulate expression, including but not limited to taRNAs, siRNAs and miRNAs. Recombinant DNA constructs are assembled using methods known to persons of ordinary skill in the art and typically comprise a promoter operably linked to DNA, the expression of which provides the enhanced agronomic trait.

Other construct components can include additional regulatory elements, such as 5' leaders and introns for enhancing transcription, 3' untranslated regions (such as polyadenylation signals and sites), and DNA for transit or targeting or signal peptides.

Percent identity describes the extent to which polynucleotides or protein segments are invariant in an alignment of sequences, for example nucleotide sequences or amino acid sequences. An alignment of sequences is created by manually aligning two sequences, for example, a stated sequence, as provided herein, as a reference, and another sequence, to produce the highest number of matching elements, for example, individual nucleotides or amino acids, while allowing for the introduction of gaps into either sequence. An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

As used herein, a "homolog" or "homologues" means a protein in a group of proteins that perform the same biological function, for example, proteins that belong to the same Pfam protein family and that provide a common enhanced trait in transgenic plants of this disclosure. Homologs are expressed by homologous genes. With reference to homologous genes, homologs include orthologs, for example, genes expressed in different species that evolved from common ancestral genes by speciation and encode proteins retain the same function, but do not include paralogs, i.e., genes that are related by duplication but have evolved to encode proteins with different functions. Homologous genes include naturally occurring alleles and artificially-created variants.

Degeneracy of the genetic code provides the possibility to substitute at least one base of the protein encoding sequence of a gene with a different base without causing the amino acid sequence of the polypeptide produced from the gene to be changed. When optimally aligned, homolog proteins, or their corresponding nucleotide sequences, have typically at least about 60% identity, in some instances at least about 70%, at least about 75%, at least about 80%, at least about 85%, at least about 90%, at least about 92%, at least about 94%, at least about 95%, at least about 96%, at least about 97%, at least about 98%, at least about 99%, or even at least about 99.5% identity over the full length of a protein or its corresponding nucleotide sequence identified as being associated with imparting an enhanced trait or altered phenotype when expressed in plant cells. In one aspect of the disclosure homolog proteins have at least about 80%, at least about 85%, at least about 90%, at least about 92%, at least about 94%, at least about 95%, at least about 96%, at least about 97%, at least about 98%, at least about 99%, or at least about 99.5% identity to a consensus amino acid sequence of proteins and homologs that can be built from sequences disclosed herein.

Homologs are inferred from sequence similarity, by comparison of protein sequences, for example, manually or by use of a computer-based tool using known sequence comparison algorithms such as BLAST and FASTA. A sequence search and local alignment program, for example, BLAST, can be used to search query protein sequences of a base organism against a database of protein sequences of various organisms, to find similar sequences, and the summary Expectation value (E-value) can be used to measure the level of sequence similarity. Because a protein hit with the lowest E-value for a particular organism may not necessarily be an ortholog or be the only ortholog, a reciprocal query is used to filter hit sequences with significant E-values for ortholog identification. The reciprocal query entails search of the significant hits against a database of protein sequences of the base organism. A hit can be identified as an ortholog, when the reciprocal query's best hit is the query protein itself or a paralog of the query protein. With the reciprocal query process orthologs are further differentiated from paralogs among all the homologs, which allows for the inference of functional equivalence of genes. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of known conservative amino acid substitutions, for example, valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side 30 chains is cysteine and methionine. Naturally conservative amino acids substitution groups are: valine-leucine, valine-isoleucine, phenylalanine-tyrosine, lysine-arginine, alaninevaline, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

In general, the term "variant" refers to molecules with some differences, generated synthetically or naturally, in their nucleotide or amino acid sequences as compared to a reference (native) polynucleotides or polypeptides, respectively. These differences include substitutions, insertions, deletions or any desired combinations of such changes in a native polynucleotide or amino acid sequence.

With regard to polynucleotide variants, differences between presently disclosed polynucleotides and polynucleotide variants are limited so that the nucleotide sequences of the former and the latter are similar overall and, in many regions, identical. Due to the degeneracy of the genetic code, differences between the former and the latter nucleotide sequences may be silent (for example, the amino acids encoded by the polynucleotide are the same, and the variant polynucleotide sequence encodes the same amino acid sequence as the presently disclosed polynucleotide). Variant nucleotide sequences can encode different amino acid sequences, in which case such nucleotide differences will result in amino acid substitutions, additions, deletions, insertions, truncations or fusions with respect to the similarly disclosed polynucleotide sequences. These variations can result in polynucleotide variants encoding polypeptides that share at least one functional characteristic. The degeneracy of the genetic code also dictates that many different variant polynucleotides can encode identical and/or substantially similar polypeptides.

As used herein "gene" or "gene sequence" refers to the partial or complete coding sequence of a gene, its complement, and its 5' and/or 3' untranslated regions (UTRs) and their complements. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application. Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock.

Sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252, zein Z27 as disclosed by Russell et al. (1997) *Transgenic Res.* 6(2):157-166, globulin 1 as disclosed by Belanger et al (1991) *Genetics* 129:863-872, glutelin 1 as disclosed by Russell (1997) *supra*, and peroxiredoxin antioxidant (Per1) as disclosed by Stacy et al. (1996) *Plant Mol Biol.* 31 (6): 1205-1216.

As used herein, the term "leader" refers to a DNA molecule isolated from the untranslated 5' region (5' UTR) of a genomic copy of a gene and is defined generally as a nucleotide segment between the transcription start site (TSS) and the protein coding sequence start site. Alternately, leaders can be synthetically produced or manipulated DNA elements. A leader can be used as a 5' regulatory element for modulating expression of an operably linked transcribable polynucleotide molecule. As used herein, the term "intron" refers to a DNA molecule that can be isolated or identified from the genomic copy of a gene and can be defined generally as a region spliced out during mRNA processing prior to translation. Alternately, an intron can be a synthetically produced or manipulated DNA element. An intron can contain enhancer elements that effect the transcription of operably linked genes. An intron can be used as a regulatory element for modulating expression of an operably linked transcribable polynucleotide molecule. A DNA construct can comprise an intron, and the intron may or may not be with respect to the transcribable polynucleotide molecule.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide. Unlike promoters, enhancer elements do not usually include a transcription start site (TSS) or TATA box or equivalent sequence. A promoter can naturally comprise one or more enhancer elements that affect the transcription of an operably linked polynucleotide. An isolated enhancer element can also be fused to a promoter to produce a chimeric promoter cis-element, which confers an aspect of the overall modulation of gene expression. A promoter or promoter fragment can comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template and that facilitate selective opening of the double helix at the site of transcriptional initiation. An enhancer element can function to bind transcription factors that regulate transcription. Some enhancer elements bind more than one transcription factor, and transcription factors can interact with different affinities with more than one enhancer domain.

Expression cassettes of this disclosure can include a "transit peptide" or "targeting peptide" or "signal peptide" molecule located either 5' or 3' to or within the gene(s). These terms generally refer to peptide molecules that when linked to a protein of interest directs the protein to a particular tissue, cell, subcellular location, or cell organelle. Examples include, but are not limited to, chloroplast transit peptides (CTPs), chloroplast targeting peptides, mitochondrial targeting peptides, nuclear targeting signals, nuclear exporting signals, vacuolar targeting peptides, and vacuolar sorting peptides. For description of the use of chloroplast transit peptides see U.S. Pat. Nos. 5,188,642 and 5,728,925. For description of the transit peptide region of an *Arabidopsis* EPSPS gene in the present disclosure, see Klee, H. J. Et al (MGG (1987) 210:437-442. Expression cassettes of this disclosure can also include an intron or introns. Expression cassettes of this disclosure can contain a DNA near the 3' end of the cassette that acts as a signal to terminate transcription from a heterologous nucleic acid and that directs polyadenylation of the resultant mRNA. These are commonly referred to as "3'-untranslated regions" or "3'-non-coding sequences" or "3'-UTRs". The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation signal can be derived from a natural gene, from a variety of plant genes, or from T-DNA. An example of a polyadenylation sequence is the nopaline synthase 3' sequence (nos 3'; Fraley et al., *Proc. Natl. Acad. Sci. USA* 80: 4803-4807, 1983). The use of different 3' non-translated sequences is exemplified by Ingelbrecht et al., *Plant Cell* 1:671-680, 1989.

Expression cassettes of this disclosure can also contain one or more genes that encode selectable markers and confer resistance to a selective agent such as an antibiotic or an herbicide. A number of selectable marker genes are known in the art and can be used in the present disclosure: selectable marker genes conferring tolerance to antibiotics like kanamycin and paromomycin (nptII), hygromycin B (aph IV), spectinomycin (aadA), U.S. Patent Publication 2009/0138985A1 and gentamycin (aac3 and aacC4) or tolerance to herbicides like glyphosate (for example, 5-enolpyruvyl-shikimate-3-phosphate synthase (EPSPS), U.S. Pat. Nos. 5,627,061; 5,633,435; 6,040,497; 5,094,945), sulfonyl herbicides (for example, acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761,373; 5,633,437; 6,613,963; 5,013,659; 5,141,870; 5,378,824; 5,605,011)), bialaphos or phosphinothricin or derivatives (e.g., phosphinothricin acetyltransferase (bar) tolerance to phosphinothricin or glufosinate (U.S. Pat. Nos. 5,646,024; 5,561,236; 5,276,268; 5,637,489; 5,273,894); dicamba (dicamba monooxygenase, Patent Application Publications US2003/0115626A1), or sethoxydim (modified acetyl-coenzyme A carboxylase for conferring tolerance to cyclohexanedione (sethoxydim)), and aryloxyphenoxypropionate (haloxyfop, U.S. Pat. No. 6,414,222).

Transformation vectors of this disclosure can contain one or more "expression cassettes", each comprising a native or non-native plant promoter operably linked to a polynucleotide sequence of interest, which is operably linked to a 3' UTR termination signal, for expression in an appropriate host cell. It also typically comprises sequences required for proper translation of the polynucleotide or transgene. As used herein, the term "transgene" refers to a polynucleotide molecule artificially incorporated into a host cell's genome. Such a transgene can be heterologous to the host cell. The term "transgenic plant" refers to a plant comprising such a transgene. The coding region usually codes for a protein of interest but can also code for a functional RNA of interest, for example an antisense RNA, a nontranslated RNA, in the sense or antisense direction, a miRNA, a noncoding RNA, or a synthetic RNA used in either suppression or over expression of target gene sequences. The expression cassette comprising the nucleotide sequence of interest can be chimeric, meaning that at least one of its components is heterologous with respect to at least one of its other components. As used herein the term "chimeric" refers to a DNA molecule that is created from two or more genetically diverse sources, for example a first molecule from one gene or organism and a second molecule from another gene or organism.

Recombinant DNA constructs in this disclosure generally include a 3' element that typically contains a polyadenylation signal and site. Known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in US Patent Application Publication 2002/0192813 A1; and the pea (*Pisum sativum*) ribulose biphosphate carboxylase gene (rbs 3'), and 3' elements from the genes within the host plant.

As used herein "operably linked" means the association of two or more DNA fragments in a recombinant DNA construct so that the function of one, for example, protein-encoding DNA, is controlled by the other, for example, a promoter.

Transgenic plants can comprise a stack of one or more polynucleotides disclosed herein resulting in the production of multiple polypeptide sequences. Transgenic plants comprising stacks of polynucleotides can be obtained by either or both of traditional breeding methods or through genetic engineering methods. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or genes carried separately on multiple vectors.

Transgenic plants comprising or derived from plant cells of this disclosure transformed with recombinant DNA can be further enhanced with stacked traits, for example, a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects, or improved quality traits such as improved nutritional value. Herbicides for which transgenic plant tolerance has been demonstrated and the method of the present disclosure can be applied include, but are not limited to, glyphosate, dicamba, glufosinate, sulfonylurea, bromoxynil and norflurazon herbicides. Polynucleotide molecules encoding proteins involved in herbicide tolerance known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and U.S. Pat. No. 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in US Patent Application Publication 2003/0083480 A1 also for imparting glyphosate tolerance; dicamba monooxygenase disclosed in US Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in US Patent Application Publication 2003/010609 A1 for imparting N-amino methyl phosphonic acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication 2002/0112260. Molecules and methods for imparting insect/nematode/virus resistance are disclosed in U.S. Pat. Nos. 5,250,515; 5,880,275; 6,506,599; 5,986,175 and US Patent Application Publication 2003/0150017 A1.

Plant Cell Transformation Methods

Numerous methods for transforming chromosomes in a plant cell with recombinant DNA are known in the art and are used in methods of producing a transgenic plant cell and plant. Two effective methods for such transformation are *Agrobacterium*-mediated transformation and microprojectile bombardment-mediated transformation. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). *Agrobacterium*-mediated transformation methods are described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 8,044,260 (cotton); U.S. Pat. No. 6,384,301 (soybean), U.S. Pat. No. 7,026,528 (wheat) and U.S. Pat. No. 6,329,571 (rice), US Patant Application Publication 2004/0087030 A1 (cotton), and US Patent Application Publication 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA construct, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

For transformation, DNA is typically introduced into only a small percentage of target plant cells in any one transformation experiment. Marker genes are used to provide an efficient system for identification of those cells that are stably transformed by receiving and integrating a recombinant DNA construct into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708; 6,118,047 and U.S. Pat. No. 8,030,544. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to a selective agent, or plant cells that have been scored positive in a screening assay, may be cultured in vitro to regenerate plantlets. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2} s^{-1}$ of light, prior to transfer to a greenhouse or growth chamber for maturation. Plants are regenerated from about 6 weeks to 10 months after a transformant is identified, depending on the initial tissue, and plant species. Plants can be pollinated using conventional plant breeding methods known to those of skill in the art to produce seeds, for example self-pollination is commonly used with transgenic corn. The regenerated transformed plant or its progeny seed or plants can be tested for expression of the recombinant DNA and selected for the presence of an enhanced agronomic trait.

Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits that contribute to increased yield or other traits that provide increased plant value, including, for example, improved seed quality. Of particular interest are plants having increased water use efficiency or drought tolerance, enhanced high temperature or cold tolerance, increased yield, and increased nitrogen use efficiency.

Table 1 provides a list of sequences of protein-encoding genes as recombinant DNA for production of transgenic plants with enhanced traits. The elements of Table 1 are described by reference to:

"NUC SEQ ID NO." which identifies a DNA sequence.

"PEP SEQ ID NO." which identifies an amino acid sequence.

"Gene ID" which refers to an arbitrary identifier.

"Gene Name and Description" which is a common name and functional description of the gene.

TABLE 1

Sequences for Protein-Coding Genes

| NUC SEQ ID NO. | PEP SEQ ID NO. | Gene ID | Gene Name and Description |
|---|---|---|---|
| 1 | 28 | TRDX4-01 | *Arabidopsis* mitochondrial import receptor subunit TOM5 homolog (TOM5) |
| 2 | 29 | TRDX4-02 | *Arabidopsis* K+ independent Asparaginase |
| 3 | 30 | TRDX4-03 | *Arabidopsis* plasma membrane (PM)-localized cyclic nucleotide gated channels (CNGCs) |
| 4 | 31 | TRDX4-04 | *Arabidopsis* receptor like kinase |
| 5 | 32 | TRDX4-05 | Rice gibberellin receptor gene GID1 |
| 6 | 33 | TRDX4-06 | Corn plastidial phosphoenolpyruvate (PEP) phosphate translocator (PPT) |
| 7 | 34 | TRDX4-07 | *Arabidopsis* sulfolipid biosynthesis protein SQD1 |
| 8 | 35 | TRDX4-08 | *Arabidopsis* cytochrome P450 family protein |
| 9 | 36 | TRDX4-09 | *Pseudomonas syringae* phosphoglycerate kinase |
| 10 | 37 | TRDX4-10 | Corn phospholipase A (PLA1) |
| 11 | 38 | TRDX4-11 | *Arabidopsis* plastidal glycolate/glycerate translocator 1 (PLGG1) |
| 12 | 39 | TRDX4-12 | Corn coiled coil domain protein |
| 13 | 40 | TRDX4-13 | Corn iron-phytosiderophore transporter protein yellow stripe 1 (YS1) |
| 14 | 41 | TRDX4-14 | *Arabidopsis* ACT domain-containing protein 3 (ACR3) |
| 15 | 42 | TRDX4-15 | *E coli* arginine-insensitive acetylglutamate kinase (NAGK) |
| 16 | 43 | TRDX4-16 | Soybean NOS1 (mitochondrial constitutive NOS) |
| 17 | 44 | TRDX4-17 | Corn thylakoid lumen protein CYP38 |
| 18 | 45 | TRDX4-18 | *Arabidopsis* glutaredoxin family protein |
| 19 | 46 | TRDX4-19 | *E coli* aminobutyrate aminotransferase |

TABLE 1-continued

Sequences for Protein-Coding Genes

| NUC SEQ ID NO. | PEP SEQ ID NO. | Gene ID | Gene Name and Description |
|---|---|---|---|
| 20 | 47 | TRDX4-20 | *Synechocystis* sp. gene of unknown function |
| 21 | 48 | TRDX4-21 | Corn putative forever young oxidoreductase |
| 22 | 49 | TRDX4-22 | Corn MSH2 gene |
| 23 | 50 | TRDX4-23 | *Arabidopsis* mitogen-activated protein kinase kinase kinase 19 (MAPKKK19) |
| 24 | 51 | TRDX4-24 | *Arabidopsis* carbamoyl phosphate synthase EC 6.3.3.5 large subunit |
| 25 | 52 | TRDX4-25 | Soybean gene improving Nitrogen Utilization Efficiency (NUE) |
| 26 | 53 | TRDX4-26 | *Arabidopsis* casparian strip membrane protein 1 (CASP1) |
| 27 | 54 | TRDX4-27 | *E. coli* codon redesigned asparagine synthetase A (AsnA) gene |

Table 2 provides a list of sequences for suppression of target protein-coding genes, as recombinant DNA for production of transgenic plants with enhanced traits. The elements of Table 2 are described by reference to:

"Target NUC SEQ ID NO." which identifies a nucleotide coding sequence of the suppression target gene.

"Target PEP SEQ ID NO." which identifies an amino acid sequence of the suppression target gene.

"Target Gene ID" which is an arbitrary identifier of the suppression target gene.

"Engineered miRNA precursor SEQ ID NO." which identifies a nucleotide sequence of the miRNA construct.

"miRNA recognition site SEQ ID NO." which identifies a nucleotide sequence of the miRNA recognition site.

"Target Gene Name and Description" which is a common name and functional description of the suppression target gene.

TABLE 2

Sequences for Gene Suppression

| Target NUC SEQ ID NO. | Target PEP SEQ ID NO. | Target Gene ID | Engineered miRNA precursor SEQ ID NO. | miRNA recognition site SEQ ID NO. | Target Gene Name and Description |
|---|---|---|---|---|---|
| 55 | 61 | TRDX4-1T | 67 | 73 | corn homolog of NOX1 gene, Plastidial phosphoenolpyruvate (PEP) phosphate translocator (PPT) |
| 56 | 62 | TRDX4-3T | 68 | 74 | soybean SOUL gene |
| 57 | 63 | TRDX4-4T | 69 | 75 | soybean Elongated Hypocotyl 5 (Hy5) |
| 58 | 64 | TRDX4-5T | 70 | 76 | corn Proliferating cell nuclear antigen 2 (PCNA2) |
| 59 | 65 | TRDX4-6T | 71 | 77 | corn putative dolichyl-di-phosphooligosaccharide protein |
| 60 | 66 | TRDX4-7T | 72 | 78 | corn Peroxisomal_fatty_acid_beta-oxidation |

Selection Methods for Transgenic Plants With Enhanced Traits

Within a population of transgenic plants each regenerated from a plant cell with recombinant DNA many plants that survive to fertile transgenic plants that produce seeds and progeny plants will not exhibit an enhanced agronomic trait. Selection from the population is necessary to identify one or more transgenic plants with an enhanced trait. Transgenic plants having enhanced traits are selected from populations of plants regenerated or derived from plant cells transformed as described herein by evaluating the plants in a variety of assays to detect an enhanced trait, for example, increased water use efficiency or drought tolerance, enhanced high temperature or cold tolerance, increased yield, increased nitrogen use efficiency, enhanced seed composition such as enhanced seed protein and enhanced seed oil. These assays can take many forms including, but not limited to, direct screening for the trait in a greenhouse or field trial or by screening for a surrogate trait. Such analyses can be directed to detecting changes in the chemical composition, biomass, physiological property, or morphology of the plant. Changes in chemical compositions such as nutritional composition of grain can be detected by analysis of the seed composition and content of protein, free amino acids, oil, free fatty acids, starch or tocopherols. Changes in chemical compositions can also be detected by analysis of contents in leaves, such as chlorophyll or carotenoid contents. Changes in biomass characteristics can be evaluated on greenhouse or field grown plants and can include plant height, stem diameter, root and shoot dry weights, canopy size; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant to appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green or delayed senescence, stalk lodging, root lodging, plant health, bareness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density and physical grain quality.

Assays for screening for a desired trait are readily designed by those practicing in the art. The following illustrates screening assays for corn traits using hybrid corn plants. The assays can be adapted for screening other plants such as canola, wheat, cotton and soybean either as hybrids or inbreds.

Transgenic corn plants having increased nitrogen use efficiency can be identified by screening transgenic plants in the field under the same and sufficient amount of nitrogen supply as compared to control plants, where such plants provide higher yield as compared to control plants. Transgenic corn plants having increased nitrogen use efficiency can also be identified by screening transgenic plants in the field under reduced amount of nitrogen supply as compared to control plants, where such plants provide the same or similar yield as compared to control plants.

Transgenic corn plants having increased yield are identified by screening using progenies of the transgenic plants over multiple locations for several years with plants grown under optimal production management practices and maximum weed and pest control or standard agronomic practices (SAP). Selection methods can be applied in multiple and diverse geographic locations, for example up to 16 or more locations, over one or more planting seasons, for example at least two planting seasons, to statistically distinguish yield improvement from natural environmental effects.

Transgenic corn plants having increased water use efficiency or drought tolerance are identified by screening plants in an assay where water is withheld for a period to induce stress followed by watering to revive the plants. For example, a selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Although the plant cells and methods of this disclosure can be applied to any plant cell, plant, seed or pollen, for example, any fruit, vegetable, grass, tree or ornamental plant, the various aspects of the disclosure are applied to corn, soybean, cotton, canola, rice, barley, oat, wheat, turf grass, alfalfa, sugar beet, sunflower, quinoa and sugar cane plants.

Example 1. Corn Transformation

This example illustrates transformation methods in producing a transgenic corn plant cell, seed, and plant having altered phenotypes as shown in Tables 4-6, or an enhanced trait, for example, increased water use efficiency, increased nitrogen use efficiency, and increased yield as shown in Tables 7 and 9.

For *Agrobacterium*-mediated transformation of corn embryo cells corn plants were grown in the greenhouse and ears were harvested when the embryos were 1.5 to 2.0 mm in length. Ears were surface-sterilized by spraying or soaking the ears in 80% ethanol, followed by air drying. Immature embryos were isolated from individual kernels on surface-sterilized ears. Shortly after excision, immature maize embryos were inoculated with overnight grown *Agrobacterium* cells, and incubated at room temperature with *Agrobacterium* for 5-20 minutes. Inoculated immature embryos were then co-cultured with *Agrobacterium* for 1 to 3 days at 23° C. in the dark. Co-cultured embryos were transferred to selection media and cultured for approximately two weeks to allow embryogenic callus to develop. Embryogenic calli were transferred to culture medium containing glyphosate and subcultured at about two week intervals. Transformed plant cells were recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

To regenerate transgenic corn plants individual transgenic calli resulting from transformation and selection were placed on media to initiate shoot and root development into plantlets. Plantlets were transferred to potting soil for initial growth in a growth chamber at 26° C. followed by a mist bench before transplanting to 5 inch pots where plants were grown to maturity. The regenerated plants were self-fertilized and seeds were harvested for use in one or more methods to select seeds, seedlings or progeny second generation transgenic plants (R2 plants) or hybrids, for example, by selecting transgenic plants exhibiting an enhanced trait as compared to a control plant.

The above process can be repeated to produce multiple events of transgenic corn plants from cells that were transformed with recombinant DNA from the genes identified in Table 1 or with recombinant DNA from Table 2 that is transcribed into a non-coding miRNA. Progeny transgenic plants and seeds of the transformed plants were screened for the presence and single copy of the inserted gene, and for increased water use efficiency, increased yield, increased nitrogen use efficiency, and altered phenotypes as shown in Tables 4-6. From each group of multiple events of transgenic plants with a specific recombinant DNA from Table 1 or Table 2, the event(s) that showed increased yield, increased water use efficiency, increased nitrogen use efficiency, and altered phenotypes was (were) identified.

Example 2. Soybean Transformation

This example illustrates plant transformation in producing a transgenic soybean plant cell, seed, and plant having altered phenotypes, or an enhanced trait, for example, increased water use efficiency or drought tolerance and increased yield as shown in Tables 7 and 9.

For *Agrobacterium* mediated transformation, soybean seeds were imbibed overnight and the meristem explants excised. Soybean explants were mixed with induced *Agrobacterium* cells containing plasmid DNA with the gene of interest cassette and a plant selectable marker cassette no later than 14 hours from the time of initiation of seed imbibition, and wounded using sonication. Following wounding, explants were placed in co-culture for 2-5 days at which point they were transferred to selection media to allow selection and growth of transgenic shoots. Resistant shoots were harvested in approximately 6-8 weeks and placed into selective rooting media for 2-3 weeks. Shoots producing roots were transferred to the greenhouse and potted in soil. Shoots that remained healthy on selection, but did not produce roots were transferred to non-selective rooting media for an additional two weeks. Roots from any shoots that produced roots off selection were tested for expression of the plant selectable marker before they were transferred to the greenhouse and potted in soil.

The above process can be repeated to produce multiple events of transgenic soybean plants from cells that were transformed with recombinant DNA from the genes identified in Table 1 or recombinant DNA transcribed into a miRNA identified in Table 2. Progeny transgenic plants and seed of the transformed plant cells were screened for the presence and single copy of the inserted gene, and for increased water use efficiency and increased yield as shown in Tables 7 and 9.

Example 3. Identification of Altered Phenotypes in Automated Greenhouse

This example illustrates screening and identification of transgenic plants for altered phenotypes in an automated greenhouse (AGH). The apparatus and the methods for automated phenotypic screening of plants are disclosed in US Patent publication No. US20110135161 (filed on Nov. 10, 2010), which is incorporated by reference herein in its entirety.

Screening and Identification of Transgenic Corn Plants for Altered Phenotypes.

Corn plants were tested in 3 screens in AGH under different conditions including non-stress, nitrogen deficit and water deficit stress conditions. All screens began with a non-stress condition during day 0-5 germination phase, after which the plants were grown for 22 days under screen specific conditions as shown in Table 3.

TABLE 3

Description of the 3 AGH screens for corn plants

| Screen | Description | Germination phase (5 days) | Screen specific phase (22 days) |
|---|---|---|---|
| Non-stress | well watered sufficient nitrogen | 55% VWC water | 55% VWC 8 mM nitrogen |
| Water deficit | limited watered sufficient nitrogen | 55% VWC water | 30% VWC 8 mM nitrogen |
| Nitrogen deficit | well watered low nitrogen | 55% VWC water | 55% VWC 2 mM nitrogen |

Water deficit is defined as a specific Volumetric Water Content (VWC) that is lower than the VWC of non-stress plant. For example, a non-stressed plant might be maintained at 55% VWC and the VWC for a water-deficit assay might be defined around 30% VWC as shown in Table 3. Data were collected using visible light and hyperspectral imaging as well as direct measurement of pot weight and amount of water and nutrient applied to individual plants on a daily basis.

Nitrogen deficit is defined in part as a specific mM concentration of nitrogen that is lower than the nitrogen concentration of non-stress plants. For example, a non-stress plant might be maintained at 8 mM nitrogen while the nitrogen concentration applied in a nitrogen-deficit assay might be maintained at a concentration of 2 mM.

Up to ten parameters were measured for each screen. The visible light color imaging based measurements are: biomass, canopy area and plant height. Biomass (Bmass) is defined as estimated shoot fresh weight (g) of the plant obtained from images acquired from multiple angles of view. Canopy Area (Cnop) is defined as area of leaf as seen in top-down image ($mm^2$). Plant Height (PlntH) refers to the distance from the top of the pot to the highest point of the plant derived from side image (mm). Anthocyanin score and area, chlorophyll score and concentration, and water content score are hyperspectral imaging based parameters. Anthocyanin Score (AntS) is an estimate of anthocyanin in the leaf canopy obtained from a top-down hyperspectral image. Anthocyanin Area (AntA) is an estimate of anthocyanin in the stem obtained from a side-view hyperspectral image. Chlorophyll Score (ClrpS) and Cholrophyll Concentration (ClrpC) are both measurements of chlorophyll in the leaf canopy obtained from a top-down hyperspectral image, where Chlorophyll Score measures in relative units and is done for soybean plants, and Chlorophyll Concentration measures in ppm units and is done for corn plants. Water Content Score (WtrCt) is a measurement of water in the leaf canopy obtained from a top-down hyperspectral image. Water Use Efficiency (WUE) is derived from the grams of plant biomass per liter of water added. Water Applied (WtrAp) is a direct measurement of water added to a pot (pot with no hole) during the course of an experiment.

These physiological screen runs were set up so that tested transgenic lines were compared to a control line. The collected data were analyzed against the control using % delta and certain p-value cutoff. Tables 4-6 are summaries of transgenic corn plants comprising the disclosed recombinant DNA constructs with altered phenotypes under non stress, nitrogen deficit, and water deficit conditions, respectively.

The test results are represented by three numbers: the first number before letter "p" denotes number of events with an increase in the tested parameter at $p \leq 0.1$; the second number before letter "n" denotes number of events with an decrease in the tested parameter at $p \leq 0.1$; the third number before letter "t" denotes total number of transgenic events tested for a given parameter in a specific screen. The increase or decrease is measured in comparison to non-transgenic control plants. A "-" means that it has not been tested. For example, 2p1n5t indicates that 5 transgenic plant events were screened, of which 2 events showed increase and 1 showed decrease of the measured parameter. Note that two constructs of gene TRDX4-19 were tested, and the results are listed as TRDX4-19 and TRDX4-19x.

TABLE 4

Summary of transgenic corn plants with altered phenotypes in AGH non-stress screens

| Gene_ID | AntA | AntS | Bmass | ClrpC | ClrpS | Cnop | PlntH | WUE | WtrAp | WtrCt |
|---|---|---|---|---|---|---|---|---|---|---|
| TRDX4-01 | 0p0n5t | 1p0n5t | 0p2n5t | 0p1n5t | — | 0p3n5t | 0p0n5t | 0p1n5t | 0p3n5t | — |
| TRDX4-02 | 0p1n5t | 0p1n5t | 0p2n5t | 0p2n5t | — | 0p3n5t | 0p2n5t | 0p2n5t | 0p3n5t | — |
| TRDX4-03 | — | 0p2n5t | 0p1n5t | 1p0n5t | — | 0p2n5t | 0p1n5t | 0p2n5t | 0p1n5t | — |
| TRDX4-04 | 1p0n5t | 0p0n5t | 0p2n5t | 0p0n5t | — | 0p1n5t | 0p3n5t | 0p1n5t | 0p1n5t | — |

TABLE 4-continued

Summary of transgenic corn plants with altered phenotypes in AGH non-stress screens

| Gene_ID | AntA | AntS | Bmass | ClrpC | ClrpS | Cnop | PlntH | WUE | WtrAp | WtrCt |
|---|---|---|---|---|---|---|---|---|---|---|
| TRDX4-05 | 1p0n5t | 0p0n5t | 0p0n5t | 0p0n5t | — | 0p0n5t | 0p1n5t | 0p0n5t | 0p1n5t | — |
| TRDX4-07 | — | 0p0n5t | 1p0n5t | — | 1p0n5t | 1p0n5t | 0p1n5t | 0p0n5t | 3p0n5t | 1p0n5t |
| TRDX4-09 | 0p0n5t | 0p0n5t | 0p0n5t | 0p0n5t | — | 0p0n5t | 1p0n5t | 0p2n5t | 1p0n5t | — |
| TRDX4-11 | 0p1n5t | 0p0n5t | 0p1n5t | 0p0n5t | — | 0p0n5t | 0p1n5t | 0p0n5t | 1p1n5t | — |
| TRDX4-12 | 0p2n5t | 0p2n5t | 0p0n5t | 1p0n5t | — | 0p0n5t | 0p0n5t | 0p0n5t | 2p0n5t | — |
| TRDX4-13 | 1p0n5t | 0p0n5t | 0p0n5t | 0p1n5t | — | 0p1n5t | 0p1n5t | 0p0n5t | 0p0n5t | — |
| TRDX4-14 | 0p0n5t | 1p0n5t | 0p2n5t | 1p0n5t | — | 0p2n5t | 0p4n5t | 0p2n5t | 0p2n5t | — |
| TRDX4-16 | 0p0n5t | 0p0n5t | 0p0n5t | 0p0n5t | — | 0p1n5t | 0p1n5t | 0p0n5t | 0p0n5t | — |
| TRDX4-17 | 0p1n5t | 0p0n5t | 1p0n5t | 1p0n5t | — | 2p0n5t | 0p0n5t | 0p0n5t | 4p0n5t | — |
| TRDX4-18 | 0p2n5t | 0p0n5t | 2p1n5t | 0p0n5t | — | 1p1n5t | 0p1n5t | 1p1n5t | 3p1n5t | — |
| TRDX4-19 | 0p1n4t | 0p0n4t | 0p1n4t | 0p0n4t | — | 0p1n4t | 0p1n4t | 0p1n4t | 0p1n4t | — |
| TRDX4-19x | 1p0n5t | 1p0n5t | 0p0n5t | 0p0n5t | — | 0p3n5t | 0p1n5t | 0p0n5t | 0p1n5t | — |
| TRDX4-1T | 0p0n5t | 0p0n5t | 0p1n5t | 3p0n5t | — | 0p1n5t | 0p1n5t | 0p0n5t | 0p1n5t | — |
| TRDX4-20 | 0p0n3t | 0p1n3t | 0p1n3t | 0p1n3t | — | 0p1n3t | 0p1n3t | 0p1n3t | 0p1n3t | — |
| TRDX4-21 | 1p1n5t | 0p0n5t | 0p0n5t | 0p0n5t | — | 1p0n5t | 0p0n5t | 0p0n5t | 1p0n5t | — |
| TRDX4-22 | 0p0n3t | 1p0n5t | 0p0n3t | 0p0n3t | — | 0p1n3t | 0p0n3t | 0p0n3t | 0p1n3t | — |
| TRDX4-23 | 0p0n5t | 1p0n5t | 0p0n5t | 1p0n5t | — | 0p1n5t | 0p0n5t | 0p0n5t | 0p1n5t | — |
| TRDX4-25 | 1p0n5t | 0p0n5t | 0p0n5t | 2p0n5t | — | 0p1n5t | 0p0n5t | 0p0n5t | 0p0n5t | — |
| TRDX4-26 | 0p0n5t | 0p0n5t | 0p2n5t | 0p1n5t | — | 0p2n5t | 0p1n5t | 0p3n5t | 0p0n5t | — |
| TRDX4-27 | 0p0n7t | 0p0n7t | 0p1n7t | 0p0n7t | — | 0p1n7t | 0p1n7t | 0p0n7t | 0p0n7t | — |
| TRDX4-5T | 0p0n3t | 0p0n3t | 0p1n3t | 0p0n3t | — | 0p1n3t | 0p0n3t | 0p1n3t | 0p1n3t | — |
| TRDX4-6T | — | 0p1n5t | 0p4n5t | 0p0n5t | — | 0p3n5t | 0p1n5t | 0p4n5t | 0p2n5t | — |
| TRDX4-7T | 1p0n2t | 0p0n2t | 0p0n2t | 0p0n2t | — | 0p0n2t | 0p1n2t | 0p0n2t | 0p0n2t | — |

TABLE 5

Summary of transgenic corn plants with altered phenotypes in AGH nitrogen-deficit screens

| Gene_ID | AntA | AntS | Bmass | ClrpC | ClrpS | Cnop | PlntH | WUE | WtrAp | WtrCt |
|---|---|---|---|---|---|---|---|---|---|---|
| TRDX4-01 | 3p0n5t | 0p1n5t | 0p1n5t | 0p0n5t | — | 0p3n5t | 0p2n5t | 0p2n5t | 1p2n5t | — |
| TRDX4-02 | 0p1n5t | 0p1n5t | 5p0n5t | 3p0n5t | — | 4p0n5t | 3p1n5t | 5p0n5t | 5p0n5t | — |
| TRDX4-03 | — | 0p0n5t | 0p3n5t | 0p0n5t | — | 0p4n5t | 0p2n5t | 0p2n5t | 0p3n5t | — |
| TRDX4-04 | 0p0n5t | 0p0n5t | 0p0n5t | 1p0n5t | — | 0p0n5t | 0p2n5t | 0p0n5t | 1p0n5t | — |
| TRDX4-05 | 5p0n5t | 0p1n5t | 0p2n5t | 0p0n5t | — | 0p1n5t | 0p0n5t | 0p3n5t | 0p4n5t | — |
| TRDX4-07 | — | 0p0n5t | 1p0n5t | — | 0p1n5t | 0p0n5t | 0p1n5t | 1p0n5t | 1p0n5t | 0p0n5t |
| TRDX4-09 | 0p0n5t | 0p0n5t | 0p0n5t | 0p0n5t | — | 0p0n5t | 0p0n5t | 0p0n5t | 0p1n5t | — |
| TRDX4-11 | 0p0n5t | 0p0n5t | 0p2n5t | 0p1n5t | — | 0p0n5t | 0p0n5t | 0p0n5t | 0p3n5t | — |
| TRDX4-12 | 0p4n5t | 0p0n5t | 1p0n5t | 1p0n5t | — | 2p0n5t | 0p0n5t | 1p0n5t | 0p0n5t | — |
| TRDX4-13 | 0p2n5t | 0p0n5t | 4p0n5t | 0p1n5t | — | 1p0n5t | 3p0n5t | 3p0n5t | 3p0n5t | — |
| TRDX4-14 | 3p0n5t | 0p0n5t | 0p2n5t | 0p0n5t | — | 0p1n5t | 0p4n5t | 0p1n5t | 0p3n5t | — |
| TRDX4-16 | 1p0n5t | 0p0n5t | 0p2n5t | 0p0n5t | — | 0p1n5t | 1p2n5t | 0p2n5t | 0p1n5t | — |
| TRDX4-17 | 0p2n5t | 1p0n5t | 0p0n5t | 1p1n5t | — | 2p0n5t | 0p1n5t | 0p0n5t | 0p4n5t | — |
| TRDX4-18 | 0p3n5t | 0p1n5t | 2p0n5t | 0p0n5t | — | 1p0n5t | 0p0n5t | 3p0n5t | 0p1n5t | — |
| TRDX4-19 | 0p1n3t | 0p0n3t | 1p0n3t | 0p0n3t | — | 2p0n3t | 1p0n3t | 0p0n3t | 2p0n3t | — |
| TRDX4-19x | 0p0n5t | 0p2n5t | 0p0n5t | 0p0n5t | — | 0p1n5t | 0p0n5t | 1p0n5t | 0p1n5t | — |
| TRDX4-1T | 1p0n5t | 0p1n5t | 1p1n5t | 0p0n5t | — | 0p1n5t | 0p2n5t | 1p1n5t | 1p0n5t | — |
| TRDX4-20 | 0p2n3t | 0p2n3t | 2p0n3t | 0p0n3t | — | 1p0n3t | 1p0n3t | 2p0n3t | 2p0n3t | — |
| TRDX4-21 | 0p2n5t | 0p0n5t | 1p1n5t | 2p0n5t | — | 1p0n5t | 0p1n5t | 2p0n5t | 0p3n5t | — |
| TRDX4-22 | 0p2n3t | 0p0n3t | 2p0n3t | 0p0n3t | — | 1p0n3t | 2p0n3t | 2p0n3t | 3p0n3t | — |
| TRDX4-23 | 0p0n5t | 0p0n5t | 1p0n5t | 0p0n5t | — | 1p0n5t | 1p0n5t | 1p0n5t | 1p0n5t | — |
| TRDX4-25 | 0p0n5t | 0p0n5t | 0p0n5t | 1p0n5t | — | 0p1n5t | 0p2n5t | 1p0n5t | 0p2n5t | — |
| TRDX4-26 | 0p0n5t | 0p2n5t | 0p0n5t | 4p0n5t | — | 0p1n5t | 0p5n5t | 0p0n5t | 0p5n5t | — |
| TRDX4-27 | 1p1n7t | 0p1n7t | 0p0n7t | 1p0n7t | — | 0p1n7t | 0p1n7t | 0p0n7t | 1p1n7t | — |
| TRDX4-5T | 0p0n3t | 0p0n3t | 0p1n3t | 0p0n3t | — | 0p2n3t | 0p1n3t | 0p2n3t | 0p3n3t | — |
| TRDX4-6T | — | 0p2n5t | 5p0n5t | 5p0n5t | — | 3p0n5t | 4p0n5t | 5p0n5t | 5p0n5t | — |
| TRDX4-7T | 0p1n3t | 0p1n3t | 3p0n3t | 0p0n3t | — | 3p0n3t | 0p0n3t | 0p0n3t | 0p0n3t | 2p0n3t |

TABLE 6

Summary of transgenic corn plants with altered phenotypes in AGH water-deficit screens

| Gene_ID | AntA | AntS | Bmass | ClrpC | ClrpS | Cnop | PlntH | WUE | WtrAp | WtrCt |
|---|---|---|---|---|---|---|---|---|---|---|
| TRDX4-01 | 0p0n5t | 1p1n5t | 1p0n5t | 1p0n5t | — | 1p1n5t | 1p1n5t | 0p0n5t | 1p0n5t | — |
| TRDX4-02 | 0p0n5t | 3p0n5t | 2p0n5t | 0p0n5t | — | 0p0n5t | 1p0n5t | 1p1n5t | 0p3n5t | — |
| TRDX4-03 | — | 0p1n5t | 0p0n5t | 1p0n5t | — | 1p0n5t | 0p0n5t | 0p1n5t | 1p0n5t | — |
| TRDX4-04 | 0p2n5t | 0p0n5t | 1p0n5t | 0p0n5t | — | 1p0n5t | 0p2n5t | 1p0n5t | 0p0n5t | — |

TABLE 6-continued

Summary of transgenic corn plants with altered phenotypes in AGH water-deficit screens

| Gene_ID | AntA | AntS | Bmass | ClrpC | ClrpS | Cnop | PlntH | WUE | WtrAp | WtrCt |
|---|---|---|---|---|---|---|---|---|---|---|
| TRDX4-05 | 1p0n5t | 0p0n5t | 0p1n5t | 0p0n5t | — | 0p1n5t | 1p0n5t | 0p1n5t | 1p2n5t | — |
| TRDX4-07 | — | 4p0n5t | 0p1n5t | — | 3p1n5t | 0p2n5t | 0p2n5t | 0p1n5t | 0p4n5t | 4p1n5t |
| TRDX4-09 | 1p0n5t | 0p0n5t | 0p0n5t | 0p1n5t | — | 0p1n5t | 0p1n5t | 0p0n5t | 1p4n5t | — |
| TRDX4-11 | 2p0n5t | 0p0n5t | 0p0n5t | 2p0n5t | — | 0p0n5t | 0p0n5t | 0p0n5t | 1p2n5t | — |
| TRDX4-12 | 1p1n5t | 0p1n5t | 1p1n5t | 0p0n5t | — | 2p1n5t | 2p0n5t | 1p1n5t | 2p0n5t | — |
| TRDX4-13 | 4p0n5t | 0p1n5t | 0p5n5t | 0p0n5t | — | 0p5n5t | 0p5n5t | 0p3n5t | 0p5n5t | — |
| TRDX4-14 | 0p0n5t | 0p0n5t | 0p1n5t | 0p1n5t | — | 0p1n5t | 1p1n5t | 0p0n5t | 0p2n5t | — |
| TRDX4-16 | 0p0n5t | 0p0n5t | 0p0n5t | 0p0n5t | — | 0p0n5t | 1p0n5t | 0p0n5t | 0p0n5t | — |
| TRDX4-17 | 0p1n5t | 0p0n5t | 4p0n5t | 2p0n5t | — | 2p0n5t | 4p0n5t | 1p0n5t | 4p0n5t | — |
| TRDX4-18 | 0p2n5t | 0p0n5t | 3p0n5t | 1p0n5t | — | 1p0n5t | 1p2n5t | 2p1n5t | 4p0n5t | — |
| TRDX4-19 | 0p1n4t | 1p0n4t | 0p2n4t | 0p0n4t | — | 1p1n4t | 0p2n4t | 0p1n4t | 0p1n4t | — |
| TRDX4-19x | 0p1n5t | 0p0n5t | 0p0n5t | 0p0n5t | — | 0p0n5t | 0p0n5t | 0p0n5t | 1p2n5t | — |
| TRDX4-1T | 0p1n2t | 0p0n2t | 1p0n2t | 0p0n2t | — | 0p0n2t | 0p0n2t | 1p0n2t | 0p0n2t | — |
| TRDX4-20 | 0p1n3t | 0p0n3t | 0p0n3t | 0p0n3t | — | 0p0n3t | 0p1n3t | 0p0n3t | 0p0n3t | — |
| TRDX4-21 | 0p1n5t | 0p0n5t | 3p1n5t | 2p0n5t | — | 3p0n5t | 2p0n5t | 1p0n5t | 4p1n5t | — |
| TRDX4-22 | 0p0n1t | 0p0n1t | 1p0n1t | 0p1n1t | — | 0p0n1t | 0p0n1t | 0p0n1t | 1p0n1t | — |
| TRDX4-23 | 0p3n5t | 0p1n5t | 4p0n5t | 1p0n5t | — | 4p0n5t | 0p0n5t | 1p0n5t | 4p0n5t | — |
| TRDX4-25 | 1p0n5t | 1p0n5t | 1p0n5t | 1p0n5t | — | 1p0n5t | 0p0n5t | 0p0n5t | 0p1n5t | — |
| TRDX4-26 | 1p0n5t | 3p0n5t | 5p0n5t | 0p0n5t | — | 5p0n5t | 2p0n5t | 3p0n5t | 1p0n5t | — |
| TRDX4-27 | 4p0n7t | 0p0n7t | 0p2n7t | 1p1n7t | — | 1p0n7t | 0p2n7t | 0p1n7t | 0p1n7t | — |
| TRDX4-5T | 2p0n3t | 0p0n3t | 0p3n3t | 0p0n3t | — | 0p3n3t | 0p3n3t | 0p3n3t | 0p3n3t | — |
| TRDX4-6T | — | 0p1n5t | 0p0n5t | 0p0n5t | — | 0p0n5t | 1p0n5t | 0p0n5t | 0p0n5t | — |
| TRDX4-7T | 0p0n3t | 0p0n3t | 0p0n3t | 0p1n3t | — | 3p0n3t | 0p0n3t | 1p0n3t | 0p0n3t | — |

Example 4. Phenotypic Evaluation of Transgenic Plants for Increased Nitrogen Use Efficiency, Increased Water Use Efficiency and Increased Yield Corn field trials were conducted to identify genes that can improve nitrogen use efficiency (NUE) under nitrogen limiting conditions leading to increased yield performance as compared to non transgenic controls. For the Nitrogen field trial results shown in Tables 7 and 9, each field was planted under nitrogen limiting condition (60 lbs/acre) and corn ear weight or yield was compared to non transgenic control plants.

Corn field trials were conducted to identify genes that can improve water use efficiency (WUE) under water limiting conditions leading to increased yield performance as compared to non transgenic controls. The water use efficiency trials for results shown in Tables 7 and 9 were conducted under managed water limiting conditions, and the corn ear weight or yield was compared to non transgenic control plants.

Corn and soybean field trials were conducted to identify genes that can improve broad-acre yield (BAY) under standard agronomic practice. The broad-acre yield trials for results shown in Tables 7 and 9 were conducted under standard agronomic practice, and the corn or soybean yield was compared to non transgenic control plants.

Table 7 provides a list of genes for producing transgenic plants with increased nitrogen use efficiency (NUE), increased water use efficiency (WUE), and increased broad-acre yield (BAY) as compared to a control plant. Polynucleotide sequences in constructs with at least one event showing significant yield or ear weight increase across multiple locations at p≤0.2 are included. The genes were expressed with constitutive promoters unless noted otherwise under "Specific Expression Pattern". Promoter of specific expression pattern was chosen over constitutive promoter, based on the understanding of the gene function, or based on the observed lack of significant yield increase when the gene was expressed with constitutive promoter. The elements of Table 7 are described by reference to:

"Crop" which refers to the crop in trial, which is either corn or soybean;

"Condition" which refers to the type of field trial, which is BAY for broad acre yield trial under standard agronomic practice (SAP), WUE for water use efficiency trial, and NUE for nitrogen use efficiency trial;

"Specific Expression Pattern" which refers to the expected expression pattern or promoter type, instead of constitutive;

"Gene ID" which refers to the gene identifier as defined in Table 1;

"Yield results" which refers to the recombinant DNA in a construct with at least one event showing significant yield increase at p≤0.2 across locations. The first number refers to the number of events with significant yield or ear weight increase, whereas the second number refers to the total number of events tested for each recombinant DNA in the construct.

TABLE 7

Recombinant DNA with protein-coding genes for increased nitrogen use efficiency, increased water use efficiency and increased yield

| Crop | Condition | Specific Expression Pattern | Gene ID | Yield Results |
|---|---|---|---|---|
| corn | BAY | leaf preferred | TRDX4-01 | 2/15 |
| corn | BAY | seed preferred | TRDX4-02 | 1/13 |
| corn | BAY | | TRDX4-03 | 2/8 |
| corn | BAY | | TRDX4-04 | 1/23 |
| corn | BAY | | TRDX4-05 | 1/23 |
| corn | BAY | | TRDX4-06 | 1/7 |
| corn | WUE | | TRDX4-07 | 2/4 |
| corn | BAY | cold inducible | TRDX4-08 | 4/26 |
| corn | BAY | | TRDX4-09 | 1/25 |
| corn | NUE | | TRDX4-10 | 1/12 |
| corn | BAY | | TRDX4-11 | 1/20 |
| corn | BAY | | TRDX4-12 | 8/20 |
| corn | BAY | | TRDX4-13 | 2/32 |
| corn | BAY | | TRDX4-14 | 2/20 |
| soybean | BAY | | TRDX4-15 | 4/13 |
| corn | BAY | | TRDX4-16 | 1/20 |
| corn | BAY | leaf preferred | TRDX4-17 | 2/13 |

TABLE 7-continued

Recombinant DNA with protein-coding genes for increased nitrogen use efficiency, increased water use efficiency and increased yield

| Crop | Condition | Specific Expression Pattern | Gene ID | Yield Results |
|---|---|---|---|---|
| corn | BAY | | TRDX4-18 | 2/19 |
| corn | WUE | leaf preferred | TRDX4-19 | 1/5 |
| corn | BAY | | TRDX4-19 | 2/22 |
| corn | BAY | leaf preferred | TRDX4-20 | 1/20 |
| corn | BAY | | TRDX4-21 | 4/19 |
| corn | NUE | | TRDX4-22 | 2/10 |
| corn | BAY | leaf preferred | TRDX4-23 | 1/19 |
| soybean | BAY | | TRDX4-24 | 3/15 |
| corn | BAY | | TRDX4-25 | 2/18 |
| corn | BAY | root preferred | TRDX4-26 | 3/21 |
| corn | BAY | | TRDX4-27 | 3/24 |

Table 8 provides a list of polynucleotide sequences of promoters with specific expression patterns. To convey the specific expression patterns, choices of promoters are not limited to those listed in Table 8.

TABLE 8

Promoter sequences and expression patterns

| Nucleotide SEQ ID NO. | Promoter Expression Pattern |
|---|---|
| 97 | Cold inducible |
| 98 | Seed preferred |
| 99 | Leaf preferred |
| 100 | Leaf preferred |

Table 9 provides a list of suppression target genes and miRNA construct elements provided as recombinant DNA for production of transgenic corn or soybean plants with increased nitrogen use efficiency, increased water use efficiency and increased yield. The elements of Table 9 are described by reference to:

"Crop" which refers to the crop in trial, which is either corn or soy;

"Condition" which refers to the type of field trial, which is BAY for broad acre yield trial under standard agronomic practice, WUE for water use efficiency trial, and NUE for nitrogen use efficiency trial;

"Target Gene ID" which refers to the suppression target gene identifier as defined in Table 2;

"Engineered miRNA precursor SEQ ID NO." which identifies a nucleotide sequence of the miRNA construct;

"Yield results" which refers to the recombinant DNA in a construct with at least one event showing significant yield increase at p≤0.2 across locations. The first number refers to the number of events with significant yield or ear weight increase, whereas the second number refers to the total number of events tested for each sequence in the construct.

TABLE 9 miRNA Recombinant DNA constructs suppressing targeted genes for increased nitrogen use efficiency, increased water use efficiency and increased yield

| Crop | Condition | Target Gene ID | Engineered miRNA precursor SEQ ID NO. | Yield Results |
|---|---|---|---|---|
| corn | BAY | TRDX4-1T | 67 | 1/13 |
| soybean | BAY | TRDX4-3T | 68 | 4/15 |
| soybean | BAY | TRDX4-4T | 69 | 3/14 |
| corn | BAY | TRDX4-5T | 70 | 2/20 |

TABLE 9-continued miRNA Recombinant DNA constructs suppressing targeted genes for increased nitrogen use efficiency, increased water use efficiency and increased yield

| Crop | Condition | Target Gene ID | Engineered miRNA precursor SEQ ID NO. | Yield Results |
|---|---|---|---|---|
| corn | NUE | TRDX4-6T | 71 | 1/6 |
| corn | WUE | TRDX4-6T | 71 | 1/6 |
| corn | BAY | TRDX4-6T | 71 | 2/20 |
| corn | WUE | TRDX4-7T | 72 | 1/5 |

Example 5. Homolog Identification

This example illustrates the identification of homologs of proteins encoded by the DNA identified in Table 1 which were used to provide transgenic seed and plants having enhanced agronomic traits. From the sequences of the homolog proteins, corresponding homologous DNA sequences can be identified for preparing additional transgenic seeds and plants with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The All Protein Database was queried using amino acid sequences provided in Table 1 using NCBI "blastp" program with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided in Table 1 using NCBI "blastp" program with E-value cutoff of 1e-4. Up to 1000 top hits were kept. A BLAST searchable database was constructed based on these hits, and is referred to as "SubDB". SubDB is queried with each sequence in the Hit List using NCBI "blastp" program with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs with at least 95% identity over 95% of the length of the polypeptide sequences provided in Table 1 are reported below in Tables 10 and 11.

Table 10 provides a list of homolog genes, of which the elements are described by reference to:

"PEP SEQ ID NO." which identifies an amino acid sequence.

"Homolog ID" which refers to an alphanumeric identifier, the numeric part of which is the NCBI Genbank GI number.

"Gene Name and Description" which is a common name and functional description of the gene.

TABLE 10

Homolog genes information

| PEP SEQ ID NO. | Homolog ID | Gene Name and Description |
|---|---|---|
| 79 | gi_735918 | gi\|735918\|emb\|CAA84367.1\| asparaginase [*Arabidopsis thaliana*] |
| 80 | gi_110742427 | gi\|110742427\|dbj\|BAE99132.1\| cyclic nucleotide-gated cation channel [*Arabidopsis thaliana*] |
| 81 | gi_215261267 | gi\|215261267\|pdb\|3EBL\|A Chain A, Crystal Structure Of Rice Gid1 Complexed With Ga4 [*Oryza sativa Japonica* group] |
| 82 | gi_193211383 | gi\|193211383\|ref\|NP_001105952.1\| plastid phosphate/phosphoenolpyruvate translocator1 [*Zea mays*] |
| 83 | gi_3164136 | gi\|3164136\|dbj\|BAA28535.1\| cytochrome P450 monooxygenase [*Arabidopsis thaliana*] |
| 84 | gi_28867617 | gi\|28867617\|ref\|NP_790236.1\| phosphoglycerate kinase [*Pseudomonas syringae* pv. tomato str. DC3000] |
| 85 | gi_71734219 | gi\|71734219\|ref\|YP_276916.1\| phosphoglycerate kinase [*Pseudomonas syringae* pv. *phaseolicola* 1448A] |
| 86 | gi_66048014 | gi\|66048014\|ref\|YP_237855.1\| phosphoglycerate kinase [*Pseudomonas syringae* pv. *syringae* B728a] |
| 87 | gi_242053823 | gi\|242053823\|ref\|XP_002456057.1\| hypothetical protein SORBIDRAFT_03g029630 [*Sorghum bicolor*] |
| 88 | gi_21593232 | gi\|21593232\|gb\|AAM65181.1\| unknown [*Arabidopsis thaliana*] |
| 89 | gi_226510490 | gi\|226510490\|ref\|NP_001148910.1\| LOC100282530 [*Zea mays*] gi\|195623174\|gb\|ACG33417.1\| pre-mRNA-splicing factor ISY1 [*Zea mays*] |
| 90 | gi_242065688 | gi\|242065688\|ref\|XP_002454133.1\| hypothetical protein SORBIDRAFT_04g025200 [*Sorghum bicolor*] |
| 91 | gi_21593552 | gi\|21593552\|gb\|AAM65519.1\| unknown [*Arabidopsis thaliana*] |
| 92 | gi_21593833 | gi\|21593833\|gb\|AAM65800.1\| glutaredoxin-like protein [*Arabidopsis thaliana*] |
| 93 | gi_226506654 | gi\|226506654\|ref\|NP_001146301.1\| DNA mismatch repair protein MSH2 [*Zea mays*] |
| 94 | gi_242050756 | gi\|242050756\|ref\|XP_002463122.1\| hypothetical protein SORBIDRAFT_02g038230 [*Sorghum bicolor*] |
| 95 | gi_255639875 | gi\|255639875\|gb\|ACU20230.1\| unknown [*Glycine max*] |
| 96 | gi_195623972 | gi\|195623972\|gb\|ACG33816.1\| triose phosphate/phosphate translocator, non-green plastid, chloroplast precursor [*Zea mays*] |

Table 11 describes the correspondence between the protein-coding genes in Table 1, suppression target genes in Table 2, and their homologs, and the level of protein sequence alignment between the gene and its homolog. Note that homologs can be from Table 1, 2 or 10.

TABLE 11

Correspondence of Genes and Homologs

| Gene ID | Homolog ID | Percent Gene Coverage | Percent Homolog Coverage | Percent Identity |
|---|---|---|---|---|
| TRDX4-02 | gi_735918 | 100 | 100 | 99 |
| TRDX4-03 | gi_110742427 | 100 | 100 | 99 |
| TRDX4-05 | gi_215261267 | 100 | 97 | 100 |
| TRDX4-06 | TRDX4-1T | 100 | 100 | 99 |
| TRDX4-06 | gi_193211383 | 100 | 100 | 99 |
| TRDX4-08 | gi_3164136 | 100 | 100 | 99 |
| TRDX4-09 | gi_28867617 | 99 | 100 | 100 |
| TRDX4-09 | gi_71734219 | 99 | 100 | 96 |
| TRDX4-09 | gi_66048014 | 99 | 100 | 96 |
| TRDX4-10 | gi_242053823 | 100 | 100 | 95 |
| TRDX4-11 | gi_21593232 | 100 | 100 | 99 |
| TRDX4-12 | gi_226510490 | 100 | 100 | 99 |
| TRDX4-12 | gi_242065688 | 100 | 100 | 98 |
| TRDX4-14 | gi_21593552 | 100 | 100 | 99 |
| TRDX4-18 | gi_21593833 | 99 | 100 | 100 |
| TRDX4-22 | gi_226506654 | 100 | 100 | 99 |
| TRDX4-22 | gi_242050756 | 100 | 100 | 95 |
| TRDX4-25 | gi_255639875 | 100 | 100 | 99 |
| TRDX4-1T | TRDX4-06 | 100 | 100 | 99 |
| TRDX4-1T | gi_195623972 | 100 | 100 | 99 |
| TRDX4-1T | gi_193211383 | 100 | 100 | 99 |

Example 6. Use of Suppression Methods to Suppress Expression of Target Genes This example illustrates monocot and dicot plant transformation with recombinant DNA constructs that are useful for stable integration into plant chromosomes in the nuclei of plant cells to provide transgenic plants having enhanced traits by suppression of the expression of target genes.

Various recombinant DNA constructs for use in suppressing the expression of a target gene in transgenic plants are constructed based on the nucleotide sequence of the gene encoding the protein that has an amino acid sequence selected from the group consisting of SEQ ID NOs: 61-66, where the DNA constructs are designed to express (a) a miRNA that targets the gene for suppression, (b) an RNA that is a messenger RNA for a target protein and has a synthetic miRNA recognition site that results in down modulation of the target protein, (c) an RNA that forms a dsRNA and that is processed into siRNAs that effect down regulation of the target protein, (d) a ssRNA that forms a trans-acting siRNA which results in the production of siRNAs that effect down regulation of the target protein.

Each of the various types of recombinant DNA constructs is used in transformation of a corn cell using the vector and method of Examples 1 and 2 to produce multiple events of transgenic corn cell. Such events are regenerated into transgenic corn plants and are screened to confirm the presence of the recombinant DNA and its expression of RNA for suppression of the target protein. The population of transgenic plants from multiple transgenic events are also screened to identify the transgenic plants that exhibit altered phenotype or enhanced trait.

We claim:

1. A recombinant DNA construct comprising a heterologous promoter functional in a plant cell and operably linked to:

a) a polynucleotide that comprises a nucleotide sequence with at least 96%, at least 97%, at least 98%, at least 99% identity, or 100% identity to SEQ ID NO: 16; or b) a polynucleotide that encodes a polypeptide having an amino acid sequence with at least 96%, at least 97%, at least 98%, at least 99% identity, or 100% identity to SEQ ID NO: 43.

2. A plant comprising a recombinant DNA construct comprising a heterologous promoter functional in a plant cell and operably linked to:

a) a polynucleotide that comprises a nucleotide sequence with at least 96%, at least 97%, at least 98%, at least 99% identity, or 100% identity to SEQ ID NO: 16; or b) a polynucleotide that encodes a polypeptide having an amino acid sequence with at least 96%, at least 97%, at least 98%, at least 99% identity, or 100% identity to SEQ ID NO: 43.

3. The plant of claim 2, wherein said plant has an altered phenotype or an enhanced trait as compared to a control plant.

4. The plant of claim 2, wherein said plant is a progeny, a propagule, or a field crop.

5. The plant of claim 2, wherein said plant is a corn, soybean, cotton, canola, rice, barley, oat, wheat, turf grass, alfalfa, sugar beet, sunflower, quinoa or sugar cane field crop.

6. The plant of claim 2, wherein said plant is a cell, pollen, ovule, flower, embryo, leaf, root, stem, shoot, meristem, grain or seed propagule.

7. The plant of claim 3, wherein said enhanced trait is increased yield, increased nitrogen use efficiency, or increased water use efficiency as compared to a control plant.

8. The plant of claim 3, wherein said phenotype is anthocyanin content, biomass, canopy area, chlorophyll content, plant height, water applied, water content or water use efficiency.

9. A method for increasing yield, increasing nitrogen use efficiency, or increasing water use efficiency in a plant comprising producing a plant comprising a recombinant DNA construct comprising a heterologous promoter functional in a plant cell and operably linked to:

a) a polynucleotide that comprises a nucleotide sequence with at least 96%, at least 97%, at least 98%, at least 99% identity, or 100% identity to SEQ ID NO: 16; or b) a polynucleotide that encodes a polypeptide having an amino acid sequence with at least 96%, at least 97%, at least 98%, at least 99% identity, or 100% identity to SEQ ID NO: 43.

10. The method of claim 9 wherein said plant is produced by transforming a plant cell or tissue with said recombinant DNA construct and regenerating a plant from said cell or tissue containing said recombinant DNA construct.

11. The method of claim 9 comprising producing said plant by crossing said plant through breeding with:
   a) itself;
   b) a second plant from the same plant line;
   c) a wild type plant; or
   d) a second plant from a different line of plants
   to produce a seed, growing said seed to produce a plurality of progeny plants; and selecting a progeny plant with increased yield, increased nitrogen use efficiency, or increased water use efficiency as compared to a control plant.

12. The recombinant DNA construct of claim 1, wherein the polynucleotide comprises a nucleotide sequence with at least 98% identity to SEQ ID NO:16.

13. The recombinant DNA construct of claim 1, wherein the polynucleotide comprises the nucleotide sequence of SEQ ID NO:16.

14. The recombinant DNA construct of claim 1, wherein the polynucleotide encodes a polypeptide having at least 98% identity to SEQ ID NO:43.

15. The recombinant DNA construct of claim 1, wherein the polynucleotide encodes a polypeptide comprising the sequence of SEQ ID NO:43.

* * * * *